United States Patent
Davidson et al.

(10) Patent No.: US 9,133,104 B2
(45) Date of Patent: Sep. 15, 2015

(54) ENZYME INHIBITORS

(71) Applicants: Chroma Therapeutics Ltd., Abingdon (GB); Margaret Struthers Drummond, Standlake (GB)

(72) Inventors: Alan Hornsby Davidson, Oxfordshire (GB); Sanjay Ratilal Patel, Oxfordshire (GB); Francesca Ann Mazzei, Oxfordshire (GB); Stephen John Davies, Abingdon (GB); Alan Hastings Drummond, Abingdon (GB); David Festus Charles Moffat, Abingdon (GB); Kenneth William John Baker, Oxfordshire (GB); Alastair David Graham Donald, Oxfordshire (GB)

(73) Assignee: Chroma Therapeutics Ltd., Abingdon, Oxfordshire (GB)

( * ) Notice: Subject to any disclaimer, the term of this patent is extended or adjusted under 35 U.S.C. 154(b) by 0 days.

(21) Appl. No.: 14/179,880

(22) Filed: Feb. 13, 2014

(65) Prior Publication Data

US 2014/0163042 A1 Jun. 12, 2014

Related U.S. Application Data

(63) Continuation of application No. 12/957,829, filed on Dec. 1, 2010, now Pat. No. 8,686,032, which is a continuation of application No. 11/918,139, filed as application No. PCT/GB2006/001605 on May 4, 2006, now Pat. No. 7,939,666.

(30) Foreign Application Priority Data

May 5, 2005 (GB) .................................. 0509223.4

(51) Int. Cl.
*C07D 471/04* (2006.01)
*C07C 237/40* (2006.01)
(Continued)

(52) U.S. Cl.
CPC .............. *C07C 237/40* (2013.01); *C07C 259/06* (2013.01); *C07C 275/24* (2013.01);
(Continued)

(58) Field of Classification Search
CPC .... A61K 31/16; C07C 259/04; C07C 237/40; C07C 317/50; C12N 9/99; C07D 471/04
USPC ............ 514/621, 623, 255.01, 292, 307, 443, 514/549, 562, 563; 562/621, 623; 435/184
See application file for complete search history.

(56) References Cited

U.S. PATENT DOCUMENTS 4,254,220 A    3/1981  Meiattini
5,369,108 A   11/1994  Breslow et al.
(Continued)

FOREIGN PATENT DOCUMENTS

DE  4421515 A1  12/1994
EP  0177366 A2   4/1986
(Continued)

OTHER PUBLICATIONS

Horig et al. Journal of Translational Medicine 2004, 2(44), p. 1-8.*
(Continued)

*Primary Examiner* — Yong Chu
(74) *Attorney, Agent, or Firm* — Norton Rose Fulbright US LLP

(57) ABSTRACT

Compounds of formula (I) are inhibitors of histone deacetylase activity, and are useful in the treatment of, for example, cancers, wherein $R_1$ is a carboxylic acid group (—COOH), or an ester group which is hydrolysable by one or more intracellular carboxyesterase enzymes to a carboxylic acid group; $R_2$ is the side chain of a natural or non-natural alpha amino acid; Y is a bond, —C(=O), —S(=O)$_2$—, —C(=O)O—, —C(O)NR$_3$—, —C(=S)—NR$_3$, —C(=NH)NR$_3$ or —S(=O)$_2$NR$_3$— wherein $R_3$ is hydrogen or optionally substituted $C_1$-$C_6$ alkyl; $L^1$ is a divalent radical of formula -(Alk$^1$)$_m$(Q)$_n$(Alk$^2$)$_p$- wherein m, n and p are independently 0 or 1, Q is (i) an optionally substituted divalent mono- or bicyclic carbocyclic or heterocyclic radical having 5-13 ring members, or (ii), in the case where both m and p are 0, a divalent radical of formula —X$^2$-Q$^1$- or -Q$^1$-X$^2$— wherein X$^2$ is —O—, S— or NR$^A$— wherein R$^A$ is hydrogen or optionally substituted $C_1$-$C_3$ alkyl, and Q$^1$ is an optionally substituted divalent mono- or bicyclic carbocyclic or heterocyclic radical having 5-13 ring members, Alk$^1$ and Alk$^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—NR$^A$—) link wherein R$^A$ is hydrogen or optionally substituted $C_1$-$C_3$ alkyl; X$^1$ represents a bond; —C(=O); or —S(=O)$_2$—; —NR$_4$C (=O)—, —C(=O)NR$_4$—, —NR$_4$C(=O)NR$_5$—, —NR$_4$S (=O)$_2$—, or —S(=O)$_2$NR$_4$— wherein $R_4$ and $R_5$ are independently hydrogen or optionally substituted $C_1$-$C_6$ alkyl; z is 0 or 1; A represents an optionally substituted mono-, bi- or tri-cyclic carbocyclic or heterocyclic ring system wherein the radicals $R_1R_2NH$—Y-L$^1$-X$^1$-[CH$_2$]$_z$— and HONHCO-[LINKER]- are attached different ring atoms; and -[Linker]- represents a divalent linker radical linking a ring atom in A with the hydroxamic acid group CONHOH, the length of the linker radical, from the terminal atom linked to the ring atom of A to the terminal atom linked to the hydroxamic acid group, is equivalent to that of an unbranched saturated hydrocarbon chain of from 3-10 carbon atoms.

(I)

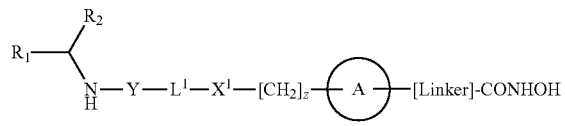

40 Claims, No Drawings

(51) Int. Cl.

| | | |
|---|---|---|
| *C07D 333/70* | (2006.01) | |
| *C07C 317/50* | (2006.01) | |
| *C07D 295/192* | (2006.01) | |
| *C07D 217/26* | (2006.01) | |
| *C07C 259/06* | (2006.01) | |
| *C07C 275/24* | (2006.01) | |
| *C07C 311/46* | (2006.01) | |
| *C07D 207/416* | (2006.01) | |
| *C07D 209/42* | (2006.01) | |
| *C07D 213/40* | (2006.01) | |
| *C07D 217/02* | (2006.01) | |
| *C07D 217/22* | (2006.01) | |
| *C07D 295/185* | (2006.01) | |

(52) U.S. Cl.
CPC ............ *C07C311/46* (2013.01); *C07C 317/50* (2013.01); *C07D 207/416* (2013.01); *C07D 209/42* (2013.01); *C07D 213/40* (2013.01); *C07D 217/02* (2013.01); *C07D 217/22* (2013.01); *C07D 217/26* (2013.01); *C07D 295/185* (2013.01); *C07D 295/192* (2013.01); *C07D 333/70* (2013.01); *C07D 471/04* (2013.01); *C07C 2101/08* (2013.01); *C07C 2101/14* (2013.01)

(56) References Cited

U.S. PATENT DOCUMENTS

| | | | |
|---|---|---|---|
| 6,204,293 | B1 | 3/2001 | Sebti et al. |
| 7,939,666 | B2 | 5/2011 | Davidson et al. |

FOREIGN PATENT DOCUMENTS

| | | | |
|---|---|---|---|
| EP | 0505321 | A2 | 9/1992 |
| IL | 186091 | | 9/2007 |
| JP | 2004516325 | A | 6/2004 |
| WO | 0063197 | A1 | 10/2000 |
| WO | WO-01/18171 | A2 | 3/2001 |
| WO | WO-01/38322 | A1 | 5/2001 |
| WO | WO-01/70675 | A2 | 9/2001 |
| WO | 0222577 | A2 | 3/2002 |
| WO | WO-02/26696 | A1 | 4/2002 |
| WO | WO-02/26703 | A1 | 4/2002 |
| WO | WO-02/30879 | A2 | 4/2002 |
| WO | 02051842 | A1 | 7/2002 |
| WO | WO-02/069947 | A2 | 9/2002 |
| WO | WO-03011851 | A2 | 2/2003 |
| WO | 03066579 | A2 | 8/2003 |
| WO | WO-03075929 | A1 | 9/2003 |
| WO | WO-03076395 | A1 | 9/2003 |
| WO | WO-03076400 | A1 | 9/2003 |
| WO | WO-03076401 | A1 | 9/2003 |
| WO | WO-03076421 | A1 | 9/2003 |
| WO | WO-03076422 | A1 | 9/2003 |
| WO | WO-03076430 | A1 | 9/2003 |
| WO | WO-03/082288 | A1 | 10/2003 |
| WO | WO-03087057 | A1 | 10/2003 |
| WO | WO-03092686 | A1 | 11/2003 |
| WO | WO-2004013130 | A1 | 2/2004 |
| WO | WO-2004092115 | A2 | 10/2004 |
| WO | 2004113336 | A1 | 12/2004 |
| WO | WO-2004110989 | A1 | 12/2004 |
| WO | WO-2005004861 | A1 | 1/2005 |
| WO | WO-2005007091 | A2 | 1/2005 |
| WO | WO-2005013958 | A1 | 2/2005 |
| WO | WO-2005014588 | A1 | 2/2005 |
| WO | WO-2005/026907 | A2 | 3/2005 |
| WO | WO-2005018578 | A2 | 3/2005 |
| WO | WO-2005019174 | A1 | 3/2005 |
| WO | WO-2005028447 | A1 | 3/2005 |
| WO | 2005034880 | A2 | 4/2005 |
| WO | 2005037272 | A1 | 4/2005 |
| WO | WO-2005030704 | A1 | 4/2005 |
| WO | 2006117567 | A2 | 11/2006 |

OTHER PUBLICATIONS

Schafer et al. Drug Discovery Today, 2008, 13 (21/22), 913-916.*
Tamaki Kazuhiko et al., "Synthesis and structure-activity relationships of gelatinase inhibitors derived from matlystatins", Chemical andPharmaceutical Bulletin, Pharmaceutical Society of Japan, Tokyo, JP, vol. 43, No. 11, 1995, pp. 1883-1893, XP002165817.
Wolz Russel L., "A kinetic comparison of the homologous proteases astacin and meprin A1" Archives of Biochemistry and Biophysics, vol. 310, No. 1, 1994, pp. 144-151, XP002392032.
Inaoka Y. et al., "Propioxatins A and B, New Enkephalinase B Inhibitors. IV. Characterization of the Active Site of the Enzyme using Synthetic Propioxatin Analogues" Nov. 1988, Journal of Biochemistry, Japanese Biochemical Society/OUP, Tokyo, JP,pp. 706-711, XP000978993.
Vippagunta et al., Advanced Drug Delivery Reviews, vol. 48, (2001), pp. 3-26.
Jung et al., "Analogues of Trichostatin A and Trapoxin B as Histone Deacetylase Inhibitors," Bioorganic & Medicinal Chemistry Letters, 1997, vol. 7, No. 13, pp. 1655-1658.
Berger, Oncogene, No. 20, 2001, pp. 3007-3013.
Blanchard et al., DDT, vol. 10, No. 3, Feb. 2005, pp. 197-204.
Darkin-Rattray et al, 1996, Proc. Soc. Natl. Acad. Sci., vol. 93, 13143-13147.
Dignam et al, Nucl. Acid. Res., vol. 11, No. 5, 1983, pp. 1475-1489.
Ferrara et al., Cancer Research, No. 61, Jan. 1, 2001, pp. 2-7.
Ghosez et al, J. C. S. Chem. Comm., 1979, pp. 1180-1181.
Gray et al., Curr. Mol. Med., vol. 1, 2001, pp. 401-429.
Grunstein, Nature, No. 389, 1997, pp. 349-353.
Hempen et al., Neuropathol. Exp. Neurol., 1996, vol. 55, No. 9, pp. 964-972.
Hockly et al, PNAS, Feb. 18, 2003, vol. 100, No. 4, 2041-2046.
Hughes, Current Biology, vol. 12, Feb. 19, 2002, pp. R141-R143.
Kelly, et al., Expert Opin. Investig. Drugs., No. 11, 2002, pp. 1695-1713.
Kramer, et al, Trends Endocrinol, 2001, vol. 12, 294-300.
McCampbell et al, Proc. Soc. Natl. Acad. Sci., vol. 98, 2001, pp. 15179-15184.
Miller et al,. Journal of Medical Chemistry, vol. 46, No. 24, 2003, pp. 5097-5116.
Mishra et al., J. Clin. Invest., vol. 111, 2003, pp. 539-552.
Mosley et al., Journal of Biological Chemistry, vol. 278, No. 22, May 30, 2003, pp. 19660-19666.
Park et al., Clinical Cancer Research, vol. 10, Aug. 1, 2004, pp. 5271-5281.
Ryu et al., PNAS, vol. 100, No. 7, 2003, 4281-4286.
Skehan et al., J. Natl. Canc. Inst., vol. 82, 1990, pp. 1107-1112.
Skov et al., Blood, Feb. 15, 2003, vol. 101, No. 4, 1430-1438.
Uphoff et al,. Leukemia vol. 7, No. 1 Jan. 1993, pp. 58-62.
Vetelino et al., Tetrahedron Letters, vol. 35, No. 2, 1994, pp. 219-222.
Vigushin et al., Anticancer Drugs, No. 12, 2002, pp. 1-13.
Wade et al, Trends. Biochem. Sci., vol. 22, 1997, pp. 128-132.
Witt et al, Blood, vol. 101, 2003, pp. 2001-2007.

* cited by examiner

ENZYME INHIBITORS

CROSS REFERENCE TO RELATED APPLICATIONS

This application is a continuation of U.S. patent application Ser. No. 12/957,829 filed on Dec. 1, 2010 issued as U.S. Pat. No. 8,686,032 on Apr. 1, 2014, which is a continuation of U.S. patent application Ser. No. 11/918,139 filed on Oct. 10, 2007 and issued as U.S. Pat. No. 7,939,666 granted May 10, 2011, which is a national phase application under 35 U.S.C. §371 that claims priority to PCT Application No. PCT/GB2006/001605 filed on May 4, 2006, which claims the benefit of Great Britain Application No. 0509223.4 filed May 5, 2005, all of which are incorporated herein by reference in their entireties.

This invention relates to compounds which inhibit members of the histone deacetylase family of enzymes and to their use in the treatment of cell proliferative diseases, including cancers, polyglutamine diseases, for example Huntingdon disease, neurodegenerative diseases for example Alzheimer disease, autoimmune disease for example rheumatoid arthritis and organ transplant rejection, diabetes, haematological disorders, inflammatory disease, cardiovascular disease, atherosclerosis, and the inflammatory sequelae of infection.

BACKGROUND TO THE INVENTION

In eukaryotic cells DNA is packaged with histones, to form chromatin. Approximately 150 base pairs of DNA are wrapped twice around an octamer of histones (two each of histones 2A, 2B, 3 and 4) to form a nucleosome, the basic unit of chromatin. The ordered structure of chromatin needs to be modified in order to allow transcription of the associated genes. Transcriptional regulation is key to differentiation, proliferation and apoptosis, and is, therefore, tightly controlled. Control of the changes in chromatin structure (and hence of transcription) is mediated by covalent modifications to histones, most notably of the N-terminal tails. Covalent modifications (for example methylation, acetylation, phosphorylation and ubiquitination) of the side chains of amino acids are enzymatically mediated (A review of the covalent modifications of histones and their role in transcriptional regulation can be found in Berger S L 2001 Oncogene 20, 3007-3013; See Grunstein, M 1997 Nature 389, 349-352; Wolffe A P 1996 Science 272, 371-372; and Wade P A et al 1997 Trends Biochem Sci 22, 128-132 for reviews of histone acetylation and transcription).

Acetylation of histones is associated with areas of chromatin that are transcriptionally active, whereas nucleosomes with low acetylation levels are, typically, transcriptionally silent. The acetylation status of histones is controlled by two enzyme classes of opposing activities; histone acetyltransferases (HATs) and histone deacetylases (HDACs). In transformed cells it is believed that inappropriate expression of HDACs results in silencing of tumour suppressor genes (For a review of the potential roles of HDACs in tumorigenesis see Gray S G and Teh B T 2001 Curr Mol Med 1, 401-429). Inhibitors of HDAC enzymes have been described in the literature and shown to induce transcriptional reactivation of certain genes resulting in the inhibition of cancer cell proliferation, induction of apoptosis and inhibition of tumour growth in animals (For review see Kelly, W K et al 2002 Expert Opin Investig Drugs 11, 1695-1713). Such findings suggest that HDAC inhibitors have therapeutic potential in the treatment of proliferative diseases such as cancer (Kramer, O H et at 2001 Trends Endocrinol 12, 294-300, Vigushin D M and Coombes R C 2002 Anticancer Drugs 13, 1-13).

In addition, others have proposed that aberrant HDAC activity or histone acetylation is implicated in the following diseases and disorders; polyglutamine disease, for example Huntingdon disease (Hughes R E 2002 Curr Biol 12, R141-R143; McCampbell A et at 2001 Proc Soc Natl Acad Sci 98, 15179-15184; Hockly E et at 2003 Proc Soc Natl Acad Sci 100, 2041-2046), other neurodegenerative diseases, for example Alzheimer disease (Hempen B and Brion J P 1996, J Neuropathol Exp Neurol 55, 964-972), autoimmune disease and organ transplant rejection (Skov S et al 2003 Blood 101, 14 30-1438; Mishra N et at 2003 J Clin Invest 111, 539-552), diabetes (Mosley A L and Ozcan S 2003 J Biol Chem 278, 19660-19666) and diabetic complications, infection (including protozoal infection (Darkin-Rattray, S J et al 1996 Proc Soc Natl Acad Sci 93, 13143-13147)) and haematological disorders including thalassemia (Witt O et at 2003 Blood 101, 2001-2007). The observations contained in these manuscripts suggest that HDAC inhibition should have therapeutic benefit in these, and other related, diseases Many types of HDAC inhibitor compounds have been suggested, and several such compounds are currently being evaluated clinically, for the treatment of cancers. For example, the following patent publications disclose such compounds:

U.S. Pat. No. 5,369,108 and WO 01/18171
U.S. Pat. No. 4,254,220
WO 01/70675
WO 01/38322
WO 02/30879
WO 02/26703
WO 02/069947
WO 02/26696
WO 03/082288
WO 02/22577
WO 03/075929
WO 03/076395
WO 03/076400
WO 03/076401
WO 03/076421
WO 03/076430
WO 03/076422
WO 03/082288
WO 03/087057
WO 03/092686
WO 03/066579
WO 03/011851
WO 04/013130
WO 04/110989
WO 04/092115
WO 04/0224991
WO 05/014588
WO 05/018578
WO 05/019174
WO 05/004861
WO 05/007091
WO 05/030704
WO 05/013958
WO 05/028447
WO 05/026907

Many of the HDAC inhibitors known in the art have a structural template, which may be represented as in formula (A):

(A)

wherein ring A is a carbocyclic or heterocyclic ring system with optional substituents R, and [Linker] is a linker radical of various types. The hydroxamate group functions as a metal binding group, interacting with the metal ion at the active site of the HDAC enzyme, which lies at the base of a pocket in the folded enzyme structure. The ring or ring system A lies within or at the entrance to the pocket containing the metal ion, with the -{Linker}- radical extending deeper into that pocket linking A to the metal binding hydroxamic acid group. In the art, and occasionally herein, the ring or ring system A is sometimes informally referred to as the "head group" of the inhibitor.

The use of prodrugs to enhance the delivery to target organs and tissues, or to overcome poor pharmacokinetic properties of the parent drug, is a well known medicinal chemistry approach. Administration of ester prodrugs, for example, which are hydrolysed by serum carboxylesterases in vivo to the active parent acids, can result in higher serum levels of the parent acid than administration of the acid itself.

BRIEF DESCRIPTION OF THE INVENTION

This invention is based on the finding that the introduction of an alpha amino acid ester grouping into the HDAC inhibitor molecular template (A) above facilitates penetration of the agent through the cell membrane, and thereby allows intracellular carboxylesterase activity to hydrolyse the ester to release the parent acid. Being charged, the acid is not readily transported out of the cell, where it therefore accumulates to increase the intracellular concentration of active HDAC inhibitor. This leads to increases in potency and duration of action. The invention therefore makes available a class of compounds whose structures are characterised by having an alpha amino acid ester moiety which is a substrate for intracellular carboxylesterase (also referred to herein as an "esterase motif") covalently linked to an HDAC inhibitor molecular template, and to the corresponding de-esterified parent acids, such compounds having pharmaceutical utility in the treatment of diseases such as cancers which benefit from intracellular inhibition of HDAC.

DETAILED DESCRIPTION OF THE INVENTION

According to the present invention there is provided a compound of formula (I) or a salt, N-oxide, hydrate or solvate thereof:

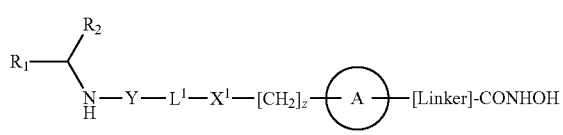

(I)

wherein
$R_1$ is a carboxylic acid group (—COOH), or an ester group which is hydrolysable by one or more intracellular carboxylesterase enzymes to a carboxylic acid group;

$R_2$ is the side chain of a natural or non-natural alpha amino acid;

Y is a bond, —C(=O)—, —S(=O)$_2$—, —C(=O)O—, —C(=O)NR$_3$—, —C(=S)—NR$_3$, —C(=NH)NR$_3$ or —S(=O)$_2$NR$_3$— wherein $R_3$ is hydrogen or optionally substituted $C_1$-$C_6$ alkyl;

$L^1$ is a divalent radical of formula -(Alk$^1$)$_m$(Q)$_n$(Alk$^2$)$_p$- wherein
  m, n and p are independently 0 or 1,
  Q is (i) an optionally substituted divalent mono- or bicyclic carbocyclic or heterocyclic radical having 5-13 ring members, or (ii), in the case where both m and p are 0, a divalent radical of formula —X$^2$-Q$^1$- or -Q$^1$-X$^2$— wherein X$^2$ is —O—, S— or NR$^A$— wherein R$^A$ is hydrogen or optionally substituted $C_1$-$C_3$ alkyl, and Q$^1$ is an optionally substituted divalent mono- or bicyclic carbocyclic or heterocyclic radical having 5-13 ring members,
  Alk$^1$ and Alk$^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—NR$^A$—) link wherein R$^A$ is hydrogen or optionally substituted $C_1$-$C_3$ alkyl;

$X^1$ represents a bond; —C(=O); or —S(=O)$_2$—; —NR$_4$C(=O)—, —C(=O)NR$_4$—, —NR$_4$C(=O)NR$_5$—, —NR$_4$S(=O)$_2$—, or —S(=O)$_2$NR$_4$— wherein $R_4$ and $R_5$ are independently hydrogen or optionally substituted $C_1$-$C_6$ alkyl;

z is 0 or 1;

A represents an optionally substituted mono-, bi- or tri-cyclic carbocyclic or heterocyclic ring system wherein the radicals $R_1R_2NH$—Y-L$^1$-X$^1$—[CH$_2$]$_z$— and HONHCO-[LINKER]- are attached different ring atoms; and -[Linker]- represents a divalent linker radical linking a ring atom in A with the hydroxamic acid group —CONHOH, the length of the linker radical, from the terminal atom linked to the ring atom of A to the terminal atom linked to the hydroxamic acid group, is equivalent to that of an unbranched saturated hydrocarbon chain of from 3-10 carbon atoms.

Although the above definition potentially includes molecules of high molecular weight, it is preferable, in line with general principles of medicinal chemistry practice, that the compounds with which this invention is concerned should have molecular weights of no more than 600.

In another broad aspect the invention provides the use of a compound of formula (I) as defined above, or an N-oxide, salt, hydrate or solvate thereof in the preparation of a composition for inhibiting the activity of an HDAC enzyme.

The compounds with which the invention is concerned may be used for the inhibition of HDAC activity, particularly HDAC1 activity, ex vivo or in vivo.

In one aspect of the invention, the compounds of the invention may be used in the preparation of a composition for the treatment of cell-proliferation disease, for example cancer cell proliferation, polyglutamine diseases for example Huntingdon disease, neurogdeenerative diseases for example Alzheimer disease, autoimmune disease for example rheumatoid arthritis, and organ transplant rejection, diabetes, haematological disorders, infection (including but not limited to protozoal and fungal), inflammatory disease, and cardiovascular disease, including atherosclerosis.

In another aspect, the invention provides a method for the treatment of the foregoing disease types, which comprises administering to a subject suffering such disease an effective amount of a compound of formula (I) as defined above.

The term "ester" or "esterified carboxyl group" means a group $R_9O(C=O)$— in which $R_9$ is the group characterising the ester, notionally derived from the alcohol $R_9OH$.

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent $(C_a-C_b)$alkylene radical" wherein a and b are integers refers to a saturated hydrocarbon chain having from a to b carbon atoms and two unsatisfied valences.

As used herein the term "$(C_a-C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent $(C_a-C_b)$alkenylene radical" means a hydrocarbon chain having from a to b carbon atoms, at least one double bond, and two unsatisfied valences.

As used herein the term "$C_a-C_b$ alkynyl" wherein a and b are integers refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent $(C_a-C_b)$alkynylene radical" wherein a and b are integers refers to a divalent hydrocarbon chain having from 2 to 6 carbon atoms, and at least one triple bond.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, $(C_1-C_6)$ alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, phenyl, halo (including fluoro, bromo and chloro), trifluoromethyl, trifluoromethoxy, nitro, nitrile (—CN), oxo, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1-C_6)$alkyl, $(C_3-C_6)$cycloalkyl, phenyl or monocyclic heteroaryl having 5 or 6 ring atoms. An "optional substituent" may be one of the foregoing substituent groups.

The term "side chain of a natural or non-natural alpha-amino acid" refers to the group $R^1$ in a natural or non-natural amino acid of formula NH$_2$—CH(R$^1$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-d ihydroxyphenylalanine, homoserine, α-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_2$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1$-$C_6$ alkyl ester), amino groups may be converted to amides (for example as a NHCOC$_1$-$C_6$ alkyl amide) or carbamates (for example as an NHC(=O)OC$_1$-$C_6$ alkyl or NHC(=O)OCH$_2$Ph carbamate), hydroxyl groups may be converted to ethers (for example an OC$_1$-$C_6$ alkyl or a O(C$_1$-$C_6$ alkyl)phenyl ether) or esters (for example a OC(=O)C$_1$-$C_6$ alkyl ester) and thiol groups may be converted to thioethers (for example a tert-butyl or benzyl thioether) or thioesters (for example a SC(=O)C$_1$-$C_6$ alkyl thioester).

Examples of side chains of non-natural alpha amino acids include those referred to below in the discussion of suitable $R_2$ groups for use in compounds of the present invention.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, mac, salicylic, citric, methanesulphonic, p-toluenesulphonic, benzoic, benzenesunfonic, glutamic, lactic, and mandelic acids and the like.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

As stated above, the esters of the invention are primarily prodrugs of the corresponding carboxylic acids to which they are converted by intracellular carboxylesterases. However, for so long as they remain unhydrolised, the esters may have HDAC inhibitory activity in their own right. The compounds of the invention include not only the ester, but also the corresponding carboxylic acid hydrolysis products.

The Hydroxamate Group —C(=O)NHOH

In the compounds of the invention, the hydroxamate group functions as a metal binding group, interacting with the metal ion at the active site of the HDAC enzyme, which lies at the base of a pocket in the folded enzyme structure.

The Ring or Ring System A

Ring or ring system A is a mono- bi- or tri-cyclic carbocyclic or heterocyclic ring system, optionally substituted. In the compounds of the invention, when bound to the HDAC enzyme's active site, ring or ring system A lies within or at the entrance to the pocket containing the metal ion, with the -{Linker}- radical extending deeper into that pocket linking A to the metal binding hydroxamic acid group. In the art, the ring or ring system A is sometimes informally referred to as the "head group" of the inhibitor. Examples of ring systems A include the following:

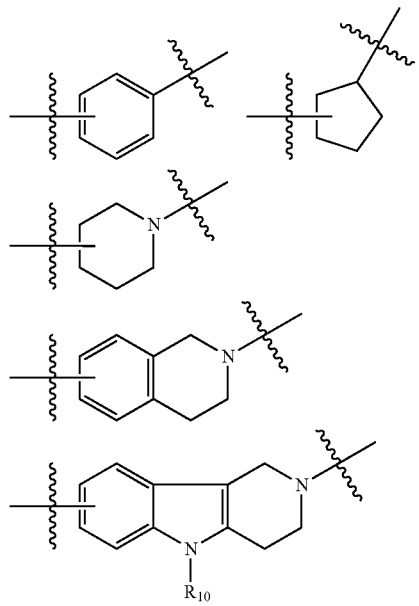

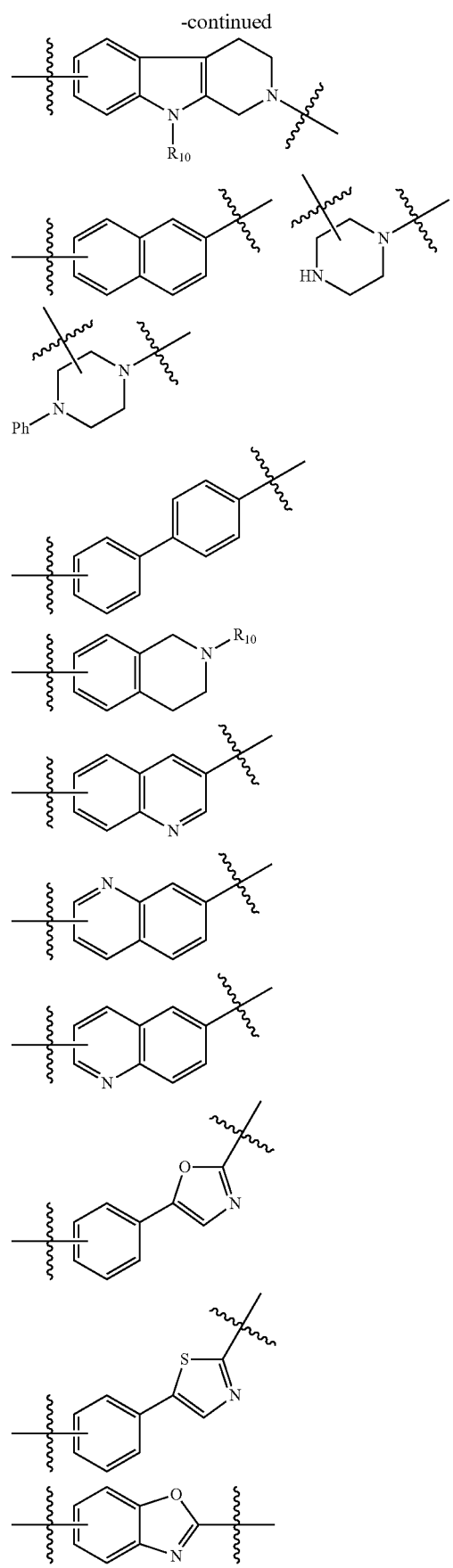

-continued
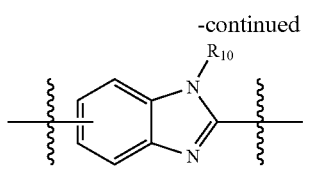
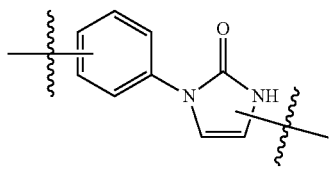
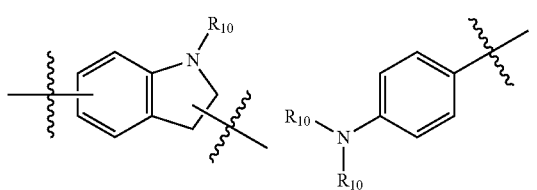
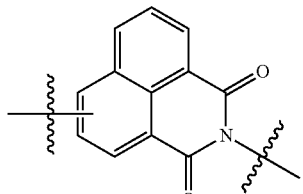
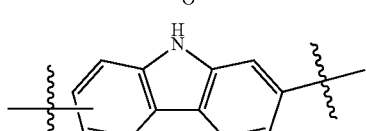
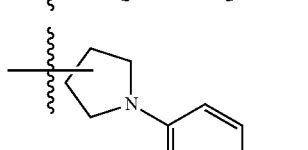
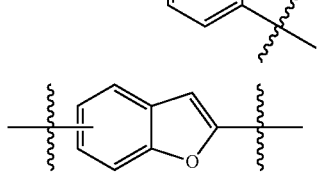
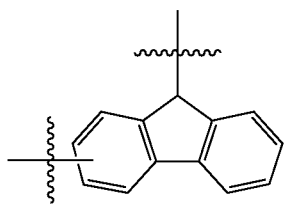
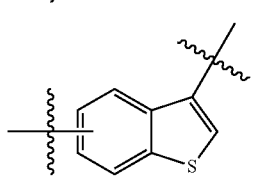
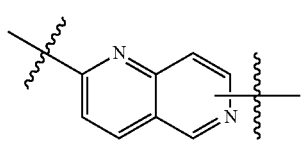
-continued
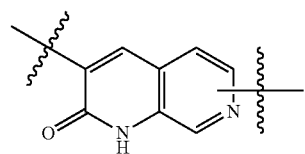
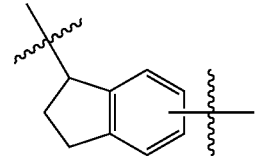
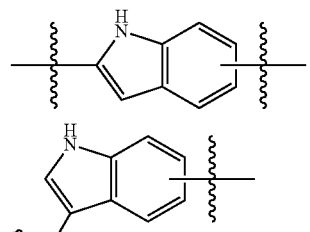
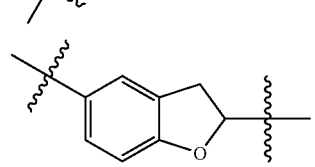
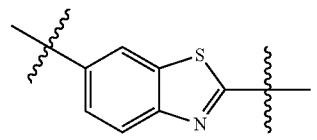
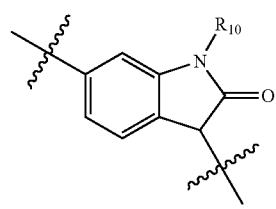
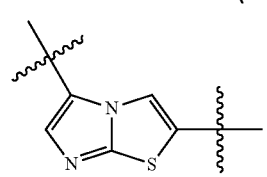
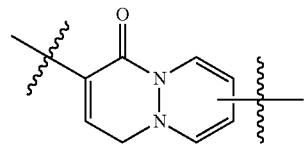
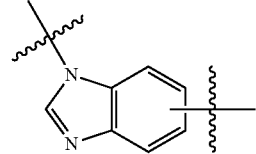
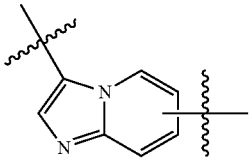

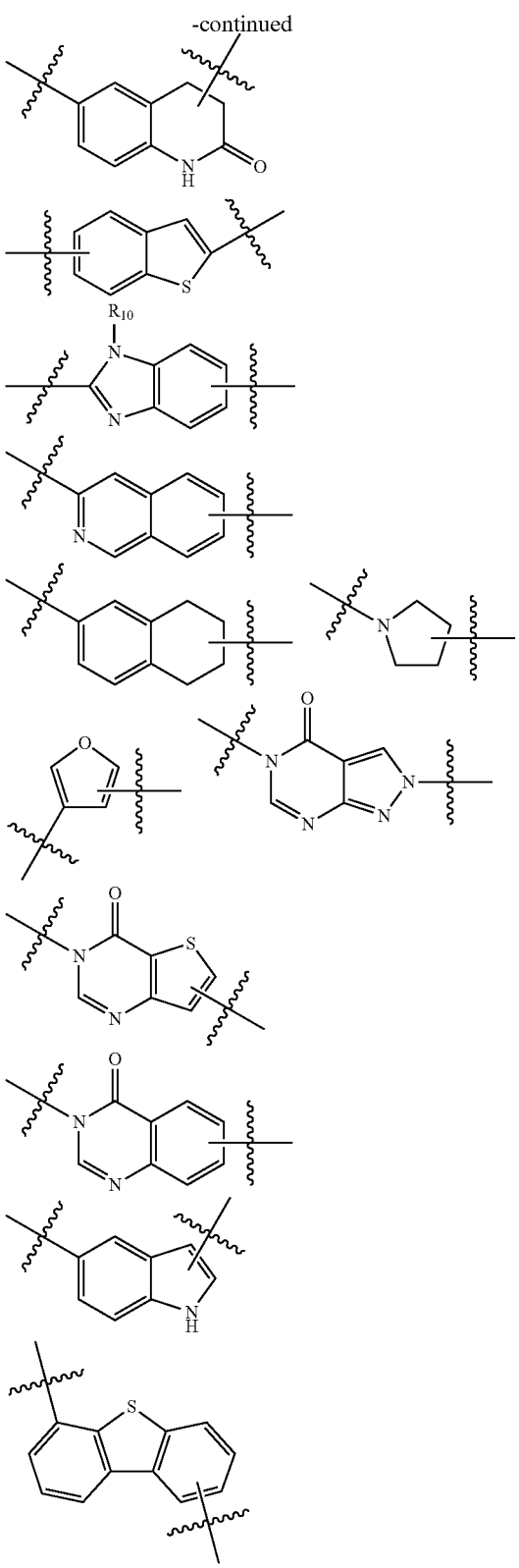

wherein $R_{10}$ is hydrogen or optionally substituted $C_1$-$C_6$ alkyl, the bond intersected by the wavy line connects to the Linker radical in the compounds (I), and wherein the grouping $R_1R_2CHNHYL_1X_1[CH_2]_z$ in the compounds (I) is linked to any convenient ring atom of the ring system shown.

The -[Linker]- Radical

-[Linker]- represents a divalent linker radical linking a ring atom in A with the hydroxamic acid group CONHOH, the length of the linker radical, from the terminal atom linked to the ring atom of A to the terminal atom linked to the hydroxamic acid group, being equivalent to that of an unbranched saturated hydrocarbon chain of from 3-10 carbon atoms. An unbranched saturated hydrocarbon chain of 3 carbon atoms has a length of about 2.5 angstroms, and one of 10 carbon atoms has a length of about 11.3 angstroms. The length of ang given -[Linker]- radical can be determined from data on atom radii and bond lengths in the literature, or can be determined using chemical structure modelling software such as DS ViewerPro (Accelrys, Inc). The defined length of the -[Linker]-radical reflects the fact that the head group A may lie at the entrance to, or within, the metal ion-containing pocket at the active site of the enzyme, and is therefore loosely related to the depth of that pocket. In many cases, the length of the linker will be equivalent to that of an unbranched saturated hydrocarbon chain of from 4 to 9 carbon atoms, for example 5, 6 or 7 carbon atoms. Specific general types of -[Linker]- radical are those discussed below as "Type 1", "Type 2", and "Type 3" linkers.

Type 1 Linkers

In this type, -[Linker]- represents a divalent radical of formula —$(CH_2)_x$—Z-$L^2$- wherein x is 0 or 1;

Z is a bond, —$NR_3$—, —$NR_3C(=O)$—, —$C(=O)NR_3$—, —$NR_4C(=O)$—$NR_3$—, —$C(=S)$—$NR_3$, —$C(=N)$—$NR_3$—$NR_3S(=O)_2$—, or —$S(=O)_2NR_3$— wherein $R_3$ is hydrogen or $C_1$-$C_6$ alkyl; —$C(=O)$; or —$S(=O)_2$—; and $L^2$ represents an optionally substituted, straight or branched, $C_4$-$C_7$ alkylene, $C_4$-$C_6$ alkenylene or $C_4$-$C_6$ alkynylene radicals which may optionally contain or terminate in an ether (—O—), thioether (—S—) or amino (—$NR^4$—) link wherein $R^4$ is hydrogen or optionally substituted $C_1$-$C_3$ alkyl.

In one sub-class of this type of linker, in any compatible combination, x is 0; Z is —NH—, —C(=O)—, —NHC(=O)— or —C(=O)NH— and $L^2$ is —$(CH_2)_5$—, —$(CH_2)_6$—, or —$(CH_2)_7$—.

Type 2 Linkers

In this type, -[Linker]- represents a divalent radical of formula —$(CH_2)_x$-$L^3$-$Ar^1$-$L^4$- wherein x is 0 or 1;

$L^3$ is Z or $L^2$ or Z-$L^2$ wherein Z is as defined in relation to Type 1 linkers and and $L^2$ is a bond or an optionally substituted divalent $C_1$-$C_3$ alkylene radical;

$Ar^1$ is a divalent phenyl radical or a divalent mono-, or bi-cyclic heteroaryl radical having 5 to 13 ring members, and $L^4$ is a bond or optionally substituted —$CH_2$— or —CH=CH—.

In one sub-class of this type of linker, in any compatible combination, x is 0 or 1; $L^3$ is Z or Z-$L^2$, wherein Z is —NH—, —NHS(=O)$_2$—, —S(=O)$_2$NH— or —S(=O)$_2$—; $L^2$ is —$CH_2$—$L^4$ is a bond or —$CH_2$—; and $Ar^1$ is divalent radical selected from the following:

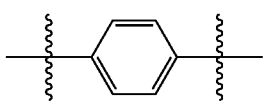

-continued

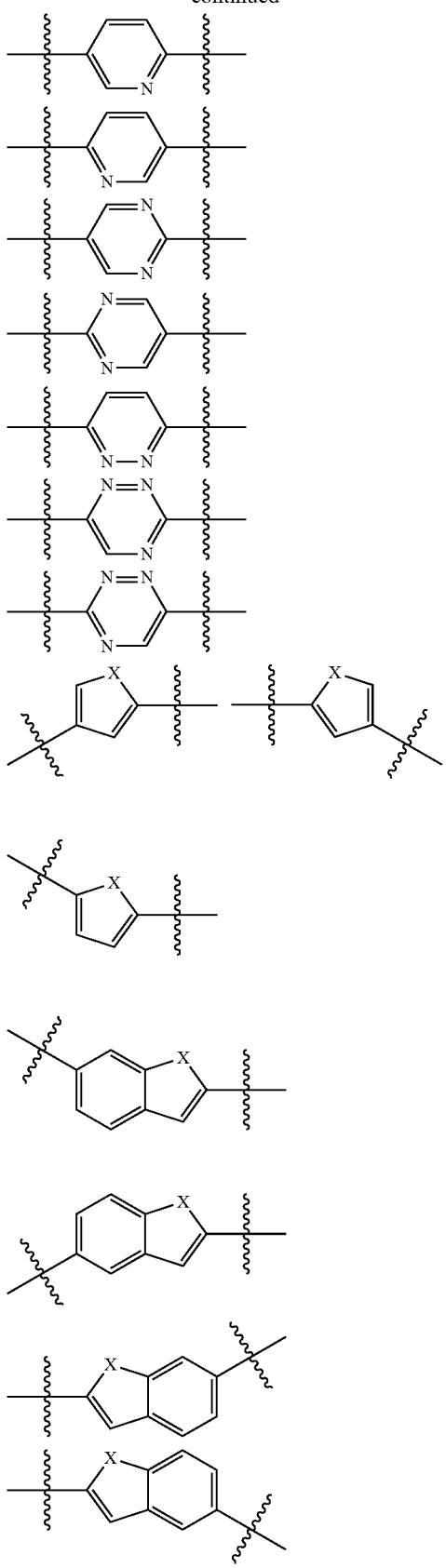

wherein X is O, S or NH.

Of the above Ar¹ radicals, the benzo[b]thiophen-6-yl radical

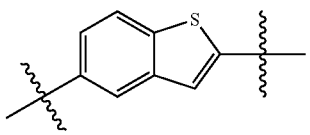 [SMILES: *c1ccc2sc(*)cc2c1]

is a particular example

In another sub-class of this type of linker, in any compatible combination, x is 0; $L^3$ is $L^2$, wherein $L^2$ is an straight chain $C_3$-$C_5$ alkylene radical which may optionally contain an ether (—O—), thioether (—S—) or amino (—$NR^A$—) link wherein $R^A$ is hydrogen or optionally substituted $C_1$-$C_3$ alkyl, for example hydroxyethyl; and Ar¹ is divalent radical selected from those listed in the preceding paragraph.

In yet another subclass of this type, x is 0, $L^3$ and $L^4$ are bonds, and Ar¹ is a divalent phenyl radical or a divalent bicyclic heteroaryl radical having 9 to 13 ring members, for example selected from the following:

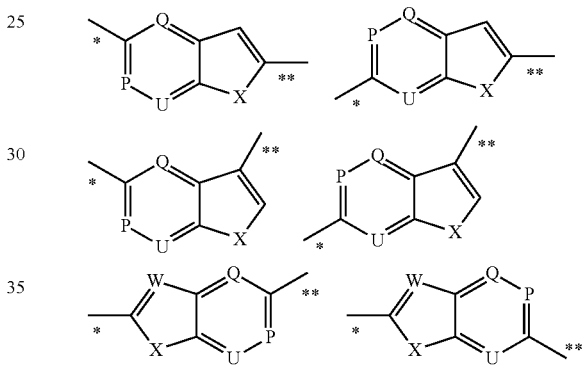

wherein X is selected from O, S and NH and P, Q, and U are independently selected from N and CH; and the bond marked ** is linked to the CONHOH group; and the bond marked * is linked to the ring or ring system A.

Type 3 Linkers

In this type, -[Linker]- represents a divalent radical of formula —$(CH_2)_x$-$L^3$-B—Ar¹-$L^4$- wherein x, Ar¹, $L^3$ and $L^4$ are as discussed with reference to Type 2 linkers above; and B is a mono- or bi-cyclic heterocyclic ring system.

In one subclass of this type of linker B is one of the following:

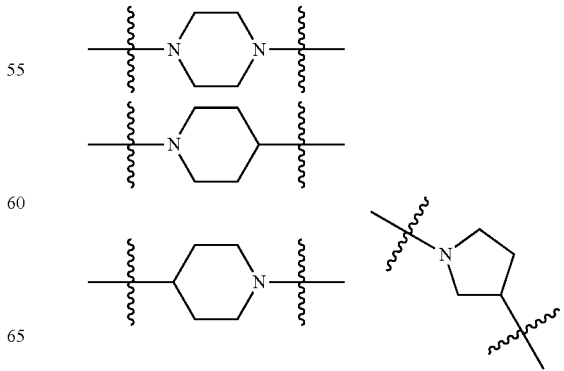

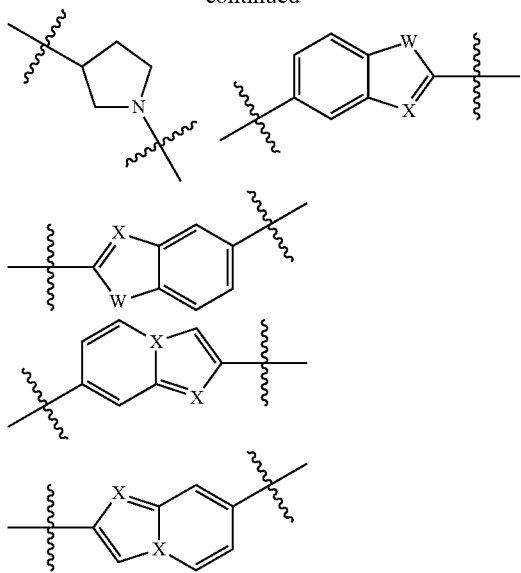

wherein X is N and W is NH, O or S.

The Ester Group $R_1$

The ester group $R_1$ must be one which in the compound of the invention is hydrolysable by one or more intracellular carboxylesterase enzymes to a carboxylic acid group. Intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes, other enzymes such as biphenylhydrolase (BPH) may also have a role in hydrolysing the ester. In general, if the carboxylesterase hydrolyses the free amino acid ester to the parent acid it will, subject to the N-carbonyl dependence of hCE-2 and hCE-3 discussed below, also hydrolyse the ester motif when covalently conjugated to the HDAC inhibitor. Hence, the broken cell assay described herein provide a straightforward, quick and simple first screen for esters which have the required hydrolysis profile. Ester motifs selected in that way may then be re-assayed in the same carboxylesterase assay when conjugated to the modulator via the chosen conjugation chemistry, to confirm that it is still a carboxylesterase substrate in that background.

Subject to the requirement that they be hydroysable by intracellular carboxylesterase enzymes, examples of particular ester groups $R_1$ include those of formula —C(=O)OR$_9$ wherein R$_9$ is (i) R$_7$R$_8$CH— wherein R$_7$ is optionally substituted $(C_1-C_3)$alkyl-$(Z^1)_a$—$(C_1-C_3)$alkyl- or $(C_2-C_3)$alkenyl-$(Z^1)_a$—$(C_1-C_3)$alkyl- wherein a is 0 or 1 and $Z^1$ is —O—, —S—, or —NH—, and R$_8$ is hydrogen or $(C_1-C_3)$alkyl- or R$_7$ and R$_8$ taken together with the carbon to which they are attached form an optionally substituted $C_3-C_7$ cycloalkyl ring or an optionally substituted heterocyclic ring of 5- or 6-ring atoms; or (ii) optionally substituted phenyl or monocyclic heterocyclic having 5 or 6 ring atoms. Within these classes, R$_9$ may be, for example, methyl, ethyl, n- or iso-propyl, n- or sec-butyl, cyclohexyl, allyl, phenyl, benzyl, 2-, 3- or 4-pyridylmethyl, N-methylpiperidin-4-yl, tetrahydrofuran-3-yl or methoxyethyl. Currently preferred is where R$_9$ is cyclopentyl.

Macrophages are known to play a key role in inflammatory disorders through the release of cytokines in particular TNFα and IL-1 (van Roon et al Arthritis and Rheumatism, 2003, 1229-1238). In rheumatoid arthritis they are major contributors to the maintenance of joint inflammation and joint destruction. Macrophages are also involved in tumour growth and development (Naldini and Carraro Curr Drug Targets Inflamm Allergy, 2005, 3-8). Hence agents that selectively target macrophage cell proliferation could be of value in the treatment of cancer and autoimmune disease. Targeting specific cell types would be expected to lead to reduced side-effects. The inventors have discovered a method of targeting HDAC inhibitors to macrophages which is based on the observation that the way in which the esterase motif is linked to the HDAC inhibitor determines whether it is hydrolysed, and hence whether or not it accumulates in different cell types. Specifically it has been found that macrophages contain the human carboxylesterase hCE-1 whereas other cell types do not. In the general formula (I) when the nitrogen of the esterase motif $R_1R_2CHNH$— is not directly linked to a carbonyl (—C(=O)—), ie when Y is not a —C(=O), —C(=O)O— or —C(=O)NR$_3$—radical, the ester will only be hydrolysed by hCE-1 and hence the HDAC inhibitors will only accumulate in macrophages. Herein, unless "monocyte" or "monocytes" is specified, the term macrophage or macrophages will be used to denote macrophages (including tumour associated macrophages) and/or monocytes.

The Amino Acid Side Chain $R_2$

Subject to the requirement that the ester group $R_1$ be hydrolysable by intracellular carboxylesterase enzymes, the identity of the side chain group $R_2$ is not critical.

Examples of amino acid side chains include $C_1-C_6$ alkyl, phenyl, 2, -3-, or 4-hydroxyphenyl, 2,- 3-, or 4-methoxyphenyl, 2,- 3-, or 4-pyridylmethyl, benzyl, phenylethyl, 2-, 3-, or 4-hydroxybenzyl, 2,- 3-, or 4-benzyloxybenzyl, 2,- 3-, or 4-$C_1-C_6$ alkoxybenzyl, and benzyloxy($C_1$-$C_6$alkyl)- groups;

the characterising group of a natural a, amino acid, in which any functional group may be protected;

groups -[Alk]$_n$R$_6$ where Alk is a $(C_1-C_6)$alkyl or $(C_2-C_6)$ alkenyl group optionally interrupted by one or more —O—, or —S— atoms or —N(R$_7$)— groups [where R$_7$ is a hydrogen atom or a $(C_1-C_6)$alkyl group], n is 0 or 1, and R$_6$ is an optionally substituted cycloalkyl or cycloalkenyl group;

a benzyl group substituted in the phenyl ring by a group of formula —OCH$_2$COR$_8$ where R$_8$ is hydroxyl, amino, $(C_1-C_6)$ alkoxy, phenyl$(C_1-C_6)$alkoxy, $(C_1-C_6)$alkylamino, di$((C_1-C_6)$alkyl)amino, phenyl$(C_1-C_6)$alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid;

a heterocyclic$(C_1-C_6)$alkyl group, either being unsubstituted or mono- or di-substituted in the heterocyclic ring with halo, nitro, carboxy, $(C_1-C_6)$alkoxy, cyano, $(C_1-C_6)$alkanoyl, trifluoromethyl $(C_1-C_6)$alkyl, hydroxy, formyl, amino, $(C_1-C_6)$ alkylamino, di-$(C_1-C_6)$alkylamino, mercapto, $(C_1-C_6)$alkylthio, hydroxy$(C_1-C_6)$alkyl, mercapto$(C_1-C_6)$alkyl or $(C_1-C_6)$alkylphenylmethyl; and a group —CR$_a$R$_b$R$_c$ in which:
  each of R$_a$, R$_b$ and R$_c$ is independently hydrogen, $(C_1-C_6)$ alkyl, $(C_2-C_6)$alkenyl, $(C_2-C_6)$alkynyl, phenyl$(C_1-C_6)$ alkyl, $(C_3-C_8)$cycloalkyl; or
  R$_c$ is hydrogen and R$_a$ and R$_b$ are independently phenyl or heteroaryl such as pyridyl; or
  R$_c$ is hydrogen, $(C_1-C_6)$alkyl, $(C_2-C_6)$alkenyl, $(C_2-C_6)$ alkynyl, phenyl$(C_1-C_6)$alkyl, or $(C_3-C_8)$cycloalkyl, and R$_a$ and R$_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently $(C_1-C_6)$alkyl, $(C_2-C_6)$alkenyl, $(C_2-C_6)$alkynyl, phenyl$(C_1-C_6)$alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —$CO_2H$, $(C_1-C_4)$perfluoroalkyl, —$CH_2OH$, —$CO_2(C_1-C_6)$alkyl, —$O(C_1-C_6)$alkyl, —$O(C_2-C_6)$alkenyl, —$S(C_1-C_6)$alkyl, —$SO(C_1-C_6)$alkyl, —$SO_2(C_1-C_6)$alkyl, —$S(C_2-C_6)$alkenyl, —$SO(C_2-C_6)$alkenyl, —$SO_2(C_2-C_6)$alkenyl or a group -Q-W wherein Q represents a bond or —O—, —S—, —SO— or —$SO_2$— and W represents a phenyl, phenylalkyl, $(C_3-C_6)$cycloalkyl, $(C_3-C_8)$cycloalkylalkyl, $(C_4-C_6)$cycloalkenyl, $(C_4-C_8)$cycloalkenylalkyl, heteroaryl or heteroarylalkyl group, which group W may optionally be substituted by one or more substituents independently selected from, hydroxyl, halogen, —CN, —$CO_2H$, —$CO_2(C_1-C_6)$alkyl, —$CONH_2$, —$CONH(C_1-C_6)$alkyl, —$CONH(C_1-C_6alkyl)_2$, —CHO, —$CH_2OH$, $(C_1-C_4)$perfluoroalkyl, —$O(C_1-C_6)$alkyl, —$S(C_1-C_6)$alkyl, —$SO(C_1-C_6)$alkyl, —$SO_2(C_1-C_6)$alkyl, —$NO_2$, —$NH_2$, —$NH(C_1-C_6)$alkyl, —$N((C_1-C_6)alkyl)_2$, —$NHCO(C_1-C_6)$alkyl, $(C_1-C_6)$alkyl, $(C_2-C_6)$alkenyl, $(C_2-C_6)$alkynyl, $(C_3-C_8)$cycloalkyl, $(C_4-C_8)$cycloalkenyl, phenyl or benzyl.

Examples of particular $R_2$ groups include hydrogen (the glycine "side chain"), benzyl, phenyl, cyclohexylmethyl, cyclohexyl, pyridin-3-ylmethyl, tert-butoxymethyl, iso-butyl, sec-butyl, tert-butyl, 1-benzylthio-1-methylethyl, 1-methylthio-1-methylethyl, 1-mercapto-1-methylethyl, and phenylethyl. Presently preferred $R_2$ groups include phenyl, benzyl, and iso-butyl.

For compounds of the invention which are to be administered systemically, esters with a slow rate of carboxylesterase cleavage are preferred, since they are less susceptible to presystemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. In the compounds of this invention, if the carbon adjacent to the alpha carbon of the alpha amino acid ester ester is monosubstituted, ie $R_2$ is $CH_2R^Z$ ($R^Z$ being the mono-substituent) then the esters tend to be cleaved more rapidly than if that carbon is di- or tri-substituted, as in the case where $R_2$ is, for example, phenyl or cyclohexyl.

The Radical —Y-$L^1$-$X^1$-[$CH_2$]$_z$—

This radical (or bond) arises from the particular chemistry strategy chosen to link the amino acid ester motif $R_1CH(R_2)$NH— to the head group A of the inhibitor. Clearly the chemistry strategy for that coupling may vary widely, and thus many combinations of the variables Y, $L^1$, $X^1$ and z are possible. However, as mentioned above, when the inhibitor is bound to the HDAC enzyme at its active site, the head group A is located at the top of, or within, the metal-ion-containing pocket of the enzyme, so by linking the amino acid ester motif to the head group it generally extends in a direction away from that pocket, and thus minimises or avoids interference with the binding mode of the inhibitor template A-[Linker]-CON-HOH. Hence the precise combination of variable making up the linking chemistry between the amino acid ester motif and the head group A will often be irrelevant to the primary binding mode of the compound as a whole. On the other hand, that linkage chemistry may in some cases pick up additional binding interactions with the enzyme at the top of, or adjacent to, the metal ion-containing pocket, thereby enhancing binding.

It should also be noted that the benefits of the amino acid ester motif described above (facile entry into the cell, carboxylesterase hydrolysis within the cell, and accumulation within the cell of active carboxylic acid hydrolysis product) are best achieved when the linkage between the amino acid ester motif and the head group is not a substrate for peptidase activity within the cell, which might result in cleavage of the amino acid from the molecule. Of course, stability to intracellular peptidases is easily tested by incubating the compound with disrupted cell contents, and analysing for any such cleavage.

With the foregoing general observations in mind, taking the variables making up the radical —Y-$L^1$-$X^1$—[$CH_2$]$_z$— in turn:

z may be 0 or 1, so that a methylene radical linked to the head group A is optional;

specific preferred examples of Y when macrophage selectivity is not required include —(C=O)—, —(C=O)NH—, and —(C=O)O—; Where macrophage selectivity is required any of the other options for Y, including the case where Y is a bond, are appropriate.

In the radical $L^1$, examples of $Alk^1$ and $Alk^2$ radicals, when present, include —$CH_2$—, —$CH_2CH_2$—$CH_2CH_2CH_2$—, —$CH_2CH_2CH_2CH_2$—, —CH=CH—, —CH=CHCH$_2$—, —$CH_2$CH=CH—, $CH_2$CH=CHCH$_2$—C≡C—, —C≡CCH$_2$—, $CH_2$C≡C—, and $CH_2$C≡CCH$_2$. Additional examples of $Alk^1$ and $Alk^2$ include —$CH_2$W—, —$CH_2CH_2$W—$CH_2CH_2$WCH$_2$—, —$CH_2CH_2$WCH($CH_3$)—, —$CH_2$WCH$_2CH_2$—, $CH_2$WCH$_2CH_2$WCH$_2$—, and —WCH$_2CH_2$— where W is —O—, —S—, —NH—, —N(CH$_3$)—, or —$CH_2CH_2$N(CH$_2CH_2$OH)CH$_2$—. Further examples of $Alk^1$ and $Alk^2$ include divalent cyclopropyl, cyclopentyl and cyclohexyl radicals.

In $L^1$, when n is 0, the radical is a hydrocarbon chain (optionally substituted and perhaps having an ether, thioether or amino linkage). Presently it is preferred that there be no optional substituents in $L^1$. When both m and p are 0, C is a divalent mono- or bicyclic carbocyclic or heterocyclic radical with 5-13 ring atoms (optionally substituted). When n is 1 and at least one of m and p is 1, $L^1$ is a divalent radical including a hydrocarbon chain or chains and a mono- or bicyclic carbocyclic or heterocyclic radical with 5-13 ring atoms (optionally substituted). When present, Q may be, for example, a divalent phenyl, naphthyl, cyclopropyl, cyclopentyl, or cyclohexyl radical, or a mono-, or bi-cyclic heterocyclicl radical having 5 to 13 ring members, such as piperidinyl, piperazinyl, indolyl, pyridyl, thienyl, or pyrrolyl radical, but 1,4-phenylene is presently preferred.

Specifically, in some embodiments of the invention, $L^1$, m and p may be 0 with n being 1. In other embodiments, n and p may be 0 with m being 1. In further embodiments, m, n and p may be all 0. In still further embodiments m may be 0, n may be 1 with Q being a monocyclic heterocyclic radical, and p may be 0 or 1. $Alk^1$ and $Alk^2$, when present, may be selected from —$CH_2$—, —$CH_2CH_2$—, and —$CH_2CH_2CH_2$— and Q may be 1,4-phenylene.

Specific examples of the radical —Y-$L^1$-$X^1$-[$CH_2$]$_z$— include —C(=O)— and —C(=O)NH— as well as —(CH$_2$)$_v$—, —(CH$_2$)$_v$O—, —C(=O)—(CH$_2$)$_v$—,
—C(=O)—(CH$_2$)$_v$O—, —C(=O)—NH—(CH$_2$)$_w$—,
—C(=O)—NH—(CH$_2$)$_w$O—
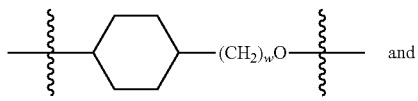 and 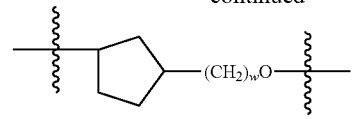
wherein v is 1, 2, 3 or 4 and w is 1, 2 or 3, such as —CH$_2$—, —CH$_2$O—, —C(=O)—CH$_2$—, —C(=O)—CH$_2$O—, —C(=O)—NH—CH$_2$—, and —C(=O)—NH—CH$_2$O—.
Examples of particular subsets of compounds of the invention include those of formulae (IA) to (IM):
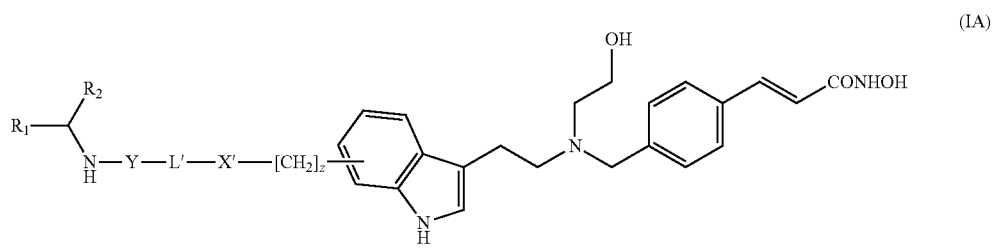
(IA)
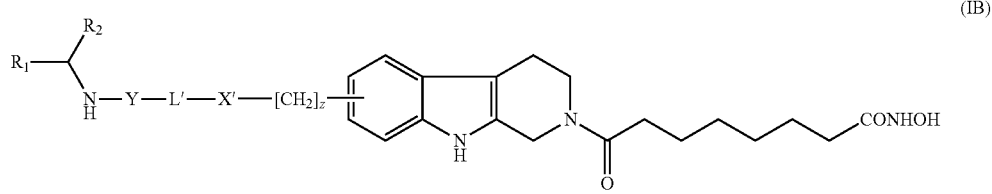
(IB)
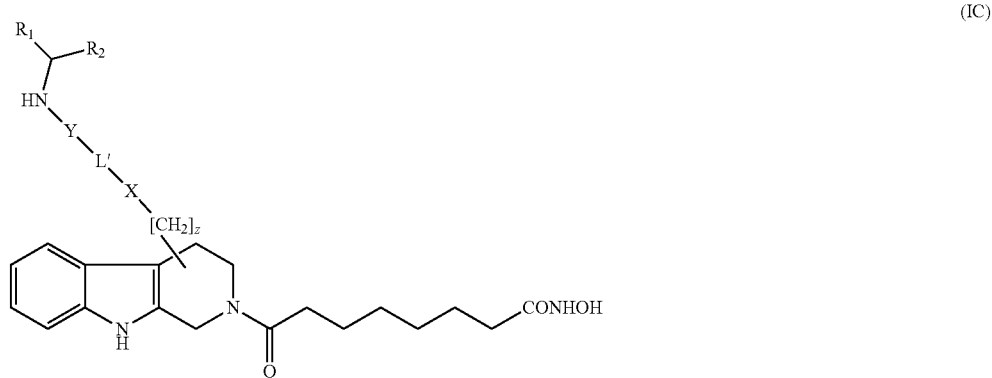
(IC)
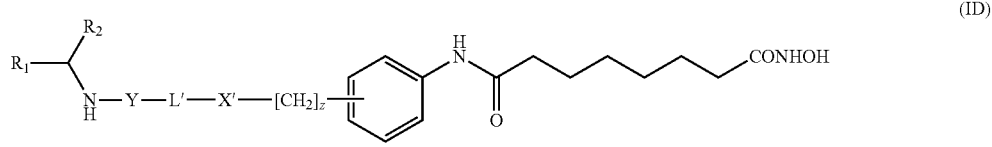
(ID)
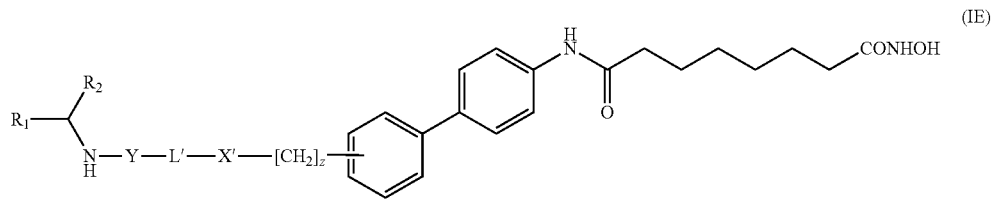
(IE)
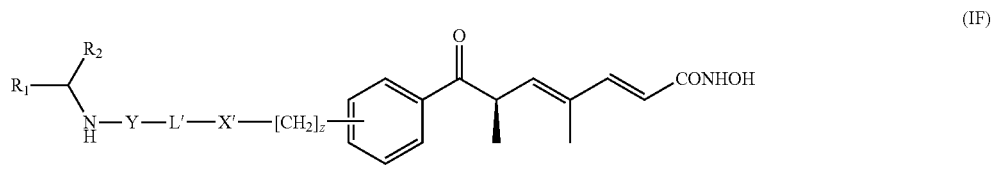
(IF)

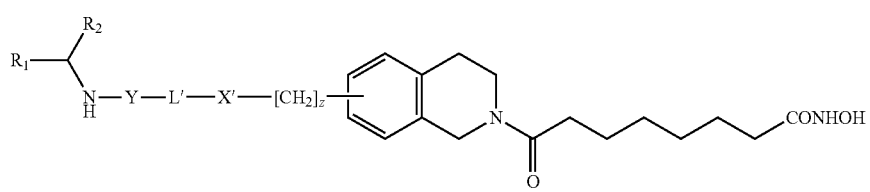

(IG)

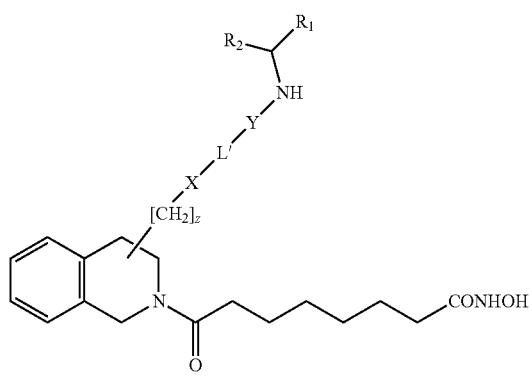

(IH)

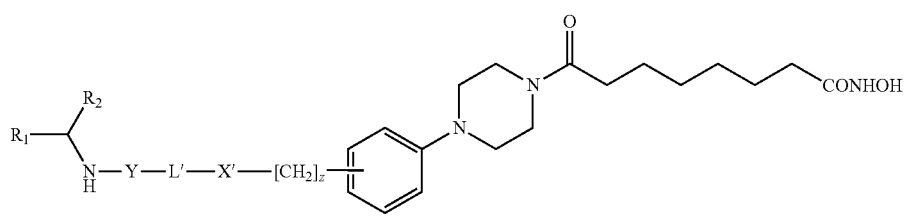

(IJ)

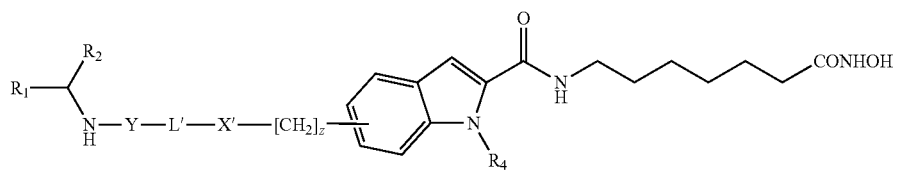

(IK)

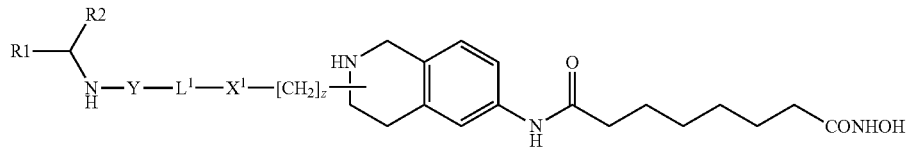

(IL)

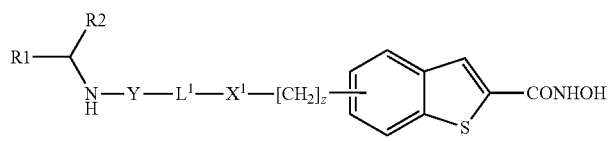

(IM)

wherein z, $R_1$, $R_2$, $R_3$, $L^1$ and $X^1$ and Y are as defined in relation to formula (I), and as discussed above, including the preferences therefor.

Examples of specific compounds of the invention include the following:

(S)-[4-(7-Hydroxycarbarnoyl-heptanoylamino)-benzylamino]-phenyl-acetic acid cyclopentyl ester (S)-2-[3-(7-Hydroxycarbamoyl-heptanoylamino)-benzylamino]-4-phenyl-butyric add cyclopentyl ester (S)-[3-(7-Hydroxycarbamoyl-heptanoylamino)-benzylamino]phenyl-acetic acid cyclopentyl ester (S)-2-[3-(7-Hydroxycarbamoyl-heptanoylamino)-benzylamino]-4-methyl-pentanoic acid cyclopentyl ester (S)-{2-[3-(7-Hydroxycarbamoyl-heptanoylamino)-phenyl]-ethylamino}-phenyl-acetic acid cyclopentyl ester (S)-2-{3-[3-(7-Hydroxycarbamoyl-heptanoylamino)-phenoxy]-propylamino}-3-phenyl-propionic acid cyclopentyl ester (S)-2-(4-{[(2-Hydroxycarbamoyl-benzo[b]thiophen-6-ylmethyl)-amino]-methyl}-benzylamino)-3-(4-hydroxy-phenyl)-propionic add cyclopentyl ester (S)-3-tert-Butoxy-2-(4-{[(2-hydroxycarbamoyl-benzo[b]thiophen-6-ylmethyl)-amino]-methyl}-benzylamino)-propionic acid cyclopentyl ester (S)-1-(4-{[(2-Hydroxycarbamoyl-benzo[b]thiophen-6-ylmethyl)-amino]-methyl}-benzyl)-pyrrolidine-2-carboxylic acid cyclopentyl ester (S)-2-(4-{[(2-Hydroxycarbamoyl-benzo[b]thiophen-6-ylmethyl)-amino]-methyl}-benzylamino)-propionic acid cyclopentyl ester (4-{[(2-Hydroxycarbamoyl-benzo[b]thiophen-6-ylmethyl)-amino]-methyl}-benzylamino)-acetic acid cyclopentyl ester Compounds of the invention may be prepared, for example, by the methods described below and in the Examples herein.

For example, compounds of the invention may be prepared from the corresponding carboxylic acids (II)

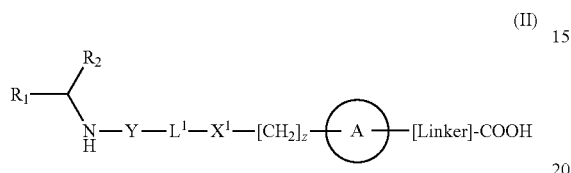

(II)

by reaction of an activated derivative thereof, such as the acid chloride, with hydroxylamine or a protected version of hydroxylamine.

Alternatively, an N- or O-protected or N,O-diprotected precursor of the desired compound (I) may be deprotected. In a useful version of this method O-protection is provided by a resin support, from which the desired hydroxamic acid (I) may be cleaved, for example by acid hydrolysis.

Carboxyl protected derivatives of compounds (II), or O-linked resin-supported derivatives of compounds (II) of the invention may be synthesised in stages by literature methods, selected according to the particular structure of the desired compound. In that connection, the patent publications listed above provide information on the synthesis of HDAC inhibitors which are structurally similar to those of the present invention.

In one approach, suitable for compounds (I) wherein Z is a sulfonamido radical —NHSO$_2$—, an amine (III)

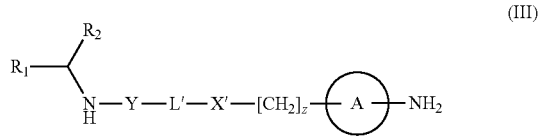

(III)

may be reacted with an activated derivative, for example the acid chloride, of a sulfonic acid HOSO$_2$-L$^2$-Z$^2$ wherein Z$^2$ is a protected carboxyl group, such as cleavable ester, or an O-linked resin-supported hydroxamic acid group.

In another approach, suitable for compounds (I) wherein Z is an amide radical —NHC(=O)—, an amine (III) may be reacted with a carboxylic acid HOC(=O)-L-Z$^2$, Z$^2$ being as defined in the preceding paragraph, in the presence of a carbodiimide coupling agent.

The case of compounds (I) where the ring or ring system A is linked to the Linker-CONHOH moiety via a ring nitrogen, and Z is —(C=O)— or —SO$_2$—, the appropriate N-heterocycle (IV)

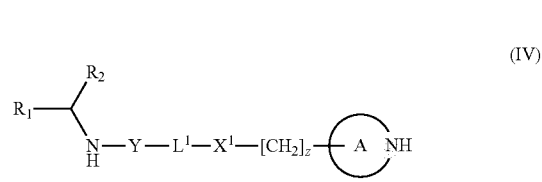

(IV)

may be reacted with the corresponding carboxylic or sulfonic acid (ie HOOC-L$^2$-Z$^2$ or HOSO$_2$-L$^2$-Z$^2$ wherein Z$^2$ is as defined above), either as an activated derivative thereof such as the chloride, or in the presence of a carbodiimide coupling agent.

By way of further illustration of the use of literature methods for the synthesis of compounds within the scope of formula (I) above, the following reaction schemes 1-6 are presented. In these schemes the group R represents the radical

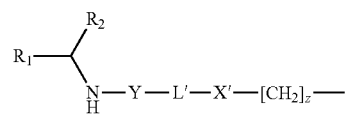

present in the compounds of the invention, or represents a functional group upon which that radical may be built up using literature methods.

Also in the schemes, the symbol

represents a solid phase resin support.

Scheme 1

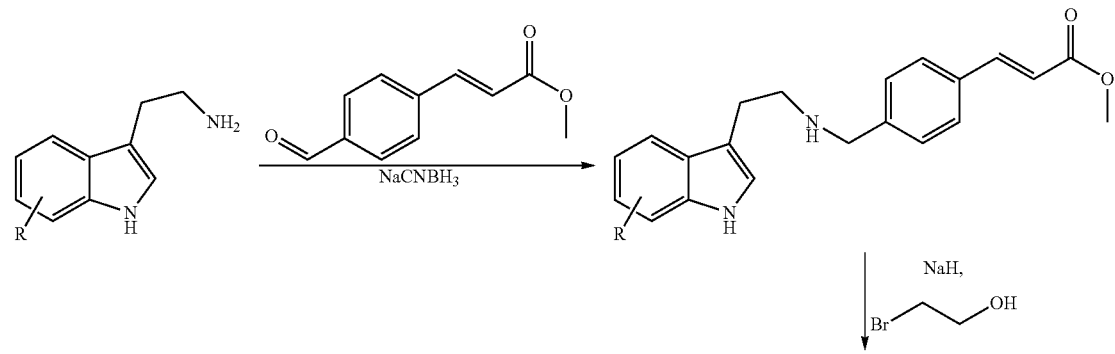

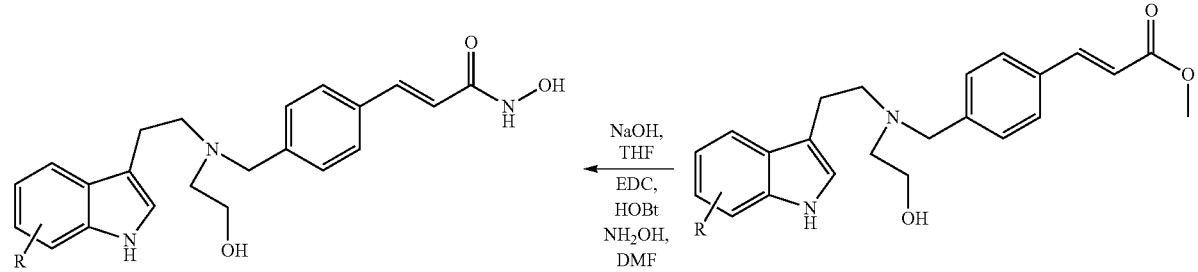
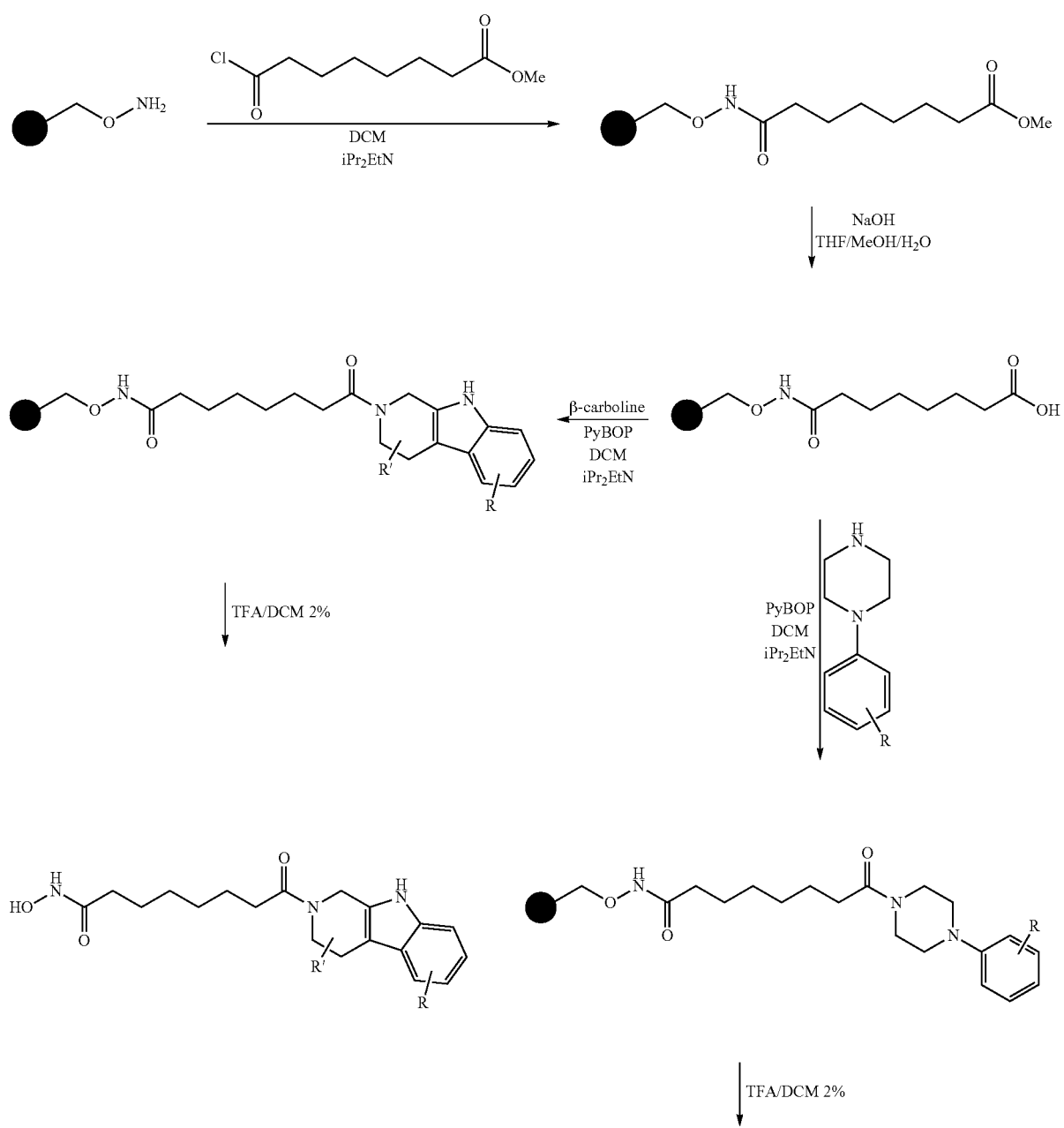
Scheme 2

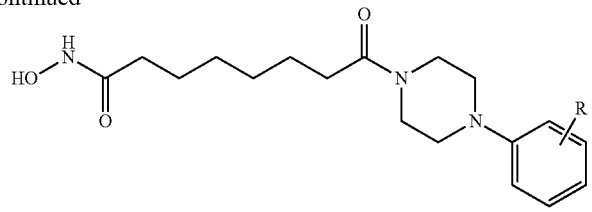
Scheme 3
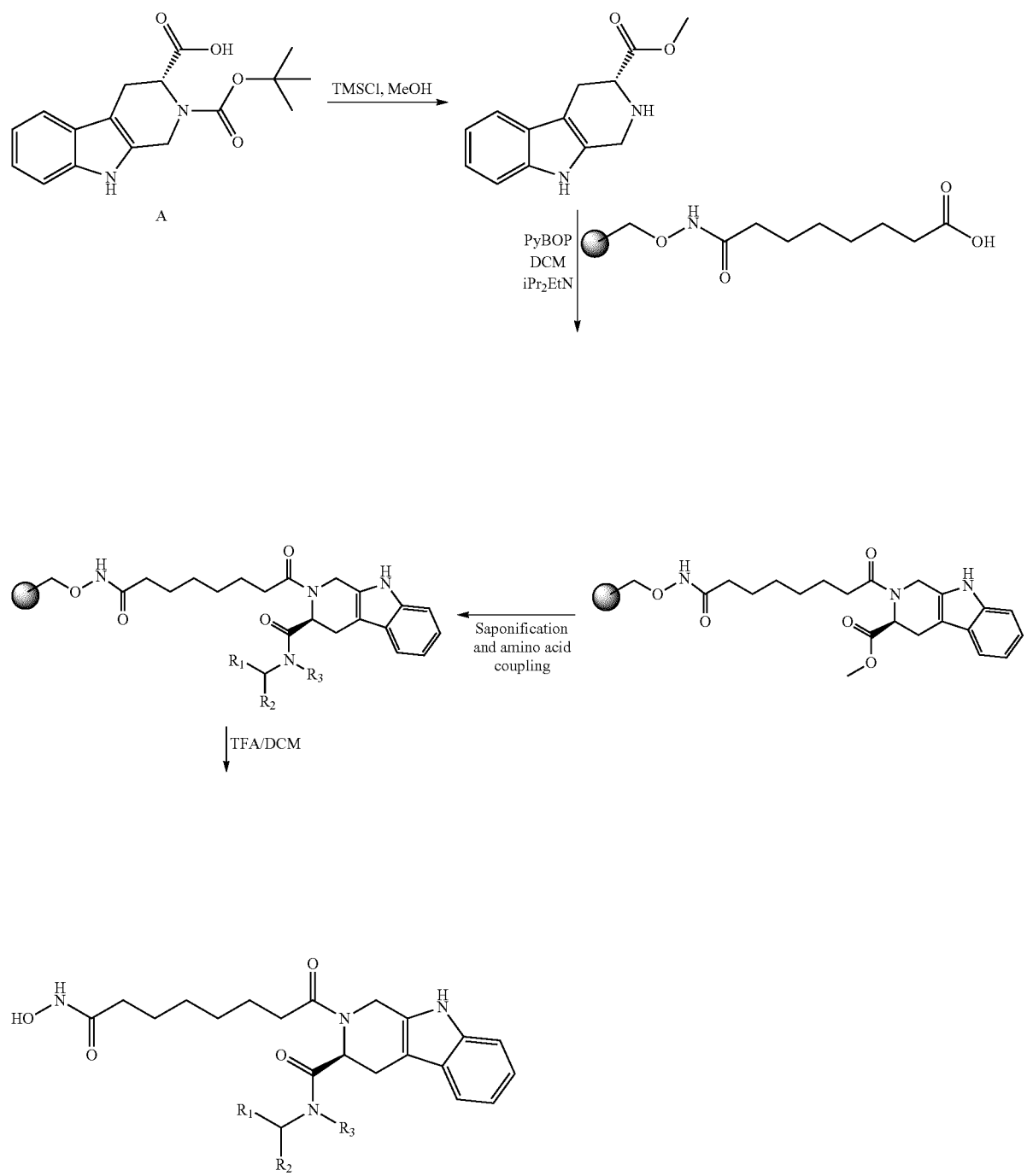

Scheme 4
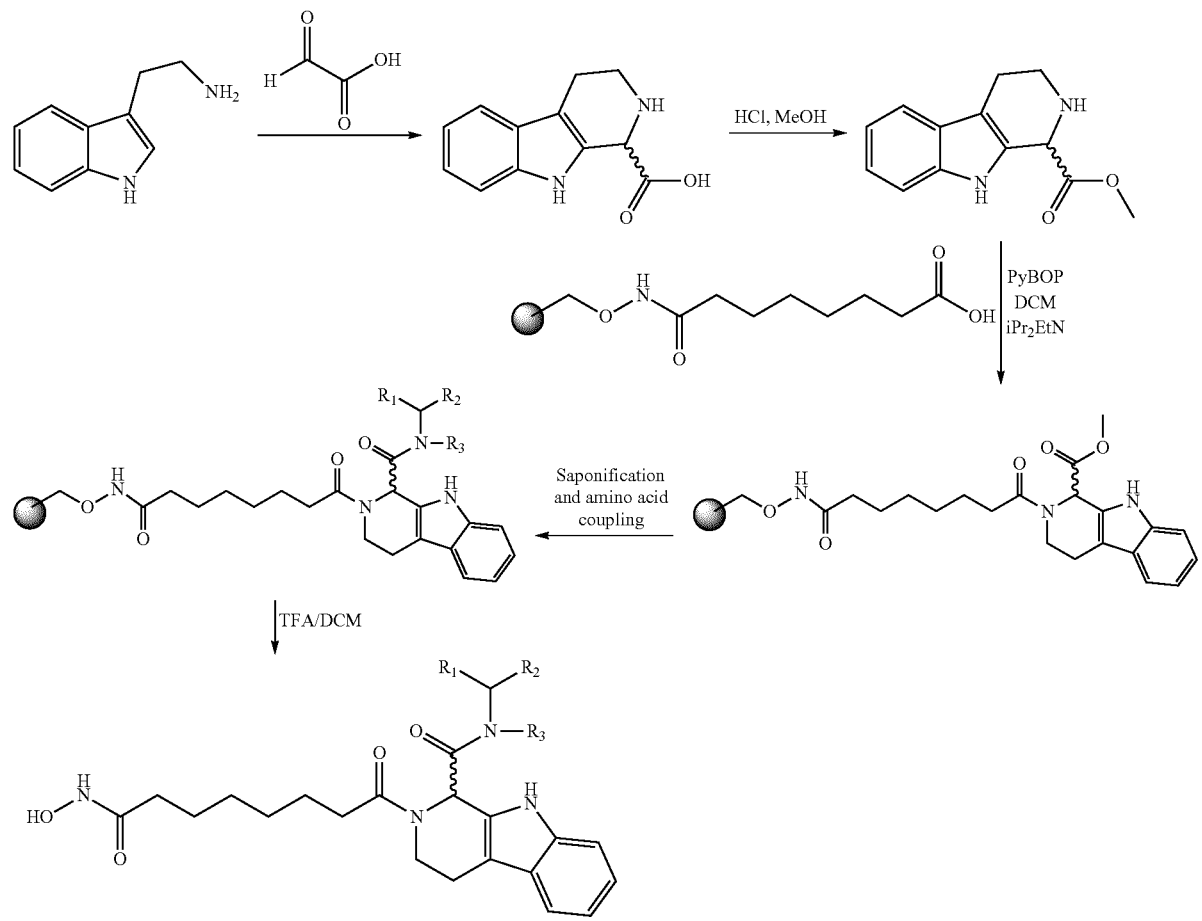
Scheme 5
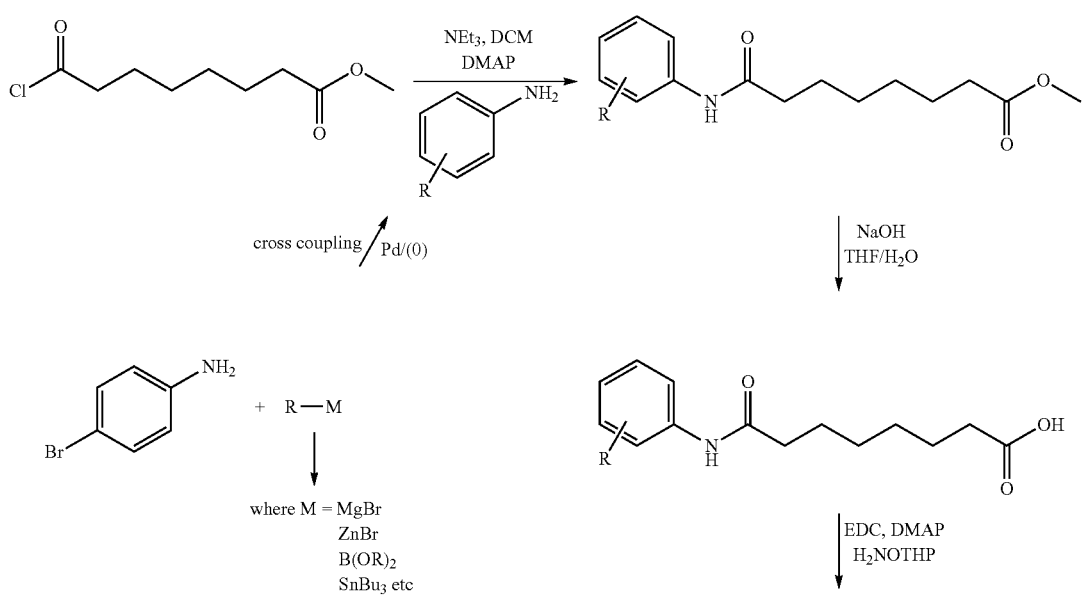

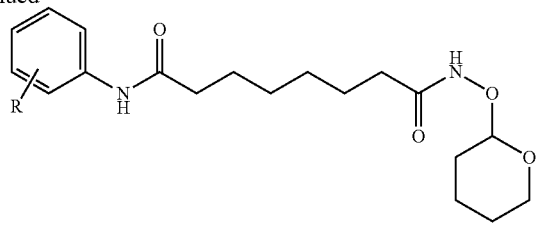

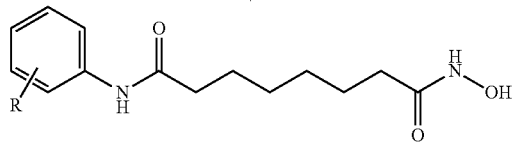

Scheme 6

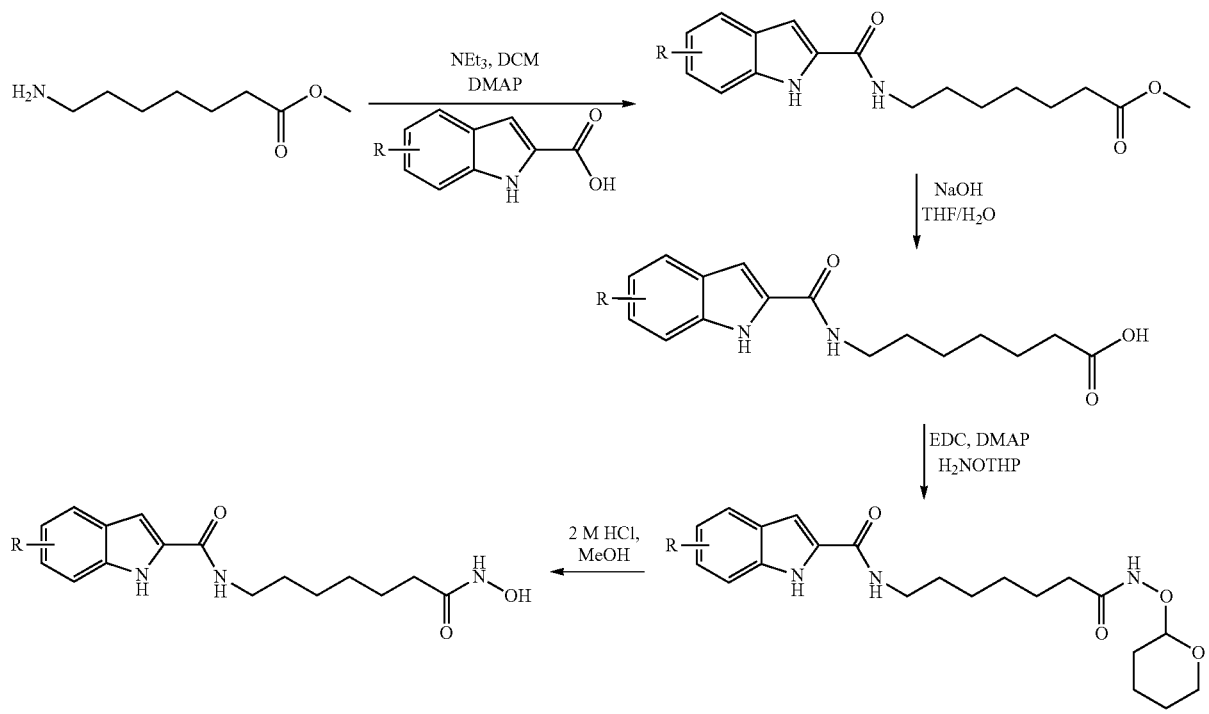

As mentioned above, the compounds with which the invention is concerned are HDAC inhibitors, and may therefore be of use in the treatment of cell proliferative disease, such as cancer, in humans and other mammals.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atom/zers or ultrasonic atom/zers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparatus are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following Examples illustrate the preparation of specific compounds of the invention, and the HDAC inhibitory properties thereof: In the Examples:

Commercially available reagents and solvents (HPLC grade) were used without further purification.

Microwave irradiation was carried out using a CEM Discover focused microwave reactor.

Solvents were removed using a GeneVac Series I without heating or a Genevac Series II with VacRamp at 30° C. or a Buchi rotary evaporator. Purification of compounds by flash chromatography column was performed using silica gel, particle size 40-63 µm (230-400 mesh) obtained from Silicycle. Purification of compounds by preparative HPLC was performed on Gilson systems using reverse phase ThermoHypersil-Keystone Hyperprep HS C18 columns (12 µm, 100× 21.2 mm), gradient 20-100% B (A=water/0.1% TFA, B=acetonitrile/0.1% TFA) over 9.5 min, flow=30 ml/min, injection solvent 2:1 DMSO:acetonitrile (1.6 ml), UV detection at 215 nm.

$^1$H NMR spectra were recorded on a Bruker 400 MHz AV spectrometer in deuterated solvents. Chemical shifts (δ) are in parts per million. Thin-layer chromatography (TLC) analysis was performed with Kieselgel 60 $F_{254}$ (Merck) plates and visualized using UV light.

Analytical HPLCMS was performed on Agilent HP1100, Waters 600 or Waters 1525 LC systems using reverse phase Hypersil BDS C18 columns (5 µm, 2.1×50 mm), gradient 0-95% B (A=water/0.1% TFA, B=acetonitrile/0.1% TFA) over 2.10 min, flow=1.0 ml/min. UV spectra were recorded at 215 nm using a Gilson G1315A Diode Array Detector, G1214A single wavelength UV detector, Waters 2487 dual wavelength UV detector, Waters 2488 dual wavelength UV detector, or Waters 2996 diode array UV detector. Mass spectra were obtained over the range m/z 150 to 850 at a sampling rate of 2 scans per second or 1 scan per 1.2 seconds using Micromass LCT with Z-spray interface or Micromass LCT with Z-spray or MUX interface. Data were integrated and reported using OpenLynx and OpenLynx Browser software The following abbreviations have been used:
MeOH=methanol
EtOH=ethanol
EtOAc=ethyl acetate
Boc=tert-butoxycarbonyl
Cbz=carbobenzyloxy
DCM=dichloromethane
DCE=dichloroethane
DMF=dimethylformamide
DMSO=dimethyl sulfoxide
TFA=trifluoroacetic acid
THF=tetrahydrofuran
$Na_2CO_3$=sodium carbonate
HCl=hydrochloric acid
DIPEA=diisopropylethylamine
NaH=sodium hydride
NaOH=sodium hydroxide
$NaHCO_3$=sodium hydrogen carbonate
Pd/C=palladium on carbon
TBME=tert-butyl methyl ether
DMAP=4-Dimethylaminopyridine
$N_2$=nitrogen
PyBop=benzotriazole-1-yl-oxy-tris-pyrrolidino-phosphonium hexafluorophosphate
$Na_2SO_4$=sodium sulphate
$Et_3N$=triethylamine
$NH_3$=ammonia
TMSCl=trimethylchlorosilane
$NH_4Cl$=ammonium chloride
$LiAlH_4$=lithium aluminium hydride
pyBrOP=Bromo-tris-pyrrolidino phosphoniumhexafluorophosphate
$MgSO_4$=magnesium sulfate
$MnO_2$=Manganese dioxide
"BuLi=n-butyllithium
$CO_2$=carbon dioxide
EDCl=N-(3-Dimethylaminopropyl)-N'-ethylcarbodiimide hydrochloride
$Et_2O$=diethyl ether LiOH=lithium hydroxide
HOBt=1-hydroxybenzotriazole
DIAD=Diisopropyl azodicarboxylate
HATU=O-(7-Azabenzotriazol-1-yl-N,N,N',N'-tetramethyluronium hexafluorophosphate
ELS=Evaporative Light Scattering
TLC=thin layer chromatography
ml=milliliter
g=gram(s)
mg=milligram(s)
mol=moles
mmol=millimole(s)
eq=mole equivalent
LCMS=high performance liquid chromatography/mass spectrometry
NMR=nuclear magnetic resonance
r.t.=room temperature
Standard Wash Procedure for Resin Chemistry Resin was washed in the following sequence: DMF, MeOH, DMF, MeOH, DCM, MeOH, DCM, MeOH×2, TBME×2.

Resin Test Cleavage

A small amount of functionalised hydroxylamine 2-chlorotrityl resin (ca 0.3 ml of reaction mixture, ca 10 mg resin) was treated with 2% TFA/DCM (0.5 ml) for 10 min at room temperature. The resin was filtered and the filtrate was concentrated by blowing with a stream of $N_2$ gas. LCMS of the residue was obtained.

(Note: For functionalized hydroxylamine Wang resin test cleavage was carried out using 50% TFA/DCM).

Preparation of Suberic Acid Derivatised Hydroxylamine 2-Chlorotrityl Resin

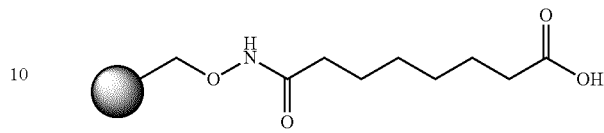

Stage 1—Immobilisation to 2-Chlorotrityl-O—$NH_2$ Resin

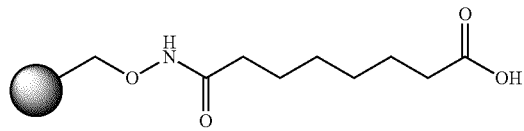

To a round bottomed flask charged with 2-chlorotrityl-O—$NH_2$ resin (6 g, loading 1.14 mmol/g, 6.84 mmol) and DCM (60 ml) was added diisopropylethylamine (5.30, 41.0 mmol, 6 eq). Methyl 8-chloro-8-oxooctanoate (4.2 g, 20.5 mmol, 3 eq) was slowly added to the reaction mixture with orbital shaking and the reaction mixture shaken for 48 hours. The resin was filtered and washed using the standard washing procedure. The resin was dried under vacuum. LCMS purity was determined by ELS detection, 100%, m/z 204 $[M^++H]^+$.

Stage 2—Saponification

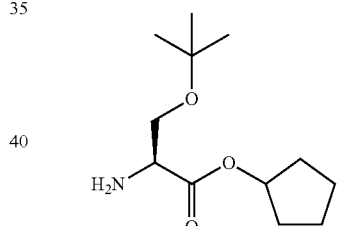

To a round bottomed flask charged with stage 1 resin (4 g, loading 1.14 mmol/g, 4.56 mmol) was added THF (16 ml) and MeOH (16 ml). To the reaction was added a solution of NaOH (0.91 g, 22.8 mmol, 5 eq) in water (16 ml). The reaction mixture was shaken for 48 hours. The resin was filtered and washed with water×2, MeOH×2, followed by the standard wash procedure. The resin was dried under vacuum. LCMS purity was determined by ELS detection, 100% m/z 190 $[M^++H]^+$.

Preparation of Cyclopentyl Esters

The esters were prepared according to one of the following methods.

Method A—Synthesis of (S)-2-Amino-3-tert-butoxy-propionic acid cyclopentyl ester

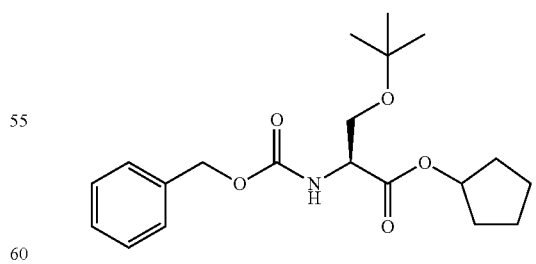

Stage 1: (S)-2-Benzyloxycarbonylamino-3-tert-butoxy-propionic acid cyclopentyl ester (S)-2-Benzyloxycarbonylamino-3-tert-butoxy-propionic acid (4 g, 0.014 mol) was dissolved in DMF (40 ml). Cyclopentanol (2.54 ml, 0.027 mol) and dimethylaminopyridine (0.165 g, 0.014 mol) were added. The solution was cooled to 0° C. using an ice bath and to it was added N-(3-dimethylaminopropyl)-N'-ethylcarbodiimide hydrochloride (2.73 g, 0.014 mol, 1.05 eq.). The mixture was stirred at 0° C. for 10 minutes and then allowed to warm to r.t. and stirred for a further 18 hours. To the reaction mixture was added water (20-30 ml) followed by EtOAc (40 ml). The layers were separated and the aqueous layer re-extracted with EtOAc (15 ml). The combined organic layers were washed with water (4×20 ml), dried (MgSO₄) and the solvent removed in vacuo to give a residue. Purification by column chromatography (1:1 EtOAc/heptane) gave the product as a colourless oil (3.82 g, 78% yield). $^1$H NMR (300 MHz, CDCl$_3$), δ: 1.15 (9H, s, CH$_3$×3), 1.50-1.90 (8H, m, CH$_2$×4), 3.57 (1H, dd, J=7.4, 1.2 Hz, CH), 3.85 (1H, dd, J=7.4, 1.2 Hz, CH), 4.45 (1H, m, CH), 5.15 (2H, s, CH$_2$), 5.25 (1H, m, CH), 5.65 (1H, d, CH, J=7.6 Hz), 7.30-7.50 (5H, m, ArH×5).

Stage 2: (S)-2-Amino-3-tert-butoxypropionic acid cyclopentyl ester

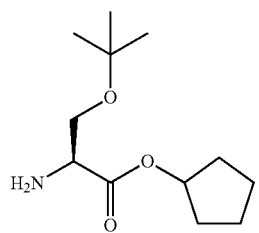 [SMILES: CC(C)(C)OC[C@H](N)C(=O)OC1CCCC1]

(S)-2-Benzyloxycarbonylamino-3-tert-butoxy-propionic acid cyclopentyl ester (3.82 g, 0.011 mol) was dissolved in EtOH (50 ml). 20% wt. Palladium hydroxide (wet) was added cautiously to the solution. The system was evacuated and put under a hydrogen atmosphere for 4 hours. The system was evacuated and the palladium residues filtered off through Celite. The Celite was thoroughly washed with EtOH (3×5 ml). The solvent of the filtrate was removed in vacuo to give the product as a colourless oil (2.41 g, 100% yield). $^1$H NMR (300 MHz, CDCl$_3$), δ: 1.15 (9H, s, CH$_3$×3), 1.50-1.90 (10H, m, CH$_2$×4, NH$_2$), 3.50-3.70 (3H, m, CH$_2$, CH), 5.22 (1H, s, CH).

Method B—Synthesis of (S)-Amino-cyclohexyl-acetic acid cyclopentyl ester

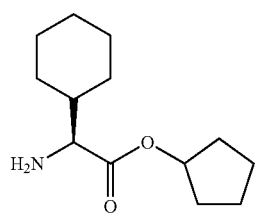

Stage 1: (S)-tert-Butoxycarbonylamino-cyclohexyl-acetic acid cyclopentyl ester

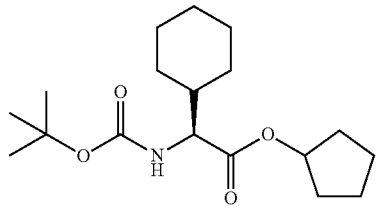 [SMILES: CC(C)(C)OC(=O)N[C@H](C(=O)OC1CCCC1)C1CCCCC1]

This was prepared in the same manner as (S)-2-benzyloxycarbonylamino-3-tert-butoxy-propionic acid cyclopentyl ester (Method A, Stage 1) but from (S)-tert-butoxycarbonylamino-cyclohexyl acetic acid. $^1$H NMR (300 MHz, CDCl$_3$), δ: 1.00-1.40 (10H, m, CH×10), 1.45 (9H, s, C(CH$_3$)$_3$), 1.60-2.00 (8H, m, 4×CH$_2$), 4.15 (1H, m, CH), 5.05 (1H, d, NH, J=7.6 Hz), 5.25 (1H, m, CH).

Stage 2: (S)-Amino-cyclohexyl-acetic acid cyclopentyl ester

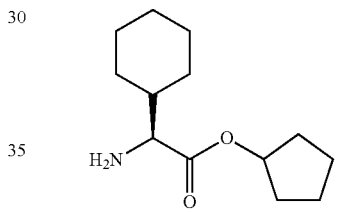

(S)-tert-butoxycarbonylamino-cyclohexyl-acetic acid cyclopentyl ester (1.17 g, 3.60 mmol) was dissolved in a TFA/DCM mixture (1:1, 10 ml) at 0° C. The solution was stirred for 90 minutes, the solvent removed in vacuo. The residue was azetroped with a DCM/heptane mixture (2×) to give a gum. The gum was redissolved in DCM (10 ml) and washed with saturated aqueous NaHCO$_3$ solution (3×10 ml), dried (MgSO$_4$) and filtered. The solvent of the filtrate was removed in vacuo to give the product as an oil (0.780 g, 78% yield). $^1$H NMR (300 MHz, CDCl$_3$), δ: 1.00-1.40 (10H, m, CH×10), 1.50-2.00 (8H, m, CH×8), 3.25 (1H, d, CH, J=7.2 Hz), 5.20 (1H, m, CH).

Method C—Synthesis of (S)-2-Amino-4-methyl-pentanoic acid cyclopentyl ester

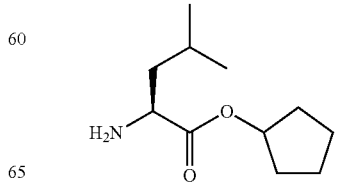

Stage 1: (S)-2-Amino-4-methyl-pentanoic acid cyclopentyl ester toluene-4-sulfonic acid

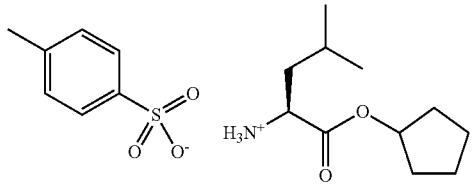

To a suspension of (S)-leucine (15 g, 0.11 mol) in cyclohexane (400 ml) was added cyclopentanol (103.78 ml, 1.14 mmol) and p-toluene sulfonic acid (23.93 g, 0.13 mol). The suspension was heated at reflux to effect solvation. After refluxing the solution for 16 hours it was cooled to give a white suspension. Heptane (500 ml) was added to the mixture and the suspension was filtered to give the product as a white solid (35 g, 85% yield). $^1$H NMR (300 MHz, MeOD), δ: 1.01 (6H, t, CH$_3$×2, J=5.8 Hz), 1.54-2.03 (11H, m, 11×CH), 2.39 (3H, s, CH$_3$), 3.96 (1H, t, CH, J=6.5 Hz), 5.26-5.36 (1H, m, CH), 7.25 (2H, d, ArH×2, J=7.9 Hz), 7.72 (2H, d, ArH×2, J=8.3 Hz).

Stage 2: Synthesis of (S)-2-Amino-4-methyl-pentanoic acid cyclopentyl ester

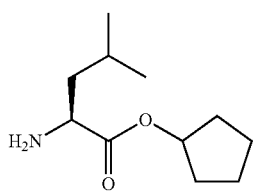

A solution of (S)-2-amino-4-methyl-pentanoic acid cyclopentyl ester toluene-4-sulfonic acid (2.57 g, 0.013 mol) in DCM (5 ml) was washed with saturated aqueous NaHCO$_3$ solution (2×3 ml). The combined aqueous layers were back extracted with DCM (3×4 ml). The combined organic layers were dried (MgSO$_4$), and the solvent removed in vacuo to give a colourless oil (1.10 g, 80% yield). $^1$H NMR (300 MHz, CDCl$_3$), δ: 0.90 (6H, t, CH$_3$×2, J=6.4 Hz), 1.23-1.94 (11H, m, 5×CH$_2$, CH), 3.38 (1H, dd, CH, J=8.4, 5.9 Hz), 5.11-5.22 (1H, m, CH).

Method D—Synthesis of (S)-2-Amino-3-tert-butylsulfanyl-propionic acid cyclopentyl ester

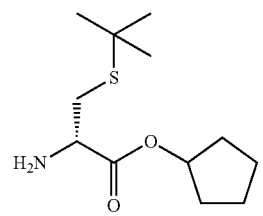

Stage 1: (S)-3-tert-Butylsulfanyl-2-(9H-fluoren-9-ylmethoxycarbonylamino)-propionic acid cyclopentyl ester

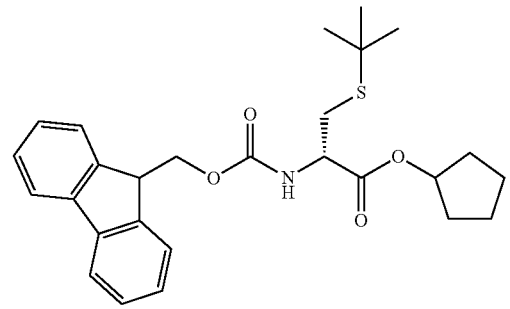 [SMILES: CC(C)(C)SC[C@@H](NC(=O)OCC1c2ccccc2-c2ccccc21)C(=O)OC1CCCC1]

This was prepared in the same manner as (S)-2-Benzyloxycarbonylamino-3-tert-butoxy-propionic acid cyclopentyl ester (Method A, Stage 1) but from (S)-3-tert-Butylsulfanyl-2-(9H-fluoren-9-ylmethoxycarbonylamino)-propionic acid. $^1$H NMR (300 MHz, CDCl$_3$), δ: 1.30 (9H, s, (CH$_3$)$_3$), 1.55-1.95 (8H, m, CH$_2$×4), 3.05 (2H, d, CH$_2$, J=4.8 Hz), 4.20-4.30 (1H, m, CH), 4.40 (2H, d, CH2, J=7.5 Hz), 4.65 (1H, m, CH), 5.25 (1H, m, CH), 5.70 (1H, d, NH, J=7.8 Hz), 7.30-7.50 (4H, m, ArH×4), 7.65 (2H, d, J=7.5 Hz, ArH×2), 7.80 (2H, d, J=7.5 Hz, ArH×2).

Stage 2: (S)-2-Amino-3-tert-butylsulfanyl-propionic acid cyclopentyl ester

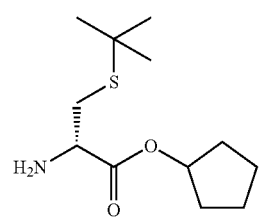 [SMILES: CC(C)(C)SC[C@@H](N)C(=O)OC1CCCC1]

(S)-3-tert-Butylsulfanyl-2-(9H-fluoren-9-ylmethoxycarbonylamino)-propionic acid cyclopentyl ester (1.63 g, 3.50 mmol) was dissolved in a CH$_3$CN (25 ml) at 0° C. Piperidine (21 ml) was added to the solution. After stirring for 30 minutes, the solvent was removed in vacuo to give a residue. Purification by column chromatography (EtOAc eluent) gave the product as a colourless oil (628 mg, 73% yield). $^1$H NMR (300 MHz, CDCl$_3$), δ: 1.30 (9H, s, (CH$_3$)$_3$), 1.55-1.95 (8H, m, CH$_2$×4), 2.75 (1H, dd, CH, J=7.2, 12.3 Hz), 2.95 (1H, dd, CH, J=4.8, 12.3 Hz), 5.25 (1H, m, CH).

The following N-Cbz protected amino acids were converted to the cyclopentyl esters according to Method A (above)
(S)-2-Benzyloxycarbonylamino-succinic acid 4-tert-butyl ester
(S)-2-Benzyloxycarbonylamino-succinamic acid
(S)-2-Benzyloxycarbonylamino-4-carbamoyl-butyric acid
(S)-2-Benzyloxycarbonylamino-3-(4-tert-butoxy-phenyl)-propionic acid
(S)-2-Benzyloxycarbonylamino-3-hydroxy-butyric acid
(S)-2-Benzyloxycarbonylamino-3,3-dimethyl-butyric acid
(S)-2-Benzyloxycarbonylamino-3-(1H-indol-2-yl)-propionic acid
(S)-2-Benzyloxycarbonylamino-6-tert-butoxycarbonylamino-hexanoic acid The following N-Boc protected amino acids were converted to the cyclopentyl esters according to Method B (above)
tert-Butoxycarbonylamino-acetic acid
(S)-2-tert-Butoxycarbonylamino-3-methyl-pentanoic acid
(S)-Pyrrolidine-1,2-dicarboxylic acid 1-tert-butyl ester
(S)-2-tert-Butoxycarbonylamino-3-methyl-butyric acid
(S)-2-tert-Butoxycarbonylamino-4-methylsulfanyl-butyric acid The following free amino acids were converted to the cyclopentyl esters according to Method C (above)
(S)-Amino-phenyl-acetic acid
(S)-2-Amino-3-phenyl-propionic acid
(S)-2-Amino-propionic acid
(S)-2-Amino-4-methyl-pentanoic acid Preparation of
6-formyl-benzo[b]thiophene-2-carboxylic acid
(1-isobutoxy-ethoxy)amide The Synthesis is outlined below in Scheme 7.
Additional literature references relating to this route can be found within *Tetrahedron Letters*, 35, 2, 219-222 & WO 05/034880

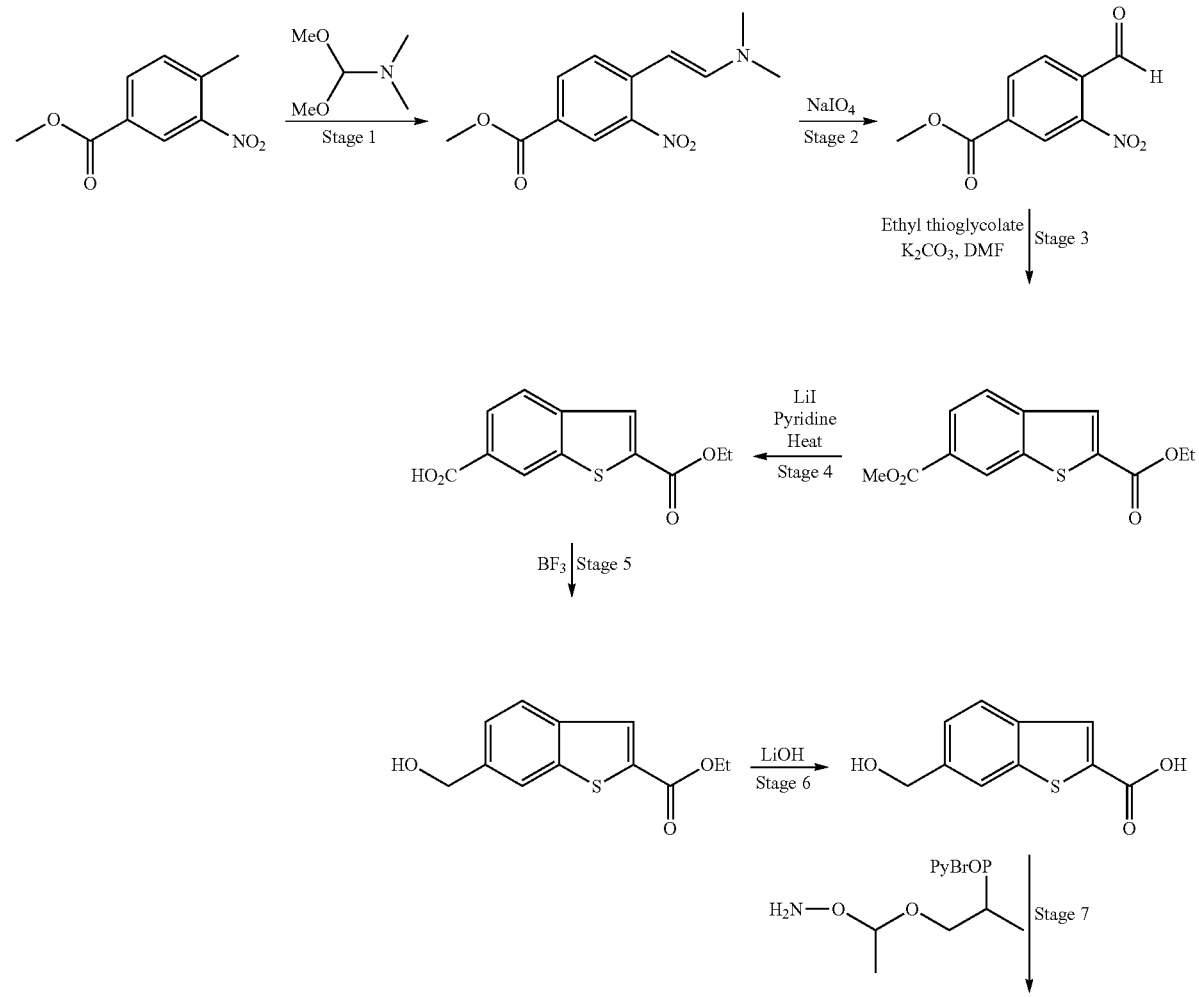

Scheme 7

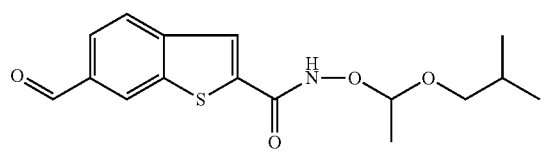 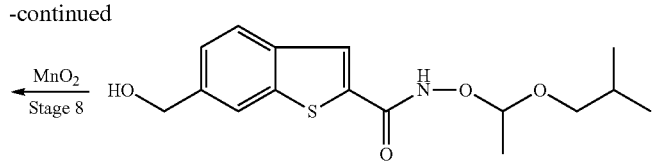

Stage 1: 4-(2-dimethylamino-vinyl)-3-nitrobenzoic acid methyl ester

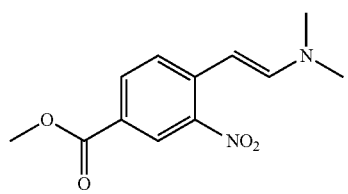

Methyl 4-methyl-3-nitrobenzoate (5 g, 25.6 mmol) was dissolved in DMF (25 mL, 5 vol) and to this was added N,N-dimethylformamide dimethylacetal (4.4 mL, 33.3 mmol). The mixture was allowed to stir at 140° C. for 3 h. The resulting deep red solution was allowed to cool and concentrated under vacuum. The residue was triturated with methanol and filtered. The filtrate was washed with methanol and dried on the sinter to yield 4-(2-dimethylamino-vinyl)-3-nitrobenzoic acid methyl ester (5.2 g, 80%). $^1$H NMR (300 MHz, DMSO), δ: 2.98 (6H, s, 2×CH$_3$), 3.87 (3H, s, CH$_3$), 5.58 (1H, m, CH), 7.72-7.83 (3H, m, ArH), 8.32 (1H, m, CH).

Stage 2: 4-Formyl-3-nitrobenzoic acid methyl ester

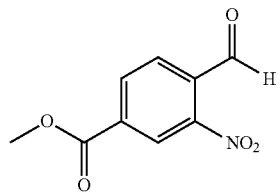

To a solution of the enamine (5 g, 20.0 mmol) in THF (50 mL, 10 vol) and water (50 mL, 10 vol) was added sodium periodate (12.8 g, 60.0 mmol) and the mixture allowed to stir for 2 h. The mixture was filtered and the resulting solids washed with EtOAc (500 mL). The organic layer was isolated, washed with NaHCO$_3$ (3×100 mL) and dried (MgSO$_4$). Concentration under vacuum afforded 4-formyl-3-nitrobenzoic acid methyl ester (3.9 g, 93%). LCMS m/z 210 [M$^+$+H]$^+$, $^1$H NMR (300 MHz, DMSO), δ: 3.96 (3H, s, OMe), 8.01 (1H, d, ArH), 8.39 (1H, d, ArH), 8.54 (1H, s, ArH), 10.31 (1H, s, CHO).

Stage 3: Benzo[b]thiophene-2,6-dicarboxylic acid 2-ethyl ester 6-methyl ester

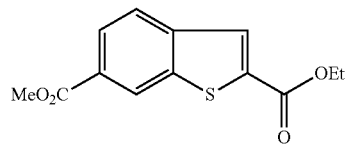 [SMILES: CCOC(=O)c1cc2ccc(C(=O)OC)cc2s1]

A mixture of 4-formyl-3-nitrobenzoic acid methyl ester (3.9 g, 18.7 mmol), mercapto-acetic acid ethyl ester (2.2 mL, 20.4 mmol) and K$_2$CO$_3$ (3.3 g, 24 mmol) in DMF (40 ml, 10 vol) was heated to 50° C. overnight. After cooling to r.t. the mixture was poured onto ice-cold water (250 mL) and the resulting mixture stirred for 40 min. The solid formed was isolated by filtration, washed with water (4×50 mL) and dried under vacuum to afford the title compound (3.9 g, 80%). LCMS m/z 265 [M$^+$+H]$^+$, $^1$H NMR (300 MHz, CDCl$_3$) δ: 1.40 (3H, t J=6.8 Hz, CH$_3$), 3.95 (3H, s, OMe), 4.40 (2H, q J=7.2 Hz, CH$_2$), 7.88 (1H, d J=8.0 Hz, ArH), 7.97-8.09 (2H, m. ArH), 8.56 (1H, s, ArH).

Stage 4: Benzo[b]thiophene-2,6-dicarboxylic acid 2-ethyl ester

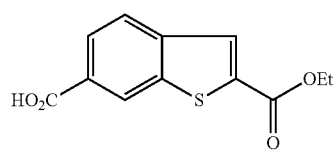 [SMILES: CCOC(=O)c1cc2ccc(C(=O)O)cc2s1]

A mixture of benzo[b]thiophene-2,6-dicarboxylic acid 2-ethyl ester 6-methyl ester (3.9 g, 14.77 mmol) and Lithium iodide (10 g, 74.6 mmol) in anhydrous pyridine (30 ml, 9 vol) was stirred at reflux for 16 h. After cooling to r.t., the mixture was added (either as a melt or chipped out) to ice-cold 2N HCl (200 mL). The solid formed was isolated by filtration and washed with water (3×50 mL). The product was purified by recrystallisation from methanol to give the title compound (1.8 g, 49%). LCMS m/z 251 [M$^+$+H]$^+$, $^1$H NMR (300 MHz, DMSO), δ: 1.35 (3H, t J=6.9 Hz, CH$_3$), 4.38 (2H, q J=7.1 Hz, CH$_2$), 7.99 (1H, d J=8.3 Hz, ArH), 8.12 (1H, d J=8.3 Hz, ArH), 8.27 (1H, s, ArH), 8.70 (1H, s, ArH).

Stage 5:
6-Hydroxymethyl-benzo[b]thiophene-2-carboxylic acid ethyl ester

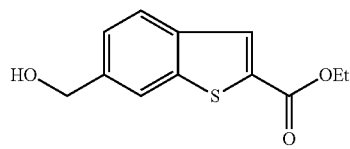 [SMILES: CCOC(=O)c1cc2ccc(CO)cc2s1]

A solution of benzo[b]thiophene-2,6-dicarboxylic acid 2-ethyl ester (1.6 g, 6.4 mmol) in anhydrous THF (40 mL, 25 vol) was cooled to 0° C. To this BH$_3$ (1M in THF, 30 mL, 30.0 mmol) was added slowly. The reaction was allowed to warm to r.t. and stirred for 3 h. The solution was then cooled to 0° C. and quenched using 1N HCl (7.5 mL). The reaction mixture was concentrated under vacuum to remove all THF and the resulting solid isolated by filtration and dried under vacuum to give 6-hydroxymethyl-benzo[b]thiophene-2-carboxylic acid ethyl ester (1.3 g, 87%). LCMS m/z 237 [M$^+$+H]$^+$, $^1$H NMR (300 MHz, DMSO), δ: 1.34 (3H, t J=6.9 Hz, CH$_3$), 4.35 (2H, q J=7.1 Hz, CH$_2$), 4.65 (2H, s, CH$_2$), 6.53 (1H, br s, OH), 7.42 (1H, d J=9.4 Hz), 7.98 (3H, m, ArH), 8.18 (1H, s, ArH).

Stage 6:
6-Hydroxymethyl-benzo[b]thiophene-2-carboxylic acid

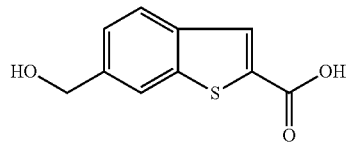

6-Hydroxymethyl-benzo[b]thiophene-2-carboxylic acid ethyl ester (2.4 g, 9.6 mmol, 1 eq) was dissolved in THF (10 mL, 4 vol) and water added (10 mL) along with LiOH (0.69 g, 28.8 mmol). The reaction mixture was stirred at 50° C. for 3 h and then concentrated to dryness and taken onto the next step without purification.

Stage 7:
6-hydroxymethyl-benzo[b]thiophene-2-carboxylic acid (1-isobutoxy-ethoxy) amide

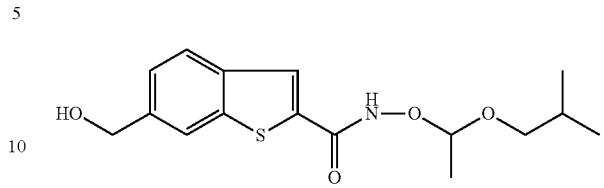

To a solution of 6-hydroxymethyl-benzo[b]thiophene-2-carboxylic acid (1.76 g, 8.4 mmol, 1 eq) in DMF was added PyBrOP (4.3 g, 9.2 mmol), O-(isobutoxy-ethyl)-hydroxylamine (11.5 mL, 84.0 mmol) (prepared via procedure in wool 60785) and DIPEA (2.9 mL, 16.7 mmol). The reaction mixture was allowed to stir at r.t. for 2 h then diluted with water (40 mL) and EtOAc (40 mL). The organic layer was isolated, washed with brine (50 mL) and concentrated. The residue was purified by chromatography on silica gel eluting with EtOAc/heptane (1:1) to afford the title compound (1.8 g, 67% over 2 steps). LCMS m/z 322 [M$^+$–H]$^+$, $^1$H NMR (300 MHz, MeOD), δ: 0.83 (6H, d J=6.6 Hz, 2×CH$_3$), 1.32 (3H, d J=5.9 Hz, CH$_3$), 1.75 (1H, m, CH), 3.38 (2H, m, CH$_2$), 4.63 (2H, s, CH$_2$), 4.95 (1H, m, CH), 7.32 (1H, d J=8.2 Hz, ArH), 7.77 (3H, m, ArH).

Stage 8: 6-formyl-benzo[b]thiophene-2-carboxylic acid (1-isobutoxy-ethoxy) amide

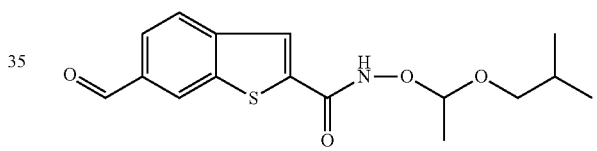

To a solution of 6-hydroxymethyl-benzo[b]thiophene-2-carboxylic acid (1-isobutoxy-ethoxy) amide (600 mg, 1.86 mmol) in DCM (3 mL) was added MnO$_2$ (2.1 g, 24.1 mmol). The mixture was stirred at ambient temperature for 30 min and then filtered through celite. The filtrate was concentrated to afford the title compound (435 mg, 82%). LCMS m/z 320 [M$^+$–H]$^+$, $^1$H NMR (300 MHz, MeOD), δ: 0.94 (6H, d J=6.7 Hz, 2×CH$_3$), 1.45 (3H, d J=5.3 Hz, CH$_3$), 1.87 (1H, m, CH), 3.40 (2H, m, CH2), 5.08 (1H, dd J=5.2, 10.6 Hz, CH), 7.89-8.09 (3H, m, ArH), 8.55 (1H, s, ArH), 10.11 (1H, s, CHO).

Synthesis of Compounds in Figure 1 as Exemplified by Compound (1) and Compound (2)

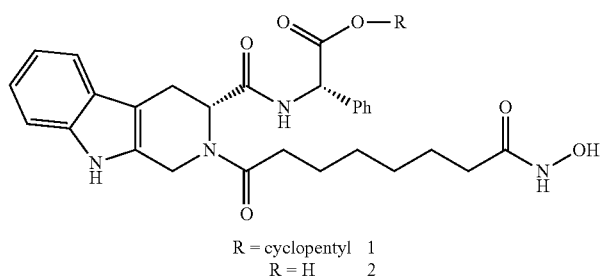

FIG. 1

R = cyclopentyl  1
R = H  2

-continued
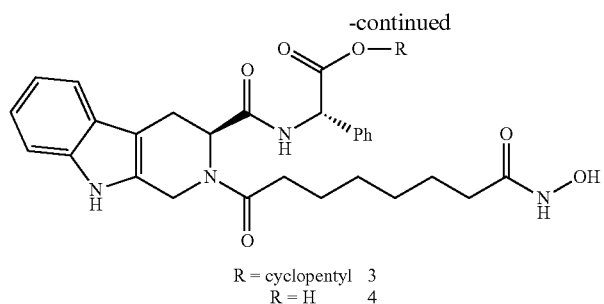
R = cyclopentyl 3
R = H 4
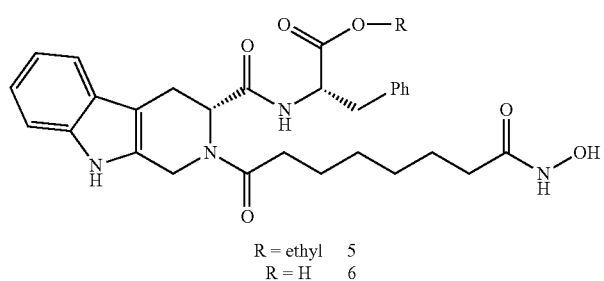
R = ethyl 5
R = H 6
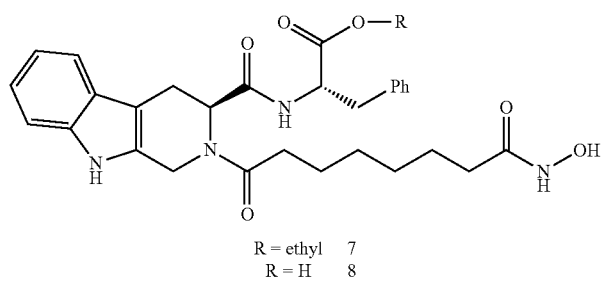
R = ethyl 7
R = H 8
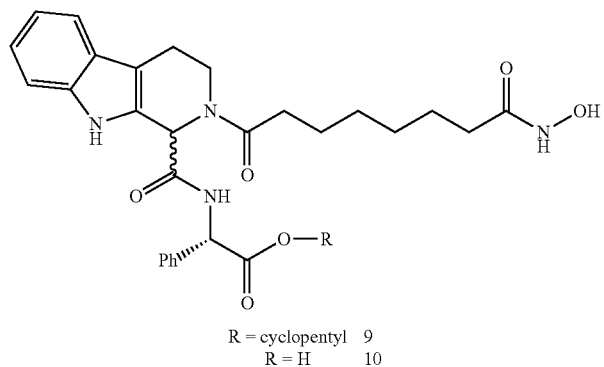
R = cyclopentyl 9
R = H 10
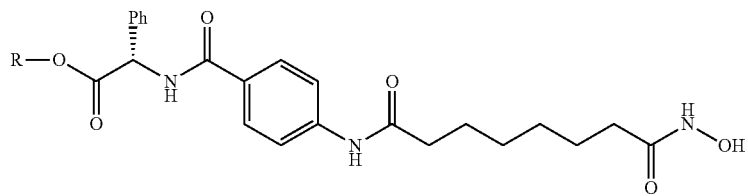

-continued
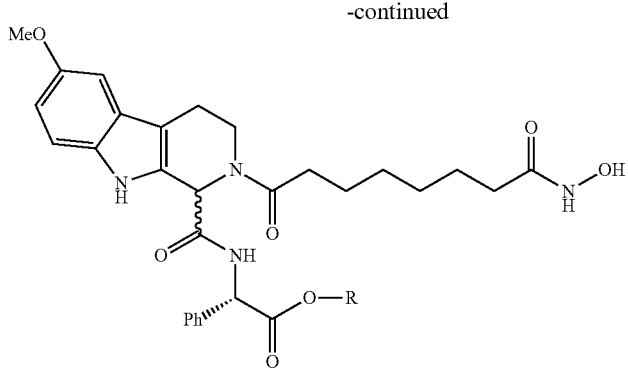
R = cyclopentyl 11
R = H 12
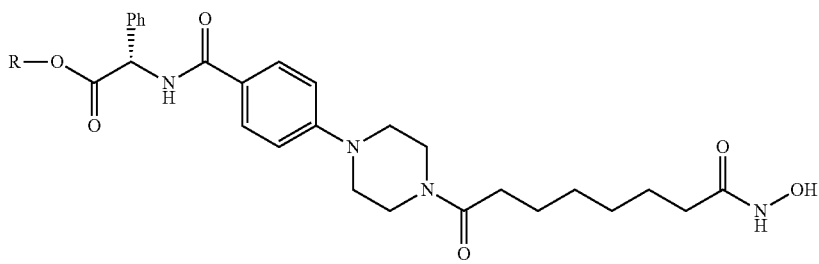
R = cyclopentyl 13
R = H 14
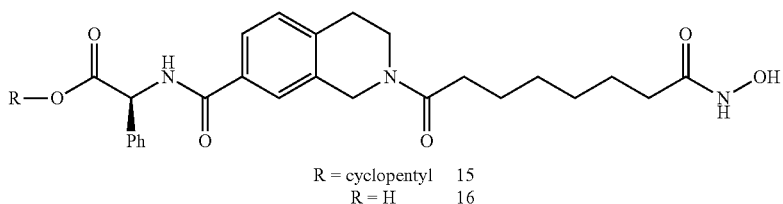
R = cyclopentyl 15
R = H 16
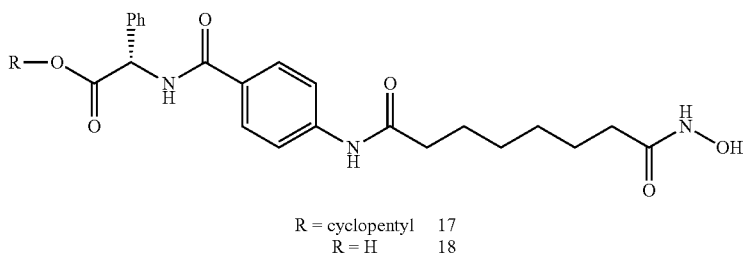
R = cyclopentyl 17
R = H 18
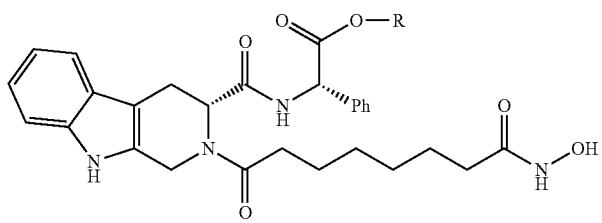
R = t-butyl 19

Preparation of Building Blocks A-G

Building Blocks A and B

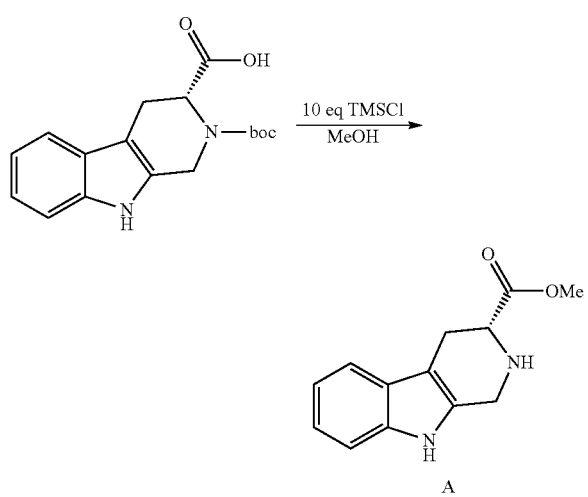

N-Boc-D-tetrahydro-beta-carboline-3-carboxylic acid (5.0 g, 15.8 mmol) and TMSCl (20 ml, 158 mmol) in MeOH (50 ml) were heated under reflux for 2 h. The reaction mixture was evaporated to dryness to yield (R)-2,3,4,9-Tetrahydro-1H-beta-carboline-3-carboxylic acid methyl ester (building block A). LCMS purity 100%. m/z 231 [M$^+$+H]$^+$, 461 [2M$^+$+H]$^+$. Building block A was used without further purification.

(S)-2,3,4,9-Tetrahydro-1H-beta-carboline-3-carboxylic acid methyl ester (building block B) was obtained by the same procedure as block A using N-boc-L-tetrahydro-beta-carboline-3-carboxylic acid.

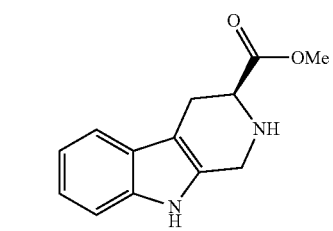

Building Block C

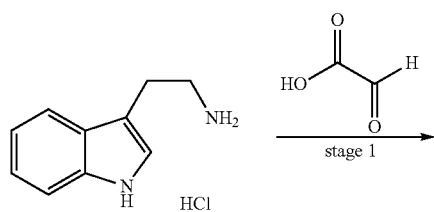

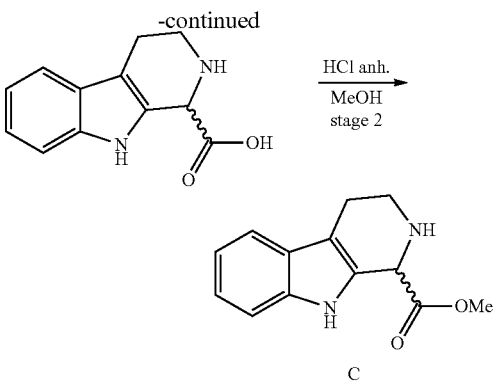

Stage 1

A solution of glyoxylic acid monohydrate (1.51 g, 16.4 mmol) in water (10 ml) was added dropwise to a stirred solution of tryptamine.HCl (3.0 g, 15.3 mmol) in water (200 ml). KOH (0.827 g, 14.7 mmol) in water (10 ml) was added. The reaction mixture was stirred at room temperature for 1 h after which time precipitation occurred. Following filtration under reduced pressure the tetrahydro-beta-carboline-1-carboxylic acid was collected and washed with water. Yield 1.9 g (58%); m/z 217 [M$^+$+H]$^+$.

Stage 2

A solution of tetrahydro-beta-carboline-1-carboxylic acid (7.4 g) in MeOH (250 ml) was saturated with HCl gas for 20 min. The reaction mixture was gently stirred at room temperature for 18 h. and ca. 80% conversion was observed. The reaction mixture was re-treated with HCl gas and allowed to stir for another 18 h. Upon completion of the reaction the mixture was concentrated in vacuo to yield 2,3,4,9-tetrahydro-1H-beta-carboline-1-carboxylic acid methyl ester (building block C), LCMS purity 95%, m/z 231 [M$^+$+H]$^+$. The product was used without further purification.

Building Block D

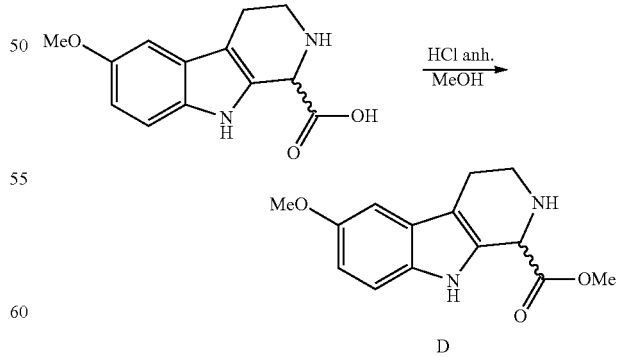

6-Methoxy-2,3,4,9-tetrahydro-1H-beta-carboline-1-carboxylic acid methyl ester (building block D) was obtained from esterification of 6-methoxy-tetrahydro-beta-carboline-1-carboxylic acid using the procedure as for building block C.

Building block D: LCMS purity 98%, m/z 261 [M++H]+. Building block D was used without further purification.

Building Block E

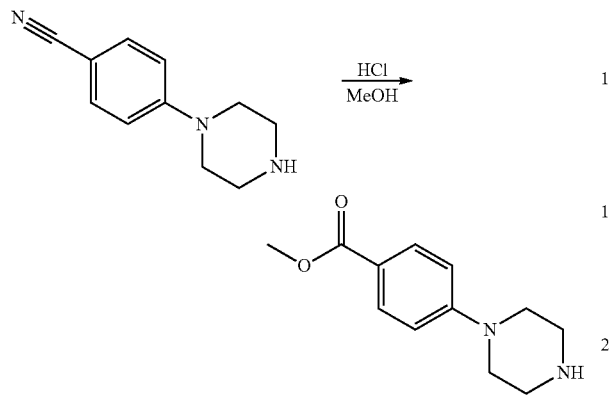

A solution 4-piperazin-1-yl-benzonitrile (1.5 g, 8.0 mmol) in MeOH (150 ml) was saturated with HCl gas. Water (0.17 ml) was added and the mixture was heated under reflux for 18 h. The reaction mixture was cooled to r.t. and was resaturated with HCl gas. This was refluxed for a further 24 h. The mixture was concentrated under reduced pressure yielding 4-Piperazin-1-yl-benzoic acid methyl ester (building block E). LCMS purity 90%, m/z 221 [M++H]+. Building block E was used without further purification.

Building Block F

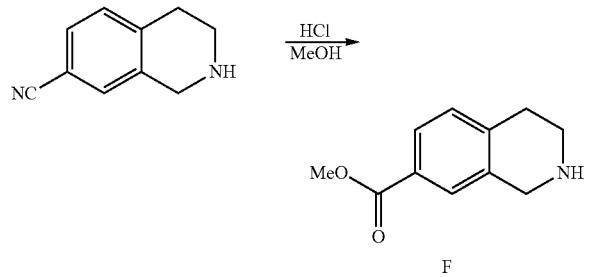

1,2,3,4-Tetrahydro-isoquinoline-7-carboxylic acid methyl ester (building block F) was prepared following the same procedure as for building block E. LCMS purity 89%. m/z 193 [M++H]+. This product was used without further purification.

Building Block G

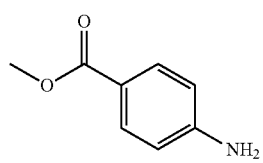

4-Amino-benzoic acid methyl ester (building block G) was commercially available

Synthesis of Compounds (1) and Compound (2)

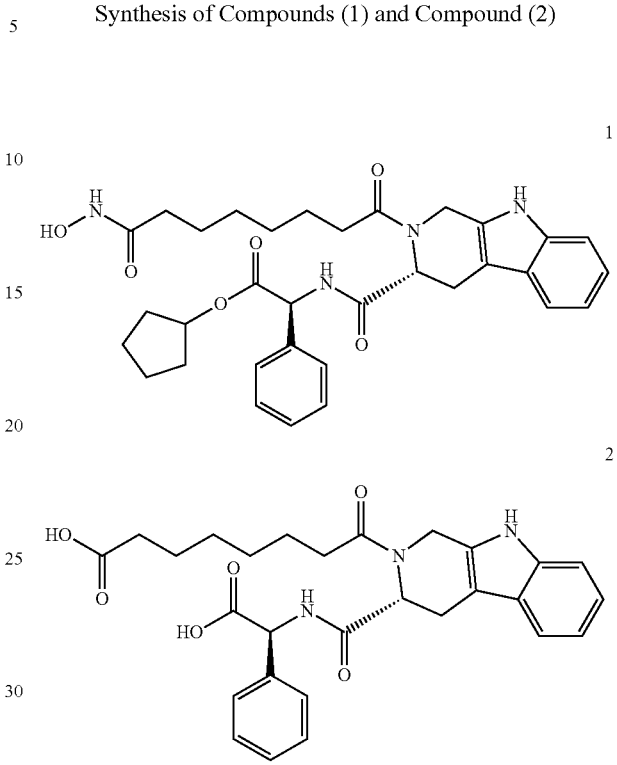

Stage 1: Coupling with Building Block

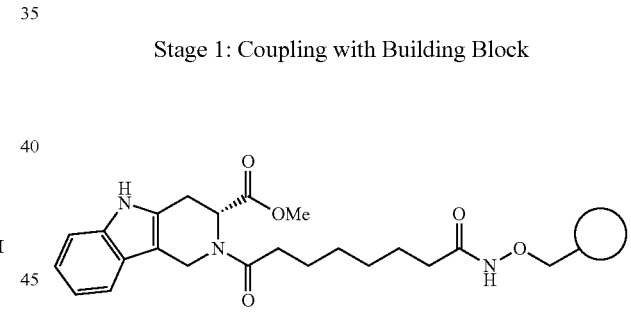

Hydroxylamine 2-chlorotrityl resin derivatized with suberic acid (4.6 g, loading 1.14 mmol, 5.24 mmol) was swollen in anhydrous DCM (50 ml). Building block A (4.76 g, 15.72 mmol) was added, followed by pyBOP (8.18 g, 15.72 mmol, 3 eq) and DIPEA (6.77 g, 52.4 mmol, 10 eq). The reaction was shaken for 18 h, filtered and washed using the standard wash procedure. The resin was dried under vacuum.

Note: For building block G, coupling using the above condition gave ca. 10% conversion. Thus an alternative condition was used: Stage 2 resin (1.0 g, loading 1.14 mmol) was swollen in anhydrous DCM (100 ml). 1-Chloro-N,N-2-trimethylpropenylamine (Ghosez reagent)[1] (7.53 ml, 57.0 mmol, 50 eq) was added at 0° C. under the atmosphere of $N_2$. The mixture was allowed to warm to room temperature and gently shaken for 1-2 h. The aniline building block G (8.6 g, 57.0 mmol, 50 eq) was added portionwise over 20 min. $Et_3N$ (8.0 ml, 57.0 mmol, 50 eq) was added. The mixture was shaken for 18 h. LCMS after a test cleave shows 70% conversion, m/z 323 [M++H]+, 645 [2M++H]+. The resin was filtered and washed using the standard wash procedure. The resin was dried under vacuum.

Stage 2: Saponification

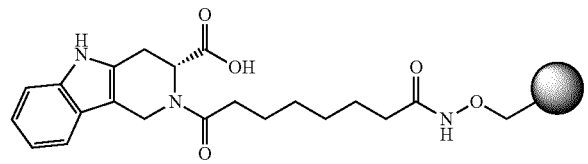 [SMILES: CCONC(=O)CCCCCCC(=O)N1Cc2c([nH]c3ccccc23)C[C@@H]1C(=O)O]

Stage 1 resin (4.8 g, loading 1.14 mmol, 5.47 mmol) was suspended in MeOH (17.5 ml) and THF (17.5 ml). A solution of NaOH (1.1 g, 27.5 mmol, 5 eq) in water (17.5 ml) was added. The mixture was shaken for 18 h. LCMS of the test cleave confirmed the completion of reaction, m/z 388 [M++H]+, 775 [2M++H]+. The resin was filtered and washed with water×2, MeOH×2, followed by the standard wash procedure. The resin was dried under vacuum.

Note: For building block E, saponification was carried out using 10 eq. of 2.7M NaOH and was shaken for 72 h.

Stage 3: Coupling with L-Phenylglycine Cyclopentyl Ester

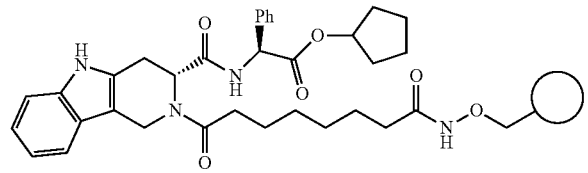 [SMILES: CCONC(=O)CCCCCCC(=O)N1Cc2c([nH]c3ccccc23)C[C@@H]1C(=O)N[C@H](C(=O)OC1CCCC1)c1ccccc1]

Stage 2 resin (2.4 g, loading 1.14 mmol, 2.7 mmol) was suspended in anhydrous DCM (30 ml). L-phenylglycine cyclopentylester tosyl salt (3.2 g, 8.1 mmol, 3 eq) was added, followed by pyBOP (4.2 g, 8.1 mmol, 3 eq) and DIPEA (3.5 g, 27.0 mmol, 10 eq). The mixture was shaken for 18 h. The LCMS of the test cleave (i.e. a small quantity of resin was washed using the standard wash procedure, dried, and cleaved in 2% TFA/DCM. Resin was filtered off and filtrate concentrated to dryness. LCMS was obtained) confirmed the completion of reaction, m/z 589 [M++H]+. The whole sample of resin was filtered and washed using the standard wash procedure. The resin was dried under vacuum.

Note.

For compounds 5-8, L-phenylalanine ethyl ester (3 eq) was used.

For compound 19, L-phenylglycine t-butyl ester (3 eq) was used.

Stage 4: (S)-{[(R)-2-(7-Hydroxycarbamoyl-heptanoyl)-2,3,4,9-tetrahydro-1H-beta-carboline-3-carbonyl]-amino}-phenyl-acetic acid cyclopentyl ester (1)

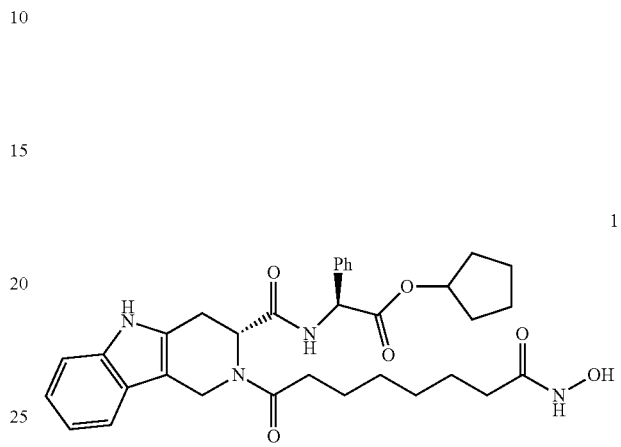

1

Stage 3 resin (1.0 g, loading 1.14 mmol) was gently shaken in 2% TFA/DCM (10 ml) for 20 mins. The resin was filtered. The filtrate was collected and evaporated under reduced pressure at room temperature. The resin was re-treated with 2% TFA/DCM (10 ml) and after 20 mins. The combined filtrates were evaporated to dryness under reduced pressure at r.t, the residue (ca. 300 mg) was purified by preparative HPLC to yield compound (1), m/z 589 [M++H]+; $^1$H NMR (400 MHz, CD$_3$OD) δ: 1.3-1.7 (16H, m, CH$_2$), 2.1-2.3 (2H, m, CH$_2$), 2.5 (2H, m, CH$_2$), 3.0-3.5 (2H, m, CH$_2$), 4.5-4.8 (2H, m, CH$_2$), 5.1 (1H, m, CO$_2$CH), 5.2 (1H, dd, CH$_2$CHNCO), 5.5-5.9 (1H, d, CONHCHPh), 7.0-7.5 (9H, m, Ar).

The corresponding carboxylic acid was obtained by the following procedure

Stage 5: Saponification

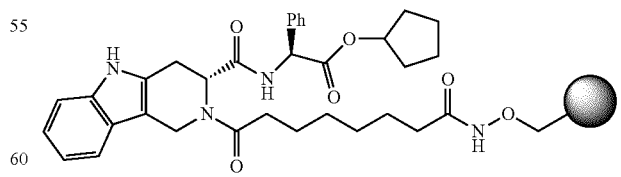

Stage 3 resin (1.0 g, loading 1.14 mmol) was suspended in MeOH (4 ml) and THF (4 ml). A solution of NaOH (0.23 g, 5.7 mmol) in water (4 ml) was added. The mixture was shaken for 18 h. LCMS of the test cleave confirmed the completion of reaction, m/z 521 [M++H]+. Resin was filtered and washed with water×2, MeOH×2, followed by the standard wash procedure. Resin was dried under vacuum.

Stage 6: (S)-{[(R)-2-(7-Hydroxycarbamoyl-heptanoyl)-2,3,4,9-tetrahydro-1H-beta-carboline-3-carbonyl]-amino}-phenyl-acetic acid (2)

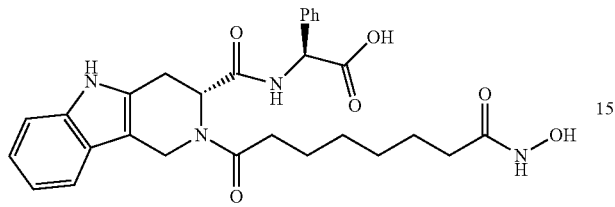

Stage 5 resin (1.0 g, loading 1.14 mmol) was cleaved using the procedure outlined for Stage 6 yielding compound (2), m/z 521 [M$^+$+H]$^+$; $^1$H NMR (400 MHz, CD$_3$OD), δ: 1.3-1.5 (4H, 2×CH$_2$), 1.6-1.8 (4H, 2×CH$_2$), 2.1-2.2 (2H, m, CH$_2$), 2.4-2.7 (2H, m, CH$_2$), 3.0-3.2 (1H, m), 3.5 (1H, m), 4.55 (m), 4.9 (m), 5.1-5.35 (2H, m), (2H, m, CH$_2$NCO), 5.75-5.8 (1H, 2×d, NHCHPh), 7.0-7.5 (9H, m, Ar), 7.6 (d), 7.7 (d), 8.35 (d), 8.95 (s), 9.05 (s).

The following compounds were prepared according to the procedure described for Compound (1) and Compound (2)

(S)-{[(S)-2-(7-Hydroxycarbamoyl-heptanoyl)-2,3,4,9-tetrahydro-1H-beta-carboline-3-carbonyl]-amino}-phenyl-acetic acid cyclopentyl ester (3)

Building Block B Used

LCMS purity 98%, m/z 589 [M$^+$+H]$^+$, $^1$H NMR (400 MHz, MeOD), δ: 1.20-1.40 (8H, m, 4×CH$_2$), 1.40-1.80 (8H, m, 4×CH$_2$), 2.10 (2H, m, CH$_2$), 3.45 (2H, m, CH$_2$), 5.0 (2H, m, CH$_2$ overlaps with D$_2$O peak), 5.25-5.45 (2H, m, 2×CH), 5.50 (1H, s, CONHCHPh), 7.00-7.50 (9H, m, Ar).

(S)-{[(S)-2-(7-Hydroxycarbamoyl-heptanoyl)-2,3,4,9-tetrahydro-1H-beta-carboline-3-carbonyl]-amino}-phenyl-acetic acid (4)

Building Block B Used

LCMS purity 100%, m/z 521 [M$^+$+H]$^+$, $^1$H NMR (400 MHz, MeOD), δ 1.30-1.50 (4H, m, 2×CH$_2$), 1.55-1.80 (4H, m, 2×CH$_2$), 2.15 (2H, m, CH$_2$), 2.60 (2H, m, CH$_2$), 3.00-3.25 (2H, m, CH$_2$), 3.40-3.55 (2H, m, CH$_2$), 5.20-5.30 (1H, m, CHCON), 5.35 (1H, s, NHCHPh), 7.05-7.50 (9H, m, Ar).

(S)-2-{[(R)-2-(7-Hydroxycarbamoyl-heptanoyl)-2,3,4,9-tetrahydro-1H-beta-carboline-3-carbonyl]-amino}-3-phenyl-propionic acid ethyl ester (5)

Building Block A Used

LCMS purity 100% m/z 563 [M$^+$+H]$^+$, $^1$H NMR (400 MHz, MeOD), δ 1.00 (3H, t, CH$_3$), 1.20-1.24 (4H, m, 2×CH$_2$), 1.50-1.70 (4H, m, 2×CH$_2$), 2.00 (2H, m, CH$_2$), 2.30-2.50 (2H, m, CH$_2$), 2.80-3.00 (2H, m, CH$_2$), 4.05 (2H, q, CO$_2$CH$_2$), 4.35-4.50 (1H, m, CH), 4.80-5.05 (2H, m, CH$_2$), 5.40 (1H, s, NHPhCO), 6.80-7.30 (9H, m, Ar).

(S)-2-{[(R)-2-(7-Hydroxycarbamoyl-heptanoyl)-2,3,4,9-tetrahydro-1H-beta-carboline-3-carbonyl]-amino}-3-phenyl-propionic acid (6)

Building Block A Used

LCMS purity 100%, m/z 534 [M$^+$+H]$^+$, $^1$H NMR (400 MHz, MeOD), δ 1.30-1.50 (4H, m, 2×CH$_2$), 1.60-1.80 (4H, m, 2×CH$_2$), 2.15 (2H, m, CH$_2$), 2.50 (2H, m, CH$_2$), 3.00 (2H, m, CH$_2$), 3.20 (2H, m, CH$_2$), 4.30-4.80 (2H, m, CH$_2$), 5.15 (1H, m, CH), 6.90-7.50 (9H, m, Ar).

(S)-2-{[(S)-2-(7-Hydroxycarbamoyl-heptanoyl)-2,3,4,9-tetrahydro-1H-beta-carboline-3-carbonyl]-amino}-3-phenyl-propionic acid ethyl ester (7)

Building Block B Used

LCMS purity 100%, m/z 563 [M$^+$+H]$^+$, $^1$H NMR (400 MHz, MeOD), δ 1.00 (3H, t, CH$_3$), 1.30-1.50 (4H, m, 2×CH$_2$), 1.60-1.70 (4H, m, 2×CH$_2$), 2.10 (2H, m, CH$_2$), 2.30-2.65 (2H, m, CH$_2$), 2.95-3.20 (2H, m, CH$_2$), 3.45 (1H, m, CH), 4.05 (2H, q, CO$_2$CH$_2$), 4.35-4.50 (1H, m, CH), 4.80-5.05 (2H, m, CH$_2$), 5.50 (1H, s, NHPhCO), 6.90-7.50 (9H, m, Ar).

(S)-2-{[(S)-2-(7-Hydroxycarbamoyl-heptanoyl)-2,3,4,9-tetrahydro-1H-beta-carboline-3-carbonyl]-amino}-3-phenyl-propionic acid (8)

Building Block B Used

LCMS purity 100%, m/z 534 [M$^+$+H]$^+$, $^1$H NMR (400 MHz, MeOD), δ 1.30-1.50 (4H, m, 2×CH$_2$), 1.60-1.80 (4H, m, 2×CH$_2$), 2.15 (2H, m, CH$_2$), 2.50 (2H, m, CH$_2$), 2.95-3.15 (2H, m, CH$_2$), 3.20-3.50 (2H, m, CH$_2$), 4.30-4.50 (2H, m, 2×CH), 4.80-5.20 (2H, m, CH$_2$), 6.90-7.50 (9H, m, Ar).

(S)-{[2-(7-Hydroxycarbarnoyl-heptanoyl)-2,3,4,9-tetrahydro-1H-beta-carboline-1-carbonyl]-amino}-phenyl-acetic acid cyclopentyl ester (9)

Building Block C Used

LCMS purity 100%, m/z 589 [M$^+$+H]$^+$, $^1$H NMR (400 MHz, CDCl$_3$), δ 1.30-1.80 (16H, m, 8×CH$_2$), 2.15 (2H, m, CH$_2$), 2.45-2.70 (2H, m, CH$_2$), 2.95 (2H, m, CH$_2$), 3.55 (1H, m, CH), 4.35 (1H, m, CH), 5.15 (1H, m, CO$_2$CH), 5.45 (1H, m, CH), 6.20 (1H, d, PhCHNH) 7.00-7.80 (9H, m, Ar), 8.80-9.20 (1H, broad m, CHNHOH).

(S)-{[2-(7-Hydroxycarbamoyl-heptanoyl)-2,3,4,9-tetrahydro-1H-beta-carboline-1-carbonyl]amino}-phenyl-acetic acid (10)

Building Block C Used

LCMS purity 100%, m/z 521 [M$^+$+H]$^+$, $^1$H NMR (400 MHz, MeOD), δ 1.30-1.50 (4H, m, 2×CH$_2$), 1.60-1.80 (4H, m, 2×CH$_2$), 2.15 (2H, m, CH$_2$), 2.50-2.65 (2H, m, CH$_2$), 2.95 (2H, m, CH$_2$), 3.70 (1H, dd, CH), 4.30 (1H, dd, CH), 5.50 (1H, m, CH), 6.10 and 6.20 (0.5H each, s, PhCHNH) 7.00-7.50 (9H, m, Ar).

(S)-{[2-(7-Hydroxycarbamoyl-heptanoyl)-6-methoxy-2,3,4,9-tetrahydro-1H-beta-carboline-1-carbonyl]-amino}-phenyl-acetic acid cyclopentyl ester (11)

Building Block D Used

LCMS purity 100%, m/z 619 [M$^+$+H]$^+$, $^1$H NMR (400 MHz, CDCl$_3$), δ 1.30-1.80 (16H, m, 8×CH$_2$), 2.15 (2H, m, CH$_2$), 2.50-2.65 (2H, m, CH$_2$), 2.85 (2H, m, CH$_2$), 3.70 (1H, dd, CH), 3.80 (3H, s, OMe), 4.30 (1H, dd, CH), 5.20 (1H, m, CO$_2$CH), 5.30-5.50 (1H, m, CH), 6.15-6.20 (1H, d, PhCHNH) 6.80-7.80 (8H, m, Ar), 8.80-9.00 (1H, m, CONHOH).

(S)-{[2-(7-Hydroxycarbamoyl-heptanoyl)-6-methoxy-2,3,4,9-tetrahydro-1H-beta-carboline-1-carbonyl]-amino}-phenyl-acetic acid (12)

Building Block D Used

LCMS purity 100%, m/z 551 [M$^+$+H]$^+$, $^1$H NMR (400 MHz, MeOD), δ 1.30-1.60 (8H, m, 4×CH$_2$), 2.05 (2H, m, CH$_2$), 2.50-2.65 (2H, m, CH$_2$), 2.80 (2H, m, CH$_2$), 3.55 (1H, dd, CH), 3.70 (3H, s, OMe), 4.30 (1H, dd, CH), 5.30-5.50 (1H, m, CH), 5.90-6.10 (0.5H each, s, PhCHNH), 6.65 (1H, m, Ar), 6.80 (1H, m, Ar), 7.10 (1H, m, Ar), 7.35 (5H, m, Ar).

(S)-{[2-(7-Hydroxycarbamoyl-heptanoyl)-6-methoxy-2,3,4,9-tetrahydro-1H-beta-carboline-1-carbonyl]amino}-phenyl-acetic acid cyclopentyl ester (13)

Building Block E Used

LCMS purity 95%, m/z 579 [M$^+$+H]$^+$, $^1$H NMR (400 MHz, CDCl$_3$), δ 1.40-1.90 (16H, m, 8×CH$_2$), 2.15 (2H, m, CH$_2$), 2.45 (2H, m, CH$_2$), 3.40 (4H, m, 2×CH$_2$N), 3.60-3.80 (4H, m, 2×CH$_2$N), 5.30 (1H, m, CO$_2$CH), 5.70 (1H, d, PhCHNH), 6.90 (2H, d, Ar), 7.30-7.50 (6H, m, Ar), 7.80 (2H, d, Ar).

(S)-{[2-(7-Hydroxycarbamoyl-heptanoyl)-6-methoxy-2,3,4,9-tetrahydro-1H-beta-carboline-1-carbonyl]-amino}-phenyl-acetic acid (14)

Building Block E Used

LCMS purity 100%, m/z 511 [M$^+$+H]$^+$, $^1$H NMR (400 MHz, MeOD), δ 1.30 (4H, m, 2×CH$_2$), 1.50 (4H, m, 2×CH$_2$), 2.00 (2H, t, CH$_2$), 2.35 (2H, t, CH$_2$), 3.30 (4H, m, 2×CH$_2$N), 3.70 (4H, m, 2×CH$_2$N), 5.55 (1H, s, PhCHNH), 6.90 (2H, d, Ar), 7.30 (3H, m, Ar), 7.40 (2H, m, Ar), 7.70 (2H, d, Ar).

(S)-{[2-(7-Hydroxycarbamoyl-heptanoyl)-1,2,3,4-tetrahydro-isoquinoline-7-carbonyl]-amino}-phenyl-acetic acid cyclopentyl ester (15)

Building Block F Used

LCMS purity 100%, m/z 550 [M$^+$+H]$^+$, $^1$H NMR (400 MHz, CDCl$_3$), δ 1.30-1.80 (16H, m, 8×CH$_2$), 2.15 (2H, m, CH$_2$), 2.45 (2H, m, CH$_2$), 2.95 (2H, m, 2×CH$_2$), 3.70-3.90 (2H, m, 2×CH$_2$), 4.60-4.70 (2H, m, CH$_2$), 5.25 (1H, m, CO$_2$CH), 5.70 (1H, m, PhCHNH), 7.20-7.70 (8H, m, Ar).

(S)-{[2-(7-Hydroxycarbamoyl-heptanoyl)-1,2,3,4-tetrahydro-isoquinoline-7-carbonyl]-amino}-phenyl-acetic acid (16)

Building Block F Used

LCMS purity 87%, m/z 482 [M$^+$+H]$^+$, $^1$H NMR (400 MHz, MeOD), δ 1.30-1.50 (4H, m, 2×CH$_2$), 1.60-1.70 (4H, m, 2×CH$_2$), 2.15 (2H, m, CH$_2$), 2.50 (2H, m, CH$_2$), 2.95 (2H, m, 2×CH$_2$), 3.70 (2H, m, CH$_2$), 4.80 (2H, m, CH$_2$), 5.70 (1H, s, PhCHNH), 7.20-7.80 (8H, m, Ar).

(S)-[4-(7-Hydroxycarbamoyl-heptanoylamino)-benzoylamino]-phenyl-acetic acid cyclopentyl ester(17)

Building Block G Used

LCMS purity 94%, m/z 510 [M$^+$+H]$^+$, $^1$H NMR (400 MHz, MeOD), δ 1.30-1.80 (16H, m, 8×CH$_2$), 2.00-2.20 (4H, m, 2×CH$_2$), 5.10-5.30 (1H, m, CO$_2$CH), 5.70 (1H, m, PhCHNH), 7.30-7.80 (9H, m, Ar).

(S)-[4-(7-Hydroxycarbamoyl-heptanoylamino)-benzoylamino]-phenyl-acetic acid (18)

Building Block G Used

LCMS purity 100%, m/z 442 [M$^+$+H]$^+$, $^1$H NMR (400 MHz, MeOD), δ 1.30-1.40 (4H, m, 2×CH$_2$), 1.50-1.70 (4H, m, 2×CH$_2$), 2.20 (2H, t, CH$_2$), 2.35 (2H, t, CH$_2$), 5.70 (1H, s, PhCHNH), 7.25-7.40 (3H, m, Ar), 7.50 (2H, d, Ar), 7.65 (2H, d, Ar), 7.80 (2H, d, Ar).

(S)-{[(R)-2-(7-Hydroxycarbamoyl-heptanoyl)-2,3,4,9-tetrahydro-1H-beta-carboline-3-carbonyl]-amino}-phenyl-acetic acid tert-butyl ester (19)

Building Block A Used

LCMS purity 100%, m/z 577 [M$^+$+H]$^+$, $^1$H NMR (400 MHz, CDCl$_3$), δ 1.20-1.40 (17H, m, 4×CH$_2$ and C(CH$_3$)$_3$), 2.10 (2H, m, CH$_2$), 2.45 (2H, m, CH$_2$), 3.15-3.60 (2H, m, CH$_2$), 4.75 (2H, m, CH$_2$), 5.35 (2H, m, PhCHNH and CH), 6.90-7.50 (9H, m, Ar).

Synthesis of Compound (20) and Compound (21)

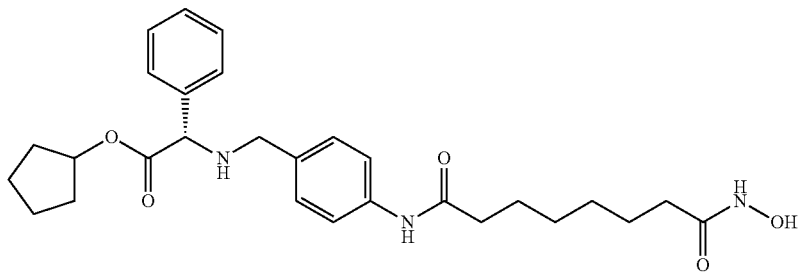

20

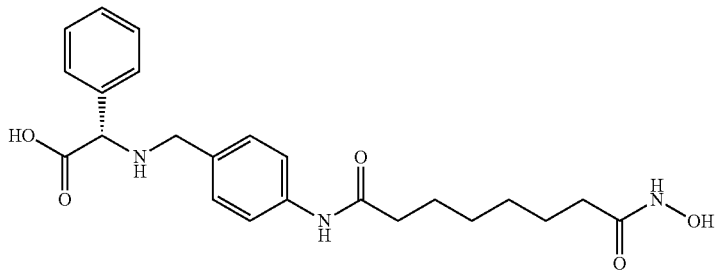

21

Stage 1: (S)-(4-Nitro-benzylamino)-phenyl-acetic acid cyclopentyl ester

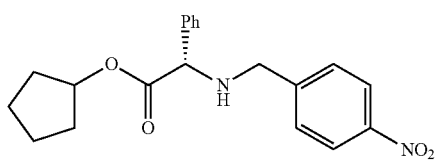 [SMILES: O=C(OC1CCCC1)[C@@H](NCc1ccc([N+](=O)[O-])cc1)c1ccccc1]

A mixture of 4-nitrobenzyl bromide (15 g, 69.4 mmol), L-phenylglycine cyclopentylester tosyl salt (27.1 g, 60.4 mmol) and potassium carbonate (19.6 g, 138.8 mmol) in DMF (250 ml) was stirred at room temperature for 18 h. The reaction mixture was diluted with EtOAc (300 ml) and washed with water (3×200 ml). The EtOAc layer was isolated, dried (Na$_2$SO$_4$), filtered and concentrated to dryness yielding an orange colour oil. A crude weight of 21 g was isolated. LCMS purity 81%, m/z 355 [M$^+$+H]$^+$, This product was used without further purification.

Stage 2: (S)-[tert-Butoxycarbonyl-(4-nitro-benzyl)-amino]-phenyl-acetic acid cyclopentyl ester

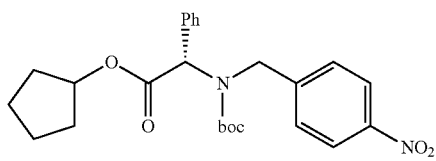

To a solution of Stage 1 product (15 g, 42.37 mmol) in THF (150 ml) was added K$_2$CO$_3$ (6.9 g, 50.8 mmol), followed by di-t-butyldicarbonate (22.2 g, 101.7 mmol). Water (150 ml) was added and the reaction stirred at room temperature for 36 h. The reaction mixture was evaporated to dryness. The residue was redissolved in EtOAc (300 ml) washed consecutively with OA M HCl (150 ml), sat. aq. NaHCO$_3$ and water (150 ml). The EtOAc layer was dried (Na$_2$SO$_4$), filtered and concentrated to dryness yielding a yellow oil. After purification by column chromatography (10% EtOAc/hexane) the product was obtained as clear yellow oil (12 g, 62% yield). LCMS purity 95%, m/z 455 [M$^+$+H]$^+$, 496 [M$^+$+H+41]$^+$.

Stage 3: (S)-[(4-Amino-benzyl)-tert-butoxycarbonyl-amino]-phenyl-acetic acid cylopentyl ester

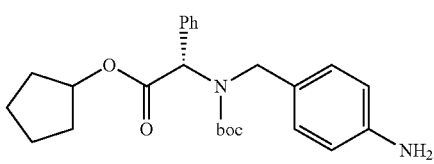

A mixture of Stage 2 product (12 g, 26.4 mmol) and 10% Pd/C (2.0 g) in EtOAc (350 ml) was hydrogenated at room temperature for 18 h. The Pd/C catalyst was filtered off through a pad of celite. The filtrate was concentrated under reduced pressure to yield a white solid (10.1 g, 90% yield). LCMS purity 100%, m/z 425 [M$^+$+H]$^+$, 466 [M$^+$+H+41]$^+$.

Stage 4: Coupling of Stage 3 Aniline

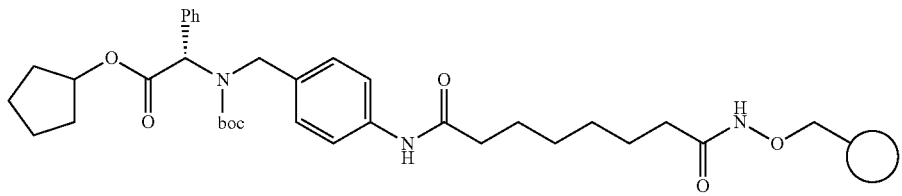

Hydroxylamine 2-chlorotrityl resin derivatized with suberic acid (1.0 g, loading 0.94 mmol) was swollen in anhydrous DCM (100 ml). 1-Chloro-N,N-2-trimethylpropenylamine (Ghosez reagent)[1] (0.373 ml, 2.82 mmol, 3 eq) was added at 0° C. under the atmosphere of $N_2$. The mixture was allowed to warm to room temperature and gently shaken for 1-2 h. Stage 3 aniline (1.2 g, 2.82 mmol, 3 eq) was added portionwise over 20 min. $Et_3N$ (0.53 ml, 3.76 mmol, 4 eq) was added. The mixture was shaken for 1 h. LCMS after a test cleave shows 70% conversion, m/z 596 $[M^++H]^+$. The resin was filtered and washed using the standard wash procedure. The resin was dried under vacuum.

Stage 5: (S)-[4-(7-Hydroxycarbamoyl-heptanoylamino)-benzylamino]-phenyl-acetic acid cyclopentyl ester (20)

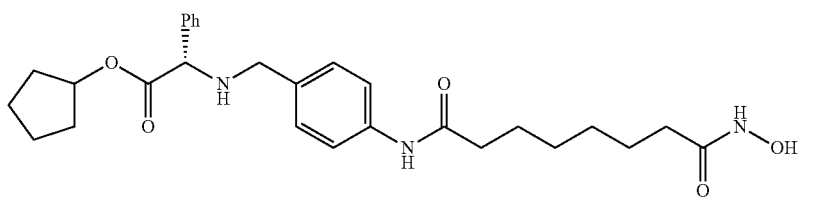

Stage 4 resin (1.5 g, loading 0.94 mmol) was gently shaken in 2% TFA/DCM (10 ml) for 20 mins. The resin was filtered. The filtrate was collected and evaporated under reduced pressure at room temperature. The resin was re-treated with 2% TFA/DCM (10 ml) and after 20 mins filtered. The combined filtrates were evaporated to dryness under reduced pressure at r.t to give a residue. This residue was allowed to stand in 20% TFA/DCM for 40 mins. After evaporation to dryness, also under reduced pressure at r.t, the residue was purified by preparative HPLC to yield compound (20) as the TFA salt, LCMS purity 95%, m/z 496 $[M^++H]^+$, $^1$H NMR (400 MHz, DMSO), δ: 1.30-1.50 (6H, m, 3×$CH_2$), 1.50-1.70 (8H, m, 4×$CH_2$), 1.80 (2H, m, $CH_2$), 2.10 (2H, t, $CH_2$), 2.45 (2H, t, $CH_2$), 4.1 (2H, dd, C$\underline{H}_2$ NH), 5.25 (1H, m, C$\underline{H}$OCO), 5.35 (1H, m, OCOC$\underline{H}$Ph), 7.45 (2H, d, Ar), 7.60 (5H, m, Ar), 7.80 (2H, d, Ar), 10.00-10.10 (2H, br s), 10.50 (1H, s).

Stage 6: Saponification of Cyclopentyl Ester

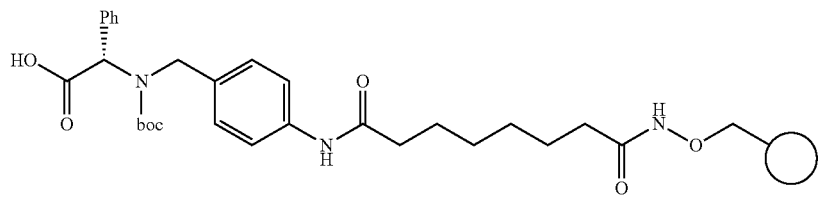

Stage 4 resin (2.5 g, loading, 0.94 mmol, 2.35 mmol) was suspended in MeOH (8.7 ml) and THF (8.7 ml). An eq. solution of 2.7 N NaOH (8.8 ml, 10 eq, 23.5 mmol) was added. The mixture was shaken for 36 h. LCMS of the test cleave confirmed the completion of reaction, m/z 528 [M$^+$+H]$^+$. The resin was filtered and washed with water×2, MeOH× 2, followed by the standard wash procedure. The resin was dried under vacuum.

Stage 7: (S)-[4-(7-Hydroxycarbamoyl-heptanoylamino)-benzylamino]-phenyl-acetic acid (21)

Stage 6 resin (2.5 g, loading 0.94 mmol, 2.35 mmol) was cleaved and boc deprotected using the procedure outlined for Stage 5. The crude product (0.40 g) was purified by preparative HPLC giving compound (21) as the TFA salt. LCMS purity 100%, m/z 428 [M$^+$+H], $^1$H NMR (400 MHz, CD$_3$OD), δ: 1.30 (4H, 2×CH$_2$), 1.55 (4H, 2×CH$_2$), 2.00 (2H, t, CH$_2$), 2.30 (2H, t, CH$_2$), 3.90 (1H, s, NHCH$_2$), 4.05 (2H, dd, NHCH$_2$), 4.95 (1H, s, CHPh), 7.35 (2H, d, Ar), 7.40 (5H, m, Ar), 7.55 (2H, d, Ar).

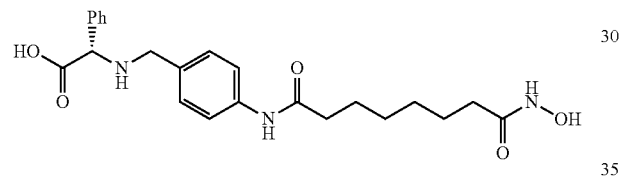

21

Synthesis of Compound (22) and Compound (23)

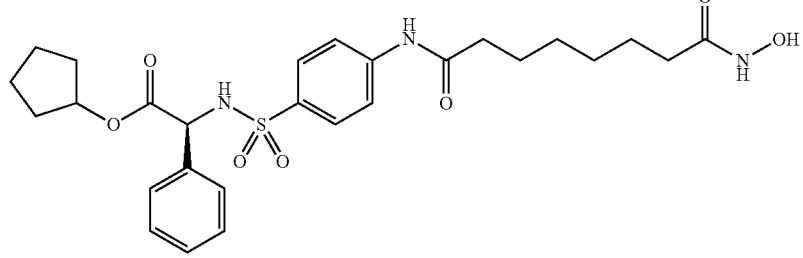

22

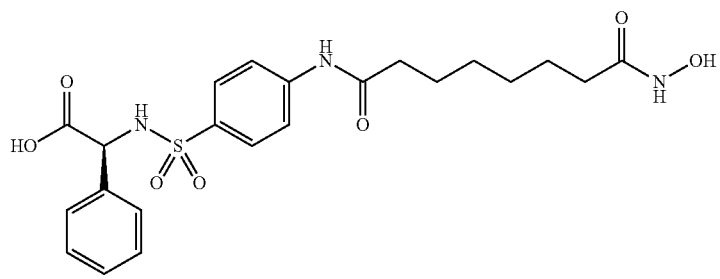

23

Stage 1:
(S)-(4-Nitro-benzenesulfonylamino)-phenyl-acetic acid

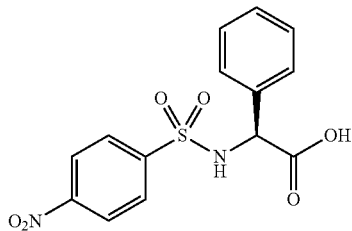 [SMILES: O=C(O)[C@@H](NS(=O)(=O)c1ccc([N+](=O)[O-])cc1)c1ccccc1]

To a solution of L-phenylglycine (0.227 g, 1.5 mmol) in water (5 ml) and dioxane (5 ml) was added triethylamine (0.42 ml, 3.0 mmol) followed by slow addition of 4-nitrobenzene sulphonyl chloride (0.5 g, 2.3 mmol) in dioxane (5 ml) at 0° C. After stirring for 45 minutes the reaction mixture was evaporated to dryness, re-dissolved in EtOAc and washed with saturated NaHCO$_3$ solution (2×20 ml) and water (10 ml). The EtOAc layer was dried over Na$_2$SO$_4$, filtered and evaporated to dryness. LCMS purity 75%, (molecular ion not observed) yield 0.58 g, (76%). This material was used without any purification.

Stage 2:
(S)-(4-Nitro-benzenesulfonylamino)-phenyl-acetic acid cyclopentyl ester

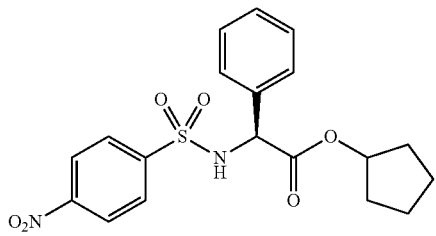 [SMILES: O=C(OC1CCCC1)[C@@H](NS(=O)(=O)c1ccc([N+](=O)[O-])cc1)c1ccccc1]

To a solution of stage 1 acid (4.32 g, 12.8 mmol) in cyclopentanol (60 ml) at 0° C. was added slowly thionyl chloride (9.3 ml, 128 mmol). The reaction mixture was stirred and heated under reflux at 70° C. for 2 hours. The excess thionyl chloride was removed by evaporation in vacuo, the reaction mixture was extracted into EtOAc and washed with saturated NaHCO$_3$ solution and dried over Na$_2$SO$_4$, filtered and evaporated to dryness. Flash column chromatography purification with DCM gave the required product (3.6 g, 70% yield). LCMS purity of 100%, (molecular ion not observed).

Stage 3:
(S)-(4-Amino-benzenesulfonylamino)-phenyl-acetic acid cyclopentyl ester

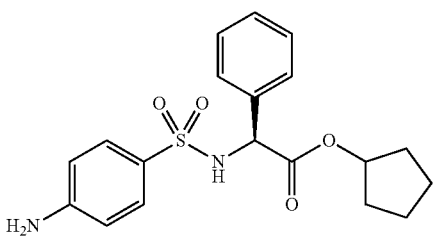

A mixture of (S)-(4-Nitro-benzenesulfonylamino)-phenyl-acetic acid cyclopentyl ester (5.29 g, 13.1 mmol) and 10% Pd/C (5.0 g) in EtOAc (350 ml) was hydrogenated under balloon pressure at room temperature for 24 h. The Pd/C catalyst was filtered off through a pad of celite. The filtrate was concentrated under reduced pressure to yield the required product (4.54 g, 92% yield). LCMS purity 100%, m/z 375 [M$^+$+H]$^+$.

Stage 4: Coupling of Anline

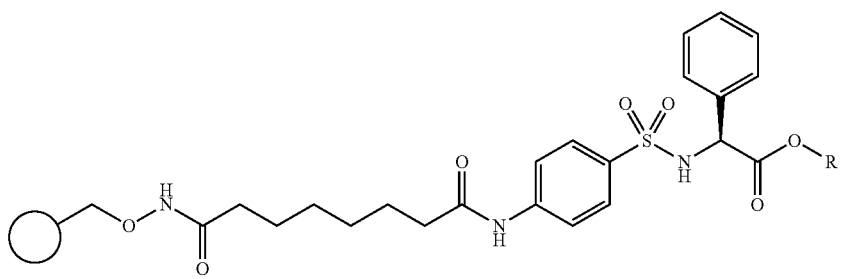

Hydroxylamine 2-chlorotrityl resin derivatized with suberic acid (0.39 g, loading 1.14 mmol/g) was swollen in anhydrous DCM (25 ml) and at 0° C. under N$_2$ atmosphere 1-chloro-N,N, 2-trimethylpropenylamine (0.175 ml, 1.33 mmol) added dropwise. The reaction mixture was shaken for 1.5 hours. A solution of stage 3 aniline (0.5 g, 1.33 mmol) in DCM (25 ml) was added followed by triethylamine (0.25 ml, 1.76 mmol). The reaction mixture was shaken for a further 10 minutes. LCMS after a test cleave showed 61% conversion, m/z 546 [M++H]+. The resin was filtered and washed using the standard wash procedure. The resin was dried under vacuum and used in the next step.

Stage 5: (S)-[4-(7-Hydroxycarbamoyl-heptanoy-lamino)-benzenesulfonylamino]-phenyl-acetic acid cyclopentyl ester (22)

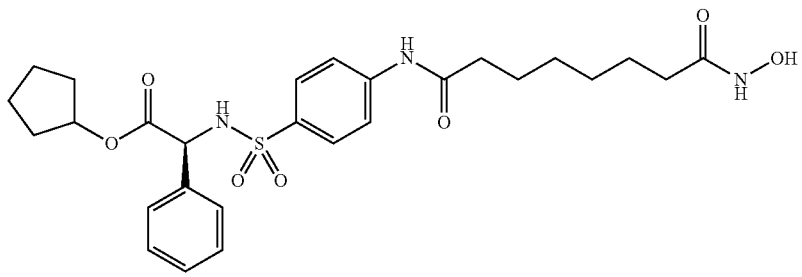 [SMILES: O=C(CCCCCCC(=O)Nc1ccc(S(=O)(=O)N[C@H](C(=O)OC2CCCC2)c2ccccc2)cc1)NO]

Stage 4 resin (1.12 g, loading 1.14 mmol/g) was gently shaken in 2% TFA/DCM (10 ml) for 20 mins. The resin was filtered. The filtrate was collected and evaporated under reduced pressure at room temperature. The resin was re-treated with 2% TFA/DCM (10 ml) and after 20 mins filtered. The combined filtrates were evaporated to dryness under reduced pressure at room temperature to give a residue. The residue was purified by preparative HPLC to yield compound (22). LCMS purity 93%, m/z 546 [M++H]+, $^1$H NMR (400 MHz, DMSO), δ: 1.20-1.68 (16H, m, 8×CH$_2$), 1.93 (2H, t, CH$_2$), 2.33 (2H, t, CH$_2$), 4.80 (1H, m, CHOCO), 4.81 (1H, d, OCOCHPh), 7.27 (5H, m, Ar), 7.65 (2H, d, Ar), 7.71 (2H, d, Ar), 8.67 (1H, br s), 8.75 (1H, d), 10.24 (1H, s), 10.34 (1H, s).

Stage 6: Saponification of Cyclopentyl Ester

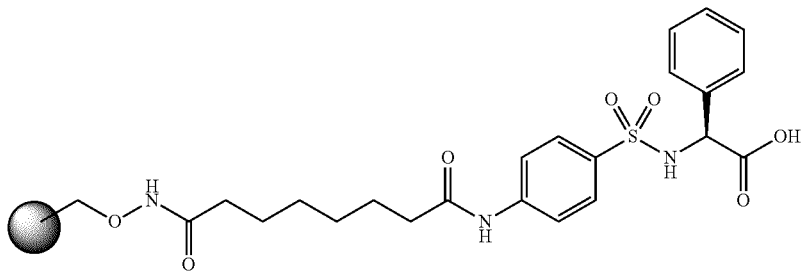 [SMILES: CCONC(=O)CCCCCCC(=O)Nc1ccc(S(=O)(=O)N[C@H](C(=O)O)c2ccccc2)cc1]

Stage 4 resin (1.2 g, loading 1.14 mmol/g) was suspended in THF (8 ml) and methanol (8 ml) and 2.7M sodium hydroxide (5.1 ml, 13.68 mmol) was added. The mixture was shaken for 48 h. LCMS of the test cleave confirmed the completion of reaction, m/z 478 [M++H]+. The resin was filtered and washed with water×2, MeOH×2, followed by the standard wash procedure. The resin was dried under vacuum.

71

Stage 7: (S)-[4-(7-Hydroxycarbamoyl-heptanoy-lamino)-benzenesulfonylamino]-phenyl-acetic acid (23)

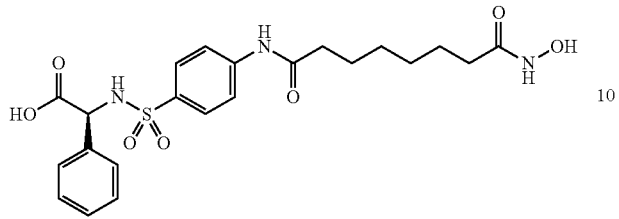

Stage 6 resin (1.2 g, loading 1.14 mmol/g) was gently shaken in 2% TFA/DCM (10 ml) for 20 mins. The resin was filtered. The filtrate was collected and evaporated under reduced pressure at room temperature. The resin was retreated with 2% TFA/DCM (10 ml) and after 20 mins filtered. The combined filtrates were evaporated to dryness under reduced pressure at room temperature to give a residue. The residue was purified by preparative HPLC to yield compound (23). LCMS purity 91%, m/z 478 [M$^+$+H]$^+$, $^1$H NMR (400 MHz, MeOD), δ: 1.44 (4H, m, 2×CH$_2$), 1.62-1.74 (4H, m, 2×CH$_2$), 2.12 (2H, t, CH$_2$), 2.34 (1H, m, OCOCHPh), 2.41 (2H, t, CH$_2$), 7.25 (5H, m, Ar), 7.69 (2H, d, Ar), 7.72 (2H, d, Ar).

Synthesis of Compounds (24) and Compound (25)

72

Stage 1: (2,3,4,9-Tetrahydro-1H-beta-carbolin-6-yloxy)-acetic acid methyl ester

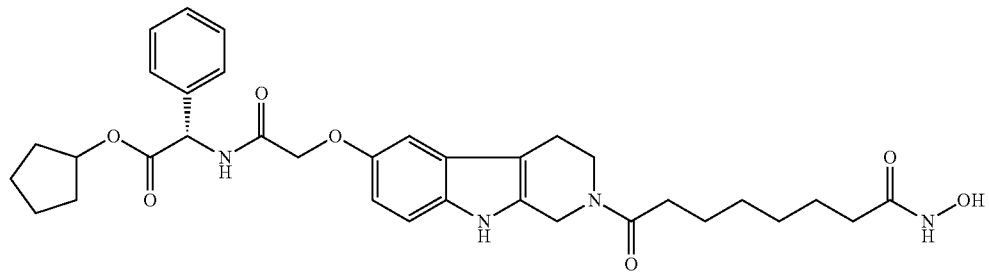

A mixture of 5-carboxymethoxy tryptamine (1.24 g, 4.56 mmol), 36% aq formaldehyde and MeOH (25 ml) was heated under reflux for 1.5 h. The reaction mixture was evaporated to dryness. MeOH (50 ml) and TMSCl (1.24 ml) were sequentially added. Reflux was continued for 1 h. Reaction mixture was evaporated to dryness and was used in the next stage without purification.

24

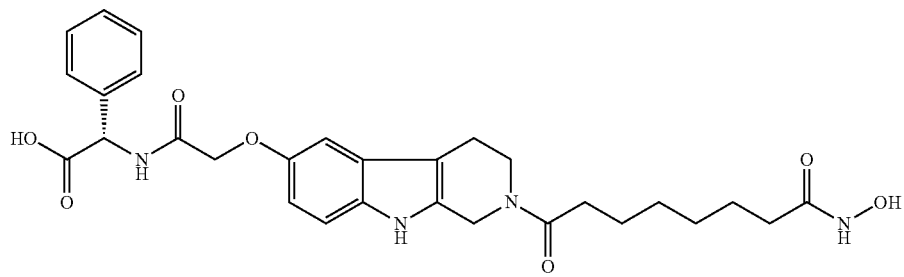

25

Stage 2: Amidation

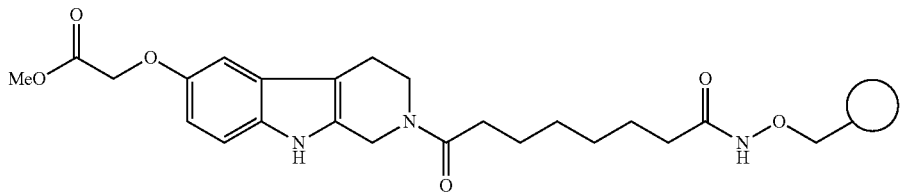 [SMILES: CCONC(=O)CCCCCCC(=O)N1CCc2c([nH]c3ccc(OCC(=O)OC)cc23)C1]

Hydroxylamine 2-chlorotrityl resin derivatized with suberic acid (2.0 g, loading 1.14 mmol/g, 2.28 mmol) was suspended in DCM (40 ml). pyBOP (3.56 g) was added followed by a DCM solution (40 ml) of Stage 1 amine (4.56 mmol) and DIPEA (3.9 ml, 22.8 mmol). The reaction was shaken at room temperature for 18 h. LCMS after test cleave confirmed the completion of reaction. The resin was filtered and washed using the standard wash procedure and was thoroughly dried.

Stage 3: Saponification of Methyl Ester

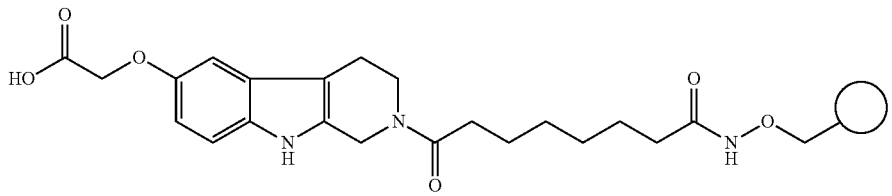 [SMILES: CCONC(=O)CCCCCCC(=O)N1CCc2c([nH]c3ccc(OCC(=O)O)cc23)C1]

Stage 2 resin (2.0 g, 1.14 mmol/g, 2.28 mmol) was suspended in a mixture of THF (10 ml) and MeOH (10 ml). 1.4M NaOH (10 ml) was added over 5 min. The mixture was shaken for 18 h. LCMS after test cleave confirmed the completion of reaction. The resin was filtered and washed using the standard wash procedure.

Stage 4: Coupling with L-phenylglycine cyclopentyl ester

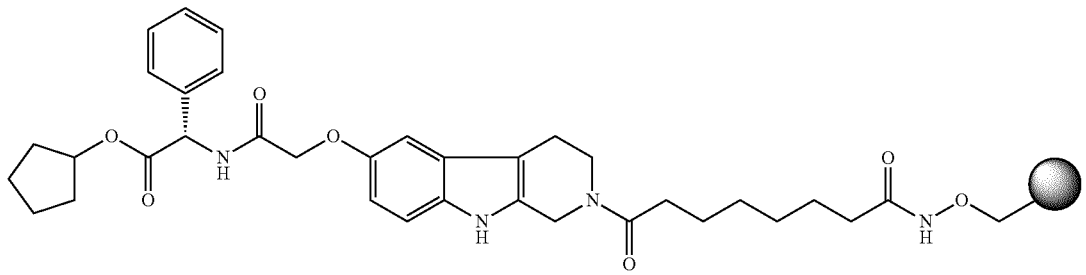 [SMILES: CCONC(=O)CCCCCCC(=O)N1CCc2c([nH]c3ccc(OCC(=O)N[C@H](C(=O)OC4CCCC4)c4ccccc4)cc23)C1]

Stage 3 resin (2.0 g, loading 1.14 mmol/g, 2.28 mmol) was suspended in DCM (30 ml). pyBOP (3.56 g, 6.84 mmol) was added, followed by L-phenylglycine cyclopentyl ester (2.59 g, 6.84 mmol) and DIPEA (3.9 ml, 22.8 mmol). The mixture was shaken for 18 h. LCMS after test cleave confirmed completion of reaction. The resin was filtered, washed using standard wash procedure and dried under vacuum.

Stage 5: (S)-{2-[2-(7-Hydroxycarbamoyl-heptanoyl)-2,3,4,9-tetrahydro-1H-beta-carbolin-6-yloxy]-acetylamino}-phenyl-acetic acid cyclopentyl ester (24)

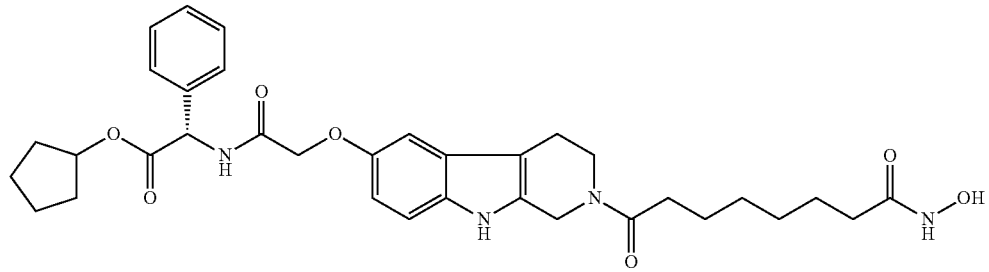 [SMILES: O=C(CCCCCCC(=O)N1CCc2c([nH]c3ccc(OCC(=O)N[C@H](C(=O)OC4CCCC4)c4ccccc4)cc23)C1)NO]

Stage 4 resin (0.8 g, loading 1.14 mmol/g, 0.91 mmol) was cleaved using 2% TFA/DCM (3×10 ml). The filtrate was evaporated to dryness at room temperature under reduced pressure to give an oily residue (200 mg) which was purified by preparative HPLC to give compound (24) as the TFA salt. LCMS purity 95%, m/z 619 [M$^+$+H]$^+$, $^1$H NMR (400 MHz, DMSO), δ: 1.05-1.66 (16H, m, 8×CH$_2$), 1.79 (2H, m, CH$_2$), 2.16-2.31 (2H, m, 2.41-2.56 (2H, m, CH$_2$), 3.60 (2H, m, CH$_2$), 4.42 (2H, s, CH$_2$), 4.49 (2H, s, CH$_2$), 4.93 (1H, m, CHOCO), 5.28 (1H, m, OCOCHPh), 6.59 (1H, d, Ar), 6.65 (1H, s, Ar), 7.04 (1H, d, Ar), 7.21 (5H, m, Ar), 8.57 (1H, m), 10.17 (1H, s), 10.58 (1H, s, Ar).

Stage 6: Saponification of Cyclopentyl Ester

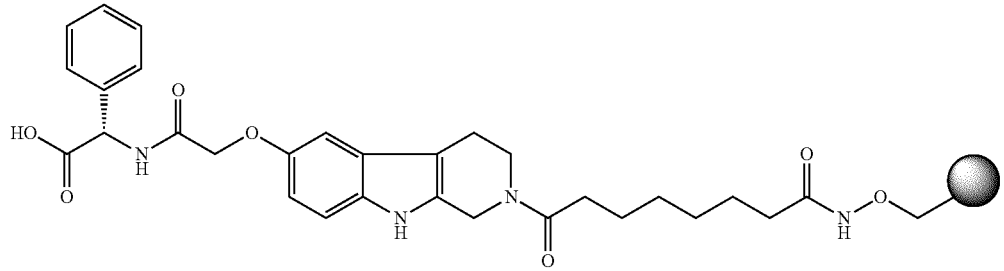 [SMILES: CCONC(=O)CCCCCCC(=O)N1CCc2c([nH]c3ccc(OCC(=O)N[C@H](C(=O)O)c4ccccc4)cc23)C1]

Stage 4 resin (1.0 g, loading 1.14 mmol/g, 1.14 mmol) was saponified according to the the procedure described in Stage 3.

Stage 7: (S)-{2-[2-(7-Hydroxycarbamoyl-heptanoyl)-2,3,4,9-tetrahydro-1H-beta-carbolin-6-yloxy]-acetylamino}-phenyl-acetic acid cyclopentyl ester (25)

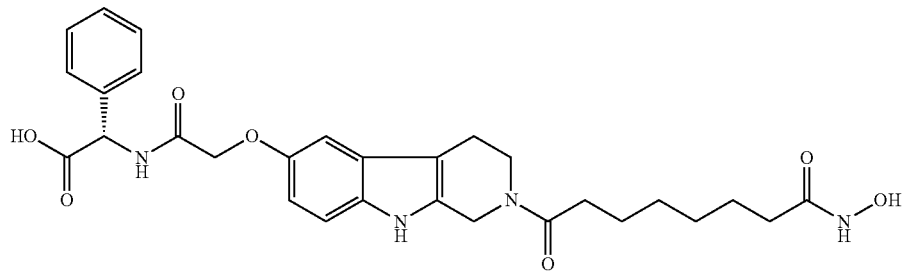 [SMILES: O=C(CCCCCCC(=O)N1CCc2c([nH]c3ccc(OCC(=O)N[C@H](C(=O)O)c4ccccc4)cc23)C1)NO]

Stage 6 resin (1.0 g, loading 1.14 mmol/g, 1.14 mmol) was cleaved and purified using the procedure detailed in stage 5. Compound (25): LCMS purity 97%, m/z 551 [M⁺+H]⁺, ¹H NMR (400 MHz, MeOD), δ: 1.33-1.49 (4H, m, 2×CH₂), 1.58-1.75 (4H, m, 2×CH₂), 2.06-2.17 (2H, m, CH₂), 2.51-2.60 (2H, m, CH₂), 2.70-2.83 (2H, m, CH₂), 3.85-3.96 (2H, m, CH₂), 4.61 (2H, m, CH₂), 4.78 (2H, m, CH₂), 5.56 (1H, s, OCOC$\underline{H}$Ph), 6.89 (1H, m, Ar), 7.00 (1H, s, Ar), 7.26 (1H, m, Ar), 7.35 (5H, m, Ar).

Synthesis of Compounds in Figure 2 as Exemplified by Compound (26) and Compound (27)

-continued

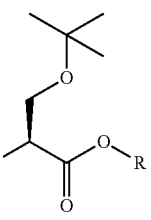

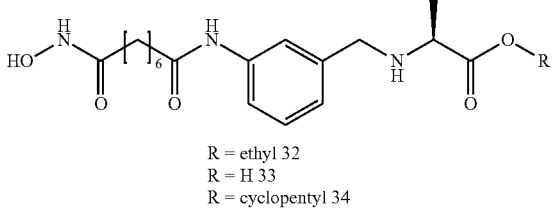

R = ethyl 32
R = H 33
R = cyclopentyl 34

Figure 2

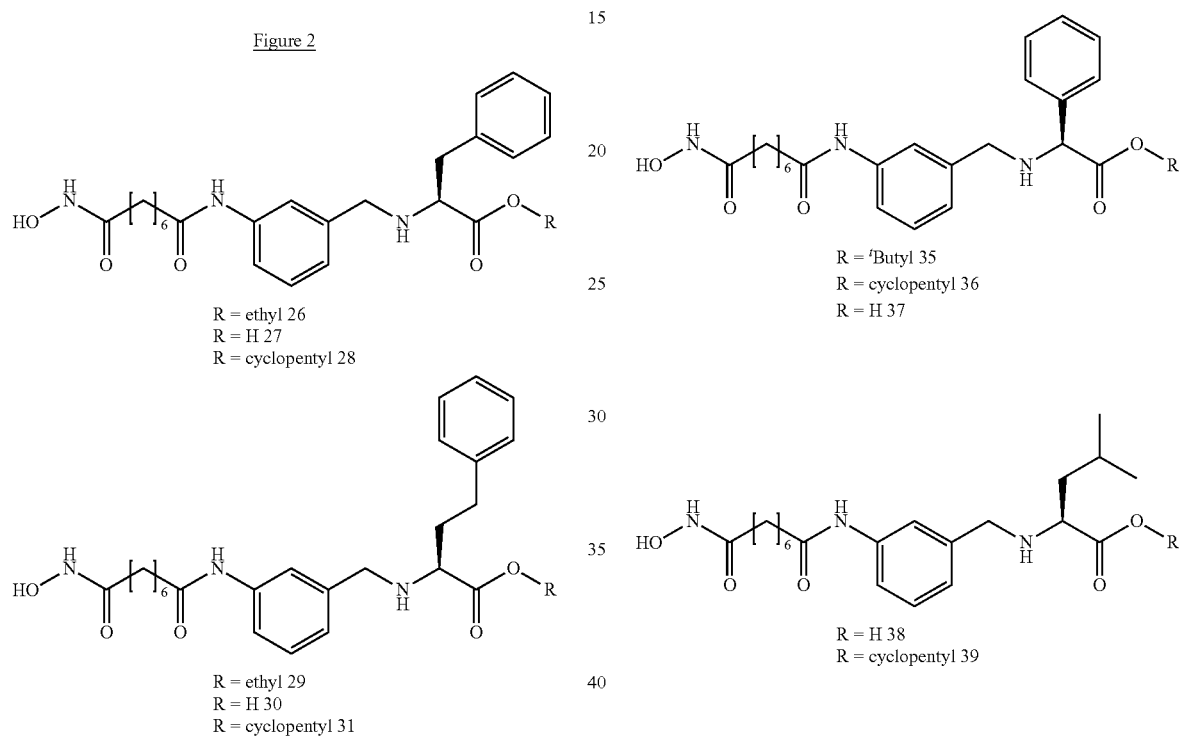

R = ethyl 26
R = H 27
R = cyclopentyl 28

R = ᵗButyl 35
R = cyclopentyl 36
R = H 37

R = ethyl 29
R = H 30
R = cyclopentyl 31

R = H 38
R = cyclopentyl 39

Synthesis of Compound (26) and Compound (27)

26

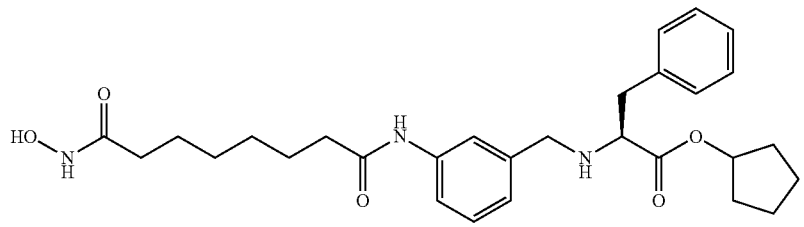

27

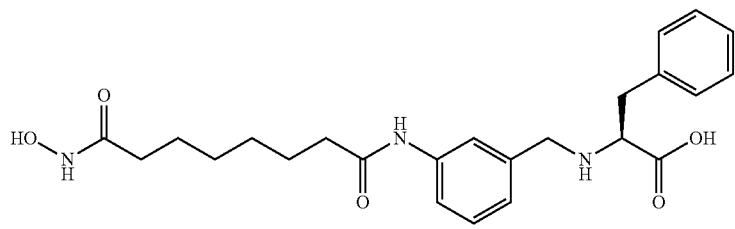

Stage 1: (S)-2-(3-Nitro-benzylamino)-3-phenyl-propionic acid ethyl ester

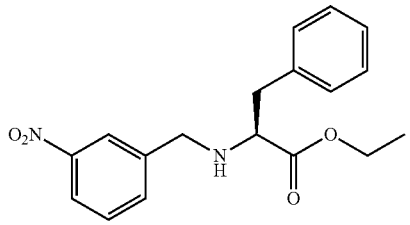 [SMILES: CCOC(=O)[C@H](Cc1ccccc1)NCc1cccc([N+](=O)[O-])c1]

3-Nitrobenzyl bromide (10.0 g, 46 mmol) was dissolved in DMF (180 ml) and potassium carbonate (12.7 g, 92 mmol) added, followed by L-phenylalanine ethyl ester hydrochloride (10.6 g, 46 mmol). The reaction was stirred for 17 h at room temperature before evaporating to dryness. The residue was re-dissolved in EtOAc (150 ml) and washed with water (3×80 ml), dried (Na$_2$SO$_4$) filtered and concentrated to dryness. After purification by flash column chromatography (30% EtOAc/hexane) the product was obtained (3.7 g, 24% yield). LCMS purity 86%, m/z 329 [M$^+$+H]$^+$.

Stage 2: (S)-2-[tert-Butoxycarbonyl-(3-nitro-benzyl)-amino]-3-phenyl-propionic acid ethyl ester

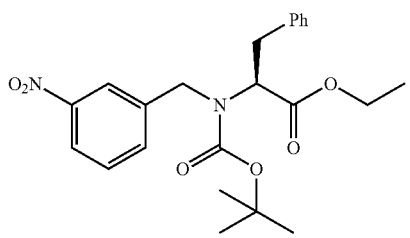 [SMILES: CCOC(=O)[C@H](Cc1ccccc1)N(Cc1cccc([N+](=O)[O-])c1)C(=O)OC(C)(C)C]

Stage 1 amine (13.4 g, 40.9 mmol) was dissolved in THF (250 ml) before addition of potassium carbonate (8.46 g, 61.4 mmol) and water (150 ml). Di-$^t$butyl-dicarbonate (35.6, 163 mmol) was added and the reaction mixture heated to 50° C. for 18 h. DCM was added the resultant mixture washed consecutively with 0.1 M HCl (150 ml), sat. aq. NaHCO$_3$ and water (150 ml). The DCM layer was dried (Na$_2$SO$_4$), filtered and concentrated to dryness. After purification by flash column chromatography (5% EtOAc/hexane) the product was isolated (9.4 g, 54% yield). LCMS purity 95%, m/z 428 [M$^+$+H]$^+$.

Stage 3: (S)-2-[(3-Amino-benzyl)-tert-butoxycarbonyl-amino]-3-phenyl-propionic acid ethyl ester

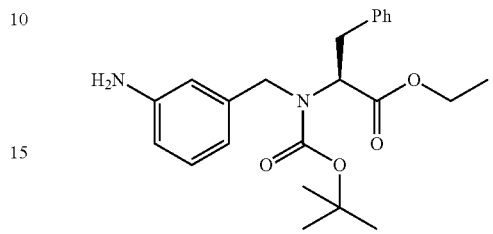

Stage 2 carbamate (4.92 g, 11.5 mmol) was dissolved in EtOAc (150 ml) before addition of Pd/C (10% wet) catalyst (0.8 g) and hydrogenated under balloon pressure at room temperature for 18 h. The reaction mixture was filtered through a pad of celite and evaporated to dryness to give a red solid (4.0 g, 89% yield). LCMS purity 100%, m/z 399 [M$^+$+H]$^+$.

Stage 4: Coupling to Resin

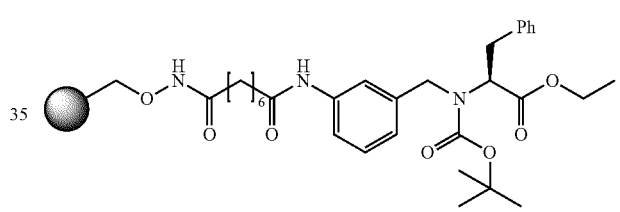

Hydroxylamine 2-chlorotrityl resin derivatized with suberic acid (1.0 g, loading 0.83 mmol/g) was swollen in DMF (15 ml) and PyBOP (1.36 g, 2.61 mmol) added, followed by DIPEA (1.5 ml, 8.7 mmol). Stage 3 aniline (1.04 g, 2.61 mmol) was dissolved in DCM (15 ml) and added to the reaction mixture. The reaction was shaken for 24 h at room temperature. LCMS after a test cleave indicated 86% conversion, m/z 570 [M$^+$+H]$^+$. The resin was filtered and washed using the standard wash procedure. The resin was dried under vacuum.

Stage 5: (S)-2-[3-(7-Hydroxycarbamoyl-heptanoylamino)-benzylamino]-3-phenyl-propionic acid ethyl ester (26)

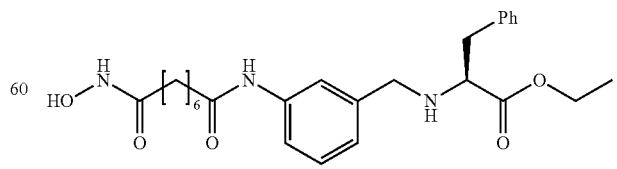

Stage 4 resin (1.3 g, loading 0.83 mmol) was gently shaken in 2% TFA/DCM (10 ml) for 20 mins. The resin was filtered. The filtrate was evaporated under reduced pressure at room temperature. The resin was re-treated with 2% TFA/DCM (10 ml) and was filtered after 20 mins. The combined filtrates were evaporated to dryness under reduced pressure at room temperature to give an oily residue. The residue was allowed to stand in 20% TFA/DCM for 40 mins. After evaporation to dryness, also under reduced pressure at room temperature, the crude product was purified by preparative HPLC to yield compound (26). LCMS purity 100%, m/z 470 [M$^+$+H]$^+$, $^1$H NMR (400 MHz, MeOD), δ: 1.08 (3H, t, CH$_3$), 1.35-1.45 (4H, m, 2×CH$_2$), 1.60-1.80 (4H, m, 2×CH$_2$), 2.10 (2H, t, CH$_2$), 2.40 (2H, t, CH$_2$), 3.13 (1H, dd, PhCHH), 3.40 (1H, dd, PhCHH), 4.11 (2H, q, CH$_2$CH$_3$), 4.14-4.22 (3H, m), 7.20-7.48 (8H, m, Ar), 7.92 (1H, s, Ar).

Stage 6: Saponification

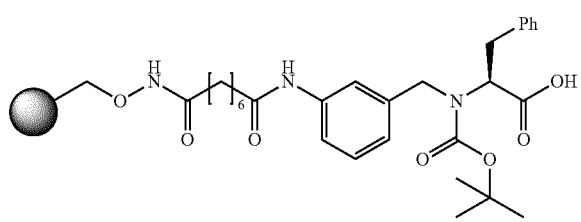

Stage 4 resin (1.4 g, loading 0.83 mmol) was suspended in THF (8.6 ml) and methanol (8.6 ml) and 1.4M sodium hydroxide solution (8.6 ml, 5.98 mmol) was added. The mixture was shaken for 24 hours before test cleavage revealed 83% conversion to required acid, m/z 541 [M$^+$+H] The resin was filtered and washed with water×2, MeOH×2, followed by the standard wash procedure. The resin was dried under vacuum.

Stage 7: (S)-2-[3-(7-Hydroxycarbamoyl-heptanoy-lamino)-benzylamino]-3-phenyl-propionic acid (27)

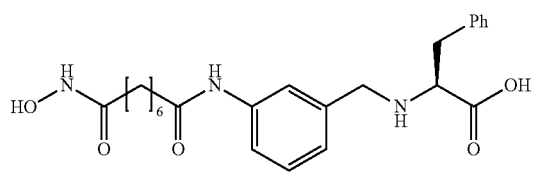

Stage 6 resin (1.44 g, loading 0.83 mmol) was gently shaken in 2% TFA/DCM (10 ml) for 20 mins. The resin was filtered. The filtrate was evaporated under reduced pressure at room temperature. The resin was re-treated with 2% TFA/DCM (10 ml) and was filtered after 20 mins. The combined filtrates were evaporated to dryness under reduced pressure at room temperature to give an oily residue. The residue was allowed to stand in 20% TFA/DCM for 40 mins. After evaporation to dryness, under reduced pressure at room temperature, the crude product was purified by preparative HPLC to yield compound (27). LCMS purity 100%, m/z 442 [M$^+$+H]$^+$, $^1$H NMR (400 MHz, MeOD), δ: 1.35-1.48 (4H, m, 2×CH$_2$), 1.60-1.78 (4H, m, 2×CH$_2$), 2.10 (2H, t, CH$_2$), 2.40 (2H, t, CH$_2$), 3.20 (1H, dd, PhCHH), 3.28 (1H, dd, PhCHH), 3.90 (1H, t, OCOCH), 4.14 (2H, m), 7.15 (1H, d, Ar), 7.26 (6H, m, Ar), 7.51 (1H, d, Ar), 7.73 (1H s, Ar).

The following compounds were prepared according to the procedure described for compound (26) and compound (27)

(S)-2-[3-(7-Hydroxycarbamoyl-heptanoylamino)-benzylamino]-3-phenyl-propionic acid cyclopentyl ester (28)

LCMS purity 100%, m/z 510 [M$^+$+H]$^+$, $^1$H NMR (400 MHz, MeOD), δ: 1.00-1.61 (16H, m, 8×CH$_2$), 1.90 (2H, t, CH$_2$), 2.20 (2H, d, CH$_2$), 2.90 (1H, dd, PhCHH), 3.20 (1H, dd, PhCHH), 4.00-4.11 (3H, m), 4.91 (1H, m), 7.00-7.25 (8H, m, Ar), 7.75 (1H, s, Ar).

(S)-2-[3-(7-Hydroxycarbamoyl-heptanoylamino)-benzylamino]-4-phenyl-butyric acid ethyl ester (29)

LCMS purity 100%, m/z 484 [M$^+$+H]$^+$, $^1$H NMR (400 MHz, MeOD), δ: 1.23-1.29 (7H, m, CH$_3$, 2×CH$_2$), 1.53 (2H, t, CH$_2$), 1.62 (2H, t, CH$_2$), 1.99 (2H, t, CH$_2$), 2.11-2.16 (2H, m, CH$_2$), 2.28 (2H, t, CH$_2$), 2.53-2.61 (1H, m, CH), 2.65-2.76 (1H, m, CH), 3.80-3.90, (1H, m, CHCO$_2$Et), 4.05 (2H, s, CH$_2$), 4.21 (2H, q, CH$_2$), 7.05-7.15 (4H, m, Ar), 7.15-7.22 (2H, m, Ar), 7.25-7.39 (2H, m, Ar), 7.75 (1H, s, Ar).

(S)-2-[3-(7-Hydroxycarbamoyl-heptanoylamino)-benzylamino]-4-phenyl-butyric acid (30)

LCMS purity 100%, m/z 456 [M$^+$+H]$^+$, $^1$H NMR (400 MHz, MeOD), δ: 1.27-1.32 (4H, m, 2×CH$_2$), 1.53 (2H, t, CH$_2$), 1.62 (2H, t, CH$_2$), 1.99 (2H, t, CH$_2$), 2.11-2.16 (2H, m, CH$_2$), 2.29 (2H, t, CH$_2$), 2.57-2.64 (1H, m, CH), 2.69-2.77 (1H, m, CH), 3.84-3.87 (1H, m, CHCO$_2$H), 4.12 (2H, q, CH$_2$), 7.09-7.11 (4H, m, Ar), 7.16-7.20 (2H, m, Ar), 7.27-7.35 (2H, m, Ar), 7.78 (1H, s, Ar).

(S)-2-[3-(7-Hydroxycarbamoyl-heptanoylamino)-benzylamino]-4-phenyl-butyric acid cyclopentyl ester (31)

LCMS purity 100%, m/z 524 [M$^+$+H]$^+$, $^1$H NMR (400 MHz, MeOD), δ: 1.20-1.35 (4H, m), 1.45-1.62 (10H, m), 1.85 (2H, m), 2.00 (2H, t, CH$_2$), 2.10 (2H, m), 2.28 (2H, t, CH$_2$), 2.55 (1H, m), 2.68 (1H, m), 3.88 (1H, t, OCOCHNH), 4.11 (2H, s, CH$_2$Ph), 5.24 (1H, m) 7.02-7.12 (4H, m, Ar), 7.18 (2H, m, Ar), 7.30 (2H, m, Ar), 7.80 (1H, s, Ar).

(S)-3-tert-Butoxy-2-[3-(7-hydroxycarbamoyl-heptanoylamino)-benzylamino]-propionic acid ethyl ester (32)

LCMS purity 90%, m/z 466 [M$^+$+H]$^+$, $^1$H NMR (400 MHz, MeOD), δ: 1.25 (9H, s, O(CH$_3$)$_3$), 1.35 (3H, t, CH$_2$CH$_3$), 1.35-1.45 (4H, m, 2×CH$_2$), 1.62-1.76 (4H, m, 2×CH$_2$), 2.12 (2H, t, CH$_2$), 2.40 (2H, t, CH$_2$), 3.89 (1H, m), 3.98 (1H, m), 4.20-4.40 (5H, m), 7.25 (1H, d, Ar), 7.39-7.50 (2H, m, Ar), 7.90 (1H, s, Ar).

(S)-3-tert-Butoxy-2-[3-(7-hydroxycarbamoyl-heptanoylamino)-benzylamino]-propionic acid (33)

LCMS purity 86%, m/z 438 [M$^+$+H]$^+$, $^1$H NMR (400 MHz, MeOD), δ: 1.20 (9H, s, C(CH$_3$)$_3$), 1.38 (4H, m, 2×CH$_2$), 1.57-1.75 (4H, m, 2×CH$_2$), 2.10 (2H, t, CH$_2$), 2.39 (2H, t, CH$_2$), 3.78-3.85 (3H, m), 4.26 (2H, s, CH$_2$Ph), 7.21 (1H, d, Ar), 7.39 (1H, t, Ar), 7.50 (1H, d, Ar), 7.80 (1H, s, Ar).

(S)-3-tert-Butoxy-2-[3-(7-hydroxycarbamoyl-heptanoylamino)-benzylamino]-propionic acid cyclopentyl ester (34)

LCMS purity 94%, m/z 506 [M$^+$+H]$^+$, $^1$H NMR (400 MHz, MeOD), δ: 1.25 (9H, s, C(C$\underline{H}_3$)$_3$), 1.33-1.50 (4H, m, 2×CH$_2$), 1.60-2.00 (12H, m), 2.13 (2H, t, CH$_2$), 2.42 (2H, t, CH$_2$), 3.83-4.00 (2H, m), 4.18 (1H, m), 4.28 (2H, s, CH$_2$Ph), 5.35 (1H, m), 7.25 (1H, m, Ar), 7.45 (2H, m, Ar), 7.90 (1H, s, Ar).

(S)-[3-(7-Hydroxycarbamoyl-heptanoylamino)-benzylamino]-phenyl-acetic acid tert-butyl ester (35)

LCMS purity 97%, m/z 484 [M$^+$+H]$^+$, $^1$H NMR (400 MHz, MeOD), δ: 1.30 (13H, m, 2×CH$_2$, C(C$\underline{H}_3$)$_3$), 1.45-1.65 (4H, m, CH$_2$×2), 1.93-2.05 (2H, m, CH$_2$), 2.20-2.40 (2H, m, CH$_2$), 3.99 (2H, q, CH$_2$), 4.65-4.95 (1H, m, CH, masked signal) 7.05 (1H, d, Ar), 7.25-7.33 (2H, m, Ar), 7.35-7.50 (5H, m, Ar), 7.75 (1H, s, Ar).

(S)-[3-(7-Hydroxycarbamoyl-heptanoylamino)-benzylamino]-phenyl-acetic acid cyclopentyl ester (36)

LCMS purity 100%, m/z 496 [M$^+$+H]$^+$, $^1$H NMR (400 MHz, MeOD), δ: 1.30-1.70 (16H, m, 8×CH$_2$), 2.00 (2H, t, CH$_2$), 2.30 (2H, t, CH$_2$), 4.05 (2H, dd, C$\underline{H}_2$NH), 5.00 (1H, m, OCOC$\underline{H}$Ph), 5.15 (1H, m, C$\underline{H}$OCO), 7.05 (1H, m, Ar), 7.30 (2H, m, Ar), 7.40 (5H, m, Ar), 7.75 (1H, m, Ar).

(S)-[3-(7-Hydroxycarbamoyl-heptanoylamino)-benzylamino]-phenyl-acetic acid (37)

LCMS purity 100%, m/z 428 [M$^+$+H]$^+$, $^1$H NMR (400 MHz, MeOD), δ: 1.20-1.35 (4H, m, 2×CH$_2$), 1.50-1.65 (4H, m, 2×CH$_2$), 2.00 (2H, m, CH$_2$), 2.30 (2H, m, CH$_2$), 4.00 (2H, dd, C$\underline{H}_2$NH), 4.90 (1H, m, OCOC$\underline{H}$Ph), 7.05 (1H, m, Ar), 7.25-7.50 (7H, m, Ar), 7.70 (1H, m, Ar).

(S)-2-[3-(7-Hydroxycarbamoyl-heptanoylamino)-benzylamino]-4-methyl-pentanoic acid (38)

LCMS purity 91%, m/z 408 [M$^+$+H]$^+$, $^1$H NMR (400 MHz, MeOD), δ: 0.78 (3H, d, J=6.6 Hz, CH$_3$), 0.84 Hz (3H, d, J=6.6 Hz, CH$_3$), 1.26-1.40 (6H, m, alkyl), 1.49-1.70 (5H, m, CH+2×CH$_2$), 1.95 (2H, t, J=7.32, CH$_2$), 2.25 (2H, t, J=7.36, CH$_2$), 3.00 (1H, t, J=6.88 Hz, NHC$\underline{H}$CO), 3.42 (1H, d, J=12.7 Hz, CH), 3.68 (1H, d, J=12.5 Hz, CH), 7.00 (1H, d, J=7.6 Hz, Ar), 7.15 (1H, t, J=7.8 Hz, Ar), 7.30 (1H, s. Ar), 7.47 (1H, br d, Ar)

(S)-2-[3-(7-Hydroxycarbamoyl-heptanoylamino)-benzylamino]-4-methyl-pentanoic acid cyclopentyl ester (39)

LCMS purity 100%, m/z 476 [M$^+$+H]$^+$, $^1$H NMR (400 MHz, MeOD), δ: 0.85-0.95 (6H, 2×d, 2×CH$_3$), 1.30 (4H, m, 2×CH$_2$), 1.50-1.70 (13H, m, alkyl), 1.75 (2H, m, CH$_2$), 2.00 (2H, t, CH$_2$), 2.30 (2H, t, CH$_2$), 3.90 (1H, NHC$\underline{H}$CO), 4.10 (2H, q, CH$_2$), 5.25, (1H, m, CH), 7.10 (1H, d, Ar), 7.30 (2H, m), 7.80 (1H, s, Ar)

Synthesis of Compound (40) and Compound (41)

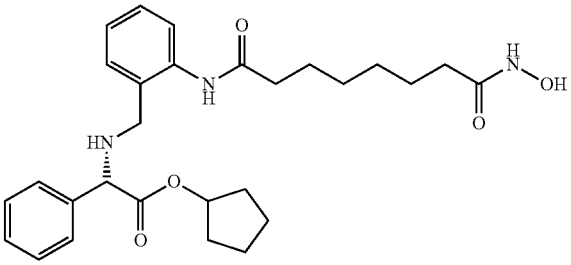

40

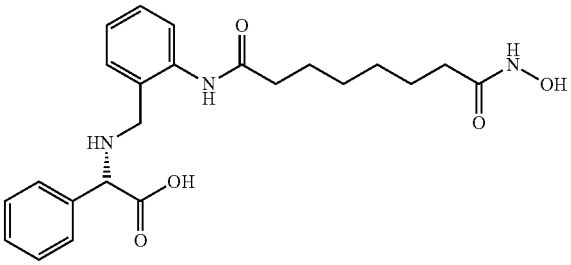

41

Stage 1: (S)-(2-Nitro-benzylamino)-phenyl-acetic acid cyclopentyl ester

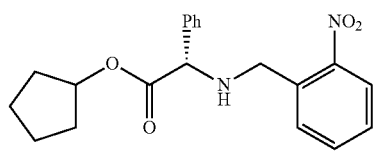 [SMILES: O=C(OC1CCCC1)[C@@H](NCc1ccccc1[N+](=O)[O-])c1ccccc1]

A mixture of 2-nitrobenzyl bromide (15 g, 69.4 mmol), L-phenylglycine cyclopentyl ester tosyl salt (27.2 g, 69.4 mmol) and potassium carbonate (19.2 g, 138.8 mmol) in DMF (300 ml) was stirred at room temperature for 18 h. The reaction mixture was diluted with EtOAc (300 ml) and washed with water (3×200 ml). The EtOAc layer was isolated, dried (Na$_2$SO$_4$), filtered and concentrated to dryness yielding an orange coloured oil. A crude weight of 24 g was isolated. LCMS purity 81%, m/z 355 [M++H]+. This product was used without further purification Stage 2: (S)-[tert-Butoxycarbonyl-(2-nitro-benzyl)-amino]-phenyl-acetic acid cyclopentyl ester

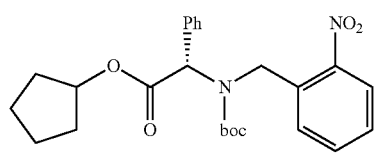

To a solution of (S)-(2-Nitro-benzylamino)-phenyl-acetic acid cyclopentyl ester (24.4 g, 69.1 mmol) in THF (150 ml) was added $K_2CO_3$ (7.6 g, 69.1 mmol), followed by di-tert-butyl dicarbonate (30.1 g, 138.1 mmol). Water (150 ml) was added and the reaction stirred at room temperature for 8 days with further di-tert-butyl dicarbonate (45.1 g, 206.6 mmol). The reaction mixture was evaporated to dryness. The residue was re-dissolved in EtOAc (300 ml), washed with 0.1 M HCl (150 ml), sat. aq.NaHCO$_3$ and water (150 ml). The EtOAc layer was dried (Na$_2$SO$_4$), filtered and concentrated to dryness yielding a yellow oil. After purification by column chromatography (20% EtOAc/hexane) the product was obtained as clear yellow oil (15 g, 48% yield).

Stage 3: (S)-[(2-Amino-benzyl)-tert-butoxycarbonyl-amino]-phenyl-acetic acid cyclopentyl ester

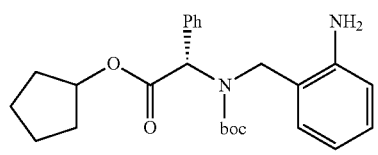

A mixture of stage 2 carbamate (4.44 g, 9.78 mmol) and 10% Pd/C (0.7 g) in EtOAc (130 ml) was hydrogenated at room temperature for 18 h under balloon pressure. The Pd/C catalyst was filtered off through a pad of celite. The filtrate was concentrated under reduced pressure to yield a white solid (4.25 g). LCMS purity 100%, m/z 425 [M++H]+, Stage 4: Coupling of Stage 3 Aniline

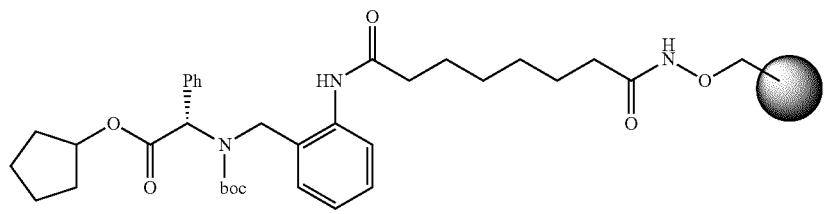

Hydroxylamine 2-chlorotrityl resin derivatized with suberic acid (1.6 g, loading 0.83 mmol) was swollen in anhydrous DCM (100 ml). 1-Chloro-N,N-2-trimethylpropenylamine (Ghosez reagent)[1] (0.56 ml, 3.3 mmol, 3 eq) was added at 0° C. under the atmosphere of N$_2$. The mixture was allowed to warm to room temperature and gently shaken for 1-2 h. Stage 3 aniline (1.4 g, 3.3 mmol, 3 eq) was added portionwise over 20 min. Et$_3$N (0.76 ml, 4.4 mmol, 4 eq) was added. The mixture was shaken for 1 h. LCMS after a test cleave shows 97% conversion, m/z 596 [M++H]+. The resin was filtered and washed using the standard wash procedure. The resin was dried under vacuum.

1. Ghosez et al, J. C. S. Chem. Comm., 1979, 1180.

Stage 5: (S)-[2-(7-Hydroxycarbamoyl-heptanoylamino)-benzylamino]-phenyl-acetic acid cyclopentyl ester (40)

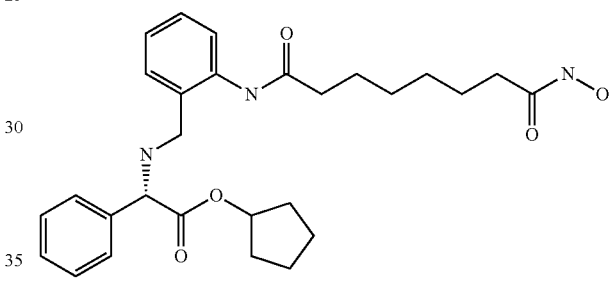

Stage 4 resin (1.34 g, loading 0.83 mmol) was gently shaken in 2% TFA/DCM (10 ml) for 20 mins. The resin was filtered. The filtrate was collected and evaporated under reduced pressure at room temperature. The resin was re-treated with 2% TFA/DCM (10 ml) and after 20 mins filtered. The combined filtrates were evaporated to dryness under reduced pressure at room temperature to give a residue. This residue was allowed to stand in 20% TFA/DCM for 40 mins. After evaporation to dryness, also under reduced pressure at room temperature, the residue was purified by preparative HPLC to yield compound 40 as the TFA salt, LCMS purity 100%, m/z 496 [M++H]+, $^1$H NMR (400 MHz, MeOD), δ: 1.40-2.00 (16H, m, 8×CH$_2$), 2.15 (2H, m, CH$_2$), 2.45 (2H, m, CH$_2$), 3.95 (1H, d, CH$_2$NH), 4.20 (1H, d, CH$_2$NH), 5.20 (1H, m, OCOCHPh), 5.35 (1H, m, CHOCO), 7.25 (1H, m, Ar), 7.40 (1H, m, Ar), 7.50-7.60 (7H, m, Ar).

Stage 6: Saponification

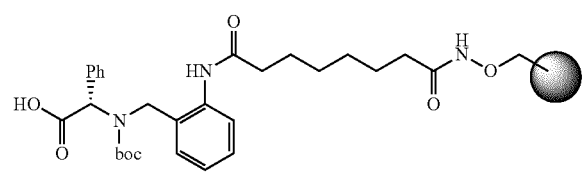

Stage 4 resin (2.0 g, loading, 0.83 mmol, 2.35 mmol) was suspended in MeOH (6.1) and THF (6.1 ml). 2.7 N NaOH (aq, 6.1 ml) was added. The mixture was shaken for 5 days. LCMS of the test cleave confirmed the completion of reaction, m/z 528 [M$^+$+H]$^+$. The resin was filtered and washed with water×2, MeOH×2, followed by the standard wash procedure. The resin was dried under vacuum.

Stage 7: (S)-[2-(7-Hydroxycarbamoyl-heptanoylamino)-benzylamino]-phenyl-acetic acid compound (41)

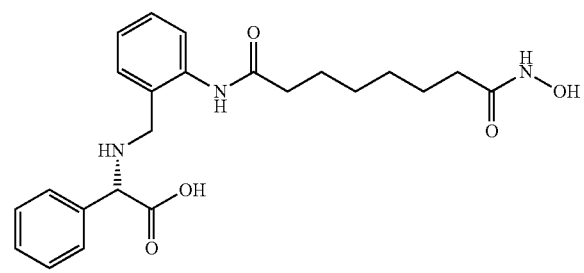

Stage 6 resin (2.0 g, loading 0.83 mmol) was cleaved and boc deprotected using the procedure outlined for stage 5. The crude product was purified by preparative HPLC yielding compound (41) as the TFA salt. LCMS purity 98%, m/z 428 [M$^+$+H]$^+$, $^1$H NMR (400 MHz, MeOD), δ: 1.25-1.35 (4H, m, 2×CH$_2$), 1.50-1.65 (4H, m, 2×CH$_2$), 2.00 (2H, m, CH$_2$), 2.30 (2H, m, CH$_2$), 3.80 (1H, d, CH$_2$NH), 4.10 (1H, d, CH$_2$NH), 5.00 (1H, m, OCOCHPh), 7.10 (1H, m, Ar), 7.30 (1H, m, Ar), 7.40-7.50 (7H, m, Ar).

Synthesis of Compound (42) and Compound (43)

42

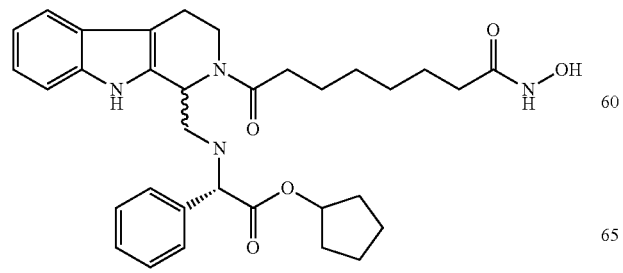

43

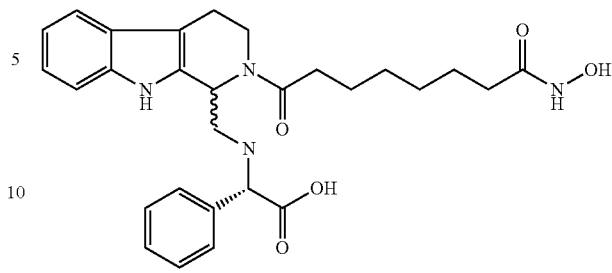

Stage 1:
1,3,4,9-Tetrahydro-beta-carboline-1,2-dicarboxylic acid 2-benzyl ester

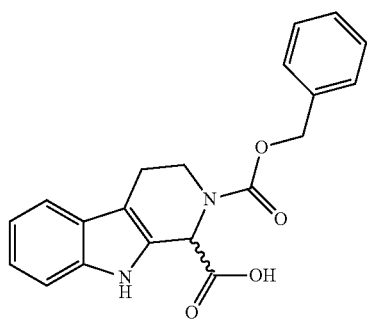 [SMILES: O=C(O)C1c2[nH]c3ccccc3c2CCN1C(=O)OCc1ccccc1]

A solution of 1,2,3,4-tetrahydrocarboline-1-carboxylic acid (5 g, 23.1 mmol) in dioxane (25 ml) and 2M NaOH (23 ml, 46 mmol) was cooled to 0° C. Benzyl chloroformate (3.95 ml, 27 mmol) was added slowly. After stirring at room temperature for 1 h further benzyl chloroformate (1.4 ml, 9.5 mmol) was added. After 2.5 h the reaction mixture was washed with ether. The aqueous layer was acidified to pH 2 and extracted with DCM, dried (MgSO$_4$), filtered and evaporated to dryness yielding a first crop of material as a yellow solid with LCMS purity of 79%, m/z 351 [M$^+$+H]$^+$. The initial crop was used without further purification. A second crop of material was obtained following concentration of the ether layers to give further crude product. The crude material was purified by flash chromatography eluting with DCM to 20% 2M methanolic NH$_3$, 80% DCM yielding further Cbz-protected compound (yield 49%) at LCMS purity 82%, m/z 351 [M$^+$+H]$^+$.

Stage 2: 1-(Methoxy-methyl-carbamoyl)-1,3,4,9-tetrahydro-beta-carboline-2-carboxylic acid benzyl ester

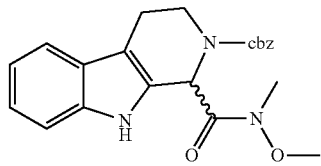

1,3,4,9-Tetrahydro-beta-carboline-1,2-dicarboxylic acid 2-benzyl ester (3 g, 8.4 mmol) was dissolved in anhydrous DCM (30 ml) and triethylamine (5.22 ml, 37.8 mmol) added. To this solution was added HOBt (2.848 g, 21.4 mmol), EDCl (4.08 g, 21.4 mmol) and N, O-dimethylhydroxylamine hydrochloride (1.86 g, 19.1 .mmol). After stirring at room temperature for 2 h the reaction mixture was evaporated to dryness, re-dissolved in EtOAc and washed with saturated NaHCO$_3$ solution (2×100 ml) and water (50 ml). The EtOAc layer was dried (Na$_2$SO$_4$), filtered and evaporated to dryness. Purification by column chromatography using DCM to 3% methanol/DCM gave the required Weinreb amide (yield 40%). LCMS purity 85%, m/z 394 [M$^+$+H]$^+$.

Stage 3: 1-Formyl-1,3,4,9-tetrahydro-beta-carboline-2-carboxylic acid benzyl ester

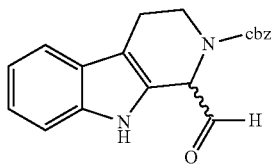

A solution of 1,3,4,9-tetrahydro-beta-carboline-1,2-dicarboxylic acid 2-benzyl ester (3.7 mg, 9.4 mmol) in THF (100 ml) under N$_2$ was cooled to −78° C. 1.5M DIBAL in toluene solution (31.2 ml, 47 mmol) was added over 2 hours. After stirring for 4 hours the reaction mixture was quenched with methanol and water, extracted into EtOAc and washed with dilute aqueous HCl. The organic layer was dried over Na$_2$SO$_4$, filtered and evaporated to dryness. LCMS purity 50%, m/z 335 [M$^+$+H]$^+$ The material was used in the next stage without further purification.

Stage 4: 1-{[((S)-Cyclopentyloxycarbonyl-phenyl-methyl)amino]-methyl}-1,3,4,9-tetrahydro-beta-carboline-2-carboxylic acid benzyl ester

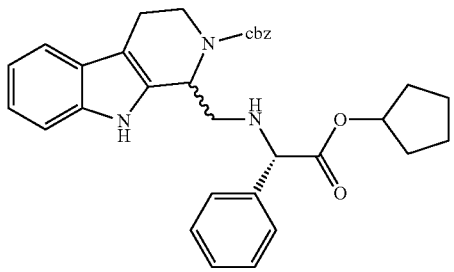

A mixture of 1-Formyl-1,3,4,9-tetrahydro-beta-carboline-2-carboxylic acid benzyl ester(1 g, 3 mmol), sodium acetate (0.68 g, 87.4 mmol), L-phenylglycine cyclopentyl ester tosyl salt (1.16 g, 3 mmol), sodium cyanoborohydride (0.26 g, 4.2 mmol) and molecular sieves in IPA (100 ml) was stirred at room temperature for 1 hour. The reaction mixture was evaporated to dryness, re-dissolved in EtOAc and washed sequentially with saturated NaHCO$_3$ solution and brine. The EtOAc layer was dried over Mg SO$_4$, filtered and evaporated to dryness. LCMS purity of 39%, m/z 538 [M$^+$+H]$^+$. The crude material was taken to the next stage without further purification.

Stage 5: 1-{[tert-Butoxycarbonyl-((S)-cyclopentyloxycarbonyl-phenyl-methyl)amino]-methyl}-1,3,4,9-tetrahydro-beta-carboline-2-carboxylic acid benzyl ester

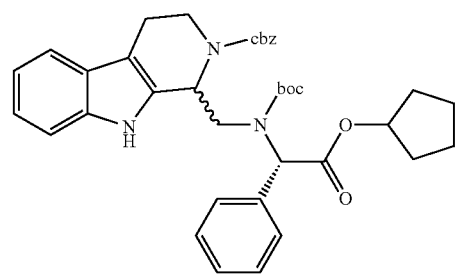

To a stirred solution of stage 4 amine (1.08 g, 2.0 mmol), in THF (20 ml) was added potassium carbonate (0.42 g, 3.0 mmol) and di-tert-butyl dicarbonate (1.75 g, 8.0 mmol). The reaction mixture was stirred at 50° C. for 96 hours and cooled to room temperature, diluted with DCM (50 ml) and washed with 0.1 M HCl solution (25 ml), saturated NaHCO$_3$ solution (2×25 ml) and water (15 ml). The DCM layer was dried, Na$_2$SO$_4$, filtered and evaporated to dryness. Purification by column chromatography using 10% EtOAc/heptane gave the product (0.89 g 70% yield). LCMS purity of 79%, m/z 638 [M$^+$+H]$^+$.

Stage 6: (S)-[tert-Butoxycarbonyl-(2,3,4,9-tetrahydro-1H-beta-carbolin-1-ylmethyl)-amino]-phenyl-acetic acid cyclopentyl ester

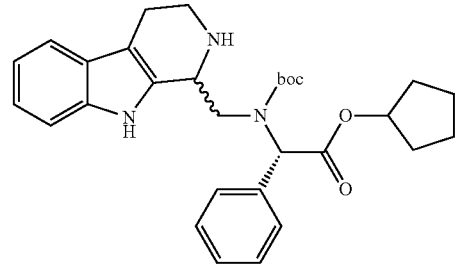

A solution of stage 5 dicarbamate (0.5 g, 0.78 mmol) in ethanol (40 ml) was stirred under the atmosphere of hydrogen in the presence of 10% Pd/C (0.4 g) for 2 h under balloon pressure. The reaction mixture was filtered through a pad of celite and evaporated to dryness yielding the required product (0.35 g, 90%), 91% purity by LCMS, m/z 504 [M⁺+H]⁺.

Stage 7: Coupling of Stage 6 Amine

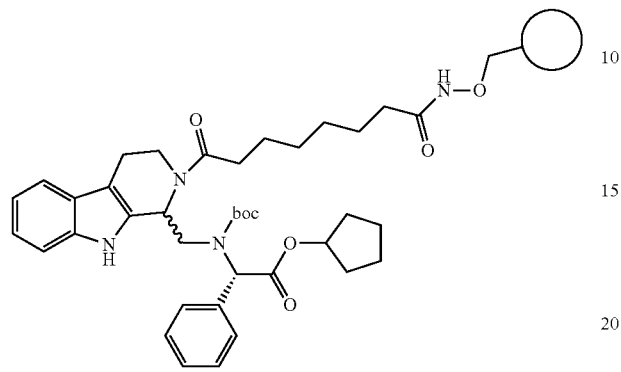

Hydroxylamine 2-chlorotrityl resin derivatized with suberic acid (703 mg, loading 0.83 mmol/g) was swollen in DCM (12 ml). PyBOP (912 mg, 1.75 mmol) was added, followed by stage 6 amine (325 mg, 0.64 mmol) and DIPEA (1.01 ml, 5.8 mmol). The reaction mixture was shaken for 18 hours. LCMS of material following test cleavage indicated 80% conversion m/z 675 [M⁺+H]⁺. The resin was filtered and washed using the standard wash procedure. The resin was dried under vacuum.

Stage 8: (S)-{[2-(7-Hydroxycarbamoyl-heptanoyl)-2,3,4,9-tetrahydro-1H-beta-carbolin-1-ylmethyl]-amino}-phenyl-acetic acid cyclopentyl ester (42)

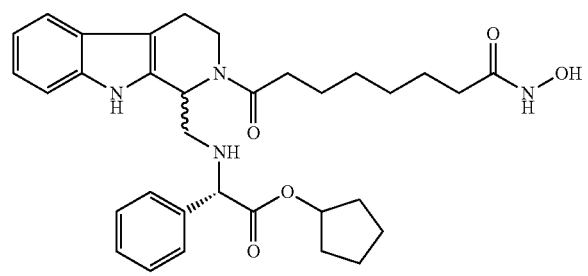 [SMILES: O=C(CCCCCCC(=O)N1CCc2c([nH]c3ccccc23)C1CN[C@H](C(=O)OC1CCCC1)c1ccccc1)NO]

Stage 7 resin (135 mg, loading 0.83 mmol) was gently shaken in 2% TFA/DCM (10 ml) for 20 mins. The resin was filtered. The filtrate was evaporated under reduced pressure at room temperature. The resin was re-treated with 2% TFA/DCM (10 ml) and was filtered after 20 mins. The combined filtrates were evaporated to dryness under reduced pressure at room temperature to give an oily residue. The residue was allowed to stand in 20% TFA/DCM for 40 mins. After evaporation to dryness, also under reduced pressure at room temperature, the crude product was purified by preparative HPLC to yield compound (42) as the TFA salt, LCMS purity 91%, m/z 575 [M⁺+H]⁺, ¹H NMR (400 MHz, MeOD), δ: 1.30-1.70 (16H, m, 8×CH₂), 2.00 (2H, m, CH₂), 2.50 (2H, m, CH₂), 2.75 (2H, m, CH₂), 3.30-3.50 (2H, m, CH₂), 4.15 (1H, m, CH₂CH), 4.80 (2H, m, CH₂NH, masked signal), 5.25 (1H, m, CHOCO), 6.00 (1H, m, OCOCHPh), 6.90 (1H, m, Ar), 7.00 (1H, m, Ar), 7.20 (1H, m, Ar), 7.30 (1H, m, Ar), 7.45 (5H, m, Ar).

Stage 9: Saponification of Cyclopentyl Ester

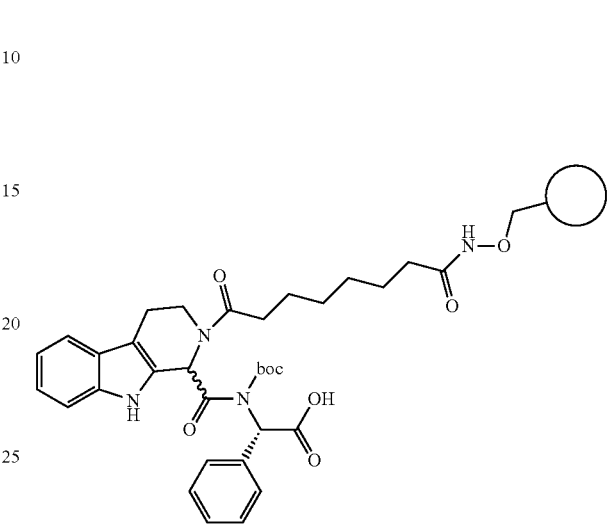

Stage 7 resin (395 mg, loading 0.83 mmol) was suspended in THF (1.5 ml) and methanol (1.5 ml) and 1.4M sodium hydroxide (aq) solution (1.17 ml, 1.6 mmol) was added. The mixture was shaken for 8 days. Test cleavage indicated 86% conversion to the acid, m/z 607 [M⁺+H]. The resin was filtered and washed with water×2, MeOH×2, followed by the standard wash procedure. The resin was dried under vacuum.

Stage 10: (S)-{[2-(7-Hydroxycarbamoyl-heptanoyl)-2,3,4,9-tetrahydro-1H-beta-carbolin-1-ylmethyl]-amino}-phenyl-acetic acid (43)

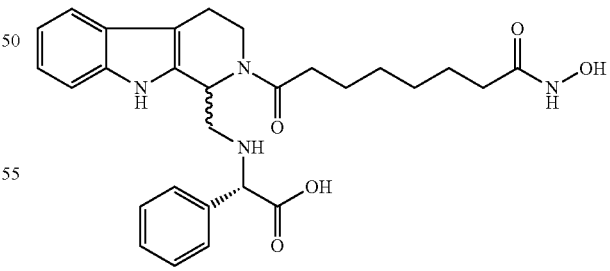

Stage 9 resin (100 mg, loading 0.83 mmol) was cleaved and boc deprotected using the procedure outlined for compound (42). Purification by preparative HPLC afforded compound (43) as the TFA salt, LCMS purity 96%, m/z 507 [M⁺+H]⁺, ¹H NMR (400 MHz, MeOD), δ: 1.25-1.40 (4H, m, 2×CH₂), 1.50-1.65 (4H, m, 2×CH₂), 2.00 (2H, m, CH₂), 2.50 (2H, m, CH₂), 2.70 (2H, m, CH₂), 3.40 (2H, m, CH₂), 4.15 (1H, m, CH₂C<u>H</u>), 4.80 (2H, m, C<u>H</u>₂NH, masked signal), 6.00 (1H, m, OCOC<u>H</u>Ph), 6.90 (1H, m, Ar), 7.00 (1H, m, Ar), 7.20 (1H, m, Ar), 7.30-7.50 (6H, m, Ar).
Synthesis of Compounds in Figure 3 as Exemplified by Compound (44) and Compound (45)
FIG. 3
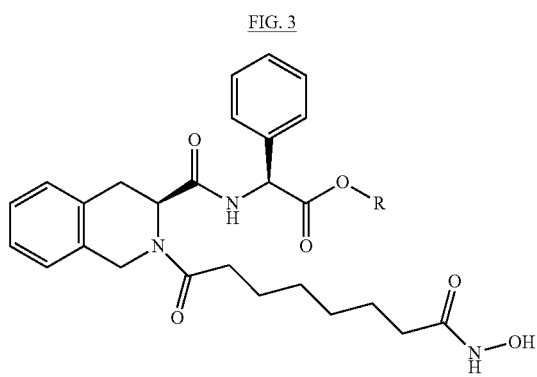
R = cyclopentyl 44
R = H 45
R = Et 46
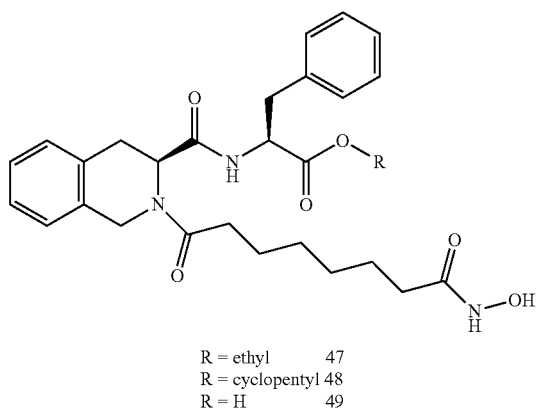
R = ethyl 47
R = cyclopentyl 48
R = H 49
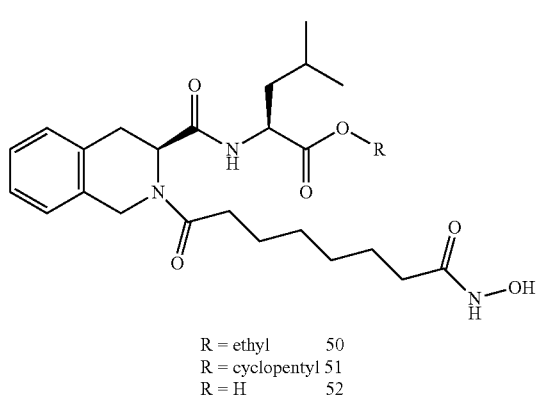
R = ethyl 50
R = cyclopentyl 51
R = H 52
-continued
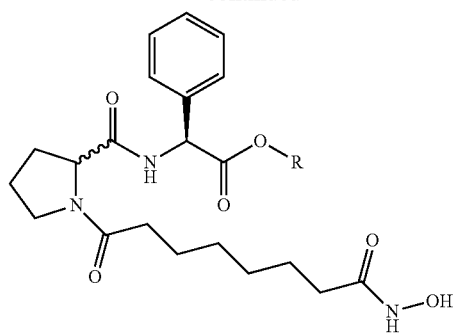
R = cyclopentyl 53
R = H 54
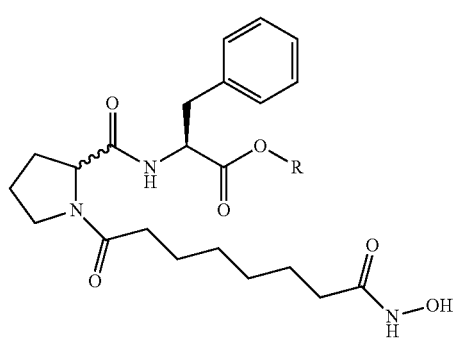
R = ethyl 55
R = cyclopentyl 56
R = H 57
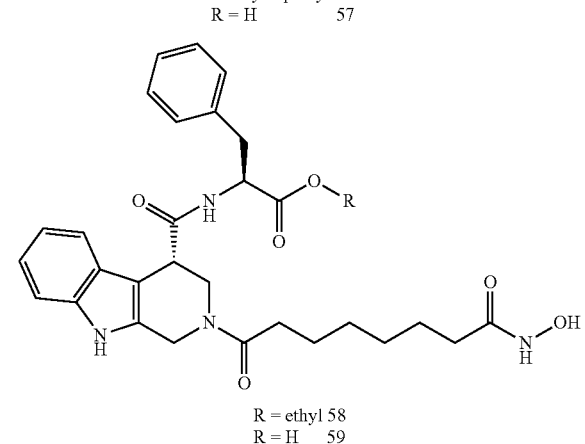
R = ethyl 58
R = H 59
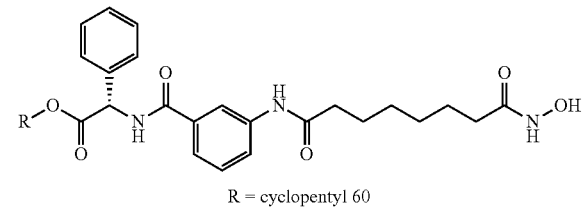
R = cyclopentyl 60
R = H 61
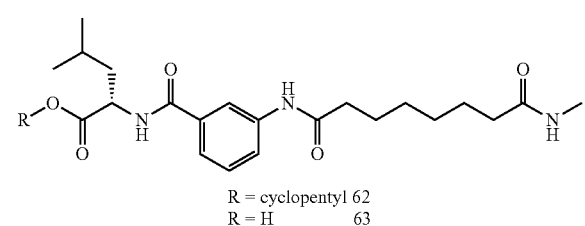
R = cyclopentyl 62
R = H 63

-continued

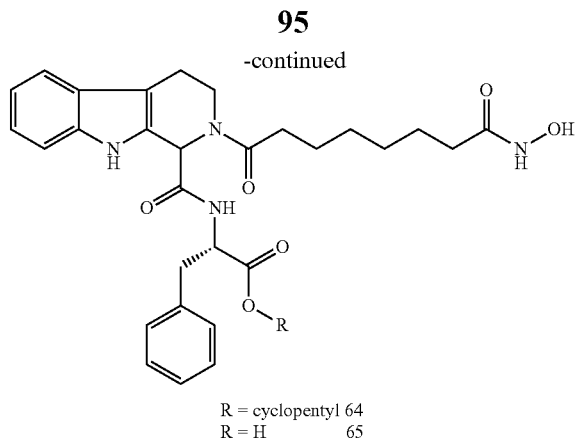

R = cyclopentyl 64
R = H 65

Preparation of Building Blocks H-L

Building Block H

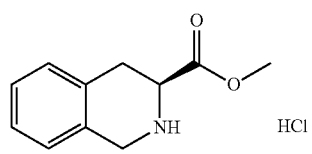

(S)-1,2,3,4-Tetrahydroisoquinoline-3-carboxylic acid (10 g, 56 mmol), TMSCl (39 ml, 310 mmol) and methanol (500 ml) were refluxed together (at 70° C.) for 2 hours. The reaction mixture was evaporated to dryness and LCMS analysis indicated 100% conversion to (S)-1,2,3,4-tetrahydro-isoquinoline-3-carboxylic acid methyl ester, m/z 192 [M$^+$+H]$^+$.

Building Block I

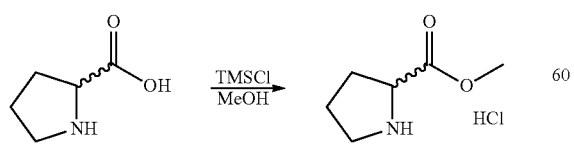

DL-Proline (10 g, 87 mmol), TMSCl (51 ml, 430 mmol) and methanol (500 ml) were refluxed together (at 70° C.) for 2 hours. The reaction mixture was evaporated to dryness and LCMS analysis indicated 100% conversion to desired product pyrrolidine-2-carboxylic acid methyl ester, m/z 130 [M$^+$+H]$^+$.

Building Block J

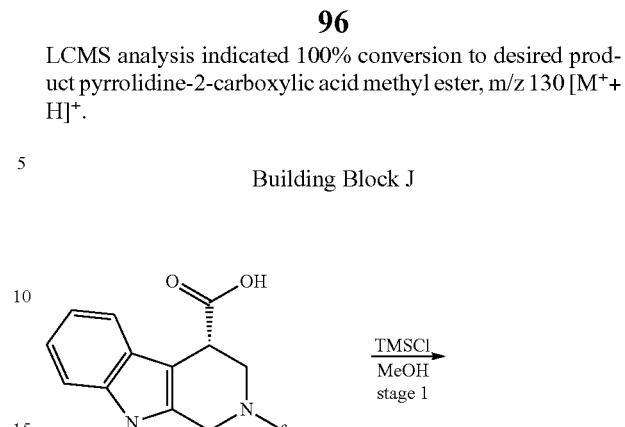

Stages 1 & 2

(R)-2-Fmoc-1,2,3,4-tetrahydronorharmane-3-carboxylic acid (2.0 g, 9.25 mmol) was added to solution of TMSCl (6 ml, 47.17 mmol) in methanol (100 ml) and heated under reflux for 2 hours. The reaction mixture was evaporated to dryness to give 1.7 g product (100% conversion by LCMS, m/z 453 [M$^+$+H]$^+$). Stage 1 ester (1.7 g) was treated with 20% piperidine in DCM (100 ml) for 30 minutes to effect fmoc removal. The crude reaction mixture was evaporated to dryness, dissolved in DCM and washed with saturated NaHCO$_3$ solution. The DCM layer was isolated, dried (Na$_2$SO$_4$), filtered and concentrated to dryness. Purification by column chromatography was carried out using 3% MeOH/DCM to give (S)-2,3,4,9-tetrahydro-1H-beta-carboline-4-carboxylic acid methyl ester. LCMS 100%, m/z 231 [M$^+$+H]$^+$.

Building Block K

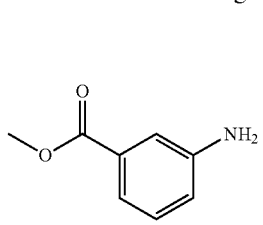

Meythl-3-aminobenzoate was obtained from commercial sources

Building Block L

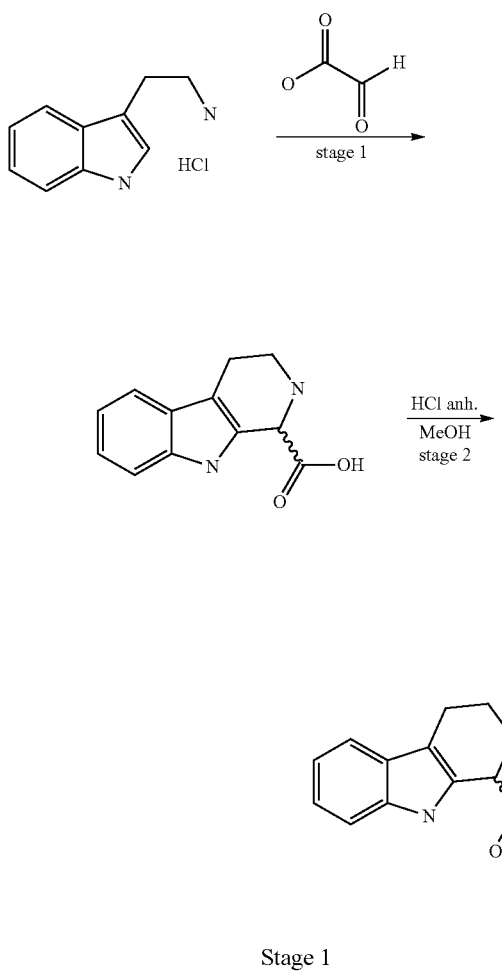

Stage 1

A solution of glyoxylic acid monohydrate (1.51 g, 16.4 mmol) in water (10 ml) was added dropwise to a stirred solution of tryptamine.HCl (3.0 g, 15.3 mmol) in water (200 ml). KOH (0.827 g, 14.7 mmol) in water (10 ml) was added. The reaction mixture was stirred at room temperature for 1 h after which time precipitation occurred. Following filtration under reduced pressure the white precipitate was collected and washed with water to furnish 2,3,4,9-tetrahydro-1H-beta-carboline-1-carboxylic acid Yield 1.9 g (58%); m/z 217 [M$^+$+H]$^+$.

Stage 2

A solution of 1,2,3,4-tetrahydro-beta-carboline-1-carboxylic acid (7.4 g) in MeOH (250 ml) was saturated with HCl gas for 20 min. The reaction mixture was gently stirred at room temperature for 18 h. The reaction mixture was re-treated with HCl gas and allowed to stir for a further 18 h. Upon completion of the reaction the mixture was concentrated in vacuo to yield building block L, LCMS purity 95%, m/z 231 [M$^+$+H]$^+$. The product (2,3,4,9-tetrahydro-1H-beta-carboline-1-carboxylic acid methyl ester) was used without further purification.

Synthesis of Compounds Outlined in Figure 3 Exemplified by Compound (44, R=Cyclopentyl) and Compound (45, R=H)

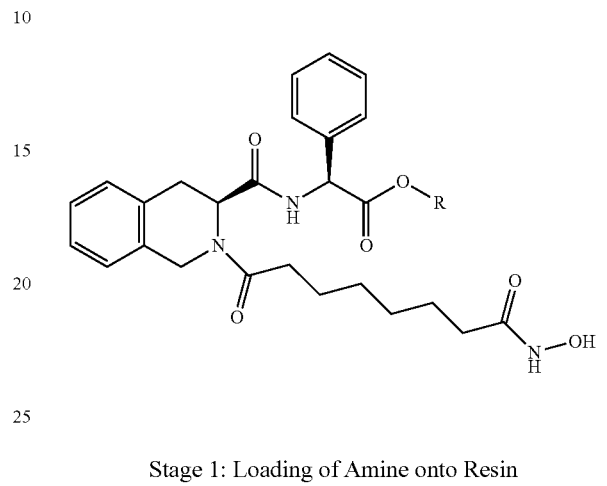

Stage 1: Loading of Amine onto Resin

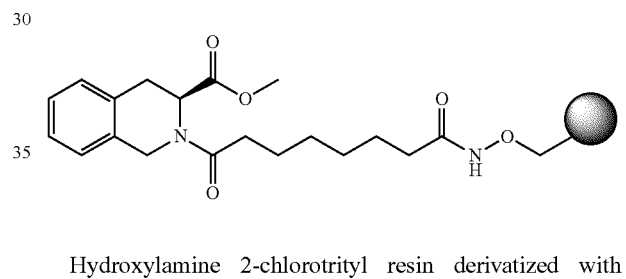

Hydroxylamine 2-chlorotrityl resin derivatized with suberic acid (6.6 g, loading, 0.83 mmol) was swollen in anhydrous DCM (65 ml). PyBOP (8.6 g, 16.43 mmol), amine building block A (3.7 g, 16.43 mmol) and DIPEA (9.5 ml, 58.4 mmol) were added. The reaction was shaken for 24 hours at room temperature. LCMS of test cleaved material indicated reaction completion. The resin was filtered and washed using the standard wash procedure. The resin was dried under vacuum.

Stage 2: Saponification of Methyl Ester

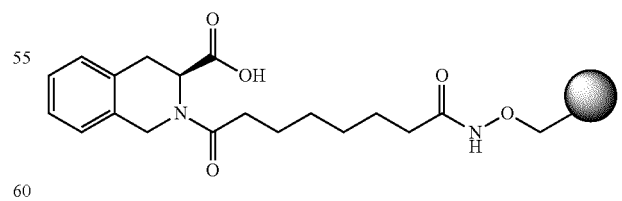

Resin bound stage 1 ester (6.95 g, loading 0.83 mmol/g) was suspended in THF (25 ml) and methanol (25 ml). Sodium hydroxide, 1.4M aqueous solution (25 ml) was added. The mixture was shaken for 48 hours and further sodium hydroxide (25 ml) added after 24 hours. LCMS of the test cleaved material indicated 65% conversion to the acid m/z 349 [M$^+$+

H]⁺. The resin was filtered and washed with water×2, MeOH×2, followed by the standard wash procedure. The resin was dried under vacuum.

Stage 3: Coupling with L-Phenylglycine Cyclopentyl Ester

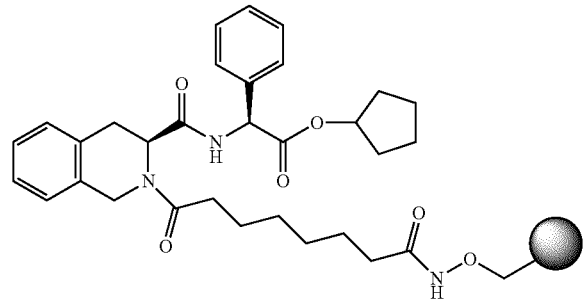

Resin bound stage 2 carboxylic acid (2.2 g, loading 0.83 mmol/g) was swollen in anhydrous DCM (25 ml). PyBOP (2.85 g, 5.48 mmol), L-phenylglycine cyclopentyl ester tosyl salt (2.14 g, 5.48 mmol) and DIPEA (3.17 ml, 18.3 mmol) were added. The mixture was shaken for 24 hours at room temperature. LCMS following test cleavage revealed 52% conversion, m/z 550 [M⁺+H]⁺. The resin was filtered and washed using standard wash procedure. The resin was dried under vacuum Stage 4: (S)-{[(S)-2-(7-Hydroxycarbamoyl-heptanoyl)-1,2,3,4-tetrahydro-isoquinoline-3-carbonyl]-amino}-phenyl-acetic acid cyclopentyl ester (44)

44

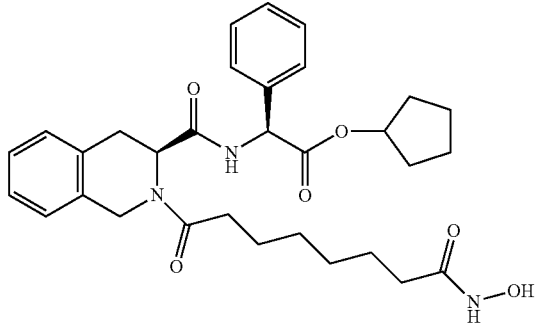

Stage 3 resin (2.2 g, loading 0.83 mmol) was gently shaken in 2% TFA/DCM (10 ml) for 20 mins. The resin was filtered. The filtrate was collected and evaporated under reduced pressure at room temperature. The resin was re-treated with 2% TFA/DCM (10 ml) and after 20 mins filtered. The combined filtrates were evaporated to dryness under reduced pressure at room temperature to give a residue. The residue was purified by preparative HPLC to yield compound (44) as the TFA salt. LCMS purity 95%, m/z 550 [M⁺+H]⁺, ¹H NMR (400 MHz, MeOD), δ: 1.12-1.75 (16H, m, 8×CH₂), 1.92-2.02 (2H, m, CH₂), 2.09-2.30 (1H, m), 2.48 (1H, m), 3.10 (2H, m, CH₂), 4.58-4.66 (2H, m, CH₂), 4.82 (1H, m), 5.04 (1H, m), 5.20 (1H, s, OCOC*H*Ph), 6.95-7.20 (9H, m, Ar).

Stage 5-Saponification of Cyclopentyl Ester

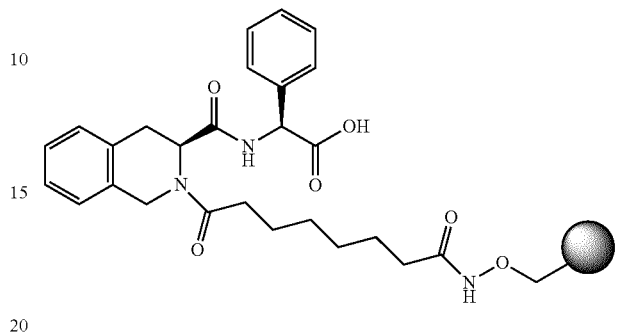

Stage 3 resin (1.3 g, 1.13 mmol) was suspended in THF (4.6 ml) and methanol (4.6 ml). Sodium hydroxide added as a 1.4M aqueous solution (4.6 ml). The mixture was shaken for 24 hours. LCMS of the test cleaved material confirmed conversion to required acid. The resin was filtered and washed with water×2, MeOH×2, followed by the standard wash procedure. The resin was dried under vacuum.

Stage 6: (S)-{[(S)-2-(7-Hydroxycarbamoyl-heptanoyl)-1,2,3,4-tetrahydro-isoquinoline-3-carbonyl]-amino}-phenyl-acetic acid (45)

45

Stage 5 resin (1.3 g, loading 0.83 mmol) was gently shaken in 2% TFA/DCM (10 ml) for 20 mins. The resin was filtered. The filtrate was collected and evaporated under reduced pressure at room temperature. The resin was re-treated with 2% TFA/DCM (10 ml) and after 20 mins filtered. The combined filtrates were evaporated to dryness under reduced pressure at room temperature to give a residue. The residue was purified by preparative HPLC to yield compound (45). LCMS purity 96%, m/z 482 [M⁺+H]⁺, ¹H NMR (400 MHz, MeOD), δ: 1.12-1.38 (4H, m, 2×CH₂), 1.45-1.61 (4H, m, CH₂), 1.98 (2H, m, CH₂), 2.10-2.58 (2H, m, CH₂), 3.04-3.20 (2H, m, CH₂), 4.48-4.65 (2H, m), 4.85 (1H, m), 5.20 (1H, m), 6.92-7.25 (9H, m, Ar).

The following compounds were prepared according to the procedure described for compounds (44) and compound (45)

(S)-{[(S)-2-(7-Hydroxycarbamoyl-heptanoyl)-1,2,3, 4-tetrahydro-isoquino line-3-carbonyl]-amino}-phenyl-acetic acid ethyl ester (46)

Building Block H Used

LCMS purity 97%, m/z 510 [M⁺+H]⁺, ¹H NMR (400 MHz, MeOD), δ: 1.19 (3H, t, CH₃), 1.32-1.48 (4H, m, 2×CH₂), 1.54-1.73 (4H, m, 2×CH₂), 2.02-2.15 (2H, m, CH₂), 2.50-2.70 (2H, m, CH₂), 3.10-3.30 (2H, m, CH₂), 4.10 (2H, m, CH₂), 4.70 (2H, m), 4.95 (1H, m), 5.35 (1H, s, OCOCHPh), 7.10-7.40 (9H, m, Ar).

(S)-2-{[(S)-2-(7-Hydroxycarbamoyl-heptanoyl)-1,2, 3,4-tetrahydro-isoquinoline-3-carbonyl]-amino}-3-phenyl-propionic acid ethyl ester (47)

Building Block H Used

LCMS purity 100%, m/z 524 [M⁺+H]⁺, ¹H NMR (400 MHz, MeOD), δ: 1.20 (3H, m, CH₃), 1.30-1.49 (4H, m, 2×CH₂), 1.55-1.70 (4H, m, CH₂), 2.10 (2H, m, CH₂), 2.60 (2H, m), 2.88-3.25 (4H, m), 4.08-4.20 (2H, m, CH₂), 4.45-4.62 (2H, m), 4.75 (1H, m), 5.03 (1H, m), 7.09-7.32 (9H, m, Ar).

(S)-2-{[(S)-2-(7-Hydroxycarbamoyl-heptanoyl)-1,2, 3,4-tetrahydro-isoquinoline-3-carbonyl]-amino}-3-phenyl-propionic acid (48)

Building Block H Used

LCMS purity 100%, m/z 564 [M⁺+H]⁺, ¹H NMR (400 MHz, MeOD), δ: 1.25-1.85 (16H, m, 8×CH₂), 2.10 (2H, m, CH₂), 2.55 (2H, t, CH₂), 2.85-3.20 (4H, m), 4.40-4.60 (2H, m), 4.75 (1H, m), 4.95-5.15 (2H, m), 7.05-7.30 (9H, m, Ar).

(S)-2-{[(S)-2-(7-Hydroxycarbamoyl-heptanoyl)-1,2, 3,4-tetrahydro-isoquinoline-3-carbonyl]amino}-3-phenyl-propionic acid (49)

Building Block H Used

LCMS purity 100%, m/z 496 [M⁺+H]⁺, ¹H NMR (400 MHz, MeOD), δ: 1.10-1.31 (4H, m, 2×CH₂), 1.40-1.55 (4H, m, 2×CH₂), 1.98 (2H, m, CH₂), 2.43 (2H, m, CH₂), 2.75-3.10 (4H, m), 4.30-4.75 (3H, m), 4.90 (1H, m), 6.90-7.15 (9H, m, Ar).

(S)-2-{[(S)-2-(7-Hydroxycarbamoyl-heptanoyl)-1,2, 3,4-tetrahydro-isoquinoline-3-carbonyl]-amino}-4-methyl-pentanoic acid ethyl ester (50)

Building Block H Used

LCMS purity 98%, m/z 490 [M⁺+H]⁺, ¹H NMR (400 MHz, MeOD), δ: 0.60 (1H, m, CH), 0.70-0.85 (6H, m, 2×CH₃), 1.25 (3H, t, CH₂CH₃), 1.38-1.65 (10H, m, 5×CH₂), 2.10 (2H, m, CH₂), 2.60 (2H, m, CH₂), 3.20 (2H, m, CH₂), 4.10 (2H, q, CH CH₃), 4.35 (1H, m, CH), 4.70-4.80 (2H, m, CH₂), 4.95 (1H, m, CH), 7.23-7.25 (4H, m, Ar).

(S)-2-{[(S)-2-(7-Hydroxycarbamoyl-heptanoyl)-1,2, 3,4-tetrahydro-isoquinoline-3-carbonyl]-amino}-4-methyl-pentanoic acid cyclopentyl ester (51)

Building Block H Used

LCMS purity 96%, m/z 530 [M⁺+H]⁺, ¹H NMR (400 MHz, MeOD), δ: 0.75 (3H, d, CH₃), 0.88 (3H, d, CH₃), 1.30-1.90 (19H, m), 2.10 (2H, t, CH₂), 2.60 (2H, m, CH₂), 3.15-3.30 (2H, m, CH₂), 4.30 (1H, m), 4.65-4.85 (2H, m), 4.95 (1H, m), 5.10 (1H, m), 7.15-7.28 (4H, m, Ar).

(S)-2-{[(S)-2-(7-Hydroxycarbamoyl-heptanoyl)-1,2, 3,4-tetrahydro-isoquinoline-3-carbonyl]-amino}-4-methyl-pentanoic acid ethyl ester (52)

Building Block H Used

LCMS purity 100%, m/z 462 [M⁺+H]⁺, ¹H NMR (400 MHz, MeOD), δ: 0.60 (1H, m, CH), 0.70-0.85 (6H, m, 2×CH₃), 1.38-1.65 (10H, m, 5×CH₂), 2.10 (2H, m, CH₂), 2.40-2.60 (2H, m, CH₂), 3.20 (2H, m, CH₂), 4.35 (1H, m, CH), 4.70-4.80 (2H, m, CH₂), 4.95 (1H, m, CH, masked signal), 7.23-7.25 (4H, m, Ar).

(S)-{[1-(7-Hydroxycarbamoyl-heptanoyl)-pyrrolidine-2-carbonyl]-amino}-phenyl-acetic acid cyclopentyl ester (53)

Building Block I Used

LCMS purity 100%, m/z 488 [M⁺+H]⁺, ¹H NMR (400 MHz, MeOD), δ: 1.30-2.45 (24H, m), 3.50-3.70 (2H, m, CH₂), 4.55 (1H, m, CH), 5.18 (1H, m, CH), 5.40 (1H, m, CH), 7.40 (5H, m, Ar).

(S)-{[1-(7-Hydroxycarbamoyl-heptanoyl)-pyrrolidine-2-carbonyl]-amino}-phenyl-acetic acid (54)

Building Block I Used

LCMS purity 90%, m/z 420 [M⁺+H]⁺, ¹H NMR (400 MHz, MeOD), δ: 1.20-1.20 (4H, m, 2×CH₂), 1.45-1.56 (4H, m, CH₂), 1.75-2.35 (8H, m), 3.35-3.60 (2H, m), 4.45 (1H, m), 5.35 (1H, m), 7.18-7.35 (5H, m, Ar).

(S)-2-{[1-(7-Hydroxycarbamoyl-heptanoyl)-pyrrolidine-2-carbonyl]-amino}-3-phenyl-propionic acid ethyl ester (55)

Building Block I Used

LCMS purity 100%, m/z 462 [M⁺+H]⁺, ¹H NMR (400 MHz, MeOD), δ: 1.20-2.20 (19H, m), 2.94-3.20 (2H, m, CH₂Ph), 3.48-3.69 (2H, m, CH₂N), 4.10-4.25 (2H, m, CH₂CH₃), 4.33-4.49 (1H, m), 4.60-4.79 (1H, m), 7.20-7.35 (5H, m, Ar).

(S)-2-{[1-(7-Hydroxycarbamoyl-heptanoyl)-pyrrolidine-2-carbonyl]-amino}-3-phenyl-propionic acid cyclopentyl ester (56)

Building Block I Used

LCMS purity 100%, m/z 502 [M⁺+H]⁺, ¹H NMR (400 MHz, MeOD), δ: 1.27-2.23 (22H, m, 11×CH₂), 2.35 (2H, m, CH₂), 2.97-3.27 (2H, m, CH₂Ph), 3.53-3.63 (2H, m, CH₂), 4.35-4.45 (1H, m, CH), 4.60-4.70 (1H, m, CHCH₂Ph), 5.10-5.20 (1H, m, CHOCO), 7.23-7.30 (5H, m, Ar).

(S)-2-{[1-(7-Hydroxycarbamoyl-heptanoyl)-pyrrolidine-2-carbonyl]-amino}-3-phenyl-propionic acid (57)

Building Block I Used

LCMS purity 90%, m/z 434 [M⁺+H]⁺, ¹H NMR (400 MHz, MeOD), δ: 1.30-1.41 (4H, m, 2×CH₂), 1.55-1.69 (4H, m, 2×CH$_2$), 1.80-1.90 (8H, m), 2.91-3.26 (2H, m), 3.45-3.70 (2H, m), 4.40 (1H, m), 4.72 (1H, m), 7.16-7.30 (5H, m, Ar).

(S)-2-{[(S)-2-(7-Hydroxycarbamoyl-heptanoyl)-2,3,4,9-tetrahydro-1H-beta-carboline-4-carbonyl]-amino}-3-phenyl-propionic acid cyclopentyl ester (58)

Building Block J Used

LCMS purity of 100%, m/z 563 [M$^+$+H]$^+$, $^1$H NMR (400 MHz MeOD), δ: 1.10-1.30 (3H, m, CH$_3$), 1.35-1.80 (8H, m, 4×CH$_2$), 2.15 (2H, m, CH$_2$), 2.4-2.65 (2H, m, CH$_2$), 2.95-3.20 (3H, m), 4.0-4.2 (2H, m CH$_2$O), 4.3-5.0 (4H, m masked signal), 5.05-5.20 (1H, m CHOCO), 6.90-7.50 (9H, m, Ar).

(S)-2-{[(S)-2-(7-Hydroxycarbamoyl-heptanoyl)-2,3,4,9-tetrahydro-1H-bet α-carboline-4-carbonyl]-amino}-3-phenyl-propionic acid (59)

Building Block J Used

LCMS purity of 100%, m/z 535 [M$^+$+H]$^+$, $^1$H NMR (400 MHz MeOD), δ: 1.20-1.40 (4H, m, 2×CH$_2$), 1.45-1.65 (4H, m, 2×CH$_2$), 1.90-2.10 (2H, m, CH$_2$), 2.30-2.50 (2H, m, CH$_2$), 2.70-3.15 (3H, m), 4.2-4.9 (4H, m masked signal), 5.00 (1H, m CHOCO), 6.75-7.40 (9H, m, Ar)

(S)-[3-(7-Hydroxycarbamoyl-heptanoylamino)-benzoylamino]-phenyl-acetic acid cyclopentyl ester (60)

Building Block K Used

LCMS purity 100%, m/z 510 [M$^+$+H]$^+$, $^1$H NMR (400 MHz, MeOD), δ: 1.28 (4H, m, 2×CH$_2$), 1.40-1.80 (12H, m, 6×CH$_2$), 1.98 (2H, t, CH$_2$), 2.27 (2H, t, CH$_2$), 5.12 (1H, m), 5.50 (1H, s, OCOCHPh), 7.21-7.32 (4H, m, Ar), 7.36 (2H, m, Ar), 7.45 (1H, d, Ar), 7.61 (1H, d, Ar), 7.90 (1H, s, Ar).

(S)-[3-(7-Hydroxycarbamoyl-heptanoylamino)-benzoylamino]phenyl-acetic acid (61)

Building Block K Used

LCMS purity 100%, m/z 442[M$^+$+H]$^+$, $^1$H NMR (400 MHz, MeOD), δ: 1.21-1.34 (4H, m, 2×CH$_2$), 1.48-1.63 (4H, m, 2×CH$_2$), 1.98 (2H, t, CH$_2$), 2.26 (2H, t, CH$_2$), 5.55 (1H, s, OCOCHPh), 7.20-7.32 (4H, m, Ar), 7.40 (2H, d, Ar), 7.48 (1H, d, Ar), 7.64 (1H, d, Ar), 7.89 (1H, s, Ar).

(S)-2-[3-(7-Hydroxycarbamoyl-heptanoylamino)-benzoylamino]-4-methyl-pentanoic acid cyclopentyl ester (62)

Building Block K Used

LCMS purity 93%, m/z 490 [M$^+$+H]$^+$, $^1$H NMR (400 MHz, MeOD), δ: 0.84 (3H, d, CH(CH$_3$)), 0.88 (3H, d, CH(CH$_3$)), 1.20-1.40 (4H, m, 2×CH$_2$), 1.40-1.85 (15H, m, 6×CH$_2$, CH(CH$_3$)$_2$, CH$_2$CH(CH$_3$)$_2$), 2.00 (2H, t, CH$_2$), 2.25 (2H, t, CH$_2$), 4.45 (1H, m, OCOCHCH$_2$), 5.10 (1H, m, CHOCO), 7.25 (1H, m Ar), 7.40 (1H, d, Ar), 7.60 (1H, d, Ar), 7.90 (1H, s, Ar).

(S)-2-[3-(7-Hydroxycarbamoyl-heptanoylamino)-benzoylamino]-4-methyl-pentanoic acid (63)

Building Block K Used

LCMS purity 97%, m/z 422 [M$^+$+H]$^+$, $^1$H NMR (400 MHz, MeOD), δ: 1.03 (3H, d, CH(CH$_3$)), 1.06 (3H, d, CH(CH$_3$)), 1.40-1.55 (4H, m, 2×CH$_2$), 1.65-1.95 (7H, m, 2×CH$_2$, CH(CH$_3$)$_2$, CH$_2$CH(CH$_3$)$_2$), 2.15 (2H, t, CH$_2$), 2.45 (2H, t, CH$_2$), 4.70 (1H, m, OCOCHCH$_2$), 7.45 (1H, m, Ar), 7.60 (1H, d, Ar), 7.80 (1H, d, Ar), 8.05 (1H, s, Ar).

(S)-2-{[2-(7-Hydroxycarbamoyl-heptanoyl)-2,3,4,9-tetrahydro-1H-beta-carboline-1-carbonyl]-amino}-3-phenyl-propionic acid cyclopentyl ester (64)

Building Block L Used

LCMS purity 100%, m/z 603 [M$^+$+H]$^+$, $^1$H NMR (400 MHz, MeOD), δ: 1.18-1.71 (16H, m, 8×CH$_2$), 2.00 (2H, t, CH$_2$), 2.45 (2H, m), 2.70 (2H, m), 2.90-3.11 (2H, m), 3.40 (1H, m), 4.10 (1H, m), 4.50 (1H, m), 5.00 (1H, m), 5.95 (1H, m), 6.90-7.11 (7H, m, Ar), 7.25 (1H, d, Ar), 7.34 (1H, d, Ar).

(S)-2-{[2-(7-Hydroxycarbamoyl-heptanoyl)-2,3,4,9-tetrahydro-1H-beta-carboline-1-carbonyl]-amino}-3-phenyl-propionic acid (65)

Building Block L Used

LCMS purity 91%, m/z 535 [M$^+$+H]$^+$, $^1$H NMR (400 MHz, MeOD δ: 1.15-1.32 (4H, m, 2×CH$_2$), 1.40-1.60 (4H, m, 2×CH$_2$), 1.98 (2H, t, CH$_2$), 2.41 (2H, m), 2.69 (2H, m), 2.90-3.11 (2H, m), 3.30 (1H, m), 4.06 (1H, m), 4.60 (1H, m), 5.92 (1H, m), 6.84 (7H, m, Ar), 7.20 (1H, d, Ar), 7.31 (1H, d, Ar).

Synthesis of Compound (66) and Compound (67)

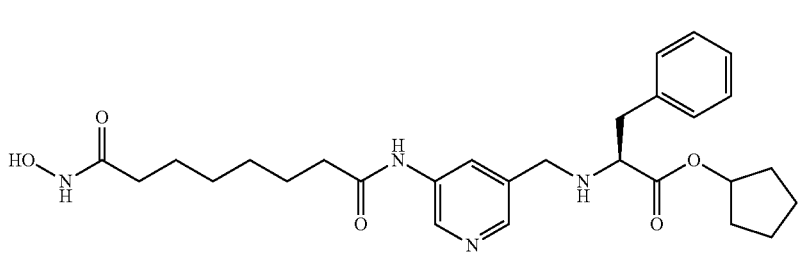

66

67

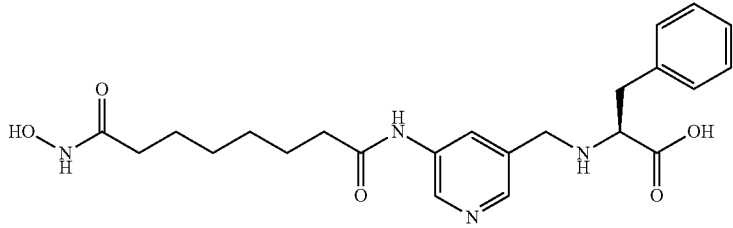

Stage 1: 5-Amino-nicotinic acid methyl ester

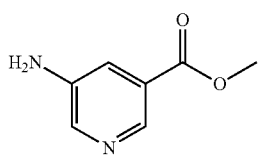

5-Aminonicotinic acid (1 g, 7.2 mmmol) was suspended in methanol (100 ml) and thionyl chloride (4.22 ml, 57.9 mmol) added dropwise at 0° C. The reaction mixture was stirred at room temperature for 18 h. The reaction mixture was evaporated to dryness and the resultant yellow oil was re-dissolved in methanol/ether (1:1) and afforded yellow crystals (HCl salt) which were collected by filtration, yield 1.2 g (85%). LCMS purity 91%, m/z 153 [M$^+$+H]$^+$,

Stage 2: (5-Amino-pyridin-3-yl)-methanol

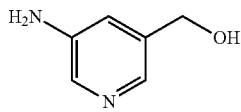

5-Amino-nicotinic acid methyl ester (5.7 g, 30.2 mmol) was dissolved in THF (150 ml) and LiAlH$_4$ (1M in THF solution 133 ml, 133 mmol) added slowly at 0° C. The reaction mixture was stirred at room temperature for 21 h. The reaction mixture was quenched and acidified to pH 3 using dilute HCl, and basified (pH 8) using solid Na$_2$CO$_3$. Solvents were removed under reduced pressure. The residue was filtered through silica gel using 20% MeOH/DCM yielding the product 3.8 g, (100%) with LCMS purity 97%, m/z 125 [M$^+$+H]$^+$, by ELS.

Stage 3: Coupling of Stage 2 Acid onto Resin

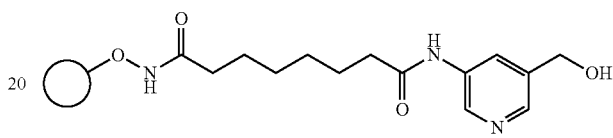

Hydroxylamine-2-chlorotrityl resin derivatized with suberic acid (0.49 g, 0.86 mmol/g, 0.42 mmol) was swollen in anhydrous DCM (6 ml) and PyBOP (0.67 g, 1.3 mmol) added. Stage 2 aniline (0.16 g, 1.3 mmol) was added in DMF (6 ml) followed by DIPEA (0.75 ml, 4.2 mmol). LCMS following test cleavage indicated 27% conversion, m/z 296 [M$^+$+H]$^+$. The resin was filtered and washed using the standard wash procedure. The resin was dried under vacuum.

Stage 4: Mesylation

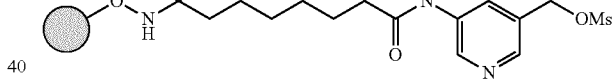

Resin bound stage 3 alcohol (1.8 g, 1.57 mmol) was swollen in anhydrous DCM (30 ml) and DIPEA (1.62 ml, 9.42 mmol) was added at 0° C. followed by mesyl chloride (0.23 ml, 3.14 mmol). The reaction mixture was shaken at 0° C. for 30 minutes. LCMS following test cleavage indicated 21% conversion, m/z 374 [M$^+$+H]$^+$ and 9% by-product derived from chloride displacement of mesylate m/z 314 [M$^+$+H]$^+$. The resin was filtered and washed using the standard wash procedure. The resin was dried under vacuum.

Stage 5: Displacement of Mesylate with L-Phenylalanine Ethyl Ester

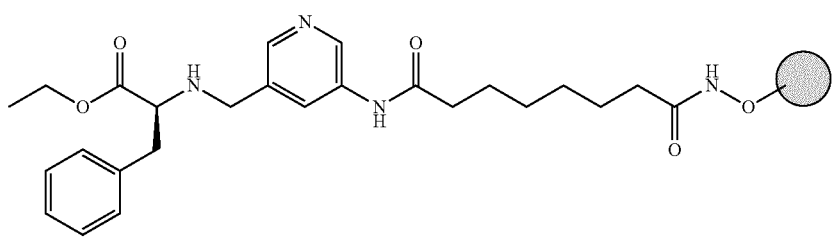

Resin bound stage 4 product (0.5 g, 0.43 mmol) was swollen in anhydrous DMF (4 ml) and sodium iodide (0.05 g, 10% w/v) added. L-Phenylalanine ethyl ester hydrochloride salt (0.3 g, 1.29 mmol) in anhydrous DMF (4 ml) was added followed by DIPEA (0.75 ml, 4.3 mmol). After shaking for 3 hours LCMS of test cleaved material indicated 35% conversion, m/z 471[M$^+$+H]$^+$. The resin was filtered and washed using the standard wash procedure. The resin was dried under vacuum.

Stage 6: (S)-2-{[5-(7-Hydroxycarbamoyl-heptanoylamino)-pyridin-3-ylmethyl]-amino}-3-phenyl-propionic acid ethyl ester (66)

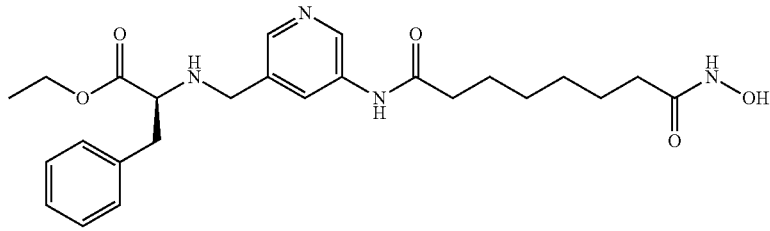

66

Stage 5 resin (2 g, loading 0.87 mmol) was gently shaken in 2% TFA/DCM (20 ml) for 20 mins. The resin was filtered. The filtrate was collected and evaporated under reduced pressure at room temperature. The resin was re-treated with 2% TFA/DCM (20 ml) and filtered after 10 mins. The combined filtrates were evaporated to dryness under reduced pressure at room temperature to give a crude product. The crude was purified by preparative HPLC to yield compound (66) as the TFA salt. LCMS purity 100%, m/z 471 [M$^+$+H]$^+$, $^1$H NMR (400 MHz, MeOD), δ: 1.10 (3H, t, CO$_2$CH$_2$C$\underline{H}_3$), 1.31-1.50 (4H, m, 2×CH$_2$), 1.58-1.80 (4H, m, 2×CH$_2$), 2.05-2.15 (1H, m, CH), 2.24-2.38 (1H, m, CH), 2.45 (2H, t, CH$_2$), 3.10-3.20 (1H, m, CH), 3.38-3.49 (1H, m, CH), 4.12 (2H, q, CH$_2$), 4.35 (3H, m, CH$_2$, CH) 7.20-7.40 (5H, m, Ar), 8.30-9.00 (3H, m, Ar).

Stage 7: (S)-2-{[5-(7-Hydroxycarbamoyl-heptanoylamino)-pyridin-3-ylmethyl]-amino}-3-phenyl-propionic acid (67)

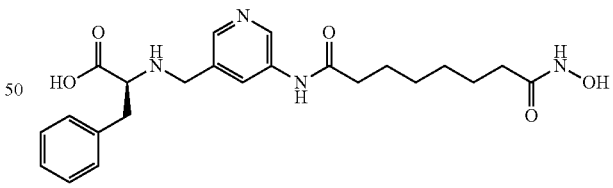

67

To a solution of Stage 6 product (30 mg, loading 1.8 mmol/g) in THF (1 ml) was added 1.4M sodium hydroxide (1 ml). The reaction mixture was stirred for 30 minutes. LCMS showed 75% conversion, m/z 442[M$^+$+H]$^+$. The reaction mixture was evaporated to dryness and was purified by preparative HPLC to yield the desired compound as the TFA salt, compound (67). LCMS purity 100%, m/z 443 [M$^+$+H]$^+$. $^1$H NMR (400 MHz, MeOD), δ: 1.30 (4H, m, 2×CH$_2$), 1.50-1.70 (4H, m, 2×CH$_2$), 2.00 (2H, t, CH$_2$), 2.30 (2H, t, CH$_2$), 3.20 (2H, m, C$\underline{H}_2$Ph, masked signal), 4.20 (3H, m), 7.20 (5H, m, Ar), 8.30 (1H, br s, Ar), 8.40 (1H, s, Ar), 8.65 (1H, br s, Ar).

Synthesis of Compound (68)

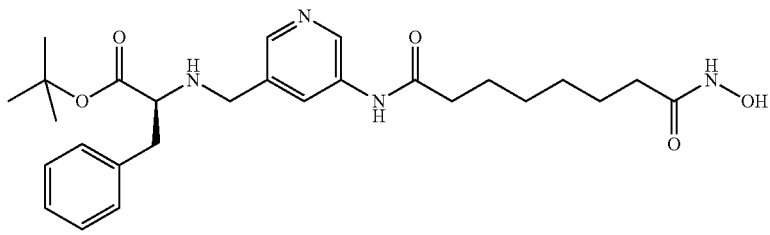

(S)-2-{[5-(7-Hydroxycarbamoyl-heptanoylamino)-pyridin-3-ylmethyl]-amino}-3-phenyl-propionic acid tert-butyl ester (68) (was prepared using the procedure outlined for the preparation of compound (66): LCMS purity 100%, m/z 499 [M$^+$+H]$^+$, $^1$H NMR (400 MHz, MeOD), δ: 1.20 (9H, s, C(CH$_3$)$_3$), 1.25-1.35 (4H, m, 2×CH$_2$), 1.49-1.65 (4H, m, 2×CH$_2$), 2.00 (2H, t, CH$_2$), 2.35 (3H, t, CH$_2$), 3.00 (1H, m), 3.32 (1H, m), 4.15-4.30 (3H, m), 7.15-7.30 (5H, m, Ar), 8.30 (1H, br s, Ar), 8.45 (1H, s, Ar), 8.65 (1H, br s, Ar).

Synthesis of Compound (69) and Compound (70)

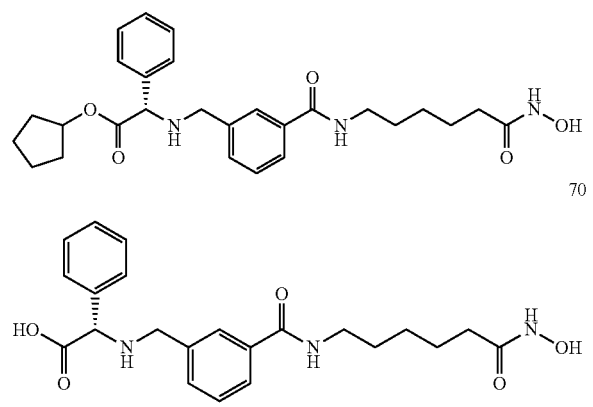

Stage 1: Loading of Fmoc Amino Caproic Acid onto Resin

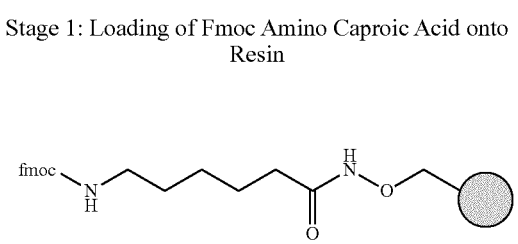

To a mixture of hydroxylamine 2-chlorotrityl resin (2.5 g, loading 0.94 mmol/g) in anhydrous DCM (10 ml) was added a solution of 1,3-diisopropylcarbodiimide (1.1 ml, 7.05 mmol) and 6-(Fmoc-amino) caproic acid (2.5 g, 7.05 mmol) in anhydrous DCM (10 ml). DMF (5 ml) was added and the reaction shaken at room temperature for 1 h. Test cleavage revealed 96% conversion to required product. The resin was filtered and washed using the standard wash procedure. The resin was dried under vacuum.

Stage 2: Fmoc Deprotection

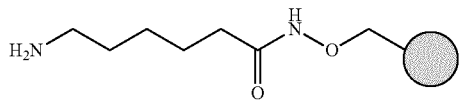

Stage 1 Fmoc protected amine resin (2.0 g, loading 0.94 mmol/g) was dissolved in a solution of 20% piperidine in DMF (25 ml, excess) and shaken at room temperature for 30 minutes. A test cleavage indicated complete conversion by LCMS, 100% (ELS detection). The resin was filtered, washed using the standard wash procedure and dried under vacuum.

Stage 3: Coupling Reaction

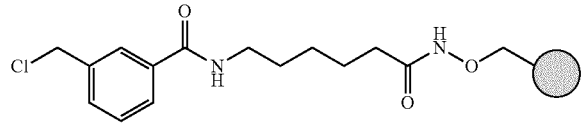

To resin bound stage 2 amine (2.0 g, loading 0.94 mmol/g) in anhydrous DCM (10 ml) and DMF (10 ml) was added DIC (0.71 ml, 5.64 mmol) and 3-(chloromethyl)benzoic acid (0.96 g, 5.64 mmol). The mixture was shaken for 1 hour before test cleavage revealed 49% conversion by LCMS, m/z 219 [M$^+$+H]$^+$. The resin was filtered and washed using the standard wash procedure. The resin was dried under vacuum.

Stage 4: Chloride Displacement with L-Phenylglycine Cyclopentyl Ester

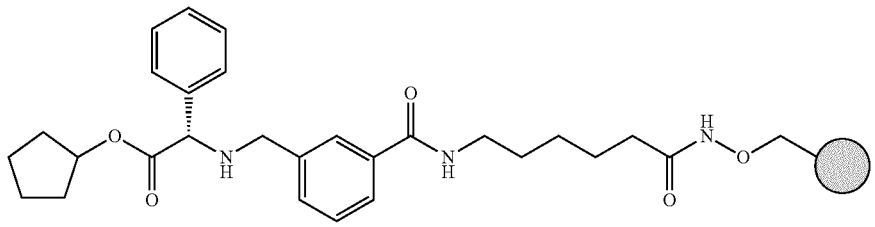

To resin bound stage 3 chloride (0.5 g, 0.47 mmol) in anhydrous DMF (5 ml) was added L-phenylglycine cyclopentyl ester tosyl salt (0.57 g, 1.41 mmol), DIPEA (0.24 ml, 1.41 mmol) and a catalytic amount of sodium iodide. The reaction mixture was heated at 60° C. for 1 hour. LCMS following test cleavage revealed 45% conversion, m/z 482 $[M^++H]^+$. The resin was filtered and washed using the standard wash procedure. The resin was dried under vacuum.

Stage 5: (S)-[3-(5-Hydroxycarbamoyl-pentylcarbamoyl)-benzylamino]-phenyl-acetic acid cyclopentyl ester (69)

69

Stage 4 resin (1.0 g, loading 0.94 mmol/g) was gently shaken in 2% TFA/DCM (10 ml) for 20 mins. The resin was filtered. The filtrate was collected and evaporated under reduced pressure at room temperature. The resin was re-treated with 2% TFA/DCM (10 ml) and after 20 mins filtered. The combined filtrates were evaporated to dryness under reduced pressure at room temperature to give a residue. The residue was purified by preparative HPLC to yield compound (69). LCMS purity 89%, m/z 482 $[M^++H]^+$, $^1$H NMR (400 MHz, MeOD), δ: 1.24-1.82 (14H, m, 7×$CH_2$), 2.03 (2H, t, $CH_2$), 3.30 (2H, t, $CH_2$), 4.08 (1H, d, CH$\underline{H}$Ph), 2.20 (1H, d, C$\underline{H}$HPh), 5.09 (1H, s, OCOC$\underline{H}$Ph), 5.18 (1H, m, C$\underline{H}$OCO), 7.39-7.54 (7H, m, Ar), 7.77 (2H, m, Ar).

Stage 6: Saponification of Cyclopentyl Ester

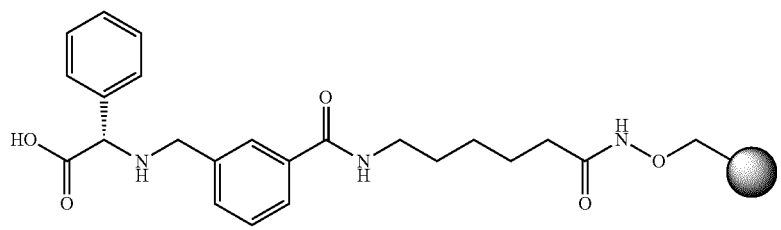 [SMILES: CCONC(=O)CCCCCNC(=O)c1cccc(CN[C@H](C(=O)O)c2ccccc2)c1]

Stage 4 resin (1.35 g, loading 0.94 mmol/g) was suspended in THF (4.7 ml) and methanol (4.7 ml). 1.4M sodium hydroxide was added (9.4 ml, 12.66 mmol). The mixture was shaken for 48 h. LCMS of the test cleave showed 49% conversion to the acid, m/z 414 [M$^+$+H]$^+$. The resin was filtered and washed with water×2, MeOH×2, followed by the standard wash procedure. The resin was dried under vacuum Stage 7: (S)-[3-(5-Hydroxycarbamoyl-pentylcarbamoyl)-benzylamino]-phenyl-acetic acid (70)

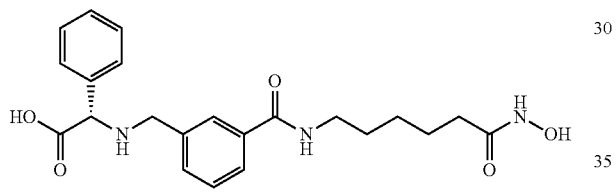

70

Stage 6 resin (1.35 g, loading 0.94 mmol/g) was gently shaken in 2% TFA/DCM (10 ml) for 20 mins. The resin was filtered. The filtrate was collected and evaporated under reduced pressure at room temperature. The resin was re-treated with 2% TFA/DCM (10 ml) and after 20 mins filtered. The combined filtrates were evaporated to dryness under reduced pressure at room temperature to give a residue. The residue was purified by preparative HPLC to yield compound (70). LCMS purity 100%, m/z 414 [M$^+$+H]$^+$, $^1$H NMR (400 MHz, MeOD), δ: 1.30 (2H, m, CH$_2$), 1.57 (4H, m, 2×CH$_2$), 2.20 (2H, t, CH$_2$), 3.30 (2H, t, CH$_2$), 4.05 (1H, d, CHHPh), 4.18 (1H, d, CHHPh), 4.90 (1H, s, OCOC HPh), 7.35-7.52 (7H, m, Ar), 7.78 (2H, m, Ar).

Synthesis of Compounds in Figure 4 Exemplified by Compound (71) and Compound (72)

FIG. 4

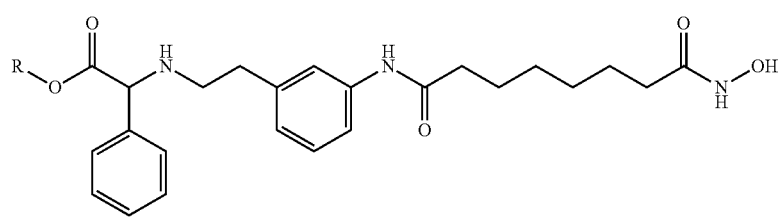

R = cyclopentyl 71
R = H        72

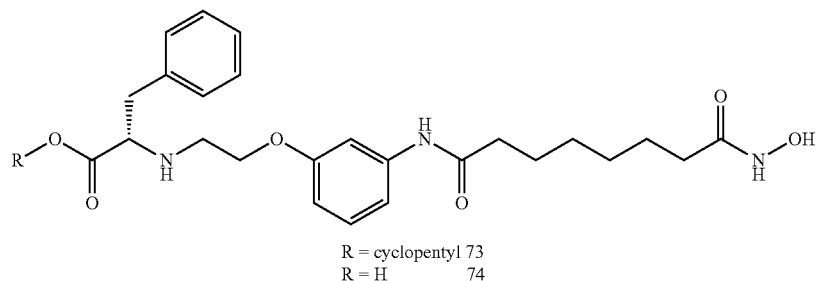

R = cyclopentyl 73
R = H        74

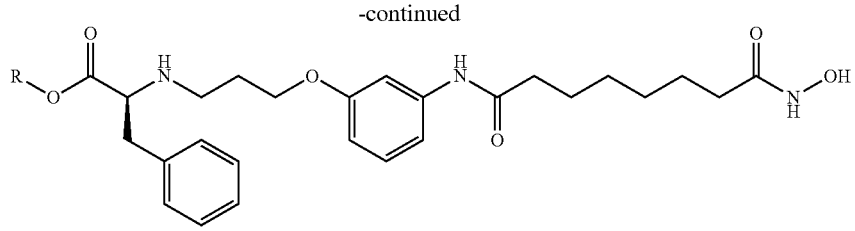

R = cyclopentyl 75
R = H          76

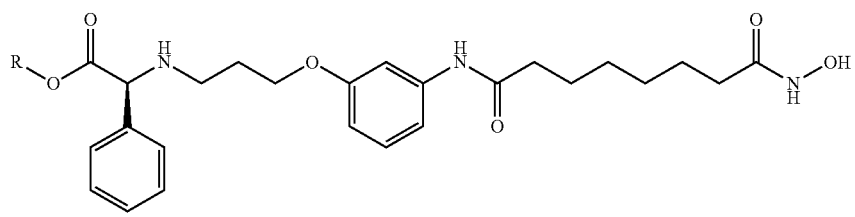

R = cyclopentyl 77
R = H          78

Preparation of Building Blocks M,N,O

Building Block M

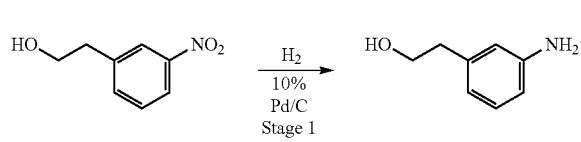

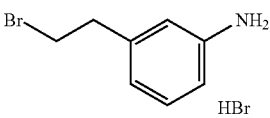

Building block M

Stage 1: 2-(3-Amino-phenyl)-ethanol

A mixture of nitro phenethyl alcohol (8.0 g, 0.047 mol) and 10% Pd/C (0.6 g) in ethanol (100 ml) was stirred under a hydrogen atmosphere (balloon pressure) for 18 h. The reaction mixture was filtered through a pad of celite and the Pd/C catalyst removed. The filtrate was concentrated under reduced pressure to yield a light brown solid 6.1 g (95% yield). LCMS purity 98%, m/z 138 [M+H]$^+$.

Stage 2: 3-(2-Bromo-ethyl)-phenylamine

A solution of 2-(3-Amino-phenyl)-ethanol (2.0 g) in 48% aq HBr (20 ml) was heated at 90° C. for 18 h. The mixture was cooled to room temperature, and the precipitate formed was collected by filtration. The solid was dried in vacuo yielding Building block M, 1.8 g (61% yield). LCMS purity 90%, m/z 200/202 [M+H]$^+$.

Building Block N

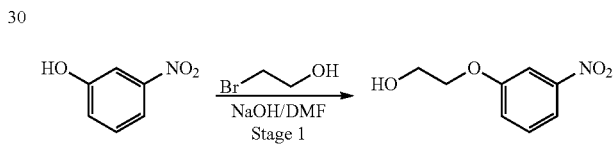

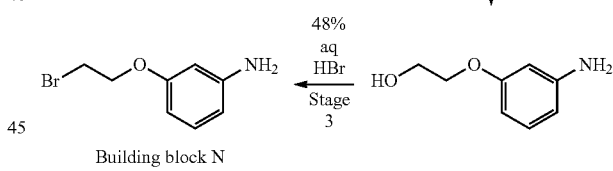

Building block N

Stage 1: 2-(3-Nitro-phenoxy)-ethanol

To a solution of 3-nitrophenol (10 g, 71.9 mmol) in DMF (40 ml) was added NaOH pellets (3.16 g, 79.1 mmol) and 2-bromoethanol (5.6 ml, 79.1 mmol). The reaction mixture was heated at 60° C. for 18 h. LCMS indicated 65% conversion to the required product. The reaction mixture was diluted with water (10 ml) and was slowly neutralised with 2M HCl. The reaction mixture was extracted with EtOAc (50 ml) and washed with water (50 ml). The EtOAc layer dried (Na$_2$SO$_4$), filtered and evaporated to dryness. Flash column chromatography purification eluting with 30% EtOAc/heptane gave the required product (8.2 g, 62% yield). LCMS purity 100%, m/z 184 [M+H]$^+$.

Stage 2: 2-(3-Amino-phenoxy)-ethanol

Reduction was carried out using the procedure outlined for Building block M.

Stage 3: 3-(2-Bromo-ethoxy)-phenylamine

Bromination was carried out using the procedure described for Building block M.

Building Block O

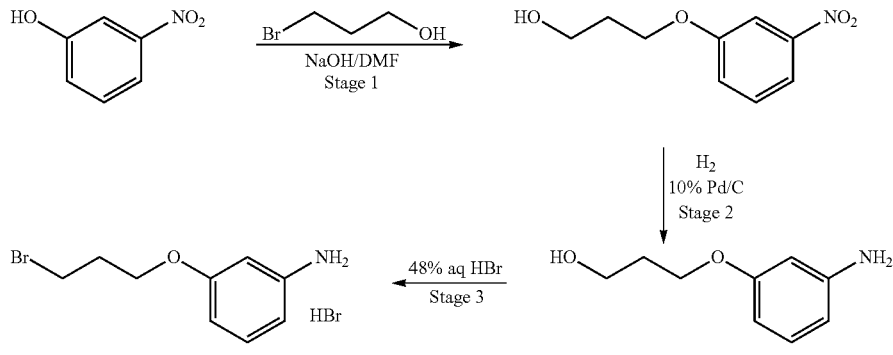

Building block O

Building block O was prepared as described for Building block G with 3-bromo-1-propanol used in place of 2-bromo-ethanol.

Synthesis of Compounds in Figure 4 Exemplified for Compound (71, R=Cyclopentyl) and Compound (72, R=H)

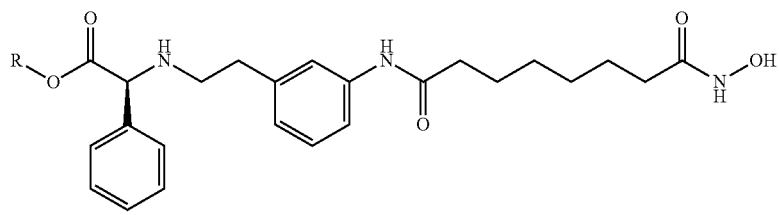

Stage 1: Coupling of Aniline Derivative to Carboxylic Acid Functionalised Resin

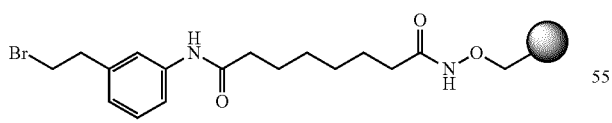

To a suspension of hydroxylamine 2-chlorotrityl resin derivatized with suberic acid (1.0 g, 0.94 mmol, loading 0.94 mmol) in DCM/DMF (10 ml/10 ml) was added DIPEA (1.75 ml) followed by building block M, 0.8 g, 2.82 mmol. PyBrOP (0.53 g, 3.76 mmol) was added and the suspension shaken for 18 h. The resin was washed using the standard wash procedure and was thoroughly dried.

Stage 2: Displacement of Bromide with L-Phenylglycine Cyclopentyl Ester

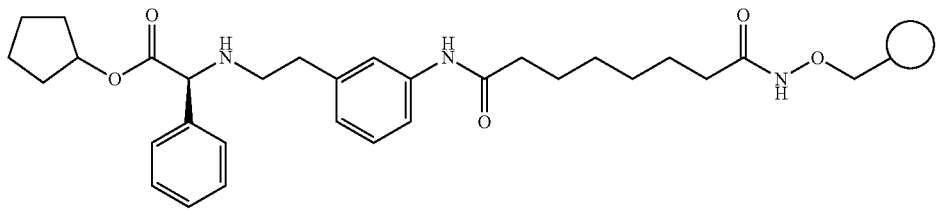 [SMILES: CCONC(=O)CCCCCCC(=O)Nc1cccc(CCN[C@H](C(=O)OC2CCCC2)c2ccccc2)c1]

To a suspension of stage 1 resin (0.4 g, 0.38 mmol) in DMF (4 ml) in a vial, was added L-phenylglycine cyclopentyl ester tosyl salt (0.44 g, 1.12 mmol) and DIPEA (0.67 ml, 3.76 mmol) followed by NaI (50 mg). The reaction was allowed to stand at 65° C. for 8 h. The resin was thoroughly washed using the standard wash procedure.

Stage 3: (S)-{2-[3-(7-Hydroxycarbamoyl-heptanoylamino)-phenyl]-ethylamino}-phenyl-acetic acid cyclopentyl ester (71)

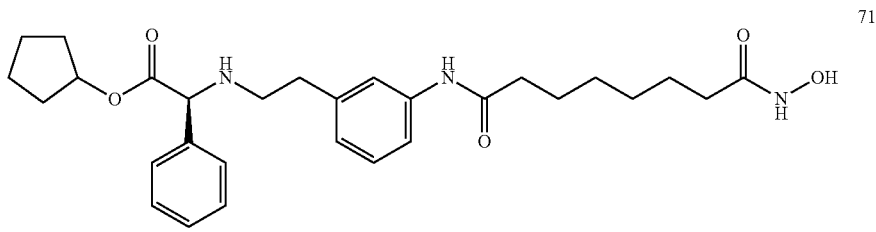 [SMILES: O=C(CCCCCCC(=O)Nc1cccc(CCN[C@H](C(=O)OC2CCCC2)c2ccccc2)c1)NO]

Stage 2 resin was cleaved with 2% TFA/DCM (10 ml×3). The filtrate was concentrated to dryness and the residue purified by preparative HPLC to afford compound (71) as the TFA salt. Yield 21 mg (11% overall), LCMS purity 99%, m/z 510 [M$^+$+H]$^+$, $^1$H NMR (400 MHz, MeOD), δ: 1.35-1.95 (16H, m 8×CH$_2$), 2.10 (2H, t, CH$_2$), 2.38 (2H, t, CH$_2$), 2.91-3.29 (4H, m), 5.18 (1H, s, OCOC$\underline{H}$Ph), 5.32 (1H, m, C$\underline{H}$OCO), 6.98 (1H, m, Ar), 7.30 (2H, m, Ar), 7.47-7.56 (5H, m, Ar), 7.62 (1H, s, Ar).

Stage 4: Saponification

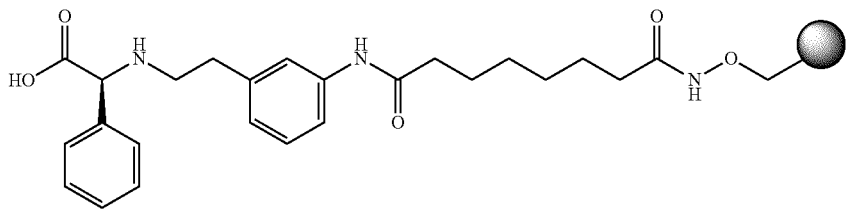 [SMILES: CCONC(=O)CCCCCCC(=O)Nc1cccc(CCN[C@H](C(=O)O)c2ccccc2)c1]

Stage 2 resin (1.2 g, 1.12 mmol) was suspended in THF/MeOH (12 ml/12 ml). 2.7M NaOH solution added and mixture was shaken for 18 h at room temperature Upon completion of reaction the resin was thoroughly washed (Standard wash procedure).

Stage 5: (S)-{2-[3-(7-Hydroxycarbamoyl-heptanoylamino)-phenyl]-ethylamino}-phenyl-acetic acid (72)

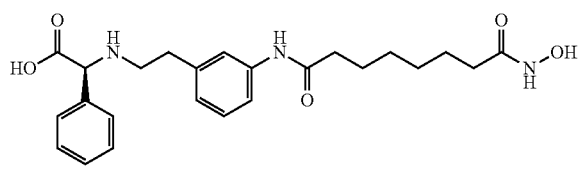

Stage 4 resin (0.8 g, 0.76 mmol) was cleaved with 2% TFA/DCM (10 ml×3). Filtrate was concentrated to dryness and residue purified by preparative HPLC to give compound (72) as a TFA salt, yield 40 mg (10% overall). LCMS purity of 100%, m/z 442 [M$^+$+H]$^+$, $^1$H NMR (400 MHz MeOD), δ: 1.20-1.35 (4H, m, 2×CH$_2$), 1.45-1.70 (4H, m, 2×CH$_2$), 1.95 (2H, t, CH$_2$), 2.25 (2H, t, CH$_2$), 2.80-3.20 (4H, m CH$_2$NH, CH$_2$Ph), 5.00 (1H, s, CHCOOH), 6.85 (1H, m, Ar), 7.15 (2H, m, Ar), 7.40 (5H, s, Ar), 7.50 (1H, s, Ar).

The following compounds were prepared according to the procedure described for compounds (71) and compound (72)

(S)-2-{2-[3-(7-Hydroxycarbamoyl-heptanoylamino)-phenoxy]-ethylamino}-3-phenyl-propionic acid cyclopentyl ester (73)

Building Block N Used

LCMS purity 94%, m/z 540 [M$^+$+H]$^+$, $^1$H NMR (400 MHz, MeOD), δ: 1.26-1.82 (16H, m, 8×CH$_2$), 2.11 (2H, t, CH$_2$), 2.39 (2H, t, CH$_2$), 3.15 (1H, dd, CHHPh), 3.44 (1H, dd, CHHPh), 3.56 (2H, m, CH$_2$), 4.30 (2H, t, CH$_2$), 4.40 (1H, m), 5.13 (1H, m, CHOCO), 6.76 (1H, d, Ar), 7.00 (1H, d, Ar), 7.24-7.41 (6H, m, Ar), 7.57 (1H, s, Ar).

(S)-2-{2-[3-(7-Hydroxycarbamoyl-heptanoylamino)-phenoxy]-ethylamino}-3-phenyl-propionic acid (74)

Building Block N Used

LCMS purity 100%, m/z 472 [M$^+$+H]$^+$, $^1$H NMR (400 MHz, MeOD), δ: 1.35-1.46 (4H, m, 2×CH$_2$), 1.61-1.77 (4H, m, 2×CH$_2$), 2.11 (2H, t, CH$_2$), 2.40 (2H, t, CH$_2$), 3.28-3.40 (2H, m, CH$_2$, masked signal), 3.53 (2H, t, CH$_2$), 4.29 (2H, t, CH$_2$), 4.38 (1H, t, OCOCHCH$_2$), 6.75 (1H, d, Ar), 7.00 (1H, d, Ar), 7.25 (1H, t, Ar), 7.30-7.41 (5H, m, Ar), 7.53 (1H, s, Ar).

(S)-2-{3-[3-(7-Hydroxycarbamoyl-heptanoylamino)-phenoxy]-propylamino}-3-phenyl-propionic acid cyclopentyl ester (75)

Building Block O Used

LCMS purity 100%, m/z 554 [M$^+$+H]$^+$, $^1$H NMR (400 MHz, MeOD), δ: 1.29-1.87 (16H, m, 8×CH$_2$), 2.10 (2H, t, CH$_2$), 2.21 (2H, m, CH$_2$), 2.37 (2H, t, CH$_2$), 3.12 (1H, dd, CHHPh), 3.25-3.43 (3H, m, CHHPh, CH$_2$), 4.11 (2H, t, CH$_2$), 4.33 (1H, m, OCOCHCH$_2$), 5.18 (1H, m, CHOCO), 6.78 (1H, d, Ar), 7.00 (1H, d, Ar), 7.22 (1H, t, Ar), 7.24-7.39 (5H, m, Ar), 7.44 (1H, s, Ar).

(S)-2-{3-[3-(7-Hydroxycarbamoyl-heptanoylamino)-phenoxy]-propylamino}-3-phenyl-propionic acid (76)

Building Block O Used

LCMS purity 100%, m/z 486 [M$^+$+H]$^+$, $^1$H NMR (400 MHz, MeOD), δ: 1.34-1.47 (4H, m, 2×CH$_2$), 1.60-1.75 (4H, m, 2×CH$_2$), 2.10 (2H, t, CH$_2$), 2.19 (2H, m, CH$_2$), 2.38 (2H, t, CH$_2$), 3.25-3.40 (4H, m, 2×CH$_2$, masked signal), 4.09 (2H, t, CH$_2$), 4.35 (1H, OCOCHCH$_2$), 6.75 (1H, d, Ar), 6.98 (1H, d, Ar), 7.20 (1H, t, Ar), 7.28-7.39 (5H, m, Ar), 7.41 (1H, s, Ar).

(S)-{3-[3-(7-Hydroxycarbamoyl-heptanoylamino)-phenoxy]-propylamino}-phenyl-acetic acid cyclopentyl ester (77)

Building Block O Used

LCMS purity of 100%, m/z 540 [M$^+$+H]$^+$, $^1$H NMR (400 MHz, MeOD), δ: 1.20-1.50 (8H, m, 4×CH$_2$), 1.50-1.80 (8H, m, 4×CH$_2$), 1.80-1.90 (2H, m, NHCH$_2$CH$_2$), 2.00 (2H, t, CH$_2$), 2.25 (211, t, CH$_2$), 2.55-2.70 (2H, m, NHCH$_2$), 3.90 (2H, t, CH$_2$CH$_2$O), 4.25 (1H, s, OCOCHPh), 5.05 (1H, m, CHOCO), 6.55 (1H, m, Ar), 6.95 (1H, m, Ar), 7.00-7.10 (1H, m, Ar), 6.15-6.35 (6H, m, Ar)

(S)-{3-[3-(7-Hydroxycarbamoyl-heptanoylamino)-phenoxy]-propylamino}-phenyl-acetic acid cyclopentyl ester (78)

Building Block O Used

LCMS purity of 100%, m/z 472 [M$^+$+H]$^+$, $^1$H NMR (400 MHz, DMSO), δ: 1.20-1.40 (4H, m, 2×CH$_2$), 1.45-1.65 (4H, m, 2×CH$_2$), 1.90 (2H, m, NHCH$_2$CH$_2$), 2.00-2.20 (2H, m, CH$_2$), 2.20-2.35 (2H, m, CH$_2$), 2.80-3.10 (2H, m, NHCH$_2$ masked signal), 3.90-4.00 (2H, m, CH$_2$CH$_2$O), 4.60-4.85 (1H, br s, OCOCHPh), 6.55 (1H, d, Ar), 7.05 (1H, d, Ar), 7.15 (1H, m, Ar), 7.30-7.60 (6H, m, Ar), 8.50-8.85 (1H, br s), 9.85 (1H, s), 10.35 (1H, s).

Synthesis of Compounds in Figure 5 Exemplified by
Compound 79 and Compound 80

FIG. 5

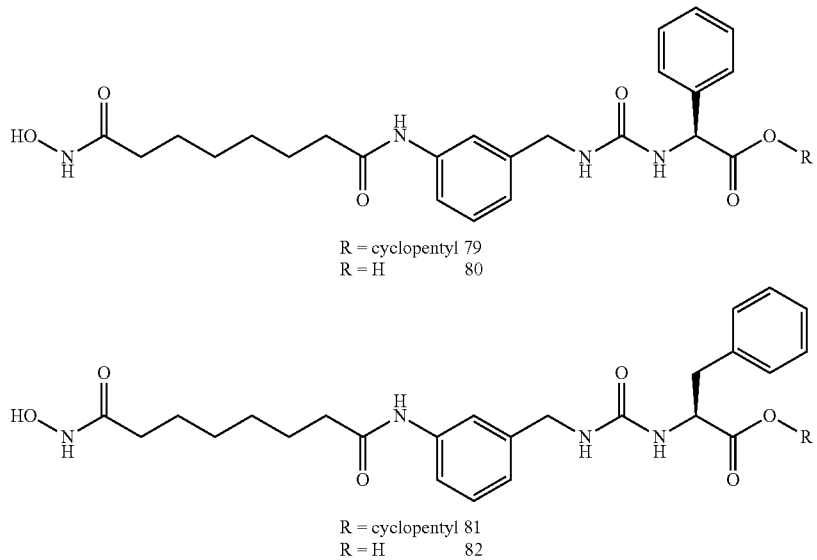

R = cyclopentyl 79
R = H 80

R = cyclopentyl 81
R = H 82

Synthesis of Compound 79 (R=Cyclopentyl) and
Compound 80 (R=H)

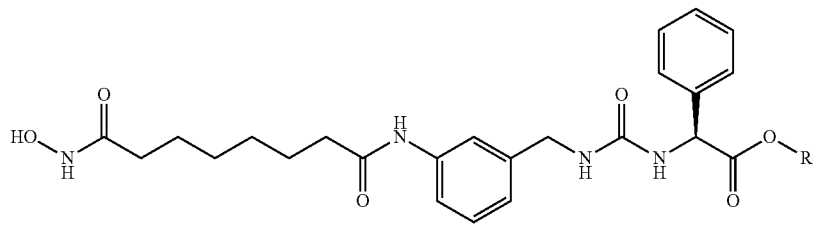

Stage 1: 3-Nitro-benzylamine

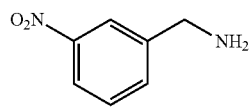 [SMILES: NCc1cccc([N+](=O)[O-])c1]

3-Nitrobenzyl bromide (10 g, 46.3 mmol) was dissolved in ethanol (200 ml) and stirred at room temperature A solution of conc.$NH_3$ (aq) (200 ml) in ethanol (300 ml) was added dropwise to the reaction over 30 minutes. The reaction was stirred for 18 h at room temperature before evaporating to dryness. Water (350 ml) was added to the residue and the solution was washed with EtOAc (2×200 ml). The aqueous layer was basified with 1M NaOH and extracted with EtOAc (2×200 ml). The organic extracts of the basic layer were combined, dried ($Na_2SO_4$) and evaporated to dryness. The product was obtained as an orange oil (4.6 g, 65% yield). LCMS purity 100%, m/z 153 $[M^++H]^+$.

Stage 2: 1-Isocyanatomethyl-3-nitro-benzene

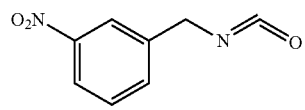 [SMILES: O=C=NCc1cccc([N+](=O)[O-])c1]

3-Nitro-benzylamine (2.3 g, 15.1 mmol) was dissolved in anhydrous dioxane (50 ml) under $N_2$ atmosphere. Diphosgene (2.2 ml, 18.2 mmol) was added, a precipitate formed which dissolved upon heating to 75° C. The reaction was stirred at 75° C. for 3 h, cooled and evaporated to dryness giving 3.4 g of crude material which was used in the next step without further purification.

Stage 3: (S)-[3-(3-Nitro-benzyl)-ureido]-phenyl-acetic acid cyclopentyl ester

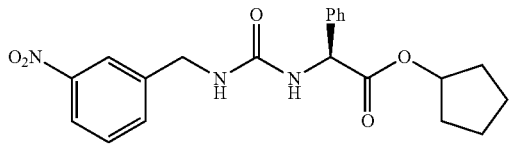 [SMILES: O=C(NCc1cccc([N+](=O)[O-])c1)N[C@H](C(=O)OC1CCCC1)c1ccccc1]

L-phenylglycine cyclopentyl ester tosyl salt (7.47 g, 19.1 mmol) was dissolved in DMF (70 ml). Triethylamine (5.8 ml, 42.0 mmol) was added and the mixture was cooled to 0° C. A solution of 1-Isocyanatomethyl-3-nitro-benzene (3.4 g, 19.1 mmol in 30 ml of DMF) was added slowly to the reaction mixture under a $N_2$ atmosphere. Stirring was continued for 18 h allowing the reaction to warm to room temperature The mixture was diluted with water (200 ml) and extracted with EtOAc (2×200 ml). The organic extracts were washed with water (3×100 ml) and brine (100 ml), dried ($Na_2SO_4$) and evaporated to dryness. The crude urea was purified by column chromatography (1% MeOH/DCM) to yield a pale yellow oil (4.6 g, 65% yield). LCMS purity 85%, m/z 398 $[M^++H]^+$.

Stage 4: (S)-[3-(3-Amino-benzyl)-ureido]-phenyl-acetic acid cyclopentyl ester

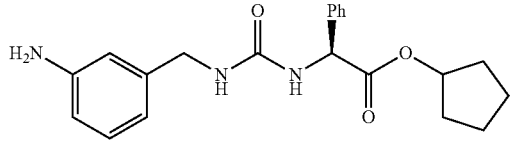

(S)-[3-(3-Nitro-benzyl)-ureido]-phenyl-acetic acid cyclopentyl ester (3.6 g, 9.0 mmol) was dissolved in ethanol (50 ml) Pd/C (10% wet) catalyst (100 mg) was added and the mixture was stirred under $H_2$ atmosphere (balloon pressure) for 18 h. The reaction mixture was filtered through a celite plug and evaporated to dryness to give a purple oil (2.34 g, 71% yield). LCMS purity 90%, m/z 368 $[M^++H]^+$.

Stage 5: Coupling to Resin

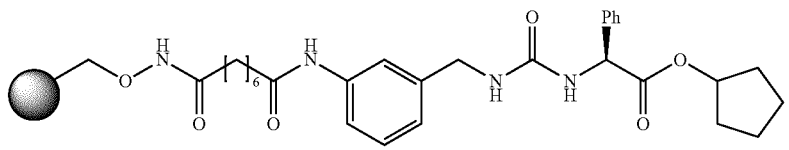

Hydroxylamine 2-chlorotrityl resin derivatized with suberic acid (1.5 g, loading 0.94 mmol/g) was swollen in DMF (15 ml) and PyBOP (2.2 g, 4.23 mmol) added, followed by DIPEA (2.4 ml, 14.1 mmol). Stage 4 aniline (1.3 g, 3.53 mmol) was dissolved in DCM (15 ml) and added to the reaction mixture. The reaction was shaken for 42 h at room temp before standard resin wash and drying.

Stage 6: (S)-{3-[3-(7-Hydroxycarbamoyl-heptanoylamino)-benzyl]-ureido}-phenyl-acetic acid cyclopentyl ester (79)

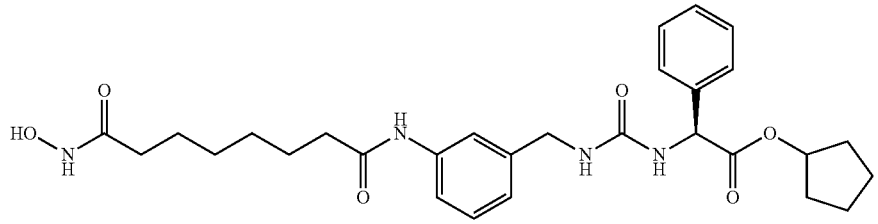

Stage 5 resin bound cyclopentyl ester (1.75 g) was shaken with 2% TFA/DCM (15 ml) for 10 min before filtering the resin and evaporating the solvent under reduced pressure at room temperature This process was repeated (×3) and the combined crude product was purified by preparative HPLC to yield compound (79). LCMS purity 100%, m/z 539 $[M^++H]^+$, $^1H$ NMR (400 MHz, MeOD), δ: 1.34-1.90 (16H, m, 8×$CH_2$), 2.11 (2H, t, $CH_2$), 2.38 (2H, t, $CH_2$), 4.30 (2H, s, $CH_2$), 5.18 (1H, m, C$\underline{H}$OCO), 5.30 (1H, s, OCOC$\underline{H}$Ph), 7.05 (1H, d, Ar), 7.26 (1H, t, Ar), 7.34-7.40 (5H, m, Ar), 7.47 (2H, m, Ar).

Stage 7: (S)-{3-[3-(7-Hydroxycarbamoyl-heptanoylamino)-benzyl]-ureido}-phenyl-acetic acid (80)

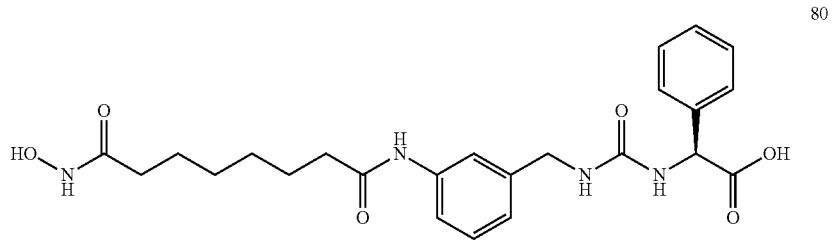 [SMILES: O=C(CCCCCCC(=O)Nc1cccc(CNC(=O)N[C@H](C(=O)O)c2ccccc2)c1)NO]

Compound (79) (75 mg) was dissolved in THF (1 ml) and 2M NaOH (aq, 1 ml) added. The reaction was stirred at room temperature for 2 h. THF was removed under a stream of $N_2$ and the aqueous layer (~1 ml) was purified by preparative HPLC to yield compound (80). LCMS purity 99%, m/z 471 [M$^+$+H]$^+$, $^1$H NMR (400 MHz, MeOD), δ: 1.20-1.35 (4H, m, 2×CH$_2$), 1.45-1.65 (4H, m, 2×CH$_2$), 2.00 (2H, t, CH$_2$), 2.25 (2H, t, CH$_2$), 4.20 (2H, s CH$_2$NH), 5.25 (1H, s CHPh), 6.90 (1H, d, Ar), 7.10 (1H, t, Ar), 7.15-7.40 (7H, m, Ar).

The following compounds were prepared according to the procedure described for compounds (79) and compound (80).

(S)-2-{3-[3-(7-Hydroxycarbamoyl-heptanoylamino)-benzyl]-ureido}-3-phenyl-propionic acid cyclopentyl ester (81)

LCMS purity 95%, m/z 553 [M$^+$+H]$^+$, $^1$H NMR (400 MHz, MeOD), δ: 1.20-1.40 (4H, m, 2×CH$_2$), 1.40-1.80 (12H, m, 6×CH$_2$), 2.00 (2H, t, CH$_2$), 2.25 (2H, t, CH$_2$), 2.90 (2H, m, CHCH$_2$Ph), 4.15 (2H, s CH$_2$NH), 4.40 (1H, m, OCOC HCH$_2$), 5.00 (1H, m, CHOCO), 6.85 (1H, d, Ar), 7.00-7.25 (6H, m, Ar), 7.35 (2H, br s, Ar).

(S)-2-{3-[3-(7-Hydroxycarbamoyl-heptanoylamino)-benzyl]-ureido}-3-phenyl-propionic acid (82)

LCMS purity 94%, m/z 485 [M$^+$+H]$^+$, $^1$H NMR (400 MHz, MeOD), δ: 1.30-1.50 (4H, m, 2×CH$_2$), 1.60-1.80 (4H, m, 2×CH$_2$), 2.10 (2H, t, CH$_2$), 2.35 (2H, t, CH$_2$), 2.95-3.25 (2H, m, CHCH$_2$Ph), 4.25 (2H, s, CH$_2$NH), 4.60 (1H, m OCOC HCH$_2$), 7.00 (1H, d, Ar), 7.15-7.35 (6H, m, Ar), 7.45 (2H, m, Ar)

Synthesis of Compounds Outlined in Figure 6
Exemplified by Compound (83) and Compound (84)

FIG. 6

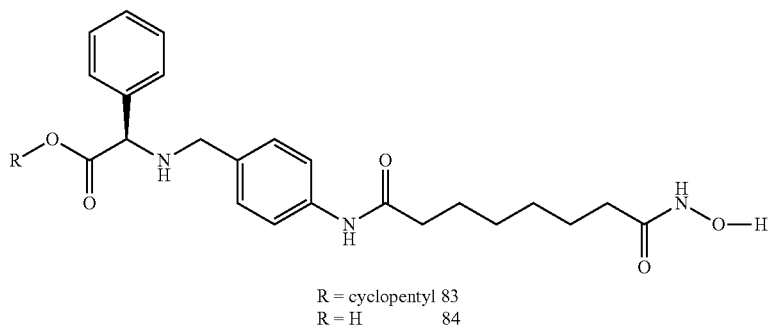

R = cyclopentyl 83
R = H 84

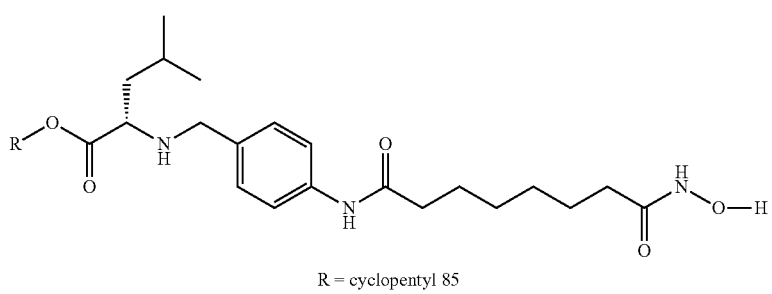

R = cyclopentyl 85

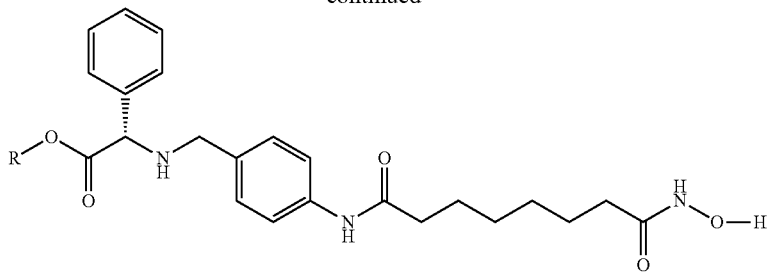

R = cyclopentyl 86
R = H 87

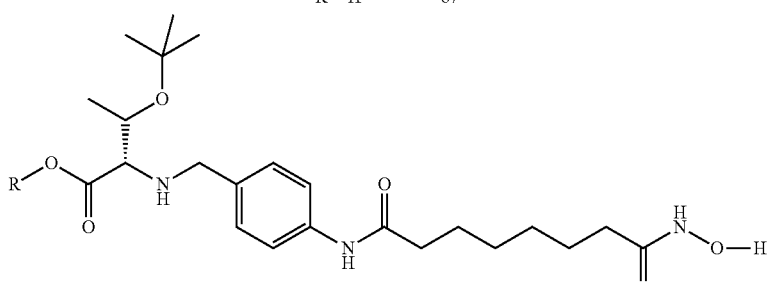

R = cyclopentyl 88

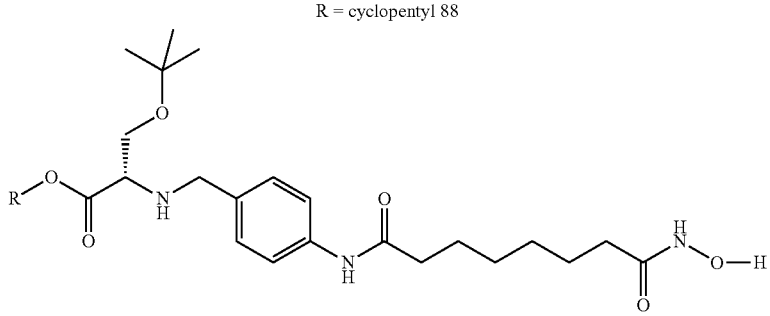

R = cyclopentyl 89
R = H 90

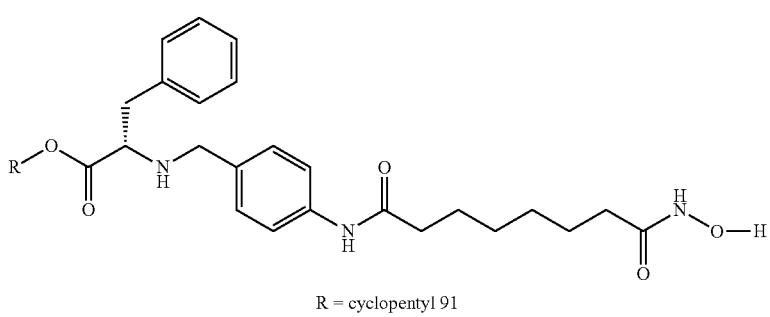

R = cyclopentyl 91

Stage 1: 7-(1-Isobutoxy-ethoxycarbamoyl)-heptanoic acid methyl ester

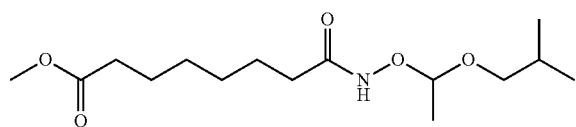 [SMILES: COC(=O)CCCCCCC(=O)NOC(C)OCC(C)C]

Monomethyl suberate (25.0 g, 13.3 mmol, 1.0 eq) was dissolved in THF (300 mL) and DCM (300 mL). EDC.HCl (25.46 g, 13.3 mmol, 1.0 eq) was added to the stirred solution, followed by HOBt (17.95 g, 13.3 mmol, 1.0 eq) and triethylamine (48.5 mL, 34.5 mmol, 2.6 eq). O-(1-Isobutoxy-ethyl)-hydroxylamine (21.9 mL, 15.9 mmol, 1.2 eq) was added to the viscous solution and the reaction allowed to stir overnight at room temperature. The reaction mixture was concentrated under vacuum, DCM (350 mL) was added and washed with water (250 mL) and brine (200 mL). The organic layer was isolated, dried ($MgSO_4$), filtered and concentrated in vacuo. The product was obtained as a white solid (36.6 g, 91% yield)

LCMS purity 88%, m/z 302 (M++H)+. This was used in the next step without further purification.

Stage 2: 7-(1-Isobutoxy-ethoxycarbamoyl)-heptanoic acid

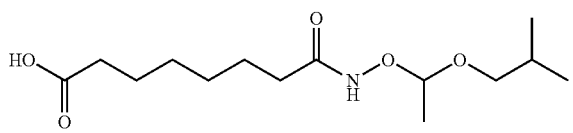 [SMILES: CC(C)COC(C)ONC(=O)CCCCCCC(=O)O]

7-(1-Isobutoxy-ethoxycarbamoyl)-heptanoic acid methyl ester (36.6 g, 12.1 mmol, 1.0 eq) was stirred in THF (200 mL) and water (200 mL) in the presence of lithium hydroxide (8.68 g, 36.2 mmol, 3.0 eq) for 3 h at 50° C. THF was evaporated under vacuum and to the mixture water (100 mL) and ethyl acetate (200 mL) were added. The mixture was acidified cautiously to pH 3 by addition of 1N HCl. The organic phase was isolated and the aqueous layer re-extracted with ethyl acetate (150 mL). The organic phases were combined, dried (MgSO₄), filtered and concentrated in vacuo. The product was obtained as a white solid (29.0 g, 83% yield), m/z 288 [M++H]+ and used in stage 4 without further purification.

Stage 3: 4-Trimethylsilanyloxymethyl-phenylamine

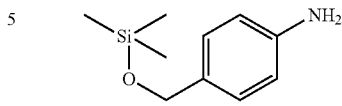

To a stirred solution of 4-amino benzyl alcohol (16.0 g, 13.0 mmol, 1.0 eq) in THF (400 mL), was added triethylamine (18.9 mL, 13.6 mmol, 1.05 eq) followed by trimethylchlorosilane (17.2 mL, 13.6 mmol, 1.05 eq). The reaction mixture was stirred under a nitrogen atmosphere overnight at room temperature. THF was evaporated under vacuum and the mixture partitioned with ethyl acetate (300 mL) and water (300 mL). The organic phase was isolated and the aqueous layer re-extracted with ethyl acetate (2×100 mL). The combined organic phases were washed with brine (2×150 mL), dried (MgSO₄), filtered and concentrated in vacuo. The product was obtained as a yellow oil (24.0 g, 95% yield) and used in stage 4 without further purification.

Stage 4: Octanedioic acid (4-hydroxymethyl-phenyl)-amide (1-isobutoxyethoxy)-amide

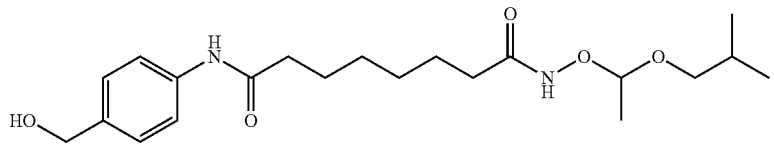 [SMILES: CC(C)COC(C)ONC(=O)CCCCCCC(=O)Nc1ccc(CO)cc1]

7-(1-Isobutoxy-ethoxycarbamoyl)-heptanoic acid (5.0 g, 1.72 mmol, 1.0 eq) and 4-trimethylsilanyloxymethyl-phenylamine (3.38 g, 1.72 mmol, 1.0 eq) were stirred together in DMF (140 mL). To the mixture was added PyBroP (10.5 g, 2.25 mmol, 1.3 eq) and DiPEA (3.9 mL, 2.25 mmol, 1.3 eq). The reaction was stirred under a nitrogen atmosphere overnight at room temperature. Ethyl acetate (200 mL) and water (200 mL) were added. The aqueous phase was isolated and re-extracted with ethyl acetate (2×100 mL). The combined organic phases were washed with water (2×50 mL) and brine (50 mL), then dried (MgSO₄), filtered and concentrated in vacuo. The crude product was dissolved in the minimum of ethyl acetate and purified by passing through a pad of silica. The product was washed through the silica using ethyl acetate and collected in 100 mL conical flasks until elution ceased by LCMS analysis. Purification gave a yellow oil (3.59 g, 53% yield). LCMS purity 61%, m/z 417 [M++Na]+

Stage 5: Octanedioic acid (4-formyl-phenyl)-amide (1-isobutoxy-ethoxy)-amide

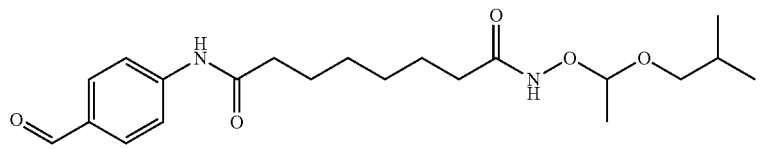 [SMILES: CC(C)COC(C)ONC(=O)CCCCCCC(=O)Nc1ccc(C=O)cc1]

Octanedioic acid (4-hydroxymethyl-phenyl)-amide (1-isobutoxyethoxy)-amide (100 mg, 0.025 mmol, 1.0 eq) was dissolved in DCM (5 mL). To the reaction mixture, was added $MnO_2$ (286 mg, 0.33 mmol, 13.0 eq) and was stirred at room temperature for 1.5 h. The reaction mixture was filtered over Celite and washed through with DCM, followed by evaporation of solvent to give a yellow oil (78.6 mg, 79% yield) LCMS purity 53%, m/z 415 $[M^++Na]^+$. The product was used in the subsequent steps without further purification.

Stage 6: (R)-{4-[7-(1-Isobutoxy-ethoxycarbamoyl)-heptanoylamino]-benzylamino}-phenyl-acetic acid cyclopentyl ester

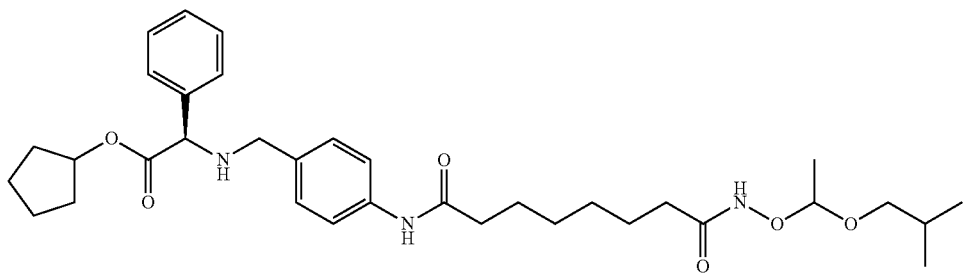 [SMILES: CC(C)COC(C)ONC(=O)CCCCCCC(=O)Nc1ccc(CN[C@@H](C(=O)OC2CCCC2)c2ccccc2)cc1]

Octanedioic acid (4-formyl-phenyl)-amide (1-isobutoxyethoxy)-amide (276 mg, 0.70 mmol, 1.0 eq) and D-phenylglycine cyclopentyl ester (170 mg, 0.77 mmol, 1.1 eq) were stirred in DCE (15 mL) for 10 min. Acetic acid (65 μL) was added and stirred for 2 min. Sodium triacetoxyborohydride (448 mg, 0.21 mmol, 3.0 eq) was introduced and the reaction mixture stirred under a nitrogen atmosphere, at room temperature for 1 h. Sodium hydrogen carbonate was added to quench the reaction. DCM was then added and the organic phase isolated. The aqueous layer was re-extracted with DCM, organic layers combined, dried ($MgSO_4$), filtered and concentrated in vacuo to give crude product (100 mg, 24%) LCMS purity 94.0%, m/z 496 $[m^++H]^+$ which was taken on without further purification.

Step 7: (R)-[4-(7-Hydroxycarbamoyl-heptanoylamino)-benzylamino]-phenyl-acetic acid cyclopentyl ester (83)

83

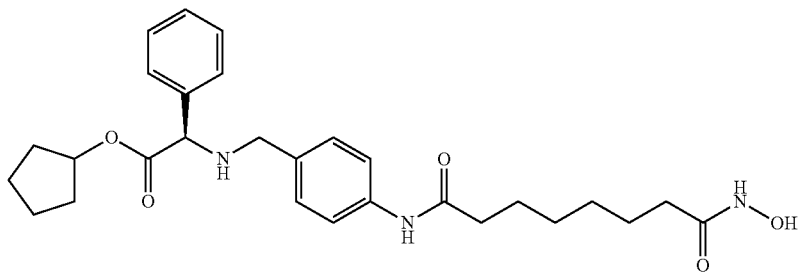

(R)-{4-[7-(1-Isobutoxy-ethoxycarbamoyl)-heptanoylamino]-benzylamino}-phenyl-acetic acid cyclopentyl ester (50 mg, 0.08 mmol, 1 eq) was dissolved in DCM (0.5 mL) and stirred with 4M HCl in dioxane (0.2 mL) for 30 min. The resulting salt was concentrated, dissolved in methanol and purified by preparative HPLC to yield compound (83). LCMS purity 94%, m/z 496 $[M^++H]^+$, $^1H$ NMR (300 MHz, MeOD), δ: 1.41-1.95 (16H, m, 8×$CH_2$), 2.15-2.17 (2H, m, $CH_2$), 2.40 (2H, t, J=7.2 Hz, $CH_2$), 4.16 (2H, q, J=13.5 Hz, $CH_2$), 5.12

(1H, s, CH), 5.27-5.30 (1H, m, CH), 7.40 (2H, d, J=8.7 Hz, Ar—H), 7.50-7.56 (5H, m, Ar—H), 7.67 (2H, d, J=8.7 Hz, Ar—H).

Stage 8: (R)-[4-(7-Hydroxycarbamoyl-heptanoylamino)-benzylamino]-phenyl-acetic acid (84)

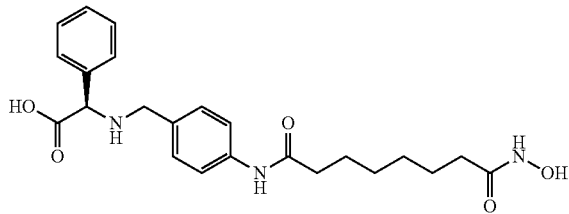

84

To a solution of CHR-003644 (50 mg, 0.008 mmol, 1.0 eq) in THF (2 mL) and water (2 mL), was added LiOH (8.0 mg, 0.033 mmol, 4.0 eq). The reaction was stirred under a nitrogen atmosphere at 40° C. overnight. THF was evaporated under vacuum and the remaining aqueous reaction solvent washed with ethyl acetate. The solution was acidified to pH 3 and the product concentrated in vacuo. The resulting salts were dissolved in methanol and the product purified by preparative HPLC to yield compound (84). LCMS purity 97%, m/z 428 [M$^+$+H]$^+$, $^1$H NMR (300 MHz, MeOD), δ: 1.39-1.41 (4H, m, 2×CH$_2$), 1.62-1.74 (4H, m, 2×CH$_2$), 2.13-2.15 (2H, m, CH$_2$), 2.40 (2H, t, J=7.5 Hz, CH$_2$), 4.14 (2H, q, J=12.9 Hz, CH$_2$), 5.06 (1H, s, CH), 7.39 (2H, d, J=8.4 Hz, Ar—H), 7.54 (5H, s, Ar—H), 7.67 (2H, d, J=8.7 Hz, Ar—H)

The following compound was prepared in a similar manner to Compound (83) and Compound (84) using the appropriate intermediates.

(S)-2-[4-(7-Hydroxycarbamoyl-heptanoylamino)-benzylamino]-4-methyl-pentanoic acid cyclopentyl ester (85)

LCMS purity 97%, m/z 476 [M$^+$+H]$^+$, $^1$H NMR (300 MHz, MeOD), δ: 0.98-1.03 (6H, m, 2×CH$_3$), 1.41-1.42 (4H, m, 2×CH$_2$), 1.71-1.96 (14H, m, 7×CH$_2$), 2.10-2.15 (2H, m, CH$_2$), 2.40 (2H, t, J=7.2 Hz, CH$_2$), 3.96-4.01 (1H, m, CH), 4.15-4.26 (2H, m, CH$_2$), 4.81 (1H, s, CH), 5.31-5.34 (1H, m, CH), 7.44 (2H, d, J=8.7 Hz, Ar—H), 7.70 (2H, d, J=8.7 Hz, Ar—H)

(S)-Cyclohexyl-[4-(7-hydroxycarbamoyl-heptanoylamino)-benzylamino]-acetic acid (87)

LCMS purity 95%, m/z 434 [M$^+$+H]$^+$, $^1$H NMR (300 MHz, MeOD), δ: 1.23-1.96 (18H, m, 9×CH$_2$), 2.10-2.15 (2H, m, CH$_2$), 2.39 (2H, m, CH$_2$), 3.71 (1H, m, CH), 4.12 (2H, q, J=7.2 Hz, CH$_2$), 4.80 (1H, s, CH), 7.43 (2H, d, J=8.4 Hz, Ar—H), 7.68 (2H, d, J=8.7 Hz, Ar—H)

(S)-3-tert-Butoxy-2-[4-(7-hydroxycarbamoyl-heptanoylamino)-benzylamino]-butyric acid cyclopentyl ester (88)

LCMS purity 83%, m/z 520 [M$^+$+H]$^+$, $^1$H NMR (300 MHz, MeOD), δ: 1.19 (9H, s, 3×CH$_3$), 1.29 (3H, d, J=7.8 Hz, CH$_3$), 1.37-1.41 (4H, m, CH$_2$), 1.64-1.89 (12H, m, CH$_2$), 2.09-2.15 (2H, m, CH$_2$), 2.40 (2H, t, J=7.2 Hz, CH$_2$), 3.36-3.37 (1H, m, CH), 3.70-3.71 (1H, m, CH), 4.24-4.27 (2H, m, CH$_2$), 5.17-5.19 (1H, m, CH), 7.42 (2H, d, J=6.9 Hz, Ar—H), 7.68 (2H, d, J=8.4 Hz, Ar—H)

(S)-3-tert-Butoxy-2-[4-(7-hydroxycarbamoyl-heptanoylamino)-benzylamino]-propionic acid cyclopentyl ester (89)

LCMS purity 95%, m/z 506 [M$^+$+H]$^+$, $^1$H NMR (300 MHz, MeOD), δ: 1.23 (9H, s, C(CH$_3$)$_3$), 1.36-2.09 (16H, m, 8×CH$_2$), 1.66 (2H, t, J=7.7 Hz, CH$_2$), 1.75 (2H, t, J=7.4 Hz, CH$_2$), 2.11 (2H, t, J=7.4 Hz, CH$_2$), 2.40 (2H, t, J=7.3 Hz, CH$_2$), 3.92 (2H, m, CH$_2$), 4.16 (1H, m, CH), 4.26 (2H, s, CH$_2$), 5.32 (1H, m, CH), 7.45 (2H, d, J=8.5 Hz, ArH), 7.67 (2H, dd, J=3.2, 8.3 Hz, ArH).

(S)-3-tert-Butoxy-2-[4-(7-hydroxycarbamoyl-heptanoylamino)-benzylamino]-propionic acid (90)

LCMS purity 95%, m/z 438 [M$^+$+H]$^+$, $^1$H NMR (300 MHz, MeOD), δ: 1.25 (9H, s, C(CH$_3$)$_3$), 1.39-1.42 (4H, m, 2×CH$_2$), 1.62-1.69 (4H, m, 2×CH$_2$), 2.08-2.17 (2H, m, CH$_2$), 2.40 (2H, t, J=7.5 Hz, CH$_2$), 3.85-3.96 (2H, m, CH$_2$), 4.01-4.04 (1H, m, CH), 4.26 (2H, s, CH$_2$), 7.46 (2H, d, J=8.4 Hz, Ar—H), 7.68 (2H, d, J=8.4 Hz, Ar—H)

(S)-2-[4-(7-Hydroxycarbamoyl-heptanoylamino)-benzylamino]-3-phenyl-propionic acid cyclopentyl ester (91)

LCMS purity 95%, m/z 510 [M$^+$+H]$^+$, $^1$H NMR (300 MHz, MeOD), δ: 1.17-2.43 (22H, m, 11×CH$_2$), 4.19-4.30 (2H, m, CH$_2$), 5.08 (1H, s, CH), 5.20-5.26 (1H, m, CH), 7.24-7.71 (9H, m, Ar—H)

Compound (86) was prepared was prepared via alternative methodology the modified conditions are detailed below Step 6b: (S)-Cyclohexyl-{4-[7-(1-isobutoxy-ethoxycarbamoyl)-heptanoylamino]-benzylamino}-acetic acid cyclopentyl ester

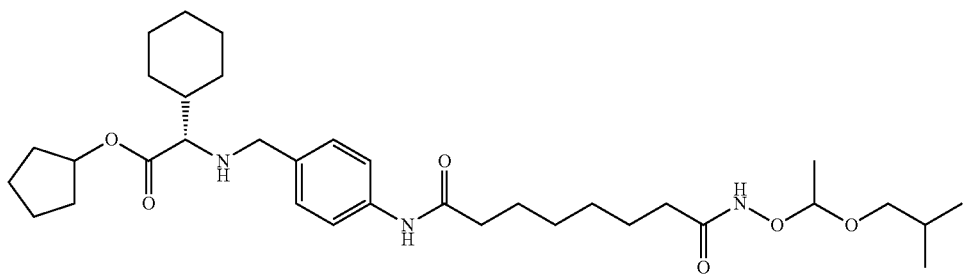 [SMILES: CC(C)COC(C)ONC(=O)CCCCCCC(=O)Nc1ccc(CN[C@H](C(=O)OC2CCCC2)C2CCCCC2)cc1]

Octanedioic acid (4-formyl-phenyl)-amide (1-isobutoxyethoxy)-amide (220 mg, 0.056 mmol, 1.0 eq) and L-cyclohexyl-glycine cyclopentyl ester (138.9 mg, 0.062 mmol, 1.1 eq) were stirred in methanol (8 mL) overnight at room temperature. Sodium borohydride (31.8 mg, 0.084 mmol, 1.5 eq) was introduced and the reaction mixture stirred for 15 min. The reaction mixture was transferred to an ice bath and 2 drops of sodium hydroxide (2M) were added. Diethyl ether was added and the organic phase isolated. The aqueous layer was re-extracted with diethyl ether, organic layers combined and washed with brine. The organic phase was then dried (MgSO$_4$) filtered and concentrated in vacuo to give crude material which was taken to the next step without further purification.

Step 7b: (S)-Cyclohexyl-[4-(7-hydroxycarbamoyl-heptanoylamino)-benzylamino]-acetic acid cyclopentyl ester (86)

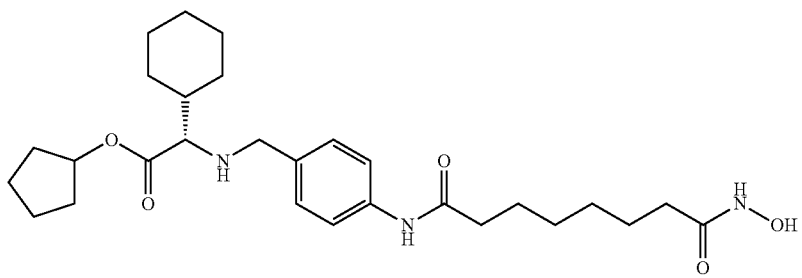

86

Material from step 6b (50 mg, 0.083 mmol, 1 eq) was dissolved in DCM/methanol (2 mL: 2 mL) and stirred with TFA (1.0 mL) for 2 h. The resulting salt was concentrated, dissolved in methanol and purified by preparative HPLC to yield compound (86). LCMS purity 100%, m/z 502 [M$^+$+H]$^+$, $^1$H NMR (300 MHz, MeOD), δ: 1.28-1.98 (26H, m, 13×CH$_2$), 2.10-2.15 (2H, m, CH$_2$), 2.40 (2H, t, J=7.8 Hz, CH$_2$), 3.81 (1H, d, J=3.9 Hz, CH), 4.21 (2H, m, CH$_2$), 5.01 (1H, s, CH), 5.23-5.25 (1H, m, CH), 7.43 (2H, d, J=8.4 Hz, Ar—H), 7.68 (2H, d, J=8.7 Hz, Ar—H)

Synthesis of 92 and 93

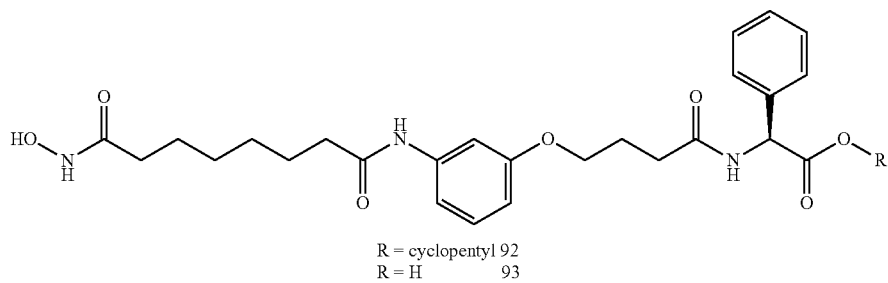

R = cyclopentyl 92
R = H          93

Stage 1: 4-(3-Nitro-phenoxy)-butyric acid methyl ester

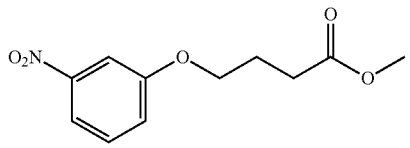 [SMILES: COC(=O)CCCOc1cccc([N+](=O)[O-])c1]

To a solution of 3-nitrophenol (8.35 g, 60 mmol), in DMF (50 ml) was added $K_2CO_3$ (16.56 g, 120 mmol) and methyl 1,4-bromobutyrate (11.95 g, 66 mmol). The reaction was stirred at room temperature for 16 h. The reaction was diluted with ethyl acetate and water. The organic phase was separated and washed with water (2×200 ml). The organic phase was dried with $Na_2SO_4$ and concentrated in vacuo. The required ether was isolated following chromatography (ethyl acetate: heptane, 1:9) as a pale yellow solid (12.2 g, 85% yield). LCMS purity 100%, m/z 240 $[M^++H]^+$.

Stage 2: 4-(3-Amino-phenoxy)-butyric acid methyl ester

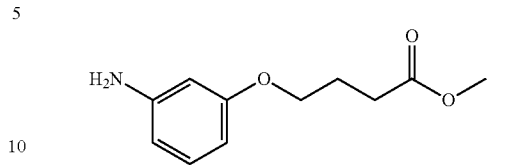

Stage 1 nitro ester (250 mg, 1 mmol) was dissolved in ethanol (3 ml). Pd/carbon (40 mg) was added and the reaction stirred under a hydrogen atmosphere (balloon pressure) for 16 h. The reaction mixture was filtered through celite. The celite pad was washed with ethanol and the combined organic fractions concentrated in vacuo to give the required product as an orange oil (210 mg, 100% yield). LCMS purity 89%, m/z 210 $[M^++H]^+$. The aniline was used in the next stage without further purification.

Stage 3: Coupling to Resin

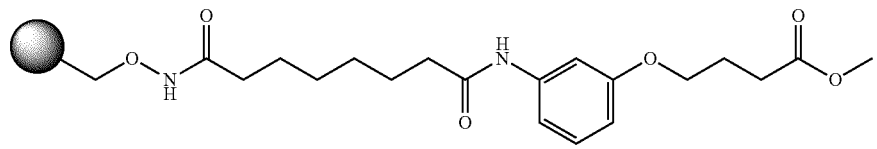 [SMILES: CCONC(=O)CCCCCCC(=O)Nc1cccc(OCCCC(=O)OC)c1]

Suberic acid derivatised hydroxylamine 2-chlorotrityl resin (8 g, 7.52 mmol, loading, 0.94 mmol/g) was swollen in DCM/DMF (80 ml/80 ml). PyBOP (11.8 g, 22.6 mmol) and diisopropylethylamine (13.1 ml, 75.2 mmol) were added to the flask followed by 4-(3-amino-phenoxy)-butyric acid methyl ester (4.73 g, 22.6 mmol). The reaction was shaken at room temperature for 72 h before standard wash and drying.

Stage 4: Ester hydrolysis

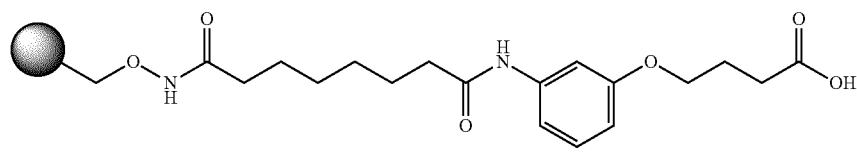 [SMILES: CCONC(=O)CCCCCCC(=O)Nc1cccc(OCCCC(=O)O)c1]

Stage 3 resin (9.5 g), was suspended in THF/MeOH (34 ml/34 ml). NaOH (1.4 M, aq, 34 ml) was added and the reaction shaken for 16 h at room temperature. The resin was washed using the standard wash procedure before air drying.

Stage 5: Amino Acid Ester Coupling

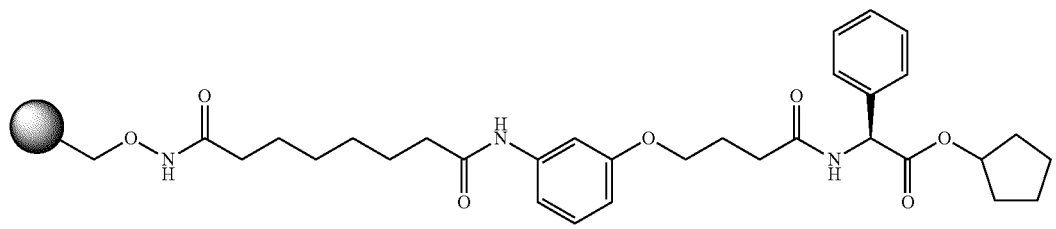 [SMILES: CCONC(=O)CCCCCCC(=O)Nc1cccc(OCCCC(=O)N[C@H](C(=O)OC2CCCC2)c2ccccc2)c1]

Stage 4 resin (2.1 g), was suspended in DCM/DMF (20 ml/20 ml). PyBOP (3.1 g, 5.92 mmol), N-phenlgiycine cyclopentyl ester (2.4 g, 5.92 mmol) and diisopropylethylamine (3.4 ml, 19.7 mmol) were added sequentially and the reaction shaken at room temperature for 72 hours. The resin was submitted to standard wash and dried.

Stage 6: (S)-{4-[3-(7-Hydroxycarbamoyl-heptanoylamino)-phenoxy]-butyrylamino}-phenyl-acetic acid cyclopentyl ester (92)

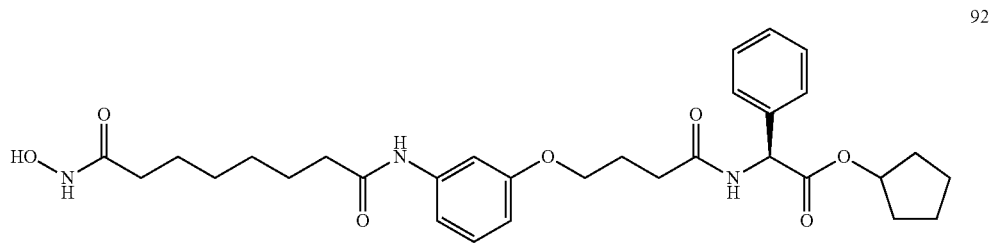 [SMILES: O=C(CCCCCCC(=O)Nc1cccc(OCCCC(=O)N[C@H](C(=O)OC2CCCC2)c2ccccc2)c1)NO]

Stage 5 resin bound cyclopentyl ester (1.1 g) was shaken with 2% TFA/DCM (10 ml) for 10 minutes before filtering the resin and evaporating the solvent under reduced pressure at room temperature. The process was repeated (×3) and the combined crude product purified by preparative HPLC to yield compound (92) (114 mg). LCMS purity 99%, m/z 568 [M$^+$+H]$^+$, $^1$H NMR (400 MHz, MeOD), δ: 1.40 (4H, m, 2×CH$_2$), 1.45-1.90 (13H, m, alkyl), 2.10 (4H, m, 2×CH$_2$), 2.40 (2H, t, CH$_2$), 2.50 (2H, m, CH$_2$), 4.00 (2H, m, CH$_2$), 5.15 (1H, m,), 5.40 (1H, s, NHCHCO), 6.65 (1H, m, Ar) 7.15 (1H, m, Ar), 7.20 (1H, t, Ar), 7.30 (1H, s, Ar), 7.40 (5H, s, Ar).

Stage 7: (S)-{4-[3-(7-Hydroxycarbamoyl-heptanoylamino)-phenoxy]-butyrylamino}-phenyl-acetic acid (93)

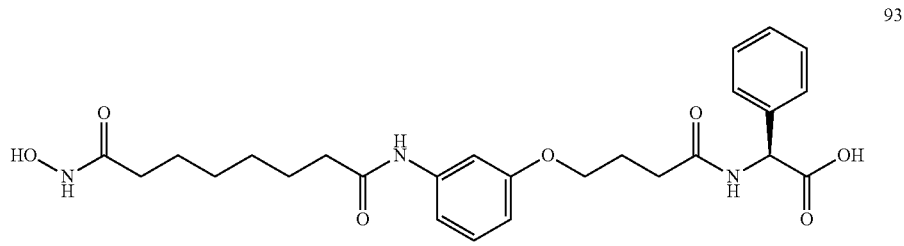 [SMILES: O=C(CCCCCCC(=O)Nc1cccc(OCCCC(=O)N[C@H](C(=O)O)c2ccccc2)c1)NO]

Stage 6 cyclopentyl ester resin (500 mg) was suspended in THF (15 ml). To the suspension was added NaOH (1.4M aq., 1.6 ml) and the reaction shaken for 16 hr at room temperature. The filtrate was removed and the resin washed and dried before cleavage. Cleavage was effected by shaking with 2% TFA/DCM (5 ml) for 10 minutes before filtering the resin and evaporating the solvent under reduced pressure at room temperature. The process was repeated (×3) and the combined crude product purified by preparative HPLC to yield compound (93) (62 mg). LCMS purity 99%, m/z 500 [M+H]+, $^1$H NMR (400 MHz, MeOD), δ: 1.40 (4H, m, 2×CH$_2$), 1.60-1.80 (4H, m, alkyl), 2.10 (4H, m, 2×CH$_2$), 2.40 (2H, t, CH$_2$), 2.50 (2H, t, CH$_2$), 4.00 (2H, m, CH$_2$), 5.45 (1H, s, NHC HCO), 6.65 (1H, d, Ar) 7.10 (1H, m, Ar), 7.20 (1H, t, Ar), 7.25 (1H, s, Ar), 7.30-7.45 (5H, m, Ar).

L-Phe-cyclopentyl ester.TsOH salt (9.42 g, 23 mmol) was suspended in DCM (40 ml). Triethylamine (6.5 ml, 47 mmol) was added and the reaction stirred at room temperature for 5 min. Stage 1 chloroformate (5 g, 23 mol) dissolved in DCM (10 ml) was added to the reaction mixture added dropwise with cooling (ice bath). The reaction was stirred for 16 h at room temperature. The solvent was removed and the residue dissolved in EtOAc (100 ml) washed with water (50 ml×3) and dried (Na$_2$SO$_4$) before concentration in vacuo. The crude material was purified by chromatography (EtOAc:heptane, 1:9) to give the required carbamate (6.4 g, 67% yield). m/z 413 [M+H]+

Synthesis of 94 and 95

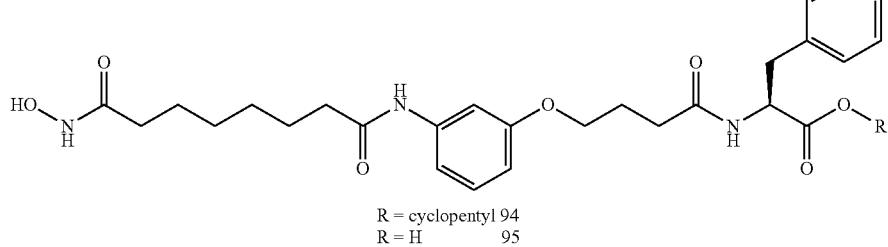

R = cyclopentyl 94
R = H          95

Stage 1: 3-nitro-benzyl-chroroformate formation

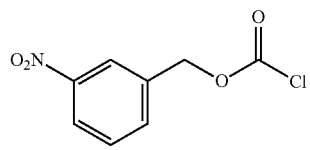 [SMILES: O=C(Cl)OCc1cccc([N+](=O)[O-])c1]

To a solution of 3-nitro benzyl alcohol (10 g, 65 mmol), in dioxane (anhydrous, 100 ml) was added trichloromethyl chloroformate (9.47 ml, 78 mmol). The reaction was heated at 75° C. under nitrogen for 16 h. The solvent was evaporated and the residue resuspended in dioxane and evaporated. The procedure was repeated (×3). The crude chloroformate was used in the next stage without further purification.

Stage 2: (S)-2-(3-Nitro-benzyloxycarbonylamino)-3-phenyl-propionic acid cyclopentyl ester

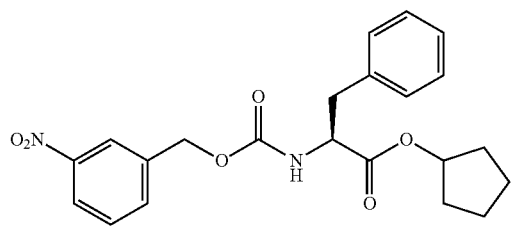

Stage 3: (S)-2-(3-Amino-benzyloxycarbonylamino)-3-phenyl-propionic acid cyclopentyl ester

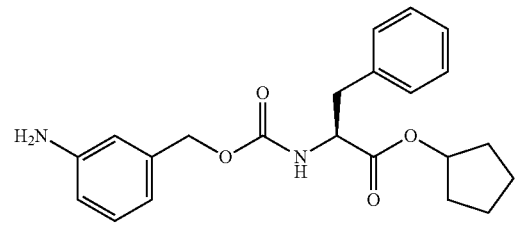 [SMILES: O=C(N[C@@H](Cc1ccccc1)C(=O)OC1CCCC1)OCc1cccc([N+](=O)[O-])c1]

Stage 2 nitro carbamate (6.4 g, 15.5 mmol) was dissolved in ethanol (64 ml). Tin chloride dihydrate (17.5 g, 77 mmol) was added and the reaction stirred for 16 h at room temperature. The solvent was evaporated and the residue dissolved in EtOAc (60 ml). A saturated solution of sodium potassium tartrate (60 ml) was added followed by a solution of saturated sodium hydrogen carbonate (120 ml). The biphasic solution was stirred for 15 min. The organic layer was separated and the aqueous phase extracted with EtOAc (60 ml×1). The organic layers were combined, dried and the solvent evaporated to give the crude product which was purified by chromatography (EtOAc heptane 1:3→1:1). The required product was isolated (3.5 g, 59% yield). LCMS purity 100%, m/z 383 [M+H]+.

Stage 4: Coupling to Resin

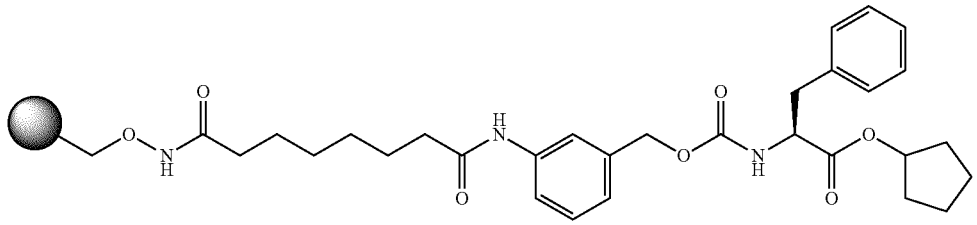 [SMILES: CCONC(=O)CCCCCCC(=O)Nc1cccc(COC(=O)N[C@@H](Cc2ccccc2)C(=O)OC2CCCC2)c1]

Suberic acid derivatised hydroxylamine 2-chlorotrityl resin (2.0 g, 1.88 mmol, loading, 0.94 mmol/g) was swollen in DMF (20 ml). PyBOP (2.93 g, 5.64 mmol) and diisopropyl ethylamine (3.25 ml, 18.8 mmol) were added. Stage 3 anilino carbamate (1.8 g, 4.7 mmol) dissolved in DCM (20 ml) was added and the reaction shaken for 4 d before filtrate removal and standard wash of the resin which was dried under air.

Stage 5: (S)-2-[3-(7-Hydroxycarbamoyl-heptanoy-lamino)-benzyloxycarbonylamino]-3-phenyl-propionic acid cyclopentyl ester (94)

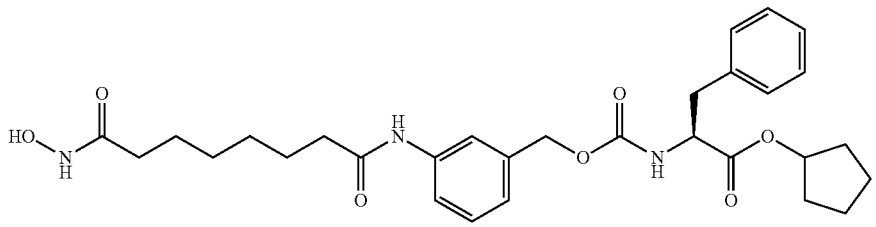

94

Stage 4 resin bound cyclopentyl ester (2 g) was shaken with 2% TFA/DCM (15 ml) for 10 minutes before filtering the resin and evaporating the solvent under reduced pressure at room temperature. The process was repeated (×3) and the combined crude product purified by preparative HPLC to yield compound (94). LCMS purity 95%, m/z 554 [M$^+$+H]$^+$, $^1$H NMR (400 MHz, MeOD), δ: 1.30 (4H, m, 2×CH$_2$), 1.40-1.90 (13H, m, alkyl), 2.00 (2H, t, CH$_2$), 2.30 (2H, t, CH$_2$), 2.90 (2H, ddd, CH$_2$), 3.80 (1H, m), 4.25 (1H, dd, NHC<u>H</u>CO), 4.90 (2H, s, CH$_2$), 5.05 (1H, m), 5.35 (1H, m), 6.95 (1H, d, Ar) 7.05-7.25 (6H, m, Ar), 7.35-7.75 (2H, m, Ar).

Stage 6: (S)-2-[3-(7-Hydroxycarbamoyl-heptanoy-lamino)-benzyloxycarbonylamino]3-phenyl-propionic acid (95)

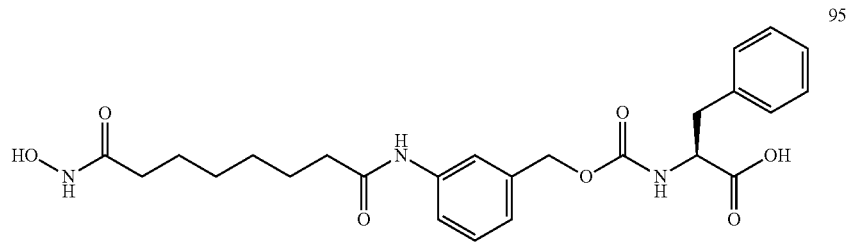 [SMILES: O=C(CCCCCCC(=O)Nc1cccc(COC(=O)N[C@@H](Cc2ccccc2)C(=O)O)c1)NO]

Compound (94) (100 mg, 0.18 mmol) was dissolved in THF (1 ml) and 2M NaOH (1 ml) added. The reaction vial was shaken for 4 h before THF removal via a stream of nitrogen. The aqueous residue was purified by preparative HPLC to yield compound (95) (62 mg). LCMS purity 95%, m/z 486 [M$^+$+H]$^+$, $^1$H NMR (400 MHz, MeOD), δ: 1.35 (4H, m, 2×CH$_2$), 1.55-1.75 (4H, m, alkyl), 2.10 (2H, t, CH$_2$), 2.35 (2H, t, CH$_2$), 2.95 (2H, dd, CH), 3.20 (1H, dd, CH), 4.45 (1H, dd, NHC$\underline{H}$CO), 5.00 (2H, s, CH$_2$), 7.05 (1H, d, Ar), 7.20-7.35 (6H, m, Ar), 7.55 (2H, m, Ar).

Synthesis of Compound (96) and Compound (97)

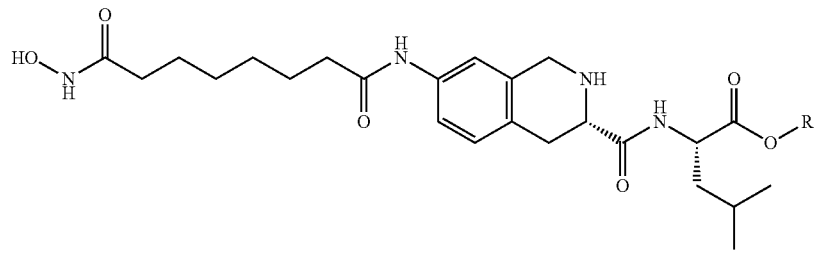

R = cyclopentyl 96
R = H 97

Stage 1: (S)-7-Nitro-1,2,3,4-tetrahydro-isoquinoline-3-carboxylic acid

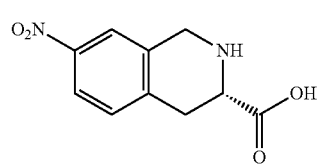 [SMILES: O=C(O)[C@@H]1Cc2ccc([N+](=O)[O-])cc2CN1]

Prepared as described in Tett Letts 42, 2001, 3507.

Stage 2: (S)-7-Nitro-3,4-dihydro-1H-isoquinoline-2,3-dicarboxylic acid-2-tert-butyl ester

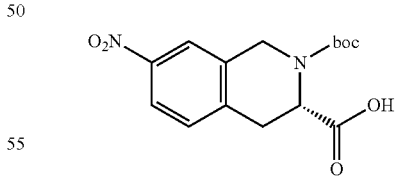

(S)-7-Nitro-1,2,3,4-tetrahydro-isoquinoline-3-carboxylic acid (7 g, 31.5 mmol) was dissolved in THF:water (1:1, 350 ml). K$_2$CO$_3$ was added (5.2 g, 37 mmol) followed by boc anhydride (13.7 g, 63 mmol) and the solution heated at 40° C. for 1 h. THF was removed by evaporation and the aqueous layer adjusted to pH=7 before extraction with EtOAc. The organic layer was washed 0.1 M HCl (×3) and dried over Na$_2$SO$_4$ before concentration in vacuo. The required N-protected product was obtained following column chromatography (EtOAc:heptane 2:3-4 EtOAc), (7.5 g, 74%), LCMS purity 92%, molecular ion not observed Stage 3: (S)-3-((S)-1-Cyclopentyloxycarbonyl-3-methyl-butylcarbamoyl)-7-nitro-3,4-dihydro-1H-isoquinoline-2-carboxylic acid tert-butyl ester

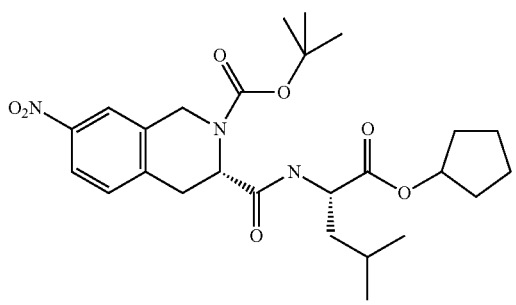 [SMILES: CC(C)C[C@H](NC(=O)[C@@H]1Cc2ccc([N+](=O)[O-])cc2CN1C(=O)OC(C)(C)C)C(=O)OC1CCCC1]

(S)-7-Nitro-3,4-dihydro-1H-isoquinoline-2,3-dicarboxylic acid-2-tert-butyl ester (2.5 g, 7.76 mmol) was dissolved in DCM (100 ml). HOBt (1.16 g, 8.53 mmol) was added, L-leucine cyclopentyl ester (3.19 g, 8.53 mmol) was added followed by triethylamine (2.38 ml, 17.1 mmol). EDCl.HCl (1.46 g, 8.5 mmol) was added and the reaction stirred at room temperature for 16 h. To the reaction was added DCM (100 ml) and the organic layer washed with water (3×300 ml), dried with $Na_2SO_4$ and the solvent removed in vacuo. The crude product was purified by chromatography (EtOAc:heptane 1:2→EtOAc) to give the required product 3.14 g (82% yield), LCMS purity 100%, m/z 504 $[M^++H]^+$ Stage 4: (S)-7-Amino-3-((S)-1-cyclopentyloxycarbonyl-3-methyl-butylcarbamoyl)-3,4-dihydro-1H-isoquinoline-2-carboxylic acid tert-butyl ester

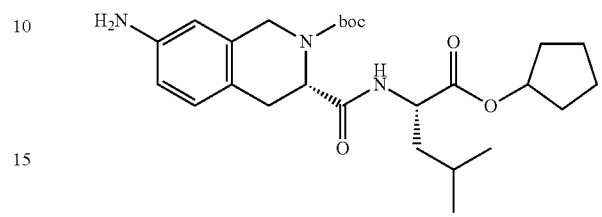

(S)-3-((S)-1-Cyclopentyloxycarbonyl-3-methyl-butylcarbamoyl)-7-nitro-3,4-dihydro-1H-isoquinoline-2-carboxylic acid tert-butyl ester (3.14 g, 6.24 mmol) and Pd/carbon (0.4 g) were suspended in EtOAc (20 ml). The reaction was stirred under a hydrogen atmosphere (balloon pressure) for 16 h. The solution was filtered through a pad of celite and the solvent removed. The crude product (3.04 g) was used in the next step without further purification. LCMS purity 83%, m/z 474 $[M^++H]^+$ Stage 5: Coupling to Resin

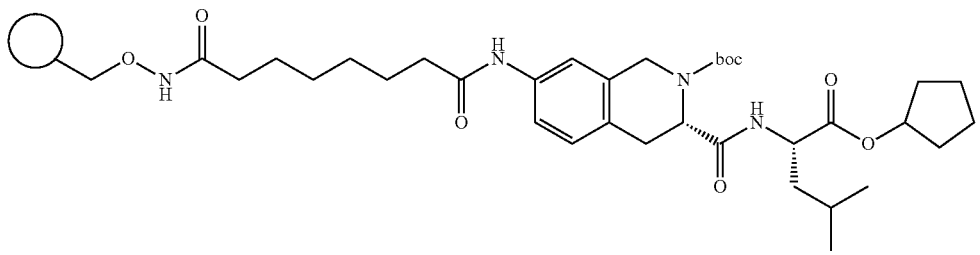

Suberic acid derivatised hydroxylamine 2-chlorotrityl resin (2.2 g, loading, 0.94 mmol/g) was swollen in DCM/DMF (1:1, 80 ml). PyBOP (3.20 g, 6.15 mmol) and diisopropylethylamine (3.54 ml, 20.7 mmol) were added. Stage 3 anilino amide (3.04 g, 6.43 mmol) dissolved in DMF (40 ml) was added and the reaction shaken for 3 days before filtrate removal and standard wash of the resin which was dried under air. Stage 6: (S)-2-{[(S)-7-(7-Hydroxycarbamoyl-heptanoylamino)-1,2,3,4-tetrahydro-isoquinoline-3-carbonyl]-amino}-4-methyl-pentanoic acid cyclopentyl ester (96)

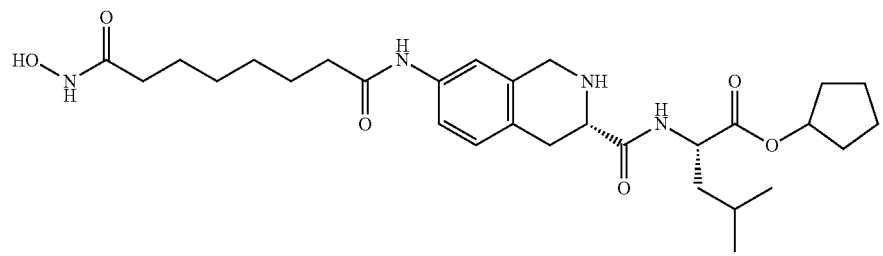

96

Stage 5 resin bound cyclopentyl ester (600 mg) was shaken with 2% TFA/DCM (8 ml) for 30 minutes before filtering the resin and evaporating the solvent under reduced pressure at room temperature. The crude product was purified by preparative HPLC to yield (S)-2-{[(S)-7-(7-Hydroxycarbamoyl-heptanoylamino)-1,2,3,4-tetrahydro-isoquinoline-3-carbonyl]-amino}-4-methyl-pentanoic acid cyclopentyl ester (17.5 mg). The boc group is removed in addition to resin cleavage. LCMS purity 98%, m/z 545 [M$^+$+H]$^+$, $^1$H NMR (400 MHz, MeOD), δ: 0.85-0.88 (6H, 2×d, J=6.4 Hz, J=6.5 Hz, 2×CH$_3$), 1.30 (4H, m, alkyl), 1.50-1.65 (13H, m, alkyl), 1.80 (2H, m, CH$_2$), 1.95 (2H, t, CH$_2$), 2.25 (2H, t, CH$_2$), 3.00 (1H, m, CH), 3.25 (1H, m, CH), 4.10 (1H, m, CH), 4.25 (2H, s, CH$_2$), 4.29 (1H, m, CH), 5.10 (1H, m, CH), 7.11 (1H, d, J=8.4 Hz, Ar), 7.25 (1H, d, J=8.3 Hz, Ar), 7.55 (2H, m, Ar).

Stage 7: (S)-2-{[(S)-7-(7-Hydroxycarbamoyl-heptanoylamino)-1,2,3,4-tetrahydro-isoquinoline-3-carbonyl]-amino}-4-methyl-pentanoic acid (96)

Synthesis of Compound (98) and Compound (99)

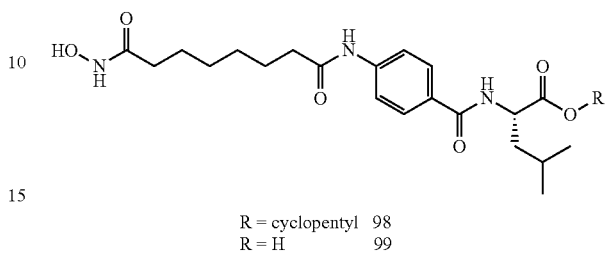

R = cyclopentyl 98
R = H 99

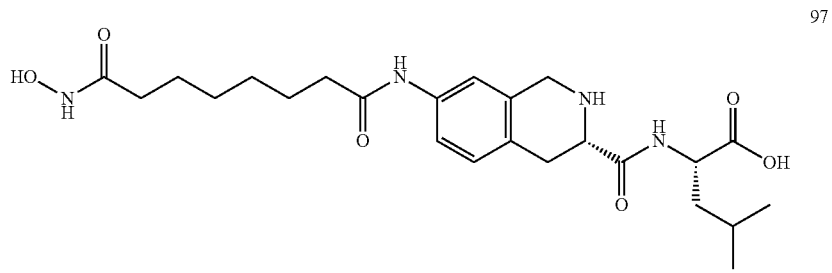 [SMILES: CC(C)C[C@H](NC(=O)[C@@H]1Cc2ccc(NC(=O)CCCCCCC(=O)NO)cc2CN1)C(=O)O]

97

Stage 5 cyclopentyl ester resin (1.55 g) was suspended in THF/MeOH (10 ml/10 ml). To the suspension was added NaOH (1.4 M aq., 5 ml) and the reaction shaken for 16 hr at r.t. The filtrate was removed and the resin washed (standard) and dried before cleavage. Cleavage (600 mg of resin) was effected by shaking with 2% TFA/DCM (8 ml) for 30 minutes before filtering the resin and evaporating the solvent under reduced pressure at room temperature. The crude product purified by preparative HPLC to yield Compound (97) (73.4 mg). The boc group is removed in addition to resin cleavage. LCMS purity 96%, m/z 477 [M$^+$+H]$^+$, $^1$H NMR (400 MHz, MeOD), δ: 0.98-1.02 (6H, 2×d, J=6 Hz, J=6.1 Hz, 2×CH$_3$), 1.40 (4H, m, alkyl), 1.60-1.80 (7H, m, alkyl), 2.10 (2H, t, J=7.4 Hz, CH$_2$), 2.39 (2H, t, 7.6 Hz, CH$_2$), 3.15 (1H, dd, J=12.5 Hz, J=16.6 Hz, CH), 3.45 (1H, dd, J=4.9 Hz, J=17 Hz, CH) 4.00 (1H, s, CH), 4.20 (1H, dd, J=4.7 Hz, J=12.2 Hz, CH), 4.40 (2H, m, CH$_2$), 4.55 (1H, dd, J=4.7 Hz, J=10 Hz, CH), 7.25 (1H, d, J=8.4 Hz, Ar), 7.25 (1H, d, J=8 Hz, Ar), 7.55 (1H, J=7 Hz, Ar).

Stage 1: (S)-4-Methyl-2-(4-nitro-benzoylamino)-pentanoic acid cyclopentyl ester

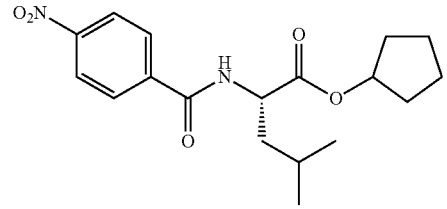 [SMILES: CC(C)C[C@H](NC(=O)c1ccc([N+](=O)[O-])cc1)C(=O)OC1CCCC1]

L-leucine cyclopentyl ester. TsOH salt (7.98 g, 21.51 mmol) was dissolved in THF (40 ml) and triethylamine (6 ml, 21.5 mmol) added. 4-Nitrobenzoyl chloride (4 g, 21.5 mmol) was added portionwise with cooling, ice bath. The reaction was stirred at room temperature for 16 h before evaporation to dryness. The residue was dissolved in DCM (100 ml) and washed with saturated sodium hydrogen carbonate (3×100 ml), 1 M HCl (3×100 ml) and brine, dried (Na$_2$SO$_4$), and the solvent removed in vacuo. to give the required product 5.25 g (70% yield) which was used in the next step without further purification, LCMS purity 100%, m/z 349 [M+ +H]+

Stage 2: (S)-2-(4-Amino-benzoylamino)-4-methyl-pentanoic acid cyclopentyl ester

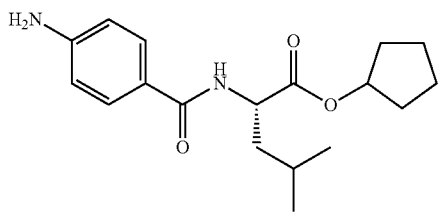

Stage 1 nitro amide (5.25 g, 15.1 mmol) was dissolved in ethanol (100 ml). Pd/carbon (200 mg) was added and the reaction stirred for 16 h at room temperature under hydrogen (balloon pressure). The reaction mixture was filtered through celite and evaporated to give the required amine amide 3.9 g (81% yield) which was used in the next step without further purification, LCMS purity 100%, m/z 319 [M+ +H]+

Stage 3: Coupling to Resin

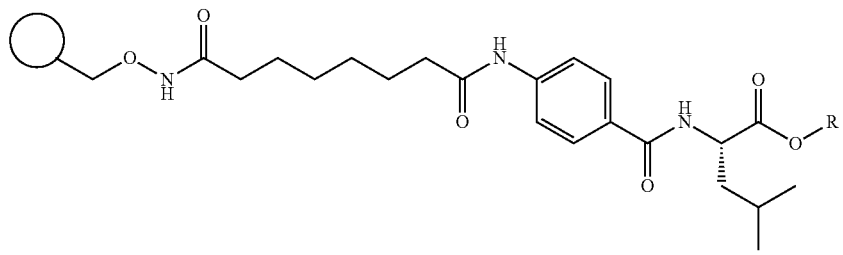

Suberic acid derivatised Wang hydroxylamine resin (1.6 g, loading, 1.8 mmol/g) was swollen in DCM (anhydrous, 20 ml). 1-Chloro-N,N-2-trimethylpropenylamine (1.15 ml, 8.64 mmol) was added dropwise before shaking at room temperature for 1 h. (S)-2-(4-Amino-benzoylamino)-4-methyl-pentanoic acid cyclopentyl ester (2.75 g, 8.64 mmol) was added followed by triethylamine (2.4 ml, 17.63 mmol) and the reaction shaken at room temperature for 16 h. The resin was washed (standard) and air dried.

Stage 4: (S)-2-[4-(7-Hydroxycarbamoyl-heptanoylamino)-benzoylamino]-4-methyl-pentanoic acid cyclopentyl ester (98)

98

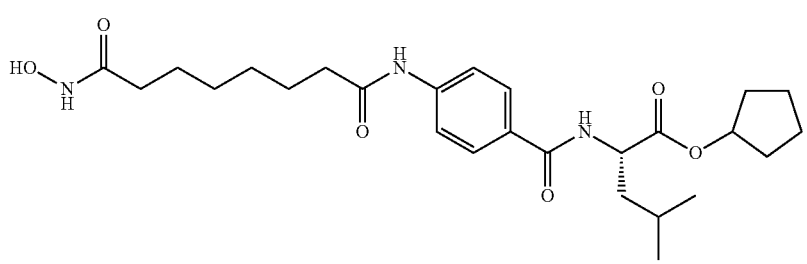

Stage 3 resin bound cyclopentyl ester was shaken with 2% TFA/DCM (10 ml) for 10 minutes before filtering the resin and evaporating the solvent under reduced pressure at room temperature. The process was repeated (×3) and the combined crude product purified by preparative HPLC to yield compound (98) (36 mg). LCMS purity 91%, m/z 490 [M+ +H]+, $^1$H NMR (400 MHz, MeOD), δ: 0.80-0.95 (6H, 2×CH$_3$), 1.25 (4H, m, alkyl), 1.40-1.85 (15H, m, alkyl), 2.00 (2H, t, CH$_2$), 2.30 (2H, t, CH$_2$), 4.45 (1H, m, CH), 5.05 (1H, m, CH), 7.60 (2H, d, Ar), 7.75 (2H, d, Ar).

Stage 5: (S)-2-[4-(7-Hydroxycarbamoyl-heptanoylamino)-benzoylamino]-4-methyl-pentanoic acid (99)

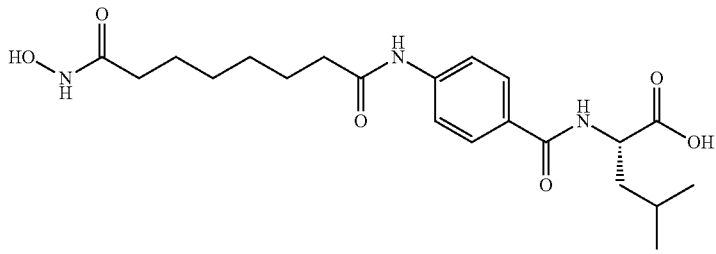

99

Compound (98) (21 mg, 0.043 mmol) was dissolved in THF (1 ml) and 2M NaOH (1 ml) added. The reaction vial was shaken for 16 h before THF removal by blowing a stream of $N_2$ gas at the surface of the solution. The aqueous residue was purified by preparative HPLC to yield compound (99) (5.2 mg). LCMS purity 92%, m/z 422 $[M^++H]^+$, $^1H$ NMR (400 MHz, MeOD), δ: 0.95-1.05 (6H, m, 2×$CH_3$), 1.30-1.50 (4H, m, alkyl), 1.55-1.85 (7H, m, alkyl), 2.10 (2H, t, $CH_2$), 2.40 (2H, t, $CH_2$), 4.65 (1H, m, CH), 7.65 (2H, d, Ar), 7.80 (2H, d, Ar).

Synthesis of Compound (100) and Compound (101)

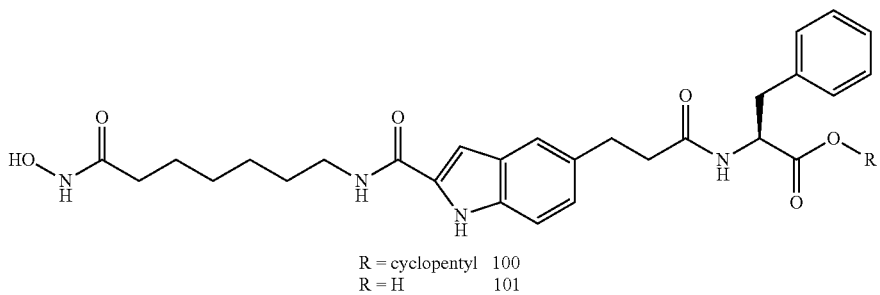

R = cyclopentyl  100
R = H            101

Stage 1: 5-((E)-2-Ethoxycarbonyl-vinyl)-1H-indole-2-carboxylic acid

50

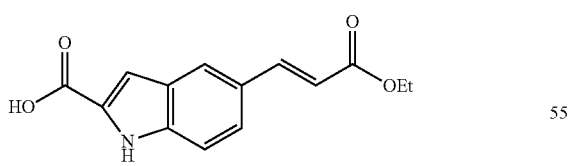

55

5-Bromoindole-2-carboxylic acid (400 mg, 1.66 mmol) and tri-O-tolylphosphine (96 mg, 0.32 mmol) were added to a microwave tube. Ethyl acrylate (0.56 ml, 5.6 mmol), $Et_3N$ (0.92 ml, 6.6 mmol), acetonitrile (2.5 ml) and Pd(OAc)$_2$ (40 mg, 0.18 mmol) were added. The reaction was placed in a CEM microwave at 150 W, 90° C. for 30 minutes with 5 min ramp time. EtOAc was added and the reaction mixture filtered through celite. The celite pad was washed with DCM and the combined organic fractions removed to give a yellow solid.

The solid was redissolved in DCM and extracted into saturated sodium hydrogen carbonate. The aqueous layer was washed with DCM and diethyl ether. The aqueous basic layer was acidified with 2M HCl (pH=5) and the product extracted into EtOAc. The solvent was removed to give the required product (370 mg, 86% yield). LCMS purity 86%, m/z 260 [M⁺+H]⁺

Stage 2: 5-((E)-2-Ethoxycarbonyl-vinyl)-1H-indole-2-carboxylic acid

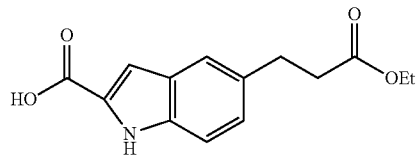 [SMILES: CCOC(=O)CCc1ccc2[nH]c(C(=O)O)cc2c1]

5-((E)-2-Ethoxycarbonyl-vinyl)-1H-indole-2-carboxylic acid (430 mg, 1.66 mmol) was dissolved in EtOAc (100 ml). Pd/carbon (100 mg) was added and the reaction stirred under a hydrogen atmosphere (balloon pressure) for 18 h. The reaction mixture was filtered through a pad of celite and washed with EtOAc. The solvent was removed to give the required product which was used in the next step without further purification (0.47 g). LCMS purity 92%, m/z 262 [M⁺+H]⁺

Stage 3: 3-{2-[6-(Tetrahydro-pyran-2-yloxycarbamoyl)-hexylcarbamoyl]-1H-indol-5-yl}-propionic acid ethyl ester

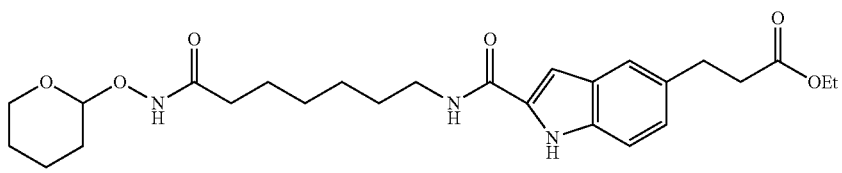 [SMILES: CCOC(=O)CCc1ccc2[nH]c(C(=O)NCCCCCCC(=O)NOC3CCCCO3)cc2c1]

5-((E)-2-Ethoxycarbonyl-vinyl)-1H-indole-2-carboxylic acid (0.427 g, 1.6 mmol) was dissolved in anhydrous DMF (20 ml). EDCl.HCl (0.38 g, 2 mmol), Et₃N (0.59 ml, 4.3 mmol), HOBt (0.27 g, 2 mmol) and 7 amino heptanoic acid (tetrahydropyran-2-yloxy) amide * (0.4 g, 1.6 mmol in anhydrous DMF 20 ml) were added and the reaction stirred at room temperature for 16 h under nitrogen. Water was added, the reaction mixture acidified to pH=6-7 (10% citric acid) and extracted with DCM. The organic layer was washed with 10% citric acid and saturated sodium hydrogen carbonate (x2). The solvent was removed in vacuo to give crude product which was purified by chromatography (EtOAc:hexane 1:2→EtOAc) to give the required product as a yellow solid (550 mg, 69% yield). LCMS purity 93%, m/z 488 [M⁺+H]⁺

Stage 4: 3-{2-[6-(Tetrahydro-pyran-2-yloxycarbamoyl)-hexylcarbamoyl]-1H-indol-5-yl}-propionic acid

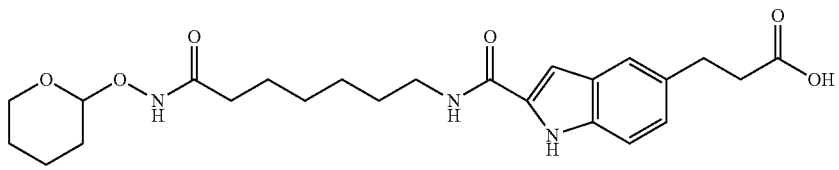 [SMILES: O=C(O)CCc1ccc2[nH]c(C(=O)NCCCCCCC(=O)NOC3CCCCO3)cc2c1]

3-{2-[6-(Tetrahydro-pyran-2-yloxycarbamoyl)-hexylcarbamoyl]-1H-indol-5-yl}-propionic acid ethyl ester (550 mg, 1.13 mmol) was dissolved in THF/methanol (50 ml/25 ml). 1.4 M NaOH solution (50 ml) was added and the reaction stirred at room temperature for 4 h. The solvent was reduced to ~50% volume and 1M HCl added to pH 6-7. The mixture was extracted with DCM and further extracted with EtOAc. The combined organic layer was dried, Na₂SO₄ and the solvent removed in vacuo to give the required product 357 mg (69% yield) as a yellow powder which was used in the next step without further purification. LCMS purity 94%, m/z 460 [M⁺+H]⁺

Stage 5: (S)-3-Phenyl-2-(3-{2-[6-(tetrahydro-pyran-2-yloxycarbamoyl)-hexyl-carbamoyl]-1H-indol-5-yl}-propionylamino)-propionic acid cyclopentyl ester

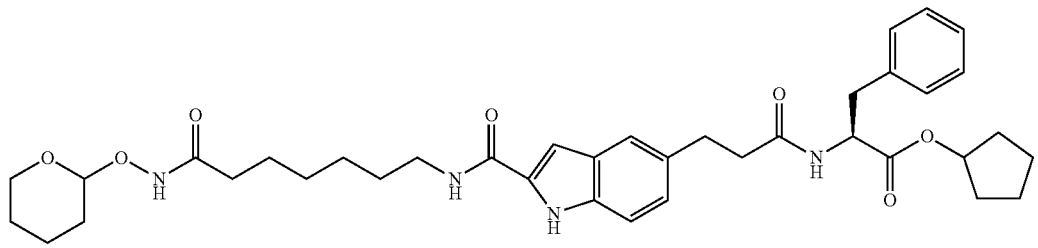 [SMILES: O=C(CCCCCCNC(=O)c1cc2cc(CCC(=O)N[C@@H](Cc3ccccc3)C(=O)OC3CCCC3)ccc2[nH]1)NOC1CCCCO1]

3-{2-[6-(Tetrahydro-pyran-2-yloxycarbamoyl)-hexylcarbamoyl]-1H-indol-5-yl}-propionic acid (0.357 g, 0.78 mmol) was dissolved in DCM/DMF (20 ml/20 ml). EDCl.HCl (0.163 mg, 0.86 mmol), triethylamine (0.24 ml, 1.7 mmol), HOBt (0.116 mg, 0.88 mmol) and L-phenylalanine cyclopentyl ester.TsOH salt (0.346 mg, 0.88 mmol) were added and the reaction mixture stirred for 16 h at room temperature under nitrogen. The solvent volume was reduced (~10 ml), DCM was added and the organic layer washed with water (×3). The organic layer was dried ($Na_2SO_4$) and the solvent removed to give the required product (500 mg, 95% yield) which was used without further purification. LCMS purity 77%, m/z 675 $[M^++H]^+$ Stage 6: (S)-2-{3-[2-(6-Hydroxycarbamoyl-hexyl-carbamoyl)-1H-indol-5-yl]-propionylamino}-3-phenyl-propionic acid cyclopentyl ester (100)

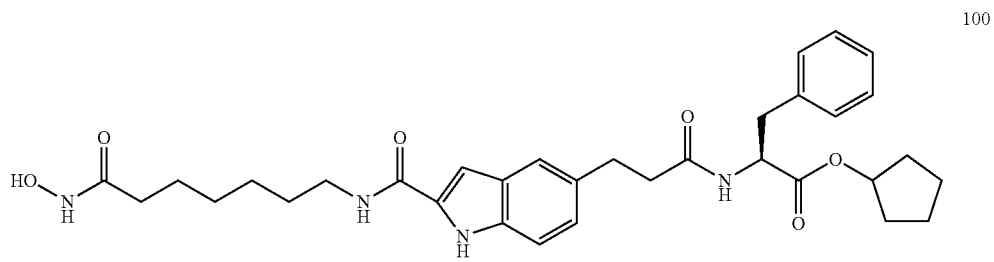 [SMILES: O=C(CCCCCCNC(=O)c1cc2cc(CCC(=O)N[C@@H](Cc3ccccc3)C(=O)OC3CCCC3)ccc2[nH]1)NO]

100

(S)-3-Phenyl-2-(3-{2-[6-(tetrahydro-pyran-2-yloxycarbamoyl)-hexyl-carbamoyl]-1H-indol-5-yl}-propionylamino)-propionic acid cyclopentyl ester (200 mg. 0.297 mmol) was stirred at room temperature for 3.5 h in TFA/DCM/MeOH (1.5 ml/15 ml/15 ml). Further TFA (0.3 ml) was added and the reaction stirred for a further 30 minutes. The solution was concentrated in vacuo, resuspended in DCM and the solvent removed (×3). The crude material was purified by prep HPLC to give pure compound (100) (19.3 mg), LCMS purity 100%, m/z 591 $[M^++H]^+$, $^1$H NMR (400 MHz, MeOD), δ: 1.27-1.70 (16 H, m, alkyl), 1.97 (2H, t, $CH_2$), 2.40 (2H, t, J=7.84 Hz, $CH_2$), 2.76-2.85 (4H, m, 2×$CH_2$), 3.25 (2H, t, J=7 Hz, $CH_2$), 4.41 (1H, m, NHCHCO, 4.95 (1H, m, CH), 6.85 (1H, s, CH), 6.95 (3H, m, Ar), 7.05 (3H, m, Ar), 7.20-7.26 (2H, s+d, J=8.5 Hz, Ar)

Stage 7: (S)-2-{3-[2-(6-Hydroxycarbamoyl-hexyl-carbamoyl)-1H-indol-5-yl]-propionylamino}-3-phenyl-propionic acid (101)

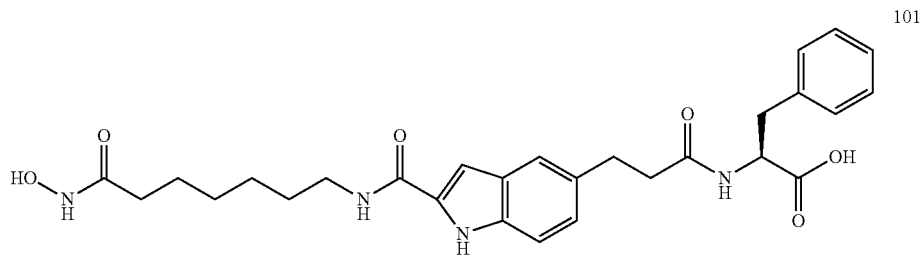 [SMILES: O=C(CCCCCCNC(=O)c1cc2cc(CCC(=O)N[C@@H](Cc3ccccc3)C(=O)O)ccc2[nH]1)NO]

101

Compound (100) (80 mg, 0.14 mmol) was dissolved in THF/MeOH (1 ml/0.5 ml) and 1.4 M NaOH (0.5 ml) added. The reaction was stirred at room temperature for 2 h. THF was removed by blowing a stream of N₂ gas at the surface of the solution and the residual material purified by preparative HPLC to give compound (101) (34.9 mg), LCMS purity 95%, m/z 523 [M⁺+H]⁺, ¹H NMR (400 MHz, MeOD), δ: 1.35-1.50 (4H, m, alkyl), 1.60-1.75 (4H, m, alkyl), 2.15 (2H, br t, CH₂), 2.55 (2H, br t, CH₂), 2.95 (3H, m, CH+CH₂), 3.10 (1H, dd, CH), 4.65, (1H, m, NHC$\underline{H}$CO), 7.00-7.15 (7H, m, Ar), 7.35-7.41 (2H, m, Ar)

Preparation of 7 amino heptanoic acid (tetrahydropyran-2-yloxy) amide

Stage 1: 6-(Tetrahydro-pyran-2-yloxycarbamoyl)-hexyl]-carbamic acid 9H-fluoren-9-ylmethyl ester

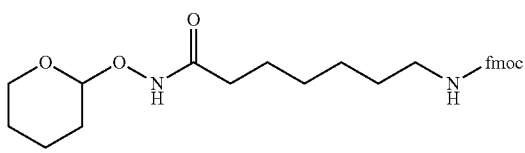

To a solution of 7-(9H-fluoren-9-yloxycarbonylamino) heptanoic acid (1 g, 2.72 mmol) in anhydrous DCM/THF (15 ml/15 ml) was added EDCl.HCl (627 mg, 3.27 mmol), HOBt (442 mg, 3.27 mmol) and O-(tetrahydro-pyran-2-yl)-hydoxy- for a further 24 h. The reaction mixture was diluted with DCM (100 ml), washed with water (3×100 ml), brine (100 ml), dried (Na₂SO₄), filtered and concentrated in vacuo. Purification by chromatography (MeOH:DCM 2:98) gave a white solid (1.03 g, 81%).

Stage 2: 7-Amino-heptanoic acid tetrahydro-pyran-2-yl ester

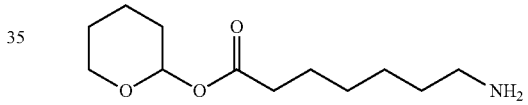

6-(Tetrahydro-pyran-2-yloxycarbamoyl)-hexyl]-carbamic acid 9H-fluoren-9-ylmethyl ester (300 mg, 0.644 mmol) was dissolved in 20% piperidine/DCM (30 ml) and the reaction stirred for 0.5 h. The reaction was evaporated to dryness, redissolved in DCM and evaporated (×3). The required product was obtained following chromatography (MeOH:DCM:NH₃), 120 mg. LCMS purity 98%, m/z 245 [M⁺+H]⁺.

Synthesis of Compound (102) and Compound (103)

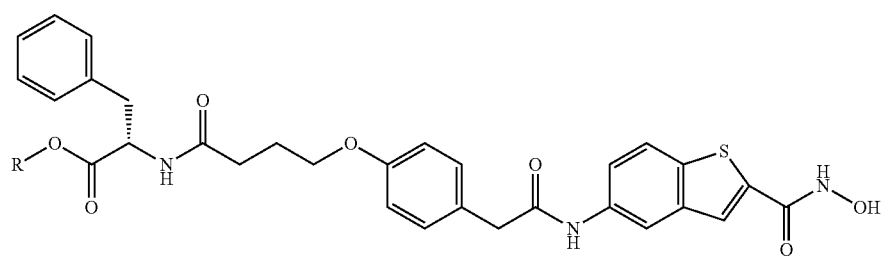

R = cyclopentyl 102
R = H 103

Stage 1: Resin Loading

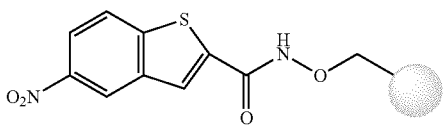

Wang hydroxylamine resin (3.72 g, 1.8 mmol/g) was swollen in DMF (50 ml). HATU (7.5 g, 19.7 mmol), 5-nitro-1-benzothiophene-2-carboxylic acid (3 g, 13.45 mmol, dissolved in DMF 150 ml) and diisopropylethylamine (4.65 ml, 26.7 mmol) were added and the resin shaken at room temperature for 4 d. The resin was filtered and washed using the standard washing procedure and air dried.

Stage 2: Nitro Reduction

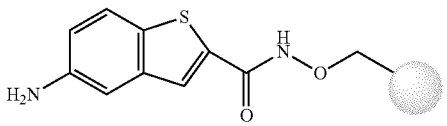

Stage 1 resin (4.9 g, 1.8 mmol/g), was swollen in DMF (200 ml) and tin chloride dihydrate (19.9 g, 88 mmol) added. The reaction was shaken at room temperature for 16 h. The resin was filtered and washed using the standard washing procedure and air dried.

Stage 3: 4-(4-Benzyloxycarbonylmethyl-phenoxy)-butyric acid methyl ester

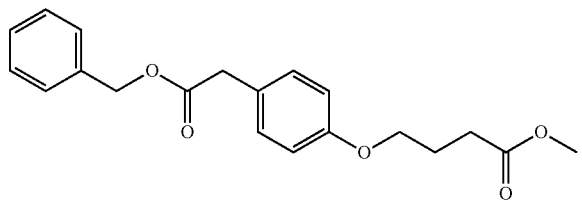 [SMILES: COC(=O)CCCOc1ccc(CC(=O)OCc2ccccc2)cc1]

Benzyl 4-hydroxyphenyl acetate (9 g, 37 mmol) was dissolved in DMF (300 ml). Ground sodium hydroxide (2.23 g, 56 mmol) and 4-methyl bromo butyrate (6.4 ml, 56 mmol) were added and the reaction heated at 60° C. for 16 h. Water was added to the cooled reaction mixture and the solution acidified (pH=5/6) with 1M HCl. The aqueous layer was extracted with EtOAc and the organic layer washed with water (×2), dried over $Na_2SO_4$, filtered and evaporated to dryness. The required diester was obtained following chromatography (EtOAc:heptane 1:2), (9.56 g, 75%) LCMS purity 90%, m/z 343 $[M^++H]^+$.

Stage 4: 4-(4-Carboxymethyl-phenoxy)-butyric acid methyl ester

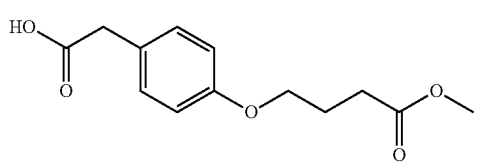 [SMILES: COC(=O)CCCOc1ccc(CC(=O)O)cc1]

4-(4-Benzyloxycarbonylmethyl-phenoxy)-butyric acid methyl ester (1.4 g, 4.09 mmol) was dissolved in EtOAc (60 ml). Pd/carbon (100 mg) was added and the reaction stirred under a hydrogen atmosphere (balloon) for 16 h at room temperature. The reaction mixture was filtered through a pad of celite and the pad washed with EtOAc. The filtrate was evaporated to dryness to give a white solid (1.03 g, 100% yield). LCMS purity 93%, m/z 253 $[M^++H]^+$.

Stage 5: Coupling to Resin

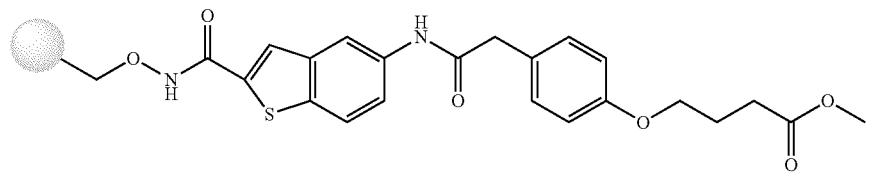

Stage 2 resin (0.18 g, 1.8 mmol/g) was swollen in DMF (5 ml). HATU (0.37 g, 0.96 mmol), 4-(4-Carboxymethyl-phenoxy)-butyric acid methyl ester (0.247 g, 0.96 mmol dissolved in DMF—10 ml) and diIsopropylamine (0.56 ml, 3.3 mmol) were added and the reaction shaken at room temperature for 16 h. The reaction was filtered and the resin washed using the standard wash procedure and air dried.

Stage 6: Ester Hydrolysis

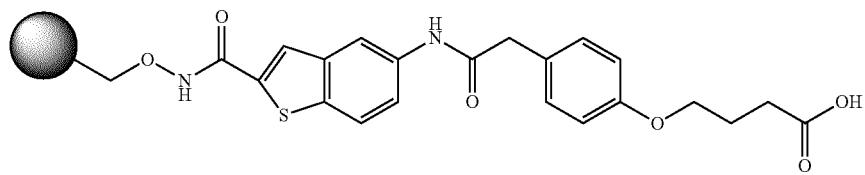 [SMILES: CCONC(=O)c1cc2cc(NC(=O)Cc3ccc(OCCCC(=O)O)cc3)ccc2s1]

Stage 5 methyl ester (280 mg, 1.8 mmol/g) was dissolved in THF/MeOH (4 ml/4 ml) and 1.4 M NaOH (8 ml) added. The reaction was shaken at r.t. for 16 h. The resin was filtered and washed using the standard wash and air dried.

Stage 7: Amino Acid Coupling

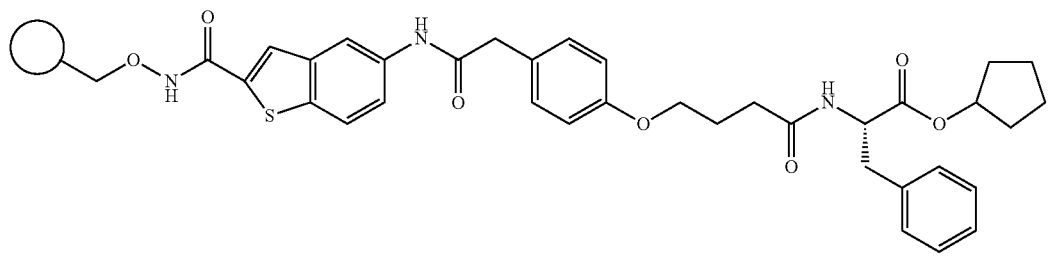 [SMILES: CCONC(=O)c1cc2cc(NC(=O)Cc3ccc(OCCCC(=O)N[C@@H](Cc4ccccc4)C(=O)OC4CCCC4)cc3)ccc2s1]

Stage 6 resin (1.6 g, 1.8 mmol/g) was swollen in anhydrous DMF (120 ml). HATU (3.3 g, 8.6 mmol), L-phenylalanine cyclopentyl ester. TsOH salt (3.4 g, 8.6 mmol) and diisopropylamine (5 ml, 2.9 mmol) were added and the reaction shaken at room temperature for 16 h. The reaction was filtered and the resin washed using the standard wash procedure and air dried.

Stage 8: (S)-2-(4-{4-[(2-Hydroxycarbamoyl-benzo[b]thiophen-5-ylcarbamoyl)-methyl]-phenoxy}-butyrylamino)-3-phenyl-propionic acid cyclopentyl ester (102)

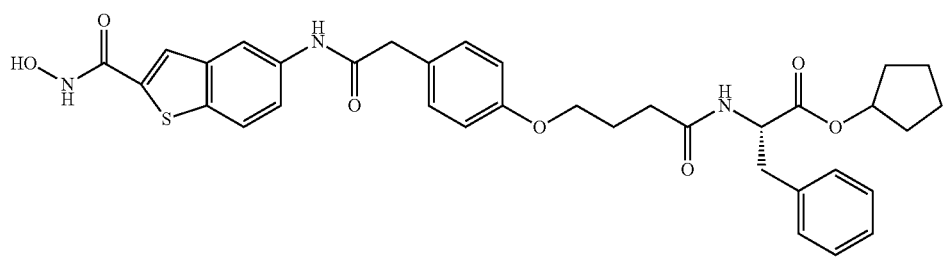

102

Stage 7 resin bound cyclopentyl ester was shaken with 2% TFA/DCM (10 ml) for 10 minutes before filtering the resin and evaporating the solvent under reduced pressure at room temperature. The process was repeated (×3) and the combined crude product purified by preparative HPLC to yield compound (102) (22.5 mg). LCMS purity 99%, m/z 644 [M++H]+, 1H NMR (400 MHz, MeOD), δ: 1.45-1.80 (6H, m, alkyl), 1.95 (2H, pent, CH$_2$), 2.34 (2H, t, J=7.3 Hz, CH$_2$), 2.90 (1H, dd, CH), 3.04 (1H, dd, CH), 3.62 (2H, s, CH$_2$), 3.86, (2H, m, CH$_2$), 4.55 (1H, m, NHCHCO), 5.07 (1H, br s, CH), 6.83 (2H, d, J=8.3 Hz, Ar), 7.14-7.18 (5H, m, Ar), 7.25 (2H, d, J=8 Hz, Ar), 7.47 (1H, d, J=9 Hz, Ar), 7.73 (1H, s, Ar), 7.81 (1H, d, J=8.8 Hz), 8.25 (1H, s, Ar)

Stage 9: (S)-2-(4-{4-[(2-Hydroxycarbamoyl-benzo[b]thiophen-5-ylcarbamoyl)-methyl]-phenoxy}-butyrylamino)-3-phenyl-propionic acid (103)

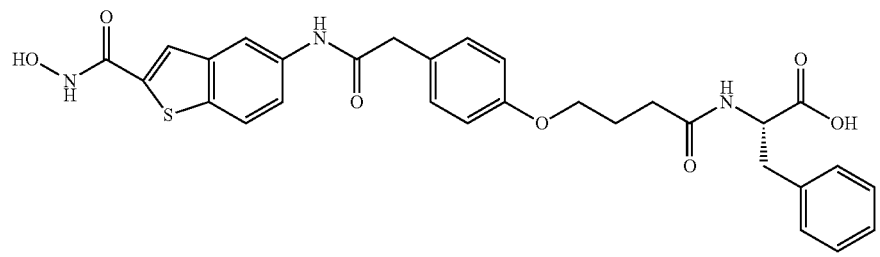

103

Stage 7 cyclopentyl ester resin (200 mg) was swollen in THF/MeOH (2 ml/2 ml) and 1.4 M NaOH (2 ml) added. The reaction was shaken at room temperature for 16 h. The resin was filtered and washed using the standard wash. Resin bound carboxylic acid was shaken with 2% TFA/DCM (3 ml) for 10 minutes before filtering the resin and evaporating the solvent under reduced pressure at room temperature. The process was repeated (×3) and the combined crude product purified by preparative HPLC to yield compound (103) (33.7 mg). LCMS purity 88%, m/z 576 [M++H]+, 1H NMR (400 MHz, d6-DMSO), δ:1.93 (2H, m, CH$_2$), 2.30 (2H, m, CH$_2$), 2.91 (1H, dd, J=9.9 Hz, J=13.8 Hz, CH), 3.13 (1H, dd, J=4.8 Hz, J=13.9 Hz, CH), 3.67 (2H, s, CH$_2$), 3.91, (2H, m, CH$_2$), 4.50 (1H, m, NHCHCO), 6.92 (2H, d, J=8.7 Hz, Ar), 7.24-7.34 (7H, m, Ar), 7.61 (1H, m), 7.92 (1H, br s, Ar), 8.00 (1H, d, J=8.8 Hz, Ar), 8.31 (1H, d, J=8.1 Hz, Ar), 8.39 (1H, s), 9.36 (1H, br s), 10.36 (1H, s), 11.52 (1H, s), 12.76 (1H, br s)

Synthesis of Compounds in Figure 7 as Exemplified for Compound (104) and Compound (105)

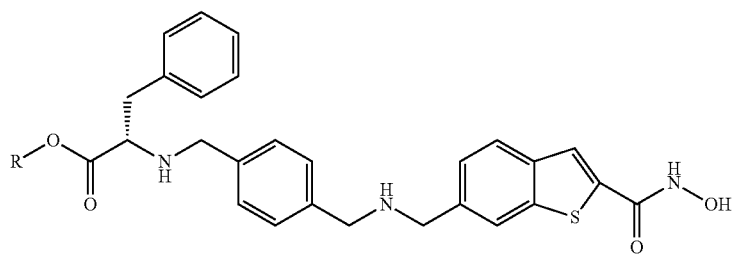

R = cyclopentyl 104
R = H 105

FIG. 7

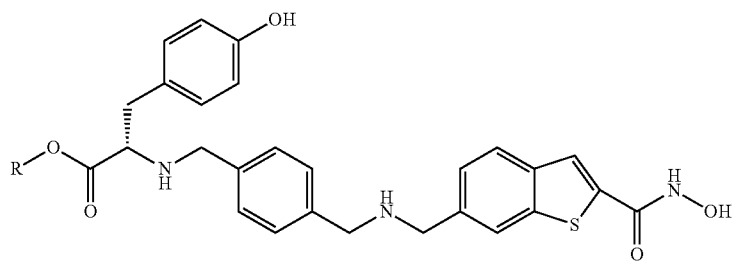
R = cyclopentyl 106
R = H 107
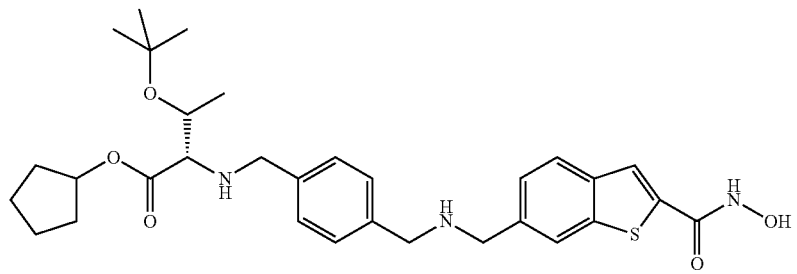
108
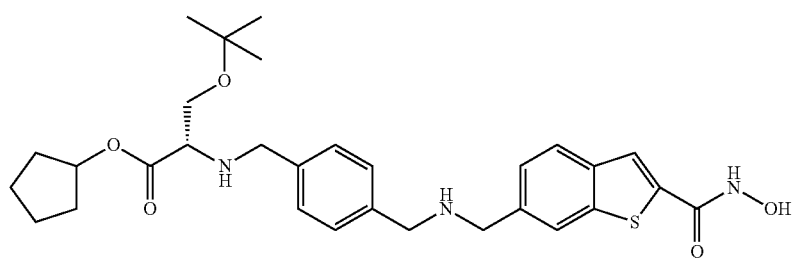
109
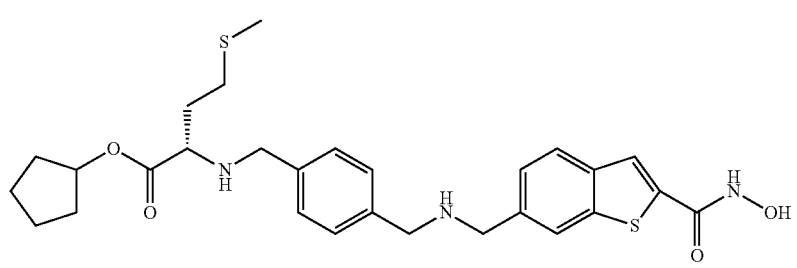
110
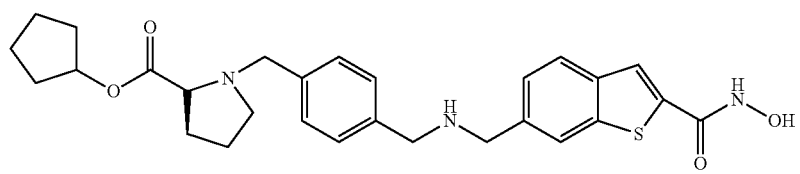
R = cyclopentyl 111
R = H 112

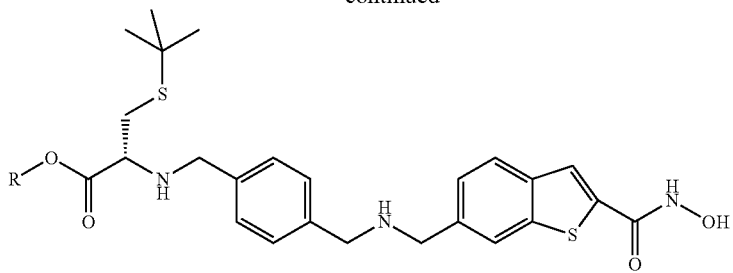
R = cyclopentyl 113
R = H 114
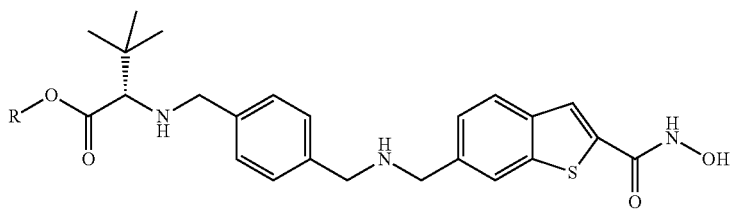
115
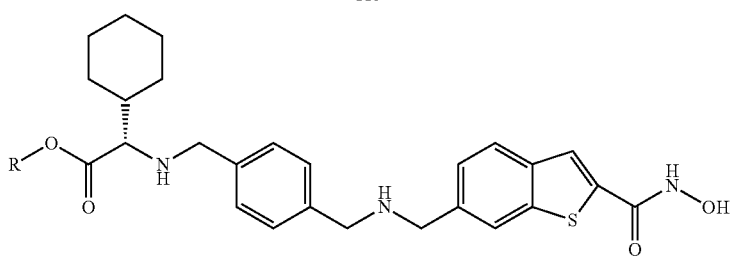
R = cyclopentyl 116
R = H 117
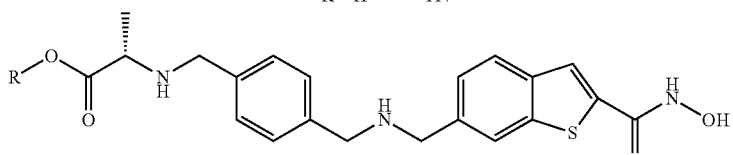
R = cyclopentyl 118
R = H 119
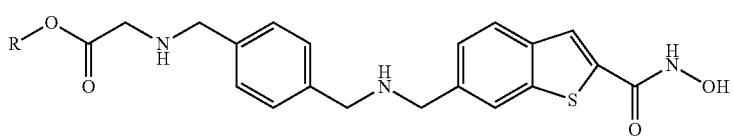
R = cyclopentyl 120
R = H 121
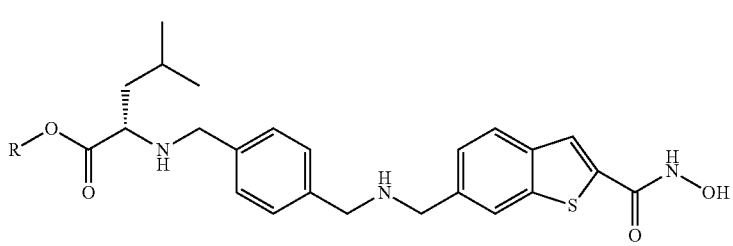
R = cyclopentyl 122
R = H 123

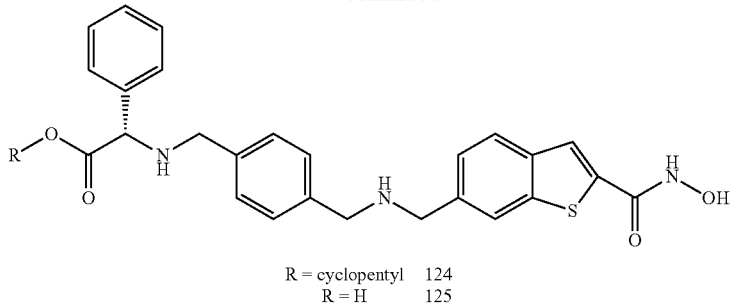

R = cyclopentyl 124
R = H 125

Step 1: 4-(tert-Butoxycarbonylamino-methyl)-benzoic acid

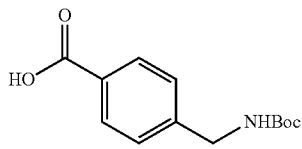 [SMILES: CC(C)(C)OC(=O)NCc1ccc(C(=O)O)cc1]

4-Aminomethylbenzyl alcohol (1.0 g, 6.60 mmol) was slurried in a mixture of THF (10 mL) and water (10 mL). A solution of saturated sodium hydrogen carbonate was added until the pH of the solution was >pH 9. The mixture was cooled to 0° C. and di-tert-butyldicarbonate (2.89 g, 13.23 mmol) added. The reaction was allowed to stir overnight then THF removed under vacuum. The aqueous mixture was extracted with EtOAc (20 mL) and then acidified to pH 3 by addition of 1N HCl. This was extracted with EtOAc (2×10 mL), the organic layers combined, dried (MgSO$_4$) and evaporated to dryness to afford the desired product (1.60 g, 97%). m/z 252 [M$^+$+H]$^+$

Step 2: (4-Hydroxymethyl-benzyl)-carbamic acid tert-butyl ester

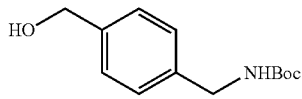

LiAl$_4$ (227 mg, 5.97 mmol) was slurried in a mixture of THF (5 mL) and dioxane (5 mL) and cooled to 0° C. under an atmosphere of N$_2$. 4-(tert-Butoxycarbonylamino-methyl)-benzoic acid was dissolved in a mixture of THF (5 mL) and dioxane (5 mL) and added to the chilled solution drop-wise over 15 min. The reaction mixture was allowed to warm to r.t and stirred for 16 h. Water (1 mL) was added to the reaction mixture which was then filtered through celite. The filtrate was evaporated to dryness and the residue partitioned between EtOAc (25 mL) and water (25 mL). The aqueous layer was extracted with EtOAC (2×25 mL), the organic layers combined, dried (Na$_2$SO$_4$) and evaporated to dryness to afford the desired product (460 mg, 100%). m/z 260 [M$^+$+Na]$^+$

Step 3: (4-Formyl-benzyl)-carbamic acid tert-butyl ester

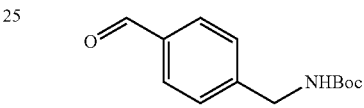

(4-Hydroxymethyl-benzyl)-carbamic acid tert-butyl ester (480 mg, 0.71 mmol) was dissolved in DCM (3 mL) and cooled to −78° C. (dry ice/acetone). Dess-Martin periodinane (331 mg, 0.78 mmol) was added to the reaction which was allowed to warm to r.t and stir for 3 h. A 1:1 solution of saturated sodium bicarbonate and sodium sulfite (20 mL) was added and the reaction mixture stirred vigorously for 15 min. The organic layer was isolated, washed with saturated sodium bicarbonate (10 mL), dried (Na$_2$SO$_4$) and evaporated to dryness to afford the desired compound (480 mg, 100%). m/z 258 [M$^+$+Na]$^+$

Step 4: (S)-2-[4-(tert-Butoxycarbonylamino-methyl)-benzylamino]-3-phenyl-propionic acid cyclopentyl ester

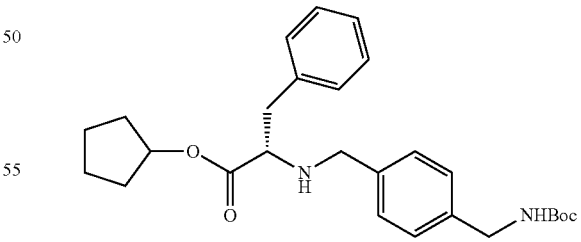

(4-Formyl-benzyl)-carbamic acid tert-butyl ester (200 mg, 0.85 mmol) was dissolved in DCE (10 mL) and to this was added phenyl alanine cyclopentyl ester (214 mg, 0.94 mmol). The reaction was stirred at r.t. for 15 min. Sodium triacetoxyborohydride (538 mg, 2.55 mmol) and acetic acid (60 uL) were added and the reaction stirred for a further 1 h. Saturated sodium bicarbonate (10 ml) was added and the solution diluted with DCM (20 mL). The organic layer was isolated and concentrated to afford the desired product which was taken onto the next step without further purification. m/z 453 [M++H+

Step 5: (S)-2-(4-Aminomethyl-benzylamino)-3-phenyl-propionic acid cyclopentyl ester

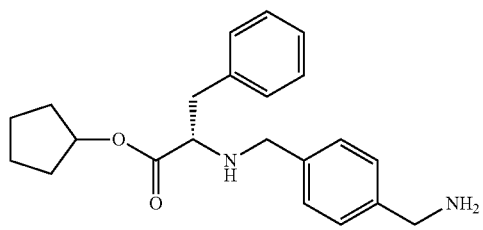 [SMILES: NCc1ccc(CN[C@@H](Cc2ccccc2)C(=O)OC2CCCC2)cc1]

(S)-2-[4-(tert-Butoxycarbonylamino-methyl)-benzylamino]-3-phenyl-propionic acid cyclopentyl ester was treated with 4M HCl in dioxane (1 mL, 0.25 mmol) and stirred at r.t. for 1 h. The mixture was evaporated to dryness and partitioned between EtOAc (20 mL) and water (20 mL). Saturated sodium bicarbonate (20 mL) was added to the aqueous layer which was then extracted with EtOAc (3×20 mL). The organic layers were combined, dried (Na$_2$SO$_4$) and evaporated to dryness to give the desired product (263 mg, 79% over 2 steps). m/z 353 [M++H]+

Step 6: (S)-2-[4-({[2-(1-Isobutoxy-ethoxycarbamoyl)-benzo[b]thiophen-6-ylmethyl]-amino}-methyl)-benzylamino]-3-phenyl-propionic acid cyclopentyl ester

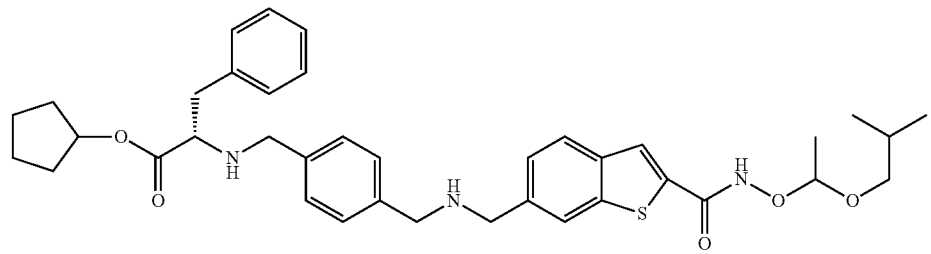 [SMILES: CC(C)COC(C)ONC(=O)c1cc2ccc(CNCc3ccc(CN[C@@H](Cc4ccccc4)C(=O)OC4CCCC4)cc3)cc2s1]

6-formyl-benzo[b]thiophene-2-carboxylic acid (1-isobutoxy-ethoxy) amide (Scheme 7) (220 mg, 0.68 mmol) and (S)-2-(4-Aminomethyl-benzylamino)-3-phenyl-propionic acid cyclopentyl ester (263 mg, 0.75 mmol) were dissolved in DCE (10 mL) under an atmosphere of N$_2$. Sodium triacetoxyborohydride (430 mg, 2.04 mmol) and acetic acid (50 µL) were added and the reaction stirred at r.t for 3 h. Sodium hydrogen carbonate (20 mL) was added and the reaction mixture extracted with dichloromethane (3×50 mL). The organic layers were combined and concentrated. The residue was purified by column chromatography (50%-100% EtOAc/heptane) to give the protected compound (80 mg, 21%). m/z 658 [M++H]+

Step 7: (S)-2-(4-{[(2-Hydroxycarbamoyl-benzo[b]thiophen-6-ylmethyl)-amino]-methyl}-benzylamino)-3-phenyl-propionic acid cyclopentyl ester (104)

104

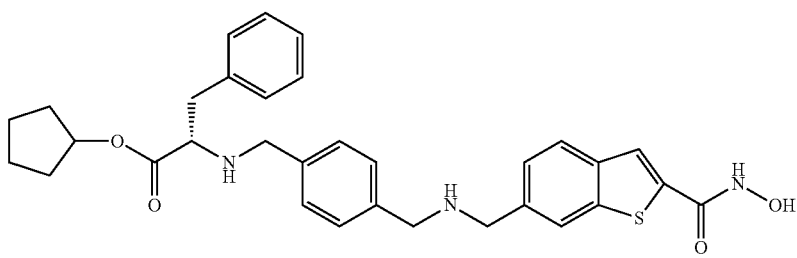

(S)-2-[4-({[2-(1-Isobutoxy-ethoxycarbamoyl)-benzo[b]thiophen-6-ylmethyl]-amino}-methyl)-benzylamino]-3-phenyl-propionic acid cyclopentyl ester was dissolved in DCM (2 mL) and MeOH (2 mL) and treated with TFA (1 mL). The mixture was stirred for 1 h at r.t then concentrated to dryness and DCM (5 mL) and heptane (5 mL) added. The mixture was evaporated to dryness. This process was repeated three times to yield compound (104) (20 mg, 59%) as a oil. LCMS purity 95%, m/z 558 [M$^+$+H]$^+$, 1H NMR (300 MHz, MeOD), δ: 1.25-1.91 (8H, m, 4×CH2), 3.12-3.47 (2H, m, CH2), 4.26 (1H, m, CH), 4.33 (2H, d, J=5.5 Hz, CH2), 4.36 (2H, s, CH2), 4.43 (1H, s, CH2), 5.16 (1H, s, CH), 5.13 (1H, m, CH), 7.25-7.37 (6H, m, ArH), 7.54-7.63 (4H, m, ArH), 7.94 (2H, m, ArH), 8.09 (1H, s, ArH).

Step 8: (S)-2-[4-({[2-(1-Isobutoxy-ethoxycarbamoyl)-benzo[b]thiophen-6-ylmethyl]amino}-methyl)-benzylamino]-3-phenyl-propionic acid

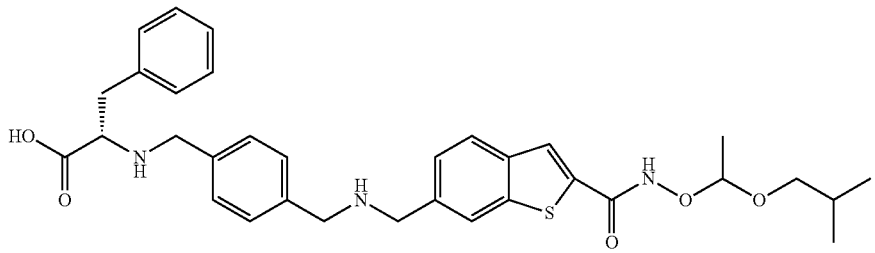 [SMILES: CC(C)COC(C)ONC(=O)c1cc2ccc(CNCc3ccc(CN[C@@H](Cc4ccccc4)C(=O)O)cc3)cc2s1]

(S)-2-[4-({[2-(1-Isobutoxy-ethoxycarbamoyl)-benzo[b]thiophen-6-ylmethyl]-amino}-methyl)-benzylamino]-3-phenyl-propionic acid cyclopentyl ester (40 mg, 0.06 mmol) was dissolved in THF (2 mL) and water (2 mL). LiOH (8 mg, 0.30 mmol) was added and the reaction mixture heated to 50° C. for 36 h. THF was removed by evaporation and the residue partitioned between water (10 mL) and EtOAc (10 mL). The aqueous layer was isolated and the pH adjusted to 3 by addition of 1M HCl. This was extracted with EtOAc (3×20 mL), the organic layers combined and evaporated to dryness.

Step 9: (S)-2-(4-{[(2-Hydroxycarbamoyl-benzo[b]thiophen-6-ylmethyl)-amino]-methyl}-benzylamino)-3-phenyl-propionic (105)

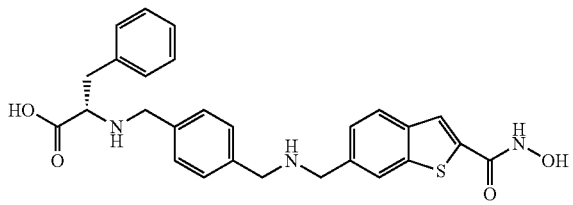

(S)-2-[4-({[2-(1-Isobutoxy-ethoxycarbamoyl)-benzo[b]thiophen-6-ylmethyl]-amino}-methyl)-benzylamino]-3-phenyl-propionic acid was dissolved in MeOH (2 mL) and THF (2 mL). TFA (1 mL) was added at the mixture stirred for 1 h at r.t. The reaction mixture was concentrated to dryness and DCM (5 mL) and heptane (5 mL) added. The mixture was evaporated to dryness. This process was repeated three times to yield compound (105) (17 mg, 57%) as a pink solid. LCMS purity 90%, m/z 490 [M$^+$+H]$^+$, 1H NMR (300 MHz, MeOD), δ: 3.33 (2H, m, CH2), 4.19 (1H, m, CH2), 4.29 (2H, s, CH2), 4.35 (2H, s, CH2), 4.42 (2H, s, CH2), 7.29-7.39 (5H, m, ArH), 7.54-7.72 (5H, m, ArH), 7.88 (1H, s, ArH), 8.00 (1H, d J=8.0 Hz, ArH), 8.08 (1H, s, ArH)

The following compounds were prepared according to the procedure described for compound (104) and compound (105)

(S)-2-(4-{[(2-Hydroxycarbamoyl-benzo[b]thiophen-6-ylmethyl)-amino]-methyl}-benzylamino)-3-(4-hydroxy-phenyl)-propionic acid cyclopentyl ester (106)

LCMS purity 98%, m/z 574 [M$^+$+H]$^+$, $^1$H NMR (300 MHz, MeOD), δ: 1.30-1.87 (8H, m, 4×CH$_2$), 2.97-3.35 (2H, m, CH$_2$), 4.17 (1H, m, CH), 4.31 (2H, d, J=5.4 Hz, CH$_2$), 4.36 (2H, s, CH$_2$), 4.42 (2H, s, CH$_2$), 5.11-5.16 (1H, m, CH), 6.77 (2H, d, J=8.4 Hz, Ar—H), 7.06 (2H, d, J=8.4 Hz, Ar—H), 7.54-7.65 (5H, m, Ar—H), 7.87 (1H, s, Ar—H), 7.99 (1H, d, J=8.4 Hz, Ar—H), 8.08 (1H, s, Ar—H)

(S)-2-(4-{[(2-Hydroxycarbamoyl-benzo[b]thiophen-6-ylmethyl)-amino]-methyl}-benzylamino)-3-(4-hydroxy-phenyl)-propionic acid (107)

LCMS purity 90%, m/z 505 [M$^+$+H]$^+$, $^1$H NMR (300 MHz, MeOD), δ: 3.09-3.27 (2H, m, CH2), 4.03 (1H, m, CH), 4.24 (2H, s, CH2), 4.34 (2H, s, CH2), 4.42 (2H, s, CH2), 6.76 (2H, d J=8.3 Hz, Ar—H), 7.11 (2H, d J=8.5 Hz, Ar—H), 7.56-7.59 (5H, m, Ar—H), 7.89 (1H, s, Ar—H), 8.02 (1H, d, J=8.4 Hz, Ar—H), 8.08 (1H, s, Ar—H)

(S)-3-tert-Butoxy-2-(4-{[(2-hydroxycarbamoyl-benzo[b]thiophen-6-ylmethyl)-amino]-methyl}-benzylamino)-butyric acid cyclopentyl ester (108)

LCMS purity 99%, m/z 568 [M$^+$+H]$^+$, $^1$H NMR (300 MHz, MeOD), δ: 1.20 (9H, s, 3×CH$_3$), 1.29 (3H, d, J=6.6 Hz, CH$_3$), 1.67-1.94 (8H, m, 4×CH$_2$), 3.75 (1H, d, J=2.7 Hz, CH), 4.29-4.32 (1H, m, CH), 4.36 (4H, d, J=2.4 Hz, 2×CH$_2$), 4.43 (2H, s, CH$_2$), 5.22-5.25 (1H, m, CH), 7.54-7.65 (5H, m, Ar—H), 7.88 (1H, s, Ar—H), 8.01 (1H, d, J=8.1 Hz, Ar—H), 8.08 (1H, s, Ar—H)

(S)-3-tert-Butoxy-2-(4-{[(2-hydroxycarbarnoyl-benzo[b]thiophen-6-ylmethyl)-amino]-methyl}-benzylamino)-propionic acid cyclopentyl ester (109)

LCMS purity 95%, m/z 554 [M$^+$+H]$^+$, $^1$H NMR (300 MHz, MeOD), δ: 1.23 (9H, s, 3×CH$_3$), 1.67-1.98 (8H, m, 4×CH$_2$), 3.87-3.98 (2H, m, CH$_2$), 4.19-4.22 (1H, m, CH), 4.34-4.36 (4H, m, 2×CH$_2$), 4.42 (2H, s, CH$_2$), 5.31-5.35 (1H, m, CH), 7.54-7.62 (5H, m, Ar—H), 7.87 (1H, s, Ar—H), 8.00 (1H, d, J=8.1 Hz, Ar—H), 8.08 (1H, s, Ar—H)

(S)-2-(4-{[(2-Hydroxycarbamoyl-benzo[b]thiophen-6-ylmethyl)-amino]-methyl}-benzylamino)-4-methylsulfanyl-butyric acid cyclopentyl ester (110)

LCMS purity 90%, m/z 541 [M$^+$+H]$^+$, $^1$H NMR (300 MHz, MeOD), δ: 1.70-1.98 (8H, m, 4×CH$_2$), 2.11 (3H, s, CH$_3$), 2.17-2.34 (2H, m, CH$_2$), 2.54-2.73 (2H, m, CH$_2$), 4.19-4.23 (1H, m, CH), 4.27-4.42 (6H, m, 3×CH$_2$), 5.35-5.39 (1H, m, CH), 7.54-7.63 (5H, m, Ar—H), 7.87 (1H, s, Ar—H), 7.97-8.00 (1H, m, Ar—H), 8.08 (1H, s, Ar—H)

(S)-1-(4-{[(2-Hydroxycarbamoyl-benzo[b]thiophen-6-ylmethyl)-amino]-methyl}-benzyl)-pyrrolidine-2-carboxylic acid cyclopentyl ester (111)

LCMS purity 96%, m/z 508 [M$^+$+H]$^+$, $^1$H NMR (300 MHz, MeOD), δ: 1.66-2.29 (12H, m, 6×CH$_2$), 3.59-3.67 (2H, m, CH$_2$), 4.38-4.46 (6H, m, 3×CH$_2$), 4.62 (1H, d, J=12.3 Hz, CH), 5.21 (1H, m, CH), 7.61-7.68 (5H, m, Ar—H), 7.88 (1H, s, Ar—H), 8.00-8.02 (1H, m, Ar—H), 8.13 (1H, s, Ar—H)

(S)-1-(4-{[(2-Hydroxycarbamoyl-benzo[b]thiophen-6-ylmethyl)-amino]-methyl}-benzyl)-pyrrolidine-2-carboxylic acid (112)

LCMS purity 100%, m/z 440 [M$^+$+H]$^+$, $^1$H NMR (300 MHz, MeOD), δ: 1.96-2.09 (2H, m, CH$_2$), 2.14-2.23 (2H, m, CH$_2$), 2.52-2.65 (1H, m, CH$_2$), 3.56-3.67 (1H, m, CH$_2$), 4.19-4.25 (1H, m, CH), 4.36-4.57 (6H, m, 3×CH$_2$), 7.55-7.64 (5H, m, Ar—H), 7.88 (1H, s, Ar—H), 7.99-8.01 (1H, m, Ar—H), 8.09 (1H, s, Ar—H)

(R)-3-tert-Butylsulfanyl-2-(4-{[(2-hydroxycarbamoyl-benzo[b]thiophen-6-ylmethyl)-amino]-methyl}-benzylamino)-propionic acid cyclopentyl ester (113)

LCMS purity 97%, m/z 570 [M+H]$^+$, $^1$H NMR (300 MHz, MeOD), δ: 1.36 (9H, s), 1.79 (8H, m), 3.16 (2H, d, 5.3 Hz), 4.25 (2H, t, J=5.6 Hz), 4.31 (2H, s), 4.36 (2H,$), 4.42 (2H, s), 5.34 (1H, m), 7.56 (1H, d, J=8.1 Hz), 7.62 (4H, s), 7.89 (1H, s), 8.09 (1H, s), 8.51 (1H, d, J=8.1 Hz),

(R)-3-tert-Butylsulfanyl-2-(4-{[(2-hydroxycarbamoyl-benzo[b]thiophen-6-ylmethyl)-amino]-methyl}-benzylamino)-propionic acid (114)

LCMS purity 97%, m/z 502 [M]$^+$, $^1$H NMR (300 MHz, MeOD), δ: 1.35 (9H, s, 3×CH$_3$), 3.09 (2H, m, CH$_2$), 3.22 (2H, m, CH$_2$), 3.83 (1H, t, J=8.8 Hz, CH), 4.34 (2H, s, CH$_2$), 4.42 (2H, s, CH$_2$), 7.57 (1H, d, J=10.0 Hz, ArH), 7.62 (4H, s, ArH×4), 7.89 (1H, s, ArH), 8.02 (1H, d, J=8.1 Hz, ArH), 8.09 (1H, s, ArH).

(S)-2-(4-{[(2-Hydroxycarbamoyl-benzo[b]thiophen-6-ylmethyl)-amino]-methyl}-benzylamino)-3,3-dimethyl-butyric acid cyclopentyl ester (115)

LCMS purity 94%, m/z 546 [M+Na]$^+$, $^1$H NMR (300 MHz, MeOD), δ: 1.08 (9H, s, 3×CH$_3$), 1.80 (8H, m, 4×CH$_2$), 3.49 (1H, s, CH), 4.29 (2H, d, J=13.5 Hz, CH$_2$), 4.29 (2H, d, J=13.5 Hz, CH$_2$), 4.36 (2H, s, CH$_2$), 4.44 (2H, s, CH$_2$), 5.19 (1H, t, J=5.7 Hz), 7.59 (5H, m, ArH×5), 7.88 (1H, ArH), 8.00 (1H, d, J=8.3 Hz), 8.09 (1H, s, ArH).

(S)-Cyclohexyl-(4-{[(2-hydroxycarbamoyl-benzo[b]thiophen-6-ylmethyl)-amino]-methyl}-benzylamino)-acetic acid cyclopentyl ester (116)

LCMS purity 100%, m/z 550 [M+H]$^+$, $^1$H NMR (300 MHz, MeOD), δ: 0.86-1.95 (18H, m, 9×CH2), 3.73 (1H, m, CH), 4.11 (1H, d J=5.7 Hz, CH), 4.19 (2H, s, CH2), 4.26 (2H, s, CH2), 4.36 (2H, s, CH2), 7.53 (5H, m, ArH), 7.77 (1H, s, CH), 7.82 (1H, d J=11.6 Hz, ArH), 8.02 (1H, s, ArH)

(S)-Cyclohexyl-(4-{[(2-hydroxycarbamoyl-benzo[b]thiophen-6-ylmethyl)-amino]-methyl}-benzylamino)-acetic acid (117)

LCMS purity 100%, m/z 482 [M+H]$^+$, $^1$H NMR (300 MHz, MeOD), δ: 0.72-1.60 (10H, m, 9×CH2), 3.89 (1H, m, CH), 4.11 (3H, m, CH), 4.23 (2H, s, CH2), 4.31 (2H, s, CH2), 7.48 (5H, m, ArH), 7.76 (1H, s, CH), 7.88 (1H, d J=11.6 Hz, ArH), 7.98 (1H, s, ArH).

(S)-2-(4-{[(2-Hydroxycarbamoyl-benzo[b]thiophen-6-ylmethyl)-amino]-methyl}-benzylamino-4-methyl-pentanoic acid cyclopentyl ester (122)

LCMS purity 94%, m/z 524 [M$^+$+H]$^+$, 1H NMR (300 MHz, MeOD), δ: 1.01 (6H, s, 2×CH3), 1.28 (1H, m, CH), 1.56-1.95 (10H, m, 4×CH2, CH2), 4.00-4.43 (6H, m, 3×CH2), 4.88 (1H, m, CH), 5.36 (1H, br s, CH), 7.47-7.62 (5H, m, ArH), 7.94 (2H, t, ArH), 8.08 (1H, s, ArH).

(S)-2-(4-{[(2-Hydroxycarbamoyl-benzo[b]thiophen-6-ylmethyl)-amino]-methyl}-benzylamino)-4-methyl-pentanoic acid (123)

LCMS purity 98%, m/z 456 [M$^+$+H]$^+$, 1H NMR (300 MHz, MeOD), δ: 1.00 (6H, m, 2×CH3), 1.86 (2H, m, CH2), 3.86 (1H, m, CH), 4.29 (2H, s, CH2), 4.36 (2H, s, CH2), 4.43 (2H, s, CH2), 7.56 (1H, m, ArH), 7.89 (1H, s, CH), 8.02 (1H, d J=8.2 Hz, ArH), 8.09 (1H, s, ArH).

(S)-(4-{[(2-Hydroxycarbamoyl-benzo[b]thiophen-6-ylmethyl)-amino]-methyl}-benzylamino)-phenyl-acetic acid cyclopentyl ester (124)

LCMS purity 90%, m/z 544 [M$^+$+H]$^+$, 1H NMR (300 MHz, MeOD), δ: 1.31-1.91 (10H, m, 4×CH2, CH2), 4.22 (2H, dd J=13.1 Hz, CH2), 4.35 (2H, s, CH2), 4.42 (1H, s, CH2), 5.16 (1H, s, CH), 5.30 (1H, m, CH), 7.47-7.62 (9H, m, ArH), 7.94 (2H, m, ArH), 8.08 (1H, s, ArH).

(S)-(4-{[(2-Hydroxycarbamoyl-benzo[b]thiophen-6-ylmethyl)-amino]-methyl}-benzylamino)-phenyl-acetic acid (125)

LCMS purity 100%, m/z 476 [M$^+$+H]$^+$, 1H NMR (300 MHz, MeOD), δ: 4.08-4.24 (3H, m, CH, CH2), 4.35 (2H, s, CH2), 4.43 (1H, s, CH2), 7.46-7.75 (10H, m, ArH), 7.89 (1H, s, ArH), 8.01 (1H, d J=7.9 Hz, ArH), 8.09 (1H, s, ArH)

The following compounds were prepared according to the procedure described for compound (104) and compound (105) using alternatives for step 3 and 4 as outlined below Step 3b: (4-Bromomethyl-benzyl)-carbamic acid tert-butyl ester

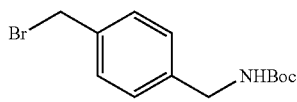

N-Bromosuccinimide (5.13 g, 28.8 mmol) was dissolved in DCM (80 mL) and cooled to 0° C. A solution of triphenylphosphine (7.18 g, 27.0 mmol) in DCM (20 mL) was prepared and added to the chilled solution followed by pyridine (1.0 mL, 1.26 mmol). Material from step 2 (2.14 g, 9.0 mmol) was dissolved in DCM (20 mL) and added and the reaction allowed to warm to r.t. and stirred for 16 h. The mixture was concentrated and the residue purified by column chromatography (50%/50% EtOAc/heptane) to afford the desired compound (864 mg, 32%). m/z 301 [M$^+$+Na]$^+$ Step 4b: (S)-2-[4-(tert-Butoxycarbonylamino-methyl)-benzylamino]-propionic acid cyclopentyl ester

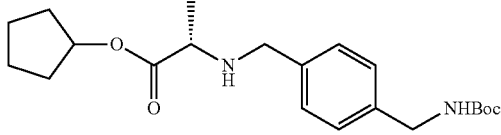 [SMILES: C[C@H](NCc1ccc(CNC(=O)OC(C)(C)C)cc1)C(=O)OC1CCCC1]

L-Alanine cyclopentyl ester (463 mg, 1.41 mmol) was dissolved in DMF (9 mL) and to this was added DIPEA (0.74 mL, 4.24 mmol). The mixture was stirred at r.t. for 15 min and then a solution of material from step 3b (212 mg, 0.706 mmol) in DMF (5 mL) added dropwise over 1 hr. The reaction was then allowed to stir at r.t. for 16 hr and was then diluted with water (50 mL) and EtOAc (50 mL). The organic layer was washed with brine (2×50 mL), dried and concentrated to give crude material (0.26 g, 100%) which was taken to the next step without further purification. m/z 377 [M$^+$+Na]$^+$ Steps 5-9 were as described for compound (104) and compound (105)

(S)-2-(4-{[(2-Hydroxycarbamoyl-benzo[b]thiophen-6-ylmethyl)-amino]-methyl}-benzylamino)-propionic acid cyclopentyl ester (118)

LCMS purity 95%, m/z 482 [M$^+$+H]$^+$, $^1$H NMR (300 MHz, MeOD), δ: 1.61 (3H, d, J=7.2 Hz, CH$_3$), 1.71-1.97 (8H, m, 4×CH$_2$), 4.13 (1H, q, J=7.2 Hz, CH), 4.30 (2H, s, CH$_2$), 4.36 (2H, s, CH$_2$), 4.43 (2H, s, CH$_2$), 5.33-5.36 (1H, m, CH), 7.54-7.63 (5H, m, Ar—H), 7.88 (1H, s, Ar—H), 8.00 (1H, d, J=8.1 Hz, Ar—H), 8.08 (1H, s, Ar—H)

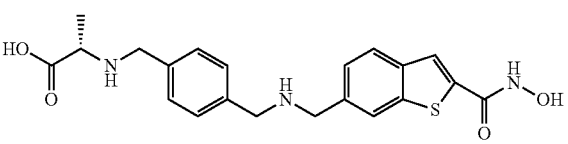 [SMILES: C[C@H](NCc1ccc(CNCc2ccc3cc(C(=O)NO)sc3c2)cc1)C(=O)O]

(S)-2-(4-{[(2-Hydroxycarbamoyl-benzo[b]thiophen-6-ylmethyl)-amino]-methyl}-benzylamino)-propionic acid (119)

LCMS purity 95%, m/z 414 [M$^+$+H]$^+$, $^1$H NMR (300 MHz, MeOD), δ: 1.64 (3H, d, J=7.1 Hz, CH$_3$), 4.06-4.14 (1H, m, CH), 4.31 (2H, s, CH$_2$), 4.36 (2H, s, CH$_2$), 4.43 (2H, s, CH$_2$), 7.55-7.63 (5H, m, Ar—H), 7.88 (1H, s, Ar—H), 8.00 (1H, d, J=8.1 Hz, Ar—H), 8.09 (1H, s, Ar—H)

The following compounds were prepared according to the procedures outlined for compound (118) and compound (119) incorporating the following alternative/additional steps Step 4b: [4-(tert-Butoxycarbonylamino-methyl)-benzylamino]-acetic acid cyclopentyl ester

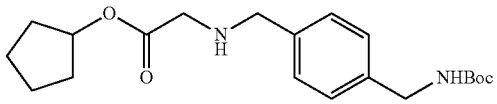 [SMILES: CC(C)(C)OC(=O)NCc1ccc(CNCC(=O)OC2CCCC2)cc1]

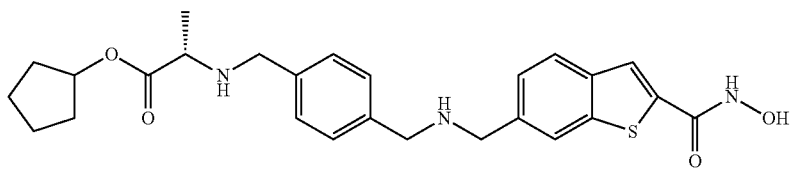

Procedure as in step 4a (using the HCl salt of the cyclopentyl ester) Product: m/z 363 [M⁺+H]⁺

Step 4c: [[4-(tert-Butoxycarbonylamino-methyl)-benzyl]-(9H-fluoren-9-ylmethoxy-carbonyl)-amino]-acetic acid cyclopentyl ester

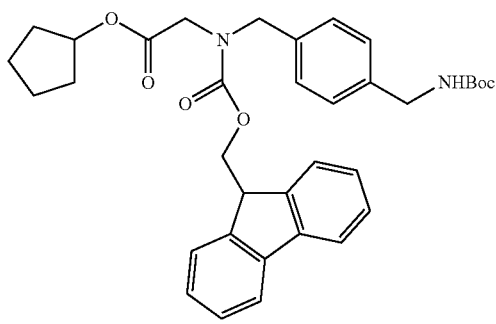 [SMILES: CC(C)(C)OC(=O)NCc1ccc(CN(CC(=O)OC2CCCC2)C(=O)OCC2c3ccccc3-c3ccccc32)cc1]

To a solution of [4-(tert-Butoxycarbonylamino-methyl)-benzylamino]-acetic acid cyclopentyl ester (0.2 g, 0.55 mmol) and 1 M Na₂CO₃ (1.1 mL, 1.1 mmol) in DCM (2 mL), was added slowly with stirring and ice bath cooling, a solution of 9-Fluorenylmethyl chloroformate (0.14 g, 0.55 mmol) in dioxane (1.4 mL). The mixture was stirred in the ice bath for 4 h and at room temperature overnight. The mixture was poured into water (90 mL) and extracted with diethyl ether. The organic extracts were combined, dried (MgSO₄) and evaporated to dryness to afford the desired product (0.32 g, 100%). m/z 607 [M⁺+Na]⁺

Step 5a: [(4-Aminomethyl-benzyl)-(9H-fluoren-9-ylmethoxycarbonyl)-amino]-acetic acid cyclopentyl ester

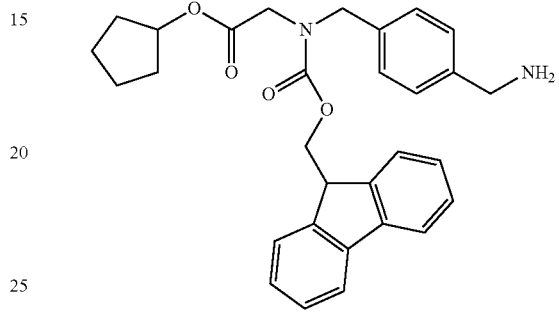

Procedure as described in step 5.
Product m/z 485 [M⁺+H]⁺

Step 6a: {(9H-Fluoren-9-ylmethoxycarbonyl)-[4-({[2-(1-isobutoxy-ethoxycarbamoyl)-benzo[b]thiophen-6-ylmethyl]-amino}-methyl)-benzyl]-amino}-acetic acid cyclopentyl ester

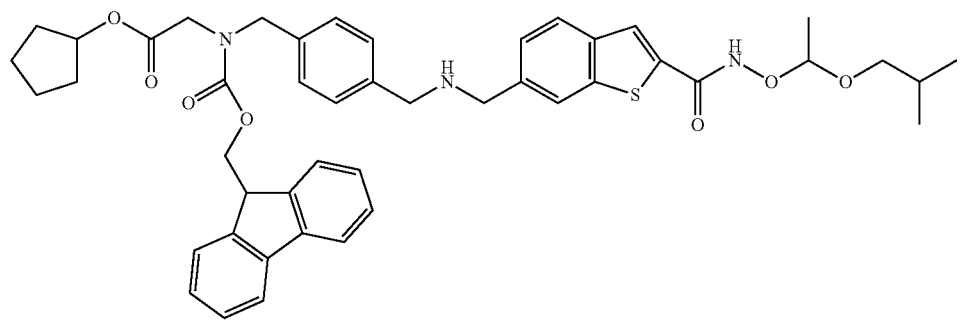 [SMILES: CC(C)COC(C)ONC(=O)c1cc2ccc(CNCc3ccc(CN(CC(=O)OC4CCCC4)C(=O)OCC4c5ccccc5-c5ccccc54)cc3)cc2s1]

Procedure as described in step 6.
Product m/z 790 [M⁺+H]⁺

Step 7a: (4-{[(2-Hydroxycarbamoyl-benzo[b]thiophen-6-ylmethyl)-amino]-methyl}-benzylamino)-acetic acid cyclopentyl ester (120)

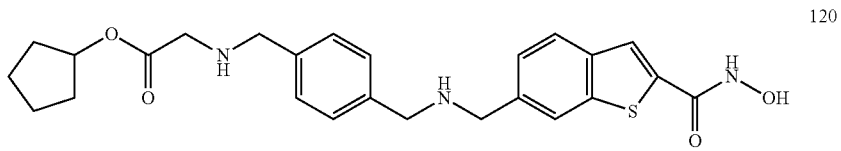 [SMILES: O=C(CNCc1ccc(CNCc2ccc3cc(C(=O)NO)sc3c2)cc1)OC1CCCC1]

{(9H-Fluoren-9-ylmethoxycarbonyl)-[4-({[2-(1-isobutoxy-ethoxycarbamoyl)-benzo[b]thiophen-6-ylmethyl]-amino}-methyl)-benzyl]-amino}-acetic acid cyclopentyl ester (0.11 g, 0.14 mmol) was dissolved in acetonitrile (3 mL) and to it was added piperidine (1.5 mL). The resulting mixture was stirred at room temperature for 1 h. The solvent was evaporated to dryness and the product separated into 2 portions. One portion was taken through to hydrolysis of the cyclopentyl ester, while the second portion was dissolved in DCM (1.5 mL) and stirred with 4M HCl in dioxane (1.0 mL) for 2 h. The solvent was evaporated to dryness and the product purified by preparative HPLC to afford the desired product as a TFA salt. LCMS purity 99%, m/z 468 [M$^+$+H]$^+$, $^1$H NMR (300 MHz, MeOD), δ: 8.09 (1H, s, ArH), 8.00 (1H, d, J=8.3 Hz, ArH), 7.88 (1H, s, ArH), 7.54-7.65 (5H, m, ArH), 5.31-5.35 (1H, m, CH), 4.43 (2H, s, CH$_2$), 4.35 (2H, s, CH$_2$), 4.31 (2H, s, CH$_2$), 3.96 (2H, s, CH$_2$), 1.65-1.93 (8H, m, 4×CH$_2$)

Step 9a: (4-{[(2-Hydroxycarbamoyl-benzo[b]thiophen-6-ylmethyl)-amino]-methyl}-benzylamino)-acetic acid (121)

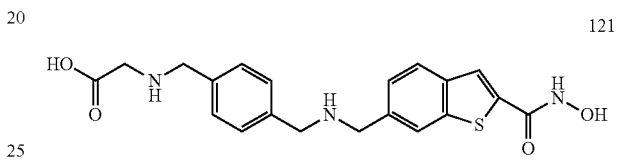

Procedure as described in step 9.
LCMS purity 99%, m/z 400 [M$^+$+H]$^+$, $^1$H NMR (300 MHz, MeOD), δ: 8.09 (1H, s, ArH), 8.00 (1H, d, J=8.3 Hz, ArH), 7.89 (1H, s, ArH), 7.54-7.62 (5H, m, ArH), 4.43 (2H, s, CH$_2$), 4.35 (2H, s, CH$_2$), 4.32 (2H, s, CH$_2$), 3.93 (2H, s, CH$_2$)

Synthesis of Compounds in Figure 8 Exemplified by Compound (126) and Compound (127)

FIG. 8

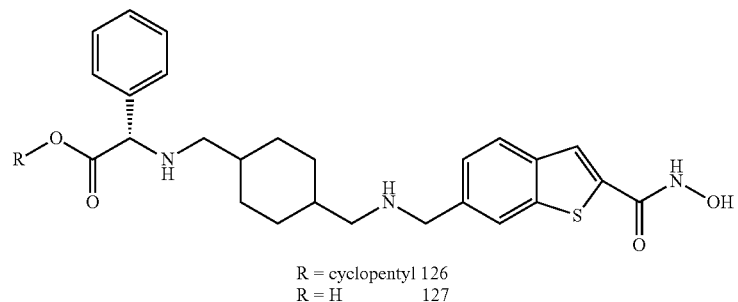

R = cyclopentyl 126
R = H 127

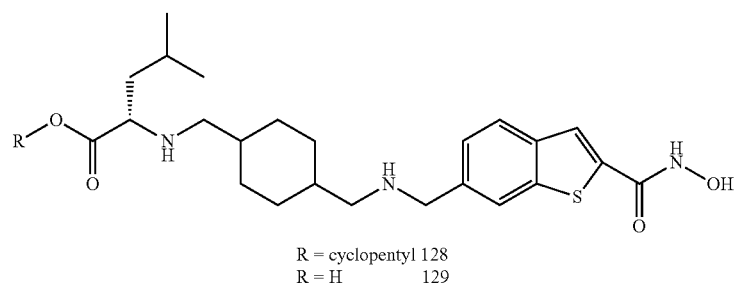

R = cyclopentyl 128
R = H 129

Stage 1: 4-(tert-Butoxycarbonylamino-methyl-cyclohexanecarboxylic acid

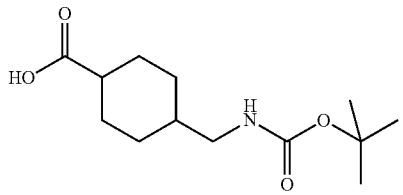 [SMILES: CC(C)(C)OC(=O)NCC1CCC(C(=O)O)CC1]

A solution of trans-4-(aminomethyl)cyclohexane carboxylic acid (1 g, 6.4 mmol) and sodium hydroxide (256 mg, 6.4 mmol) in 40 ml of dioxane and 40 ml of water was cooled in an ice-water bath while stirring. Di-tert-butyl dicarbonate (1.39 g, 6.4 mmol) was added and the mixture stirred at r.t. for 5 hours and left standing overnight. The solution was concentrated in vacuo and acidified with 2N HCl to pH 2. The acidified aqueous layer was extracted 3 times with EtOAc. The organic layers were pooled and washed with brine. The organic layer was dried over magnesium sulfate and evaporated to dryness. The product was obtained as a white solid (1.1 g, 64% yield). $^1$H NMR (300 MHz, CDCl$_3$), δ: 0.86-1.07 (2H, m, CH$_2$), 1.34-1.53 (11H, m, boc and CH$_2$), 1.84 (2H, dd, J=13.0, 2.3 Hz, CH$_2$), 2.05 (2H, dd, CH$_2$), 2.18-2.35 (1H, m, C$\underline{H}$CH$_2$), 2.99 (2H, t, J=6.3 Hz, C$\underline{H}_2$NH), 4.59 (1H, br. s, C$\underline{H}$COOH), 11.0 (1H, br. s, COOH).

Stage 2: (4-Hydroxymethyl-cyclohexylmethyl)-carbamic acid tert-butyl ester

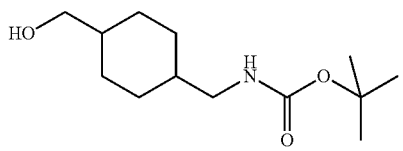 [SMILES: CC(C)(C)OC(=O)NCC1CCC(CO)CC1]

Lithium aluminium hydride (465 mg, 12.2 mmol) was suspended in anhydrous THF (10 ml) and cooled down to 0° C. under N$_2$ atmosphere. A solution of 4-(tert-butoxy-carbonyl-amino-methyl-cyclohexanecarboxylic acid (1.1 g, 4.1 mmol) in THF and dioxane (10 ml, 1:1) was added slowly and the mixture was stirred overnight at room temperature. Excess lithium aluminium hydride was quenched by adding water dropwise. The cake was filtered and washed with THF (10 ml) and MeOH (10 ml). The filtrate was concentrated in vacuo and acidified with 1N HCl to pH 2. The aqueous was extracted twice with EtOAc. The organic layer was dried over magnesium sulfate, filtered and evaporated to dryness to yield 964 mg of product (97% yield). $^1$H NMR (300 MHz, CDCl$_3$), δ: 0.81-1.08 (4H, m, 2×CH$_2$), 1.33-1.60 (10H, m, boc and CH), 1.82 (4H, d, J=5.7 Hz, 2×CH$_2$), 2.98 (2H, t, J=6.4 Hz, C$\underline{H}_2$NH), 3.46 (2H, d, J=6.4 Hz, C$\underline{H}_2$OH), 4.60 (1H, br. s, CH)

Stage 3: (4-Formyl-cyclohexylmethyl)-carbamic acid tert-butyl ester

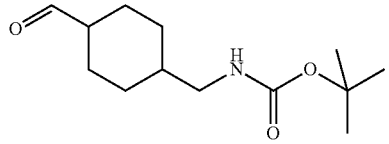 [SMILES: CC(C)(C)OC(=O)NCC1CCC(C=O)CC1]

(4-Hydroxymethyl-cyclohexylmethyl)-carbamic acid tert-butyl ester (965 mg, 4.0 mmol) was dissolved in DCM (20 ml) and cooled down to −78° C. Dess Martin reagent (2.52 g, 6.0 mmol) was dissolved in DCM (30 ml) and added slowly to the stage 2 alcohol in solution. The reaction mixture was then stirred at r.t. for 3 h. The resulting solution was poured into a vigorously stirred saturated NaHCO$_3$ and Na$_2$S$_2$O$_3$ solution (1:1, 100 ml). The organic layer was separated and washed with brine, dried over magnesium sulfate and evaporated to dryness to yield the product (786 mg, 82% yield). $^1$H NMR (300 MHz, CDCl$_3$), δ: 0.83-1.01 (2H, m, CH$_2$), 1.15-1.24 (2H, m, CH$_2$), 1.34 (9H, s, Boc), 1.75-1.88 (2H, m, CH$_2$), 1.90-2.00 (2H, m, CH$_2$), 2.05-2.18 (1H, m, CH), 2.93 (2H, t, J=6.4 Hz, C$\underline{H}_2$NH), 4.53 (1H, br. s, C$\underline{H}$CHO), 9.55 (1H, s, CHO)

Stage 4: (S)-{[4-(tert-Butoxycarbonylamino-methyl)-cyclohexylmethyl]-amino}-phenyl-acetic acid cyclopentyl ester

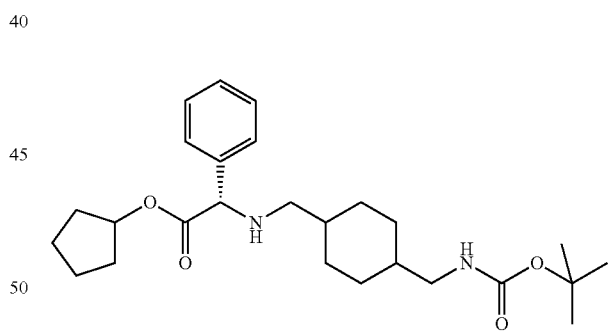

(4-Formyl-cyclohexylmethyl)-carbamic acid tert-butyl ester (390 mg, 1.6 mmol) and (S)-amino-phenyl-acetic acid cyclopentyl ester (394 mg, 1.8 mmol) were stirred in DCE (6 ml) at r.t. for 25 min. Acetic acid (9.6 ul, 0.16 mmol) and sodium triacetoxy-borohydride (1.0 g, 4.8 mmol) were added and the resulting mixture was stirred for 1 h30 at r.t. DCM (10 ml) and a saturated solution of NaHCO$_3$ (10 ml) were added and phases were separated. Aqueous were extracted with EtOAc (2×10 ml), the organics were dried over magnesium sulfate, filtered and evaporated to dryness. The crude product was purified by column chromatography (8:2 heptane/

EtOAc) to yield 223 mg of the pure amine (31% yield). LCMS purity 100%, m/z 445 [M++H]+.

Stage 5: (S)-[(4-Aminomethyl-cyclohexylmethyl)-amino]-phenyl-acetic acid cyclopentyl ester

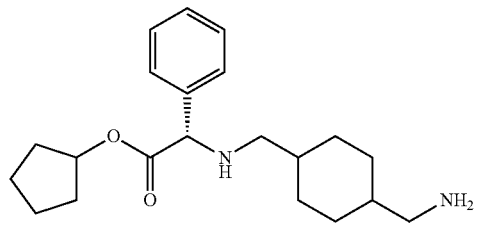 [SMILES: NCC1CCC(CN[C@H](C(=O)OC2CCCC2)c2ccccc2)CC1]

(S)-{[4-(tert-Butoxycarbonylamino-methyl)-cyclohexylmethyl]-amino}-phenyl-acetic acid cyclopentyl ester (223 mg, 0.5 mmol) was stirred in DCM (4 ml), TFA (1 ml) was added and the mixture was stirred at r.t, for 2 h. The solution was concentrated in vacuo, taken up in DCM, washed twice with a saturated solution of NaHCO$_3$ and once with a saturated solution of brine. The organic phase was dried over magnesium sulfate, filtered and evaporated to yield the expected amine as a yellow oil (130 mg, 75% yield). LCMS purity 100%, m/z 345 [M++H]+.

Stage 6: (S)-[(4-{[(2-Hydroxycarbamoyl-benzo[b]thiophen-6-ylmethyl)-amino]-meth yl}-cyclohexylmethyl)-amino]phenyl-acetic acid cyclopentyl ester (126)

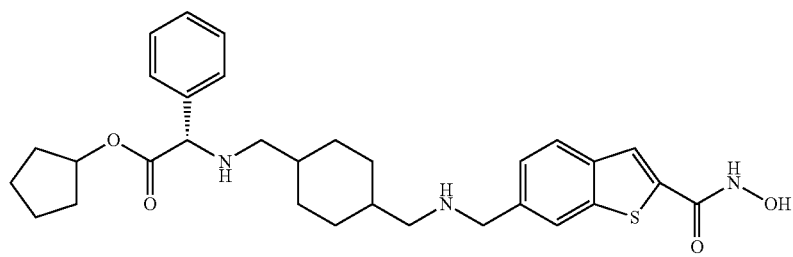

Stage 5 amine (130 mg, 0.38 mmol) was stirred with 6-formyl-benzo[b]thiophene-2-carboxylic acid (1-isobutoxy-ethoxy) amide (Scheme 7) (110 mg, 0.34 mmol) in DCE for 30 min at r.t. Acetic acid (2.1 ul, 0.03 mmol) and sodium triacetoxyborohydride (218 mg, 1.0 mmol) were added and the resulting mixture was stirred overnight at r.t. The mixture was concentrated in vacuo, taken up in EtOAc, washed with a saturated solution of NaHCO$_3$ (10 ml) and brine (10 ml). The organics were dried over magnesium sulfate, filtered and evaporated to dryness. The crude product (167 mg) was purified by preparative HPLC to yield compound (126) as a light pink solid. LCMS purity 86%, m/z 550 [M++H]+, ca. 10% carboxylic acid. $^1$H NMR (300 MHz, MeOD), δ: 1.08 (4H, m, 2×CH$_2$), 1.76 (14H, m, 6×CH$_2$ and 2×CH), 2.81 (4H, m, 2×CH$_2$NH), 4.35 (2H, s, CH$_2$NH), 5.12 (1H, s, CHNH), 5.30 (1H, m, OCH), 7.51 (6H, m, Ar), 7.85 (1H, s, Ar), 7.96 (1H, d, Ar), 8.08 (1H, s, Ar).

Synthesis of ((S)-[(4-{[(2-Hydroxycarbamoyl-benzo[b]thiophen-6-ylmethyl)-amino]-methyl}-cyclohexylmethyl)-amino]-phenyl-acetic acid (127)

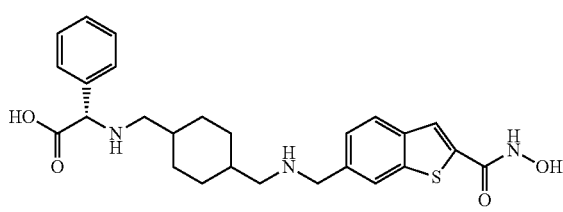

Stage 1: (S)-{[4-(tert-Butoxycarbonylamino-methyl)-cyclohexylmethyl]-amino}-phenyl-acetic acid tert-butyl ester

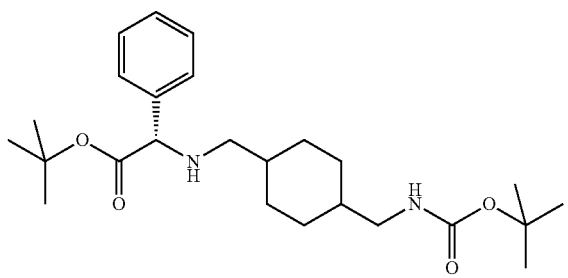 [SMILES: CC(C)(C)OC(=O)NCC1CCC(CN[C@H](C(=O)OC(C)(C)C)c2ccccc2)CC1]

(4-Formyl-cyclohexylmethyl)-carbamic acid tert-butyl ester (899 mg, 3.7 mmol) and (S)-tert-butyl phenylglycine ester (850 mg, 4.1 mmol) were stirred in DCE (20 ml) for 30 min. Acetic acid (20 ul, 0.37 mmol) and sodium triacetoxyborohydride (2.37 g, 11.1 mmol) were added and the reaction mixture was stirred at r.t. for 3 h. DCM (10 ml) and a saturated solution of NaHCO₃ (20 ml) were added and phases were separated. The aqueous phase was extracted with EtOAc (20 ml). The organics were dried over magnesium sulfate, filtered and concentrated under vacuum. The crude product (2.4 g) was purified on column chromatography (7:3 heptane/EtOAc) to yield the expected product (385 mg, 24% yield). LCMS purity 100%, m/z 433 [M$^+$+H]$^+$.

Stage 2: (S)-{[4-(tert-Butoxycarbonylamino-methyl)-cyclohexylmethyl]-amino}-phenyl-acetic acid tert-butyl ester

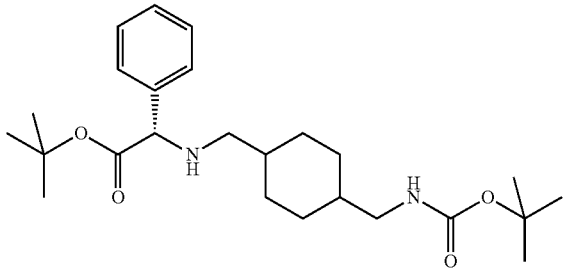 [SMILES: CC(C)(C)OC(=O)NCC1CCC(CN[C@H](C(=O)OC(C)(C)C)c2ccccc2)CC1]

(S)-{[4-(tert-Butoxycarbonylamino-methyl)-cyclohexylmethyl]-amino}-phenyl-acetic acid tert-butyl ester (385 mg, 0.9 mmol) was stirred in DCM (5 ml) and TFA (2 ml) was added and the mixture was stirred at r.t. for 30 min. The solution was concentrated in vacuo, taken up in EtOAc (5 ml), washed twice with a saturated solution of NaHCO₃ (2×5 ml) and once with a saturated solution of brine (5 ml). The organic phase was dried over magnesium sulfate, filtered and evaporated to yield the expected amine as a yellow oil (290 mg, 97% yield). LCMS purity 100%, m/z 333 [M$^+$+H]$^+$.

Stage 3: (S)-{[4-({[2-(1-Isobutoxy-ethoxycarbamoyl)-benzo[b]thiophen-6-ylmethyl]-amino}-methyl)-cyclohexylmethyl]-amino}-phenyl-acetic acid tert-butyl ester

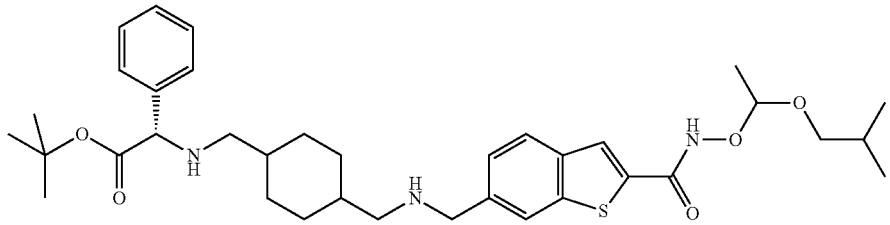 [SMILES: CC(C)COC(C)ONC(=O)c1cc2ccc(CNCC3CCC(CN[C@H](C(=O)OC(C)(C)C)c4ccccc4)CC3)cc2s1]

(S)-{[4-(tert-Butoxycarbonylamino-methyl)-cyclohexylmethyl]-amino}-phenyl-acetic acid tert-butyl ester (290 mg, 0.9 mmol) and 6-formyl-benzo[b]thiophene-2-carboxylic acid (1-isobutoxy-ethoxy) amide (Scheme 7) (255 mg, 0.8 mmol) were stirred in DCE (8 ml) for 30 min. Acetic acid (4 ul, 0.08 mmol) and sodium triacetoxyborohydride (504 mg, 2.4 mmol) were added and the reaction mixture was stirred at r.t. for 1 h30. DCM (5 ml) and a saturated solution of NaHCO₃ (10 ml) were added and phases were separated. The aqueous phase was extracted with EtOAc (15 ml). The organics were dried over magnesium sulfate, filtered and concentrated under vacuum. The crude product (543 mg) was purified on column chromatography (5 to 10% MeOH in DCM) to yield the expected pure product (172 mg, 34% yield). LCMS purity 100%, m/z 638 [M$^+$+H]$^+$.

Stage 4: (S)-{[4-({[2-(1-Isobutoxy-ethoxycarbamoyl)-benzo[b]thiophen-6-ylmethyl]-amino}-methyl)-cyclohexylmethyl]-amino}-phenyl-acetic acid tert-butyl ester (127)

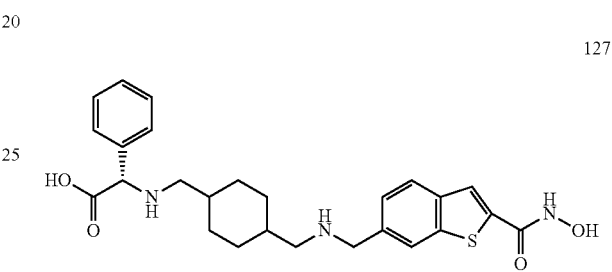

(S)-{[4-({[2-(1-Isobutoxy-ethoxycarbamoyl)-benzo[b]thiophen-6-ylmethyl]-amino}-methyl)-cyclohexylmethyl]-amino}-phenyl-acetic acid tert-butyl ester (172 mg, 0.27 mmol) was stirred in 4M HCl in dioxane solution (2 ml) at r.t. for 30 min. The solution was evaporated to dryness to yield compound (127) as a beige solid (123 mg, 95% yield). LCMS purity 98%, m/z 482 [M$^+$+H]$^+$. $^1$H NMR (300 MHz, MeOD), δ: 1.10 (4H, m, 2×CH₂), 1.80 (6H, m, 2×CH₂ and 2×CH), 2.88 (2H, dd, CH₂NH), 2.94 (2H, d, CH₂NH), 4.36 (2H, s, CH₂NH), 5.07 (1H, s, CH), 7.53 (6H, m, Ar), 7.87 (1H, s, Ar), 7.97 (1H, d, Ar), 8.12 (1H, s, Ar).

The following compounds were prepared according to the procedure described for Compound (126) and Compound (127)

(S)-2-[(4-{[(2-Hydroxycarbamoyl-benzo[b]thiophen-6-ylmethyl)-amino]-methyl}-cyclohexylmethyl)-amino]-4-methyl-pentanoic acid cyclopentylester (128)

LCMS purity 86%, m/z 530 [M$^+$+H]$^+$, $^1$H NMR (300 MHz, MeOD), δ: 0.99 (6H, t, J=6 Hz, 2×CH₃), 1.11 (4H, t, J=8.1 Hz, 2×CH₂), 1.76 (20H, m, 2×CH and 9×CH₂), 2.80 (1H, m, CH), 2.97 (4H, m, 2×CH₂NH), 3.95 (1H, m, CH), 4.35 (2H, s, C H₂NH), 5.32 (1H, m, OCH), 7.54 (1H, d, J=6 Hz, Ar), 7.84 (1H, s, Ar), 7.94 (1H, d, J=9 Hz, Ar), 8.08 (1H, s, Ar).

(S)-2-[(4-{[(2-Hydroxycarbamoyl-benzo[b]thiophen-6-ylmethyl)-amino]-methyl}-cyclohexylmethyl)-amino]-4-methyl-pentanoic acid (129)

LCMS purity 95%, m/z 462 [M⁺+H]⁺, ¹H NMR (300 MHz, MeOD), δ: 1.00 (6H, t, J=6.3 Hz, 2×CH₃), 1.10 (4H, m, 2×CH₂), 1.85 (8H, m, 2×CH and 3×CH₂), 2.94 (4H, m, 2×CH₂NH), 3.91 (1H, m, CHNH), 4.36 (2H, s, CH₂NH), 7.54 (1H, d, J=7.8 Hz, Ar), 7.85 (1H, s, Ar), 7.95 (1H, d, J=8.1 Hz, Ar), 8.08 (1H, s).

Synthesis of Compounds in Figure 9 as Exemplified for Compound (130)

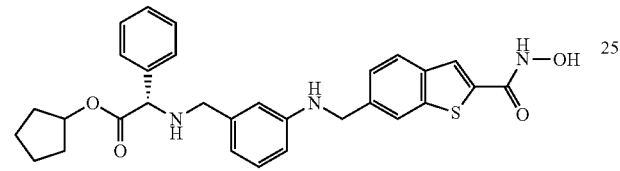

130

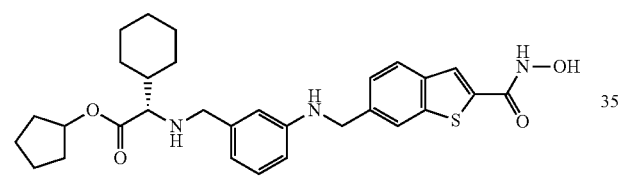

131

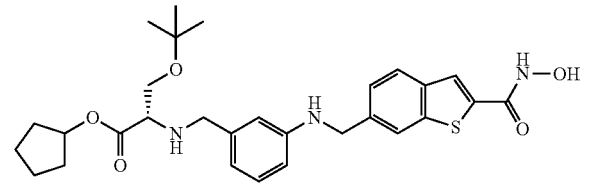

132

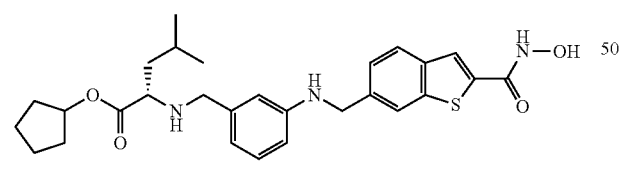

133

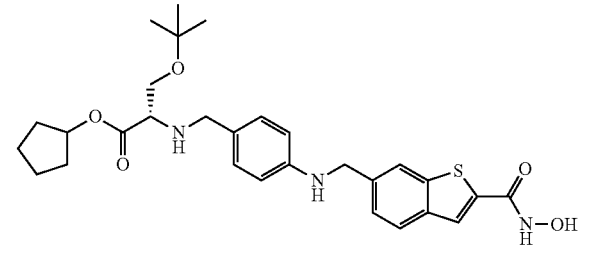

134

Stage 1: (S)-[(3-nitro-benzyl)-amino]-phenyl-acetic acid cyclopentyl ester

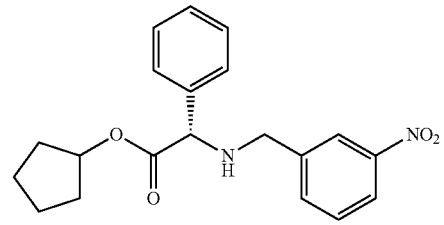 [SMILES: O=C(OC1CCCC1)[C@@H](NCc1cccc([N+](=O)[O-])c1)c1ccccc1]

To a solution of phenylglycine cyclopentyl ester tosic acid salt (3.08 g, 7.8 mmol) in DCE (120 ml) was added 3-nitrobenzaldehyde (1.01 g, 6.7 mmol) then sodium triacetoxyborohydride (3.03 g). The mixture was stirred for 3.5 h, then quenched by addition of saturated sodium bicarbonate solution (200 ml). Product was extracted with DCM (250 ml) and the organic extract was dried (MgSO₄). The product was carried forward without further purification.

Stage 2: (S)-[(3-nitro-benzyl)-tert-butoxycarbonyl-amino]-phenyl-acetic acid cyclopentyl ester

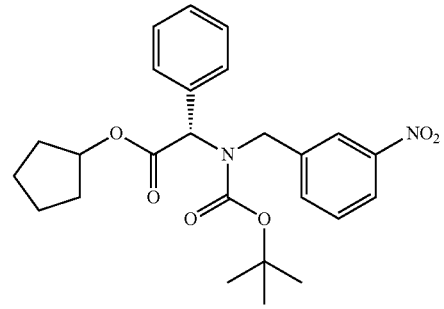

To the crude mixture of (S)-[(3-nitro-benzyl)-amino]-phenyl-acetic acid cyclopentyl ester in DCM (50 ml) was added di-ter-butyl dicarbonate (3.38 g, 15.6 mmol). The mixture was heated at 50° C. overnight, then cooled to rt. N,N,N'-trimethylethylene diamine (2 ml) was then added and the mixture stirred for 2 h. The mixture was then poured into ethyl acetate (150 ml) and washed with 1M HCl (3 times 50 ml), dried (MgSO₄) and concentrated to yield the desired product as a colourless oil (1.509 g, 42% yield). LCMS purity 98%, m/z 477 (M+Na⁺). ¹H NMR (300 MHz, d6-DMSO), δ: 7.97

(1H, dd, J=2.1, 9 Hz), 7.15-7.45 (8H, m), 5.60-6.00 (1H, m), 5.20-5.35 (1H, m), 4.65-4.82 (1H, m), 4.21 (1H, d, J=16 Hz), 1.30-1.95 (17H, m)

Stage 3: (S)-[(3-Amino-benzyl)tert-butoxycarbonyl-amino]-phenyl-acetic acid cyclopentyl ester

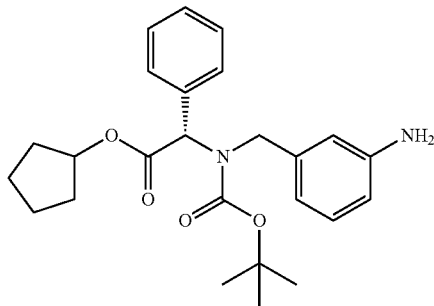 [SMILES: CC(C)(C)OC(=O)N(Cc1cccc([N+](=O)[O-])c1)[C@H](C(=O)OC1CCCC1)c1ccccc1]

To a solution of (S)-[(3-nitro-benzyl)-tert-butoxycarbonyl-amino]-phenyl-acetic acid cyclopentyl ester (1.509 g, 3.32 mmol) in ethanol (10 ml) was added palladium on carbon (10%, 0.38 g, 0.36 mmol). The flask was evacuated and back-filled with hydrogen gas. The mixture was stirred overnight, then filtered through Celite, washed with ethanol (150 ml) and then concentrated to yield the desire product as a colourless oil (1.351 g, 96% yield). $^1$H NMR (300 MHz, CDCl$_3$), δ: 7.19-7.42 (5H, m), 6.97 (1H, t, J=7.5 Hz), 6.46 (2H, dd, J=8.1, 16.5 Hz), 6.29 (1H, br s), 5.58 (1H, br s), 5.29 (1H, br s), 4.69 (1H, br s), 4.00 (1H, d, J=15.9 Hz), 3.74 (1H, q, J=6.9 Hz), 3.51 (2H, br s), 1.20-2.00 (17H, m)

Stage 4: (S)-[tert-Butoxycarbonyl-(3-{[2-(1-isobutoxy-ethoxycarbamoyl)-benzo[b]-thiophen-6-ylmethyl]-amino}-benzyl)-amino]-phenyl-acetic acid cyclopentyl ester

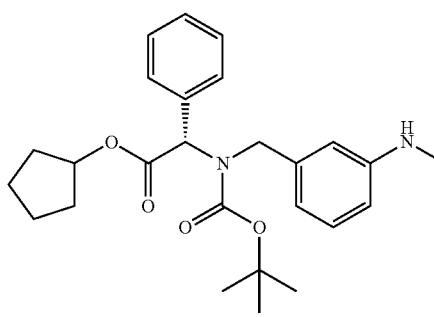

To (S)-[(3-Amino-benzyl)-tert-butoxycarbonyl-amino]-phenyl-acetic acid cyclopentyl ester (0.317 g, 0.75 mmol) was added 6-Formyl-benzo[b]thiophene-2-carboxylic acid (1-isobutoxy-ethoxy)-amide (Scheme 7) (0.210 g, 0.65 mmol) in DCE (8 ml). 2 drops of glacial acetic acid were added, and then sodium triacetoxyborohydride (0.170 g, 0.8 mmol). The mixture was stirred for 2 h and then poured into DCM (150 ml). The solution was washed with saturated sodium bicarbonate (50 ml), then dried (MgSO$_4$), concentrated and purified by flash column chromatography to yield the desired product as a pale yellow foam (0.346 g, 73% yield). $^1$H NMR (300 MHz, CDCl$_3$), δ: 8.35-8.43 (1H, m), 7.56-8.05 (2H, m), 7.01-7.41 (8H, m), 6.90-7.01 (1H, m), 6.42 (1H, dd, J=2.6, 7.9 Hz), 5.25-5.31 (1H, m), 5.12 (1H, q, J=5.2 Hz), 4.40 (1H, d, J 5.4 Hz), 4.00 (1H, dd, J=3.1, 15.8 Hz), 3.60-3.70 (1H, m), 3.35-3.40 (1H, m), 1.33-1.94 (21H, m), 0.98 (3H, d, J=6.6 Hz), 0.97 (3H, d, J=6.6 Hz)

Stage 5: (S)-{3-[(2-Hydroxycarbamoyl-benzo[b]thiophen-6-ylmethyl)-amino]-benzyl-amino}-phenyl-acetic acid cyclopentyl ester (130)

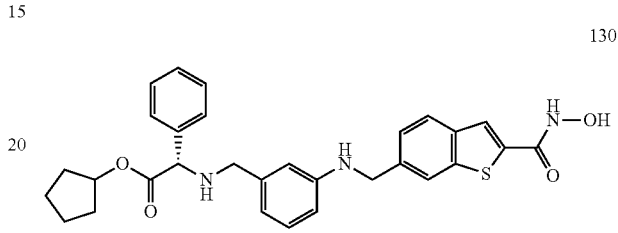

To a solution of (S)-[tert-Butoxycarbonyl-(3-{[2-(1-isobutoxy-ethoxycarbamoyl)-benzo[b]thiophen-6-ylmethyl]-amino}-benzyl)-amino]-phenyl-acetic acid cyclopentyl ester (0.100 g, 0.14 mmol) in DCM/MeOH (1 ml:1 ml) was added TFA (8 ml). The solution was stirred for 2 h, then diluted with DCM (200 ml). The solution was washed with saturated sodium bicarbonate (100 ml). The solution was dried (Na$_2$SO$_4$), concentrated and purified by reverse phase HPLC to yield the desired product (8.1 mg, 11% yield). LCMS purity 98%, m/z 531 (M+H)$^+$ 300 MHz, DMSO, δ:1.26-1.85 (8H, m), 3.47 (2H, s), 4.21 (1H, s), 4.38 (2H, d, J 5.8 Hz), 5.02-5.07 (1H, m), 6.32 (1H, t, J 6.0 Hz), 6.45 (2H, d, J 7.9 Hz), 6.57 (1H, s), 6.97 (1H, t, J 7.8 Hz), 7.23-7.35 (5H, m), 7.42 (1H, dd, J 1.2, 8.3 Hz), 7.84 (1H, s), 7.87 (1H, s), 7.93 (1H, s), 9.23 (1H, br s), 11.4 (1H, br s)

The following compounds were prepared according to the procedures described for compound (130)

(S)-{3-[(2-Hydroxycarbamoyl-benzo[b]thiophen-6-ylmethyl)-amino]-benzylamino}-cyclohexyl-acetic acid cyclopentyl ester (131)

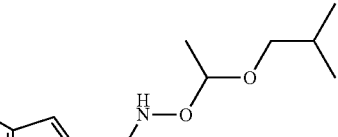

LCMS purity>98%, m/z 536.25 (M+H)$^+$, $^1$H NMR (300 MHz, d6-DMSO), δ: 0.7-1.25 (8H, m), 1.50-1.95 (14H, m), 3.69 (1H, br s), 3.98 (2H, br s), 4.43 (2H, br s), 5.14 (1H, t, J 5.4 Hz), 6.60-6.71 (2H, m), 7.05-7.28 (3H, m), 7.43 (1H, d, J 8.5 Hz), 7.83-7.98 (2H, m), 9.25 (1H, br s), 11.45 (1H, br s)

(S)-3-tert-Butoxy-2-{3-[(2-hydroxycarbamoyl-benzo[b]thiophen-6-ylmethyl)-amino]-benzylamino}-propionic acid cyclopentyl ester (132)

LCMS purity>98%, m/z 540.25 (M+H)$^+$, $^1$H NMR (300 MHz, d6-DMSO), δ: 1.05 (9H, s), 1.50-1.78 (8H, m), 3.15-3.67 (5H, m), 4.38 (2H, d, J 5.8 Hz), 5.05-5.15 (1H, m), 6.31 (1H, t, J 5.9 Hz), 6.40-6.48 (2H, m), 6.56 (1H, s), 6.96 (1H, t, J 7.8 Hz), 7.42 (1H, d, J 8.2 Hz), 7.87 (1H, s), 7.93 (1H, s), 9.24 (1H, br s), 11.43 (1H, br s)

(S)-2-{3-[(2-Hydroxycarbamoyl-benzo[b]thiophen-6-ylmethyl)-amino]-benzylamino}-4-methyl-pentanoic acid cyclopentyl ester (133)

LCMS purity 98%, m/z 510.25 (M+H)$^+$, $^1$H NMR (300 MHz, d6-DMSO), δ: 0.87 (6H, d, J 6.4 Hz), 1.50-1.94 (10H, m), 3.57-4.20 (3H, m), 4.44 (2H, s), 5.20 (1H, t, J 5.8 Hz), 6.58-6.74 (3H, m), 7.11 (1H, t, J 7.7 Hz), 7.43 (1H, d J 8.3 Hz), 7.85-7.96 (3H, m), 9.38 (2H, br s), 11.46 (1H, br s)

(S)-3-tert-Butoxy-2-{4-[(2-hydroxycarbamoyl-benzo[b]thiophen-6-ylmethyl)-amino]-benzylamino}-propionic acid cyclopentyl ester (134)

LCMS purity 98%, m/z 540.25 (M+H)$^+$, $^1$H NMR (300 MHz, d4-MeOD), δ: 7.64-7.77 (2H, m), 7.28 (1H, d, J=7.2 Hz), 6.99 (2H, d, J=6.6 Hz), 6.53 (2H, d, J=6.6 Hz), 5.06-5.08 (1H, m), 4.35 (2H, s), 3.40-3.75 (5H, m), 1.50-1.82 (8H, m), 1.04 (9H, s)

Measurement of Biological Activities

Histone Deacetylase Activity

The ability of compounds to inhibit histone deacetylase activities was measured using the commercially available HDAC fluorescent activity assay from Biomol. In brief, the Fluor de Lys™ substrate, a lysine with an epsilon-amino acetylation, is incubated with the source of histone deacetylase activity (HeLa nuclear extract) in the presence or absence of inhibitor. Deacetylation of the substrate sensitises the substrate to Fluor de Lys™ developer, which generates a fluorophore. Thus, incubation of the substrate with a source of HDAC activity results in an increase in signal that is diminished in the presence of an HDAC inhibitor.

Data are expressed as a percentage of the control, measured in the absence of inhibitor, with background signal being subtracted from all samples, as follows:—

$$\% \text{ activity} = ((S^i - B)/(S^o - B)) \times 100$$

where $S^i$ is the signal in the presence of substrate, enzyme and inhibitor, $S^o$ is the signal in the presence of substrate, enzyme and the vehicle in which the inhibitor is dissolved, and B is the background signal measured in the absence of enzyme.

IC50 values were determined by non-linear regression analysis, after fitting the results of eight data points to the equation for sigmoidal dose response with variable slope (% activity against log concentration of compound), using Graphpad Prism software.

Histone deacetylase activity from crude nuclear extract derived from HeLa cells was used for screening. The preparation, purchased from 4C (Seneffe, Belgium), was prepared from HeLa cells harvested whilst in exponential growth phase. The nuclear extract is prepared according to Dignam JD1983 Nucl. Acid. Res. 11, 1475-1489, snap frozen in liquid nitrogen and stored at −80° C. The final buffer composition was 20 mM Hepes, 100 mM KCl, 0.2 mM EDTA, 0.5 mM DTT, 0.2 mM PMSF and 20% (v/v) glycerol.

IC50 results were allocated to one of 3 ranges as follows:
Range A: IC50<100 nM,
Range B: IC50 from 101 nM to 1000 nM;
Range C: IC50>1001 nM.
NT=Not tested Results of testing the compounds of the examples in this assay are given in the second column of Table 2 below.

Cell Inhibition Assays

The corresponding cancer cell lines (Hela, U937 and HUT) growing in log phase were harvested and seeded at 1000 cells/well (200 ul final volume) into 96-well tissue culture plates. Following 24 h of cell growth cells were treated with compounds (final concentration of 20 uM). Plates were then re-incubated for a further 72 h before a sulphorhodamine B (SRB) cell viability assay was conducted according to Skehan 1990 J Natl Canc Inst 82, 1107-1112.

Data were expressed as a percentage inhibition of the control, measured in the absence of inhibitor, as follows:—

$$\% \text{ inhibition} = 100 - ((S^i/S^o) \times 100)$$

where $S^i$ is the signal in the presence of inhibitor and $S^o$ is the signal in the presence of DMSO.

IC50 values were determined by non-linear regression analysis, after fitting the results of eight data points to the equation for sigmoidal dose response with variable slope (% activity against log concentration of compound), using Graphpad Prism software.

IC50 results were allocated to one of 3 ranges as follows:
Range A: IC50<330 nM,
Range B: IC50 from 330 nM to 3300 nM;
Range C: IC50>3301 nM.
NT=Not tested Results of testing the compounds of the examples in this assay are given in the third-fifth columns of Table 2 below.

TABLE 2

| Example No. | HDAC Activity | Hela | U937 | HUT |
|---|---|---|---|---|
| 1 | B | C | B | B |
| 2 | B | C | B | B |
| 3 | C | C | B | C |
| 4 | B | C | C | C |
| 5 | B | B | B | B |
| 6 | A | C | C | C |
| 7 | B | C | B | B |
| 8 | B | C | C | C |
| 9 | B | B | B | B |
| 10 | A | C | C | C |
| 11 | B | B | B | B |
| 12 | B | C | C | C |
| 13 | B | C | B | B |
| 14 | B | C | C | C |
| 15 | C | C | B | B |
| 16 | C | C | C | C |
| 17 | B | C | B | B |
| 18 | B | C | C | C |
| 19 | B | B | B | B |
| 20 | B | B | A | B |
| 21 | B | C | C | C |
| 22 | B | B | B | B |
| 23 | B | C | C | C |
| 24 | B | C | C | B |
| 25 | B | C | C | C |
| 26 | A | B | B | B |
| 27 | B | C | NT | NT |
| 28 | B | B | B | B |
| 29 | B | B | B | B |
| 30 | B | C | NT | NT |
| 31 | B | B | A | B |
| 32 | A | B | NT | B |

TABLE 2-continued

| Example No. | HDAC Activity | Hela | U937 | HUT |
|---|---|---|---|---|
| 33 | B | C | NT | NT |
| 34 | B | B | A | B |
| 35 | B | B | B | B |
| 36 | A | B | A | B |
| 37 | B | C | C | C |
| 38 | B | NT | NT | NT |
| 39 | B | NT | A | B |
| 40 | C | C | C | C |
| 41 | C | C | C | C |
| 42 | C | B | B | B |
| 43 | B | C | C | C |
| 44 | B | C | B | B |
| 45 | C | C | NT | NT |
| 46 | C | C | B | B |
| 47 | B | C | B | B |
| 48 | C | C | B | B |
| 49 | B | C | NT | NT |
| 50 | C | C | B | B |
| 51 | B | C | B | B |
| 52 | C | C | NT | NT |
| 53 | C | C | C | C |
| 54 | C | C | NT | NT |
| 55 | C | C | C | C |
| 56 | C | C | C | C |
| 57 | C | C | NT | NT |
| 58 | B | B | B | B |
| 59 | A | C | NT | NT |
| 60 | B | B | B | B |
| 61 | B | C | NT | NT |
| 62 | B | C | C | B |
| 63 | B | NT | NT | NT |
| 64 | B | B | NT | B |
| 65 | A | C | NT | NT |
| 66 | B | C | C | C |
| 67 | B | C | NT | NT |
| 68 | B | C | B | B |
| 69 | B | B | NT | B |
| 70 | B | C | NT | NT |
| 71 | A | B | A | B |
| 72 | A | NT | NT | NT |
| 73 | A | B | A | B |
| 74 | B | NT | NT | NT |
| 75 | A | B | A | A |
| 76 | A | NT | NT | NT |
| 77 | A | B | A | A |
| 78 | A | NT | NT | NT |
| 79 | A | NT | C | C |
| 80 | B | NT | NT | NT |
| 81 | A | C | C | B |
| 82 | B | NT | NT | NT |
| 83 | B | B | B | B |
| 84 | B | NT | NT | NT |
| 85 | B | C | A | B |
| 86 | B | C | A | B |
| 87 | A | NT | NT | NT |
| 88 | B | B | A | B |
| 89 | B | C | A | B |
| 90 | B | NT | NT | NT |
| 91 | B | C | B | B |
| 92 | A | B | B | B |
| 93 | A | NT | NT | NT |
| 94 | B | NT | B | B |
| 95 | B | NT | NT | NT |
| 96 | B | C | B | B |
| 97 | B | NT | NT | NT |
| 98 | B | B | B | B |
| 99 | C | NT | NT | NT |
| 100 | A | C | B | B |
| 101 | A | NT | NT | NT |
| 102 | B | C | B | C |
| 103 | A | NT | NT | NT |
| 104 | B | B | A | B |
| 105 | A | NT | NT | NT |
| 106 | A | B | A | A |
| 107 | NT | NT | NT | NT |
| 108 | B | B | B | B |
| 109 | A | B | A | B |
| 110 | A | B | A | A |
| 111 | A | A | A | A |
| 112 | B | NT | NT | NT |
| 113 | B | B | B | B |
| 114 | B | NT | NT | NT |
| 115 | B | B | B | B |
| 116 | B | C | B | C |
| 117 | A | NT | NT | NT |
| 118 | A | A | A | A |
| 119 | A | NT | NT | NT |
| 120 | A | NT | A | A |
| 121 | A | NT | NT | NT |
| 122 | A | B | A | B |
| 123 | A | NT | NT | NT |
| 124 | B | B | A | B |
| 125 | A | NT | NT | NT |
| 126 | B | NT | A | C |
| 127 | B | NT | NT | NT |
| 128 | B | B | A | A |
| 129 | B | NT | NT | NT |
| 130 | C | C | B | C |
| 131 | C | C | B | C |
| 132 | B | C | B | B |
| 133 | B | B | B | C |
| 134 | B | NT | B | C |

Broken Cell Carboxyesterase Assay

Preparation of Cell Extract

U937 or Hct116 tumour cells (~$10^9$ were washed in 4 volumes of Dulbeccos PBS (~1 liter) and pelleted at 160 g for 10 mins at 4° C. This was repeated twice and the final cell pellet was then resuspended in 35 ml of cold homogenising buffer (Trizma 10 mM, NaCl 130 mM, $CaCl_2$ 0.5 mM PH 7.0) at 25° C. Homogenates were prepared by nitrogen cavitation (700 psi for 50 min at 4° C.). The homogenate was kept on ice and supplemented with a cocktail of inhibitors designed to give final concentrations of Leupeptin 1 μM
Aprotinin 0.1 μM
E64 8 μM
Pepstatin 1.5 μM
Bestatin 162 μM
Chymostatin 33 μM After clarification of the cell homogenate by centrifugation at 360 rpm for 10 min, the resulting supernatant was used as a source of esterase activity and could be stored at −80° C. until required.

Measurement of Ester Cleavage

Hydrolysis of ester to the corresponding carboxylic acid can be measured using this cell extract. To this effect cell extract (~30 ug/total assay volume of 0.5 ml) was incubated at 37° C. in a Tris-HCl 25 mM, 125 mM NaCl, buffer, PH 7.5 at 25° C. At zero time the relevant ester (substrate), at a final concentration of 2.5 μM was then added and samples incubated at 37° C. for the appropriate time (Usually zero or 80 minutes). Reactions were stopped by the addition of 3× volumes of Acetonitrile. For zero time samples the acetonitrile was added prior to the ester compound. After centrifugation at 12000 g for 5 minutes, samples were analysed for the parent ester and its corresponding carboxylic acid at room temperature by LCMS (Sciex API 3000, HP1100 binary pump, CTC PAL). Chromatographic conditions used were based on an AceCN (75*2.1 mm) column and a mobile phase of 5-95% acetonitrile in water/0.1% formic acid.

The invention claimed is:

1. A method of inhibiting the activity of an HDAC enzyme comprising contacting the enzyme with an amount of a compound of formula (I) or a pharmaceutically acceptable salt or N-oxide thereof which is effective for such inhibition:

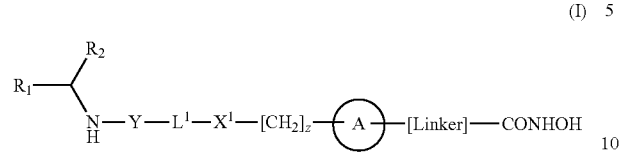

wherein
$R_1$ is an ester group which is hydrolysable by one or more intracellular carboxyesterase enzymes to a carboxylic acid group;
$R_2$ is (i) $C_1$-$C_6$ alkyl, phenyl, 2,- 3-, or 4-hydroxyphenyl, 2,- 3-, or 4-methoxyphenyl, 2,-3-, or 4-pyridylmethyl, benzyl, phenylethyl, 2-, 3-, or 4-hydroxybenzyl, 2,- 3-, or 4-benzyloxybenzyl, 2,- 3-, or 4- $C_1$-$C_6$ alkoxybenzyl, and benzyloxy($C_1$-$C_6$alkyl)-groups; or
(ii) the characterising group of a natural α amino acid, in which any functional group may be protected; or
(iii) a group -[Alk]$_n$R$_6$ where Alk is a ($C_1$-$C_6$)alkyl or ($C_2$-$C_6$)alkenyl group optionally interrupted by one or more —O—, or —S— atoms or —N(R$_7$)— groups where R$_7$ is a hydrogen atom or a ($C_1$-$C_6$)alkyl group, n is 0 or 1, and R$_6$ is an optionally substituted cycloalkyl or cycloalkenyl group;
(iv) a benzyl group substituted in the phenyl ring by a group of formula —OCH$_2$COR$_8$ where R$_8$ is hydroxyl, amino, ($C_1$-$C_6$)alkoxy, phenyl($C_1$-$C_6$)alkoxy, ($C_1$-$C_6$)alkylamino, di(($C_1$-$C_6$)alkyl)amino, phenyl($C_1$-$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or
(v) a heterocyclic($C_1$-$C_6$)alkyl group, either being unsubstituted or mono- or di-substituted in the heterocyclic ring with halo, nitro, carboxy, ($C_1$-$C_6$)alkoxy, cyano, ($C_1$-$C_6$)alkanoyl, trifluoromethyl ($C_1$-$C_6$)alkyl, hydroxy, formyl, amino, ($C_1$-$C_6$)alkylamino, di-($C_1$-$C_6$) alkylamino, mercapto, ($C_1$-$C_6$)alkylthio, hydroxy($C_1$-$C_6$)alkyl, mercapto($C_1$-$C_6$)alkyl or ($C_1$-$C_6$)alkylphenylmethyl; or
(vi) a group —CR$_a$R$_b$R$_c$ in which:
each of R$_a$, R$_b$ and R, is independently hydrogen, ($C_1$-$C_6$) alkyl, ($C_2$-$C_6$)alkenyl, ($C_2$-$C_6$)alkynyl, phenyl($C_1$-$C_6$) alkyl, ($C_3$-$C_8$)cycloalkyl; or
R$_c$ is hydrogen and R$_a$ and R$_b$ are independently phenyl or heteroaryl such as pyridyl; or
R$_c$ is hydrogen, ($C_1$-$C_6$)alkyl, ($C_2$-$C_6$)alkenyl, ($C_2$-$C_6$) alkynyl, phenyl($C_1$-$C_6$)alkyl, or ($C_3$-$C_8$)cycloalkyl, and R$_a$ and R$_b$ together with the carbon atom to which they are attached form a 3 to 8 membered cycloalkyl or a 5- to 6-membered heterocyclic ring; or
R$_a$, R$_b$ and R$_c$ together with the carbon atom to which they are attached form a tricyclic ring (for example adamantyl); or
R$_a$ and R$_b$ are each independently ($C_1$-$C_6$)alkyl, ($C_2$-$C_6$) alkenyl, ($C_2$-$C_6$)alkynyl, phenyl($C_1$-$C_6$)alkyl, or a group as defined for R$_c$ below other than hydrogen, or R$_a$ and R$_b$ together with the carbon atom to which they are attached form a cycloalkyl or heterocyclic ring, and R$_c$ is hydrogen, —OH, —SH, halogen, —CN, —CO$_2$H, ($C_1$-$C_4$)perfluoroalkyl, —CH$_2$OH, —CO$_2$($C_1$-$C_6$)alkyl, —O($C_1$-$C_6$)alkyl, —O($C_2$-$C_6$)alkenyl, —S($C_1$-$C_6$) alkyl, —SO($C_1$-$C_6$)alkyl, —SO$_2$($C_1$-$C_6$) alkyl, —S($C_2$-$C_6$)alkenyl, —SO($C_2$-$C_6$)alkenyl, —SO$_2$($C_2$-$C_6$)alkenyl or a group -Q-W wherein Q represents a bond or —O—, —S—, —SO— or —SO$_2$— and W represents a phenyl, phenylalkyl, ($C_3$-$C_8$)cycloalkyl, ($C_3$-$C_8$)cycloalkylalkyl, ($C_4$-$C_8$)cycloalkenyl, ($C_4$-$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$-$C_6$)alkyl, —CONH$_2$, —CONH($C_1$-$C_6$)alkyl, —CONH($C_1$-$C_6$alkyl)$_2$, —CHO, —CH$_2$OH, ($C_1$-$C_4$)perfluoroalkyl, —O($C_1$-$C_6$)alkyl, —S($C_1$-$C_6$)alkyl, —SO($C_1$-$C_6$)alkyl, —SO$_2$($C_1$-$C_6$)alkyl, —NO$_2$, —NH$_2$, —NH($C_1$-$C_6$) alkyl, —N(($C_1$-$C_6$)alkyl)$_2$, —NHCO($C_1$-$C_6$)alkyl, ($C_1$-$C_6$)alkyl, ($C_2$-$C_6$)alkenyl, ($C_2$-$C_6$)alkynyl, ($C_3$-$C_8$)cycloalkyl, ($C_4$-$C_8$)cycloalkenyl, phenyl or benzyl;
Y is a bond, —C(=O)—, —S(=O)$_2$—, —C(=O)O—, —C(=O)NR$_3$—, —C(=S)—NR$_3$, —C(=NH)NR$_3$ or —S(=O)$_2$NR$_3$— wherein R$_3$ is hydrogen or optionally substituted $C_1$-$C_6$ alkyl;
$L^1$ is a divalent radical of formula -(Alk$^1$)$_m$(Q)$_n$(Alk$^2$)$_p$- wherein
m, n and p are independently 0 or 1,
Q is (i) an optionally substituted divalent mono- or bicyclic carbocyclic or heterocyclic radical having 5-13 ring members, or (ii), in the case where both m and p are 0, a divalent radical of formula —X$^2$-Q$^1$- or -Q$^1$-X$^2$— wherein X$^2$ is —O—, S— or NR$^A$— wherein R$^A$ is hydrogen or optionally substituted $C_1$-$C_3$ alkyl, and Q$^1$ is an optionally substituted divalent mono- or bicyclic carbocyclic or heterocyclic radical having 5-13 ring members,
Alk$^1$ and Alk$^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—NR$^A$—) link wherein R$^A$ is hydrogen or optionally substituted $C_1$-$C_3$ alkyl;
X$^1$ represents a bond; —C(=O); or —S(=O)$_2$—; —NR$_4$C(=O)—, —C(=O)NR$_4$—, —NR$_4$C(=O) NR$_5$—, —NR$_4$S(=O)$_2$—, or —S(=O)$_2$NR$_4$— wherein R$_4$ and R$_5$ are independently hydrogen or optionally substituted $C_1$-$C_6$ alkyl;
z is 0 or 1;
A represents an optionally substituted mono-, bi- or tricyclic carbocyclic or heterocyclic ring system wherein the radicals R$_1$R$_2$NH—Y-L$^1$-X$^1$-[CH$_2$]$_z$- and HON-HCO-[LINKER]- are attached at different ring atoms; and
-[Linker]- represents a divalent linker radical of formula —(CH$_2$)$_x$—Z-L$^2$- linking a ring atom in A with the hydroxamic acid group CONHOH, wherein
x is 0 or 1;
Z is a bond, —NR$_3$C(=O)—, —C(=O)NR$_3$—,—NR$_4$C (=O)—NR$_3$—, —C(=S)—NR$_3$, —C(=NH)—NR$_3$—NR$_3$S(=O)$_2$—, or —S(=O)$_2$NR$_3$— wherein R$_3$ is hydrogen or $C_1$-$C_6$ alkyl; —C(=O); or —S(=O)$_2$—; and
$L^2$ represents an optionally substituted, straight or branched, $C_4$-$C_7$ alkylene, $C_4$-$C_6$ alkenylene or $C_4$-$C_6$ alkynylene radical which may optionally contain or terminate in an ether (—O—), thioether (—S—) or amino (—NR$^A$—) link wherein R$^A$ is hydrogen or optionally substituted C$_1$-C$_3$ alkyl.

2. A method for the selective inhibition of the activity of an HDAC enzyme in macrophages and/or monocytes relative to other cell types, comprising contacting the enzyme with an amount, effective for such inhibition, of a compound of formula (I) or a pharmaceutically acceptable salt or N-oxide thereof:

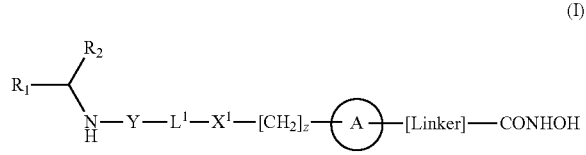

(I)

wherein
R$_1$ is an ester group which is hydrolysable by one or more intracellular carboxyesterase enzymes to a carboxylic acid group;
R$_2$ is (i) C$_1$-C$_6$ alkyl, phenyl, 2,- 3-, or 4-hydroxyphenyl, 2,- 3-, or 4-methoxyphenyl, 2,-3-, or 4-pyridylmethyl, benzyl, phenylethyl, 2-, 3-, or 4-hydroxybenzyl, 2,- 3-, or 4-benzyloxybenzyl, 2,- 3-, or 4- C$_1$-C$_6$ alkoxybenzyl, and benzyloxy(C$_1$-C$_6$alkyl)-group s; or
(ii) the characterising group of a natural α amino acid, in which any functional group may be protected; or
(iii) a group -[Alk]$_n$R$_6$ where Alk is a (C$_1$-C$_6$)alkyl or (C$_2$-C$_6$)alkenyl group optionally interrupted by one or more —O—, or —S— atoms or —N(R$_7$)— groups where R$_7$ is a hydrogen atom or a (C$_1$-C$_6$)alkyl group, n is 0 or 1, and R$_6$ is an optionally substituted cycloalkyl or cycloalkenyl group;
(iv) a benzyl group substituted in the phenyl ring by a group of formula —OCH$_2$COR$_8$ where R$_8$ is hydroxyl, amino, (C$_1$-C$_6$)alkoxy, phenyl(C$_1$-C$_6$)alkoxy, (C$_1$-C$_6$)alkylamino, di((C$_1$-C$_6$)alkyl)amino, phenyl(C$_1$-C$_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or
(v) a heterocyclic(C$_1$-C$_6$)alkyl group, either being unsubstituted or mono- or di-substituted in the heterocyclic ring with halo, nitro, carboxy, (C$_1$-C$_6$)alkoxy, cyano, (C$_1$-C$_6$)alkanoyl, trifluoromethyl (C$_1$-C$_6$)alkyl, hydroxy, formyl, amino, (C$_1$-C$_6$)alkylamino, di-(C$_1$-C$_6$) alkylamino, mercapto, (C$_1$-C$_6$)alkylthio, hydroxy(C$_1$-C$_6$)alkyl, mercapto(C$_1$-C$_6$)alkyl or (C$_1$-C$_6$)alkylphenylmethyl; or
(vi) a group —CR$_a$R$_b$R$_c$ in which:
each of R$_a$, R$_b$ and R$_c$ is independently hydrogen, (C$_1$-C$_6$) alkyl, (C$_2$-C$_6$)alkenyl, (C$_2$-C$_6$)alkynyl, phenyl(C$_1$-C$_6$) alkyl, (C$_3$-C$_8$)cycloalkyl; or
R$_c$ is hydrogen and R$_a$ and R$_b$ are independently phenyl or heteroaryl such as pyridyl; or
R$_c$ is hydrogen, (C$_1$-C$_6$)alkyl, (C$_2$-C$_6$)alkenyl, (C$_2$-C$_6$) alkynyl, phenyl(C$_1$-C$_6$)alkyl, or (C$_3$-C$_8$)cycloalkyl, and R$_a$ and R$_b$ together with the carbon atom to which they are attached form a 3 to 8 membered cycloalkyl or a 5- to 6-membered heterocyclic ring; or
R$_a$, R$_b$ and R$_c$ together with the carbon atom to which they are attached form a tricyclic ring (for example adamantyl); or
R$_a$ and R$_b$ are each independently (C$_1$-C$_6$)alkyl, (C$_2$-C$_6$) alkenyl, (C$_2$-C$_6$)alkynyl, phenyl(C$_1$-C$_6$)alkyl, or a group as defined for R$_c$ below other than hydrogen, or R$_a$ and R$_b$ together with the carbon atom to which they are attached form a cycloalkyl or heterocyclic ring, and R$_c$ is hydrogen, —OH, —SH, halogen, —CN, —CO$_2$H, (C$_1$-C$_4$)perfluoroalkyl, —CH$_2$OH, —CO$_2$(C$_1$-C$_6$)alkyl, —O (C$_1$-C$_6$)alkyl, —O(C$_2$-C$_6$)alkenyl, —S(C$_1$-C$_6$) alkyl, —SO(C$_1$-C$_6$)alkyl, —SO$_2$(C$_1$-C$_6$) alkyl, —S(C$_2$-C$_6$)alkenyl, —SO(C$_2$-C$_6$)alkenyl, —SO$_2$(C$_2$-C$_6$)alkenyl or a group -Q-W wherein Q represents a bond or —O—, —S—, —SO— or —SO$_2$— and W represents a phenyl, phenylalkyl, (C$_3$-C$_8$)cycloalkyl, (C$_3$-C$_8$)cycloalkylalkyl, (C$_4$-C$_8$)cycloalkenyl, (C$_4$-C$_8$)cycloalkenylalkyl, heteroaryl or heteroarylalkyl group, which group W may optionally be substituted by one or more substituents independently selected from, hydroxyl, halogen, —CN, —CO$_2$H, —CO$_2$(C$_1$-C$_6$)alkyl, —CONH$_2$, —CONH(C$_1$-C$_6$)alkyl, —CONH(C$_1$-C$_6$alkyl)$_2$, —CHO, —CH$_2$OH, (C$_1$-C$_4$)perfluoroalkyl, —O(C$_1$-C$_6$)alkyl, —S(C$_1$-C$_6$)alkyl, —SO(C$_1$-C$_6$)alkyl, —SO$_2$(C$_1$-C$_6$)alkyl, —NO$_2$, —NH$_2$, —NH(C$_1$-C$_6$) alkyl, —N((C$_1$-C$_6$)alkyl)$_2$, —NHCO(C$_1$-C$_6$)alkyl, (C$_1$-C$_6$)alkyl, (C$_2$-C$_6$)alkenyl, (C$_2$-C$_6$)alkynyl, (C$_3$-C$_8$)cycloalkyl, (C$_4$-C$_8$)cycloalkenyl, phenyl or benzyl;
Y is a bond, —S(=O)$_2$— or —S(=O)$_2$NR$_3$— wherein R$_3$ is hydrogen or optionally substituted C$_1$-C$_6$ alkyl;
L$^1$ is a divalent radical of formula -(Alk$^1$)$_m$(Q)$_n$(Alk$^2$)$_p$- wherein m, n and p are independently 0 or 1,
Q is (i) an optionally substituted divalent mono- or bicyclic carbocyclic or heterocyclic radical having 5-13 ring members, or (ii), in the case where both m and p are 0, a divalent radical of formula —X$^2$-Q$^1$- or -Q$^1$-X$^2$— wherein X$^2$ is —O—, S— or NR$^A$— wherein R$^A$ is hydrogen or optionally substituted C$_1$-C$_3$ alkyl, and Q$^1$ is an optionally substituted divalent mono- or bicyclic carbocyclic or heterocyclic radical having 5-13 ring members,
Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl;
X$^1$ represents a bond; —C(=O); or —S(=O)$_2$—; —NR$_4$C(=O)—, —C(=O)NR$_4$—, —NR$_4$C(=O) NR$_5$—, —NR$_4$S(=O)$_2$—, or —S(=O)$_2$NR$_4$— wherein R$_4$ and R$_5$ are independently hydrogen or optionally substituted C$_1$-C$_6$ alkyl;
z is 0 or 1;
A represents an optionally substituted mono-, bi- or tricyclic carbocyclic or heterocyclic ring system wherein the radicals R$_1$R$_2$NH—Y-L$^1$-X$^1$-[CH$_2$]$_z$— and HON-HCO-[LINKER]- are attached at different ring atoms; and
-[Linker]- represents a divalent linker radical of formula —(CH$_2$)$_x$—Z-L$^2$- linking a ring atom in A with the hydroxamic acid group CONHOH, wherein
x is 0 or 1;
Z is a bond, —NR$_3$C(=O)—, —C(=O)NR$_3$—, —NR$_4$C (=O)-NR$_3$—, —C(=S)—NR$_3$, —C(=NH)—NR$_3$—

$NR_3S(=O)_2-$, or $-S(=O)_2NR_3-$ wherein $R_3$ is hydrogen or $C_1-C_6$ alkyl; $-C(=O)$; or $-S(=O)_2-$; and $L^2$ represents an optionally substituted, straight or branched, $C_4-C_7$ alkylene, $C_4-C_6$ alkenylene or $C_4-C_6$ alkynylene radical which may optionally contain or terminate in an ether (—O—), thioether (—S—) or amino ($-NR^A-$) link wherein $R^A$ is hydrogen or optionally substituted $C_1-C_3$ alkyl;

with the proviso that the nitrogen of the amino acid ester moiety is not directly linked to a carbonyl group.

3. A method as claimed in claim 1 or claim 2, wherein the HDAC enzyme is HDAC1 and the inhibition of HDAC1 activity occurs ex vivo or in vivo in an individual.

4. A method for the treatment of cell-proliferation disease, polyglutamine disease, neurodegenerative disease, autoimmune disease, inflammatory disease, organ transplant rejection, diabetes, haematological disorders and infection, which comprises administering to a subject suffering such disease an effective amount of a compound of formula (I) or a pharmaceutically acceptable salt or N-oxide thereof,

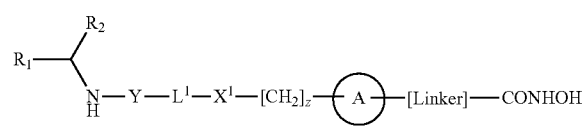

(I)

wherein $R_1$ is a an ester group which is hydrolysable by one or more intracellular carboxyesterase enzymes to a carboxylic acid group;

$R_2$ is (i) $C_1-C_6$ alkyl, phenyl, 2,- 3-, or 4-hydroxyphenyl, 2,- 3-, or 4-methoxyphenyl, 2,-3-, or 4-pyridylmethyl, benzyl, phenylethyl, 2-, 3-, or 4-hydroxybenzyl, 2,- 3-, or 4-benzyloxybenzyl, 2,- 3-, or 4-$C_1-C_6$ alkoxybenzyl, and benzyloxy($C_1-C_6$alkyl)-groups; or (ii) the characterising group of a natural α amino acid, in which any functional group may be protected; or (iii) a group -[Alk]$_n$R$_6$ where Alk is a $(C_1-C_6)$alkyl or $(C_2-C_6)$alkenyl group optionally interrupted by one or more —O—, or —S— atoms or —N(R$_7$)— groups where $R_7$ is a hydrogen atom or a $(C_1-C_6)$alkyl group, n is 0 or 1, and $R_6$ is an optionally substituted cycloalkyl or cycloalkenyl group;

(iv) a benzyl group substituted in the phenyl ring by a group of formula —OCH$_2$COR$_8$ where $R_8$ is hydroxyl, amino, $(C_1-C_6)$alkoxy, phenyl$(C_1-C_6)$alkoxy, $(C_1-C_6)$alkylamino, di$((C_1-C_6)$alkyl)amino, phenyl$(C_1-C_6)$alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or (v) a heterocyclic$(C_1-C_6)$alkyl group, either being unsubstituted or mono- or di-substituted in the heterocyclic ring with halo, nitro, carboxy, $(C_1-C_6)$alkoxy, cyano, $(C_1-C_6)$alkanoyl, trifluoromethyl $(C_1-C_6)$alkyl, hydroxy, formyl, amino, $(C_1-C_6)$alkylamino, di-$(C_1-C_6)$ alkylamino, mercapto, $(C_1-C_6)$alkylthio, hydroxy$(C_1-C_6)$alkyl, mercapto$(C_1-C_6)$alkyl or $(C_1-C_6)$alkylphenylmethyl; or (vi) a group —CR$_a$R$_b$R$_c$ in which:
each of $R_a$, $R_b$ and $R_c$ is independently hydrogen, $(C_1-C_6)$ alkyl, $(C_2-C_6)$alkenyl, $(C_2-C_6)$alkynyl, phenyl$(C_1-C_6)$ alkyl, $(C_3-C_8)$cycloalkyl; or $R_c$ is hydrogen and $R_a$ and $R_b$ are independently phenyl or heteroaryl such as pyridyl; or $R_c$ is hydrogen, $(C_1-C_6)$alkyl, $(C_2-C_6)$alkenyl, $(C_2-C_6)$ alkynyl, phenyl$(C_1-C_6)$alkyl, or $(C_3-C_8)$cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently $(C_1-C_6)$alkyl, $(C_2-C_6)$ alkenyl, $(C_2-C_6)$alkynyl, phenyl$(C_1-C_6)$alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, $(C_1-C_4)$perfluoroalkyl, —CH$_2$OH, —CO$_2(C_1-C_6)$alkyl, —O$(C_1-C_6)$alkyl, —O$(C_2-C_6)$alkenyl, —S$(C_1-C_6)$ alkyl, —SO$(C_1-C_6)$alkyl, —SO$_2(C_1-C_6)$ alkyl, —S$(C_2-C_6)$alkenyl, —SO$(C_2-C_6)$alkenyl, —SO$_2(C_2-C_6)$alkenyl or a group -Q-W wherein Q represents a bond or —O—, —S—, —SO— or —SO$_2$— and W represents a phenyl, phenylalkyl, $(C_3-C_8)$cycloalkyl, $(C_3-C_8)$cycloalkylalkyl, $(C_4-C_8)$cycloalkenyl, $(C_4-C_8)$cycloalkenylalkyl, heteroaryl or heteroarylalkyl group, which group W may optionally be substituted by one or more substituents independently selected from, hydroxyl, halogen, —CN, —CO$_2$H, —CO$_2(C_1-C_6)$alkyl, —CONH$_2$, —CONH$(C_1-C_6)$alkyl, —CONH$(C_1-C_6$alkyl)$_2$, —CHO, —CH$_2$OH, $(C_1-C_4)$perfluoroalkyl, —O$(C_1-C_6)$alkyl, —S$(C_1-C_6)$alkyl, —SO$(C_1-C_6)$alkyl, —SO$_2(C_1-C_6)$alkyl, —NO$_2$, —NH$_2$, —NH$(C_1-C_6)$ alkyl, —N$((C_1-C_6)$alkyl)$_2$, —NHCO$(C_1-C_6)$alkyl, $(C_1-C_6)$alkyl, $(C_2-C_6)$alkenyl, $(C_2-C_6)$alkynyl, $(C_3-C_8)$cycloalkyl, $(C_4-C_8)$cycloalkenyl, phenyl or benzyl;

Y is a bond, —C(=O)—, —S(=O)$_2$—, —C(=O)O—, —C(=O)NR$_3$—, —C(=S)—NR$_3$, —C(=NH)NR$_3$ or —S(=O)$_2$NR$_3$— wherein $R_3$ is hydrogen or optionally substituted $C_1-C_6$ alkyl;

$L^1$ is a divalent radical of formula -(Alk$^1$)$_m$(Q)$_n$(Alk$^2$)$_p$- wherein m, n and p are independently 0 or 1, Q is (i) an optionally substituted divalent mono- or bicyclic carbocyclic or heterocyclic radical having 5-13 ring members, or (ii), in the case where both m and p are 0, a divalent radical of formula —X$^2$-Q$^1$- or -Q$^1$-X$^2$— wherein X$^2$ is —O—, S— or NR$^A$— wherein $R^A$ is hydrogen or optionally substituted $C_1-C_3$ alkyl, and Q$^1$ is an optionally substituted divalent mono- or bicyclic carbocyclic or heterocyclic radical having 5-13 ring members, Alk$^1$ and Alk$^2$ independently represent optionally substituted divalent $C_3-C_7$ cycloalkyl radicals, or optionally substituted straight or branched, $C_1-C_6$ alkylene, $C_2-C_6$ alkenylene, or $C_2-C_6$ alkynylene radicals which may optionally contain or terminate in an ether (—O—), thioether (—S—) or amino (—NR$^A$—) link wherein $R^A$ is hydrogen or optionally substituted $C_1-C_3$ alkyl;

X$^1$ represents a bond; —C(=O); or —S(=O)$_2$—; —NR$_4$C(=O)—, —C(=O)NR$_4$—, —NR$_4$C(=O) NR$_5$—, —NR$_4$S(=O)$_2$—, or —S(=O)$_2$NR$_4$— wherein $R_4$ and $R_5$ are independently hydrogen or optionally substituted $C_1-C_6$ alkyl;

z is 0 or 1;

A represents an optionally substituted mono-, bi- or tricyclic carbocyclic or heterocyclic ring system wherein the radicals $R_1R_2NH-Y-L^1-X^1-[CH_2]_z-$ and HON-HCO-[LINKER] are attached at different ring atoms; and -[Linker]- represents a divalent linker radical of formula $-(CH_2)_x-Z-L^2-$ linking a ring atom in A with the hydroxamic acid group CONHOH, wherein x is 0 or 1;

Z is a bond, $-NR_3C(=O)-$, $-C(=O)NR_3-$, $-NR_4C(=O)-NR_3-$, $-C(=S)-NR_3$, $-C(=NH)-NR_3-NR_3S(=O)_2-$, or $-S(=O)_2NR_3-$ wherein $R_3$ is hydrogen or $C_1-C_6$ alkyl; $-C(=O)$; or $-S(=O)_2-$; and $L^2$ represents an optionally substituted, straight or branched, $C_4-C_7$ alkylene, $C_4-C_6$ alkenylene or $C_4-C_6$ alkynylene radical which may optionally contain or terminate in an ether (—O—), thioether (—S—) or amino ($-NR^A-$) link wherein $R^A$ is hydrogen or optionally substituted $C_1-C_3$ alkyl.

5. A method as claimed in claim 4 wherein the cell proliferation disease is cancer.

6. A method as claimed in claim 4 wherein the autoimmune disease is rheumatoid arthritis.

7. A method as claimed in claim 1, wherein x is 0.

8. A method as claimed in claim 1, wherein Z is $-C(=O)-$, $-NHC(=O)-$ or $-C(=O)NH-$.

9. A method as claimed in claim 1, wherein $L^2$ is $-(CH_2)_5-$, $-(CH_2)_6-$, or $-(CH_2)_7-$.

10. A method as claimed in claim 9, wherein x is 0 and Z is $-C(=O)-$, $-NHC(=O)-$ or $-C(=O)NH-$.

11. A method as claimed in claim 1 wherein A is one of the following, optionally substituted:

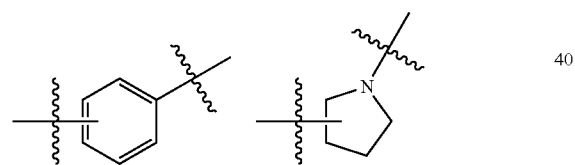

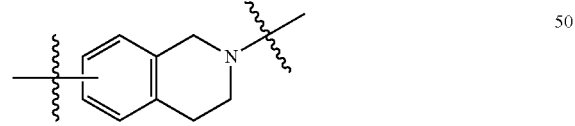

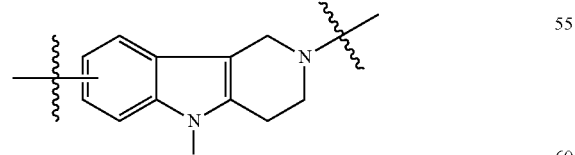

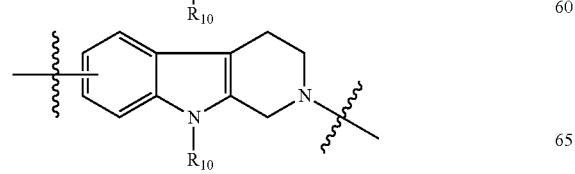

-continued

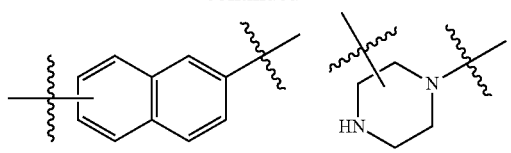

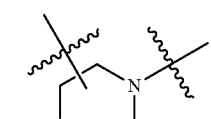

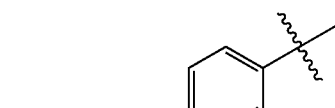

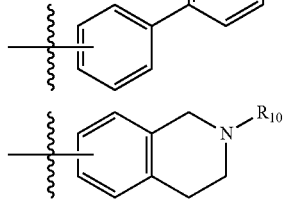

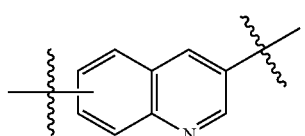

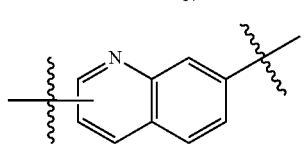

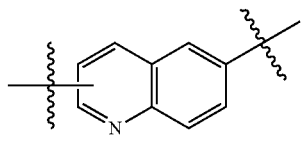

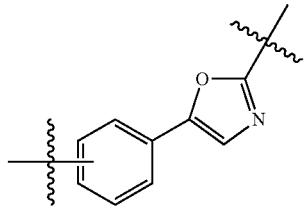

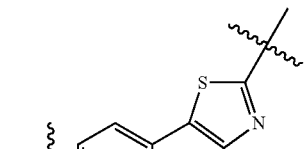

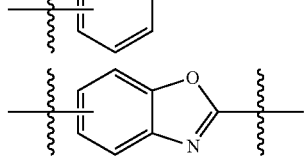

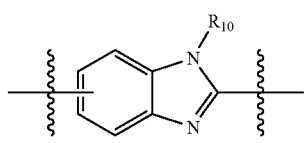

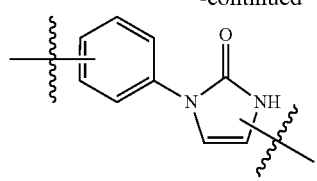
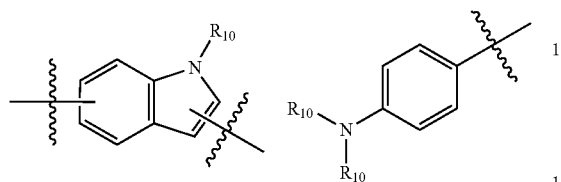
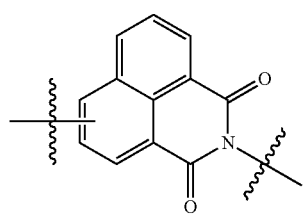
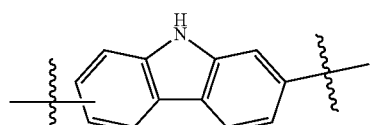
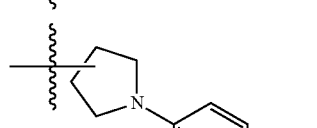
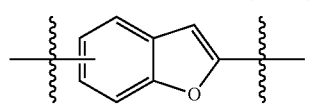
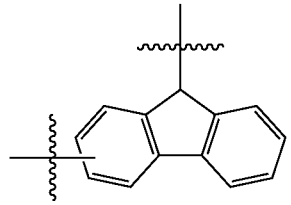
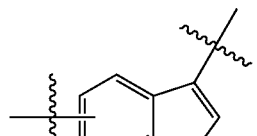
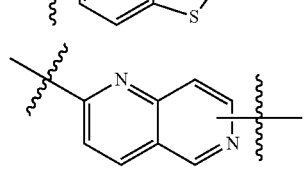
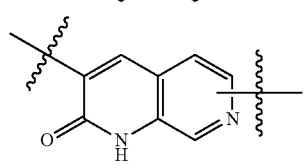
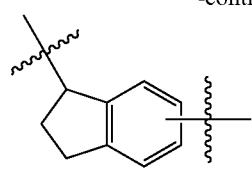
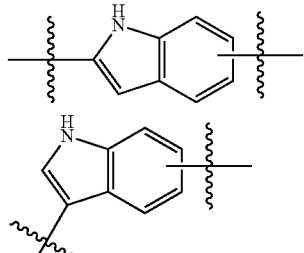
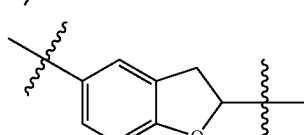
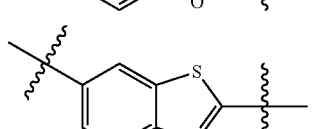
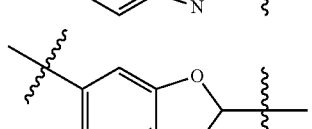
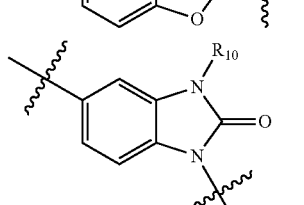
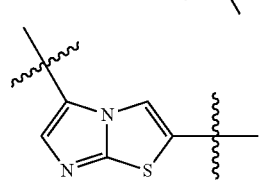
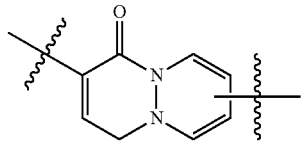
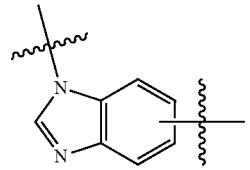
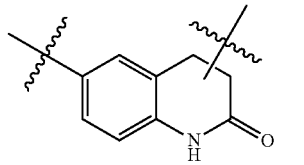

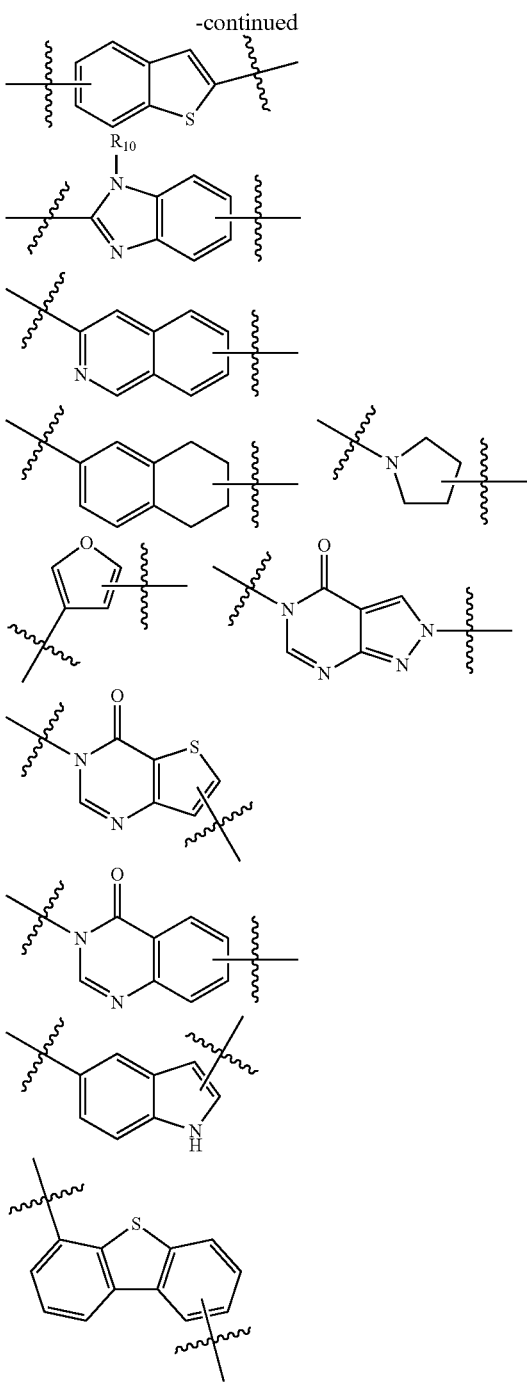

wherein $R_{10}$ is hydrogen or optionally substituted $C_1$-$C_6$ alkyl, the bond intersected by the wavy lines shown as connected to a fixed atom connects to the Linker radical in the compounds (I), and the other bond shown as floating links any convenient ring atom of the ring system shown to the grouping $R_1R_2CHNHYL^1X^1[CH2]_z$.

12. A method as claimed in claim 1, wherein A is phenyl.

13. A method as claimed in claim 1 wherein the radical —Y-L$^1$-X$^1$-[CH$_2$]$_z$— is selected from —C(=O)—, —C(=O)NH—, —(CH$_2$)$_v$—, —(CH$_2$)$_v$O—, —C(=O)—(CH$_2$)$_v$—, —C(=O)—(CH$_2$)$_v$O—, —C(=O)—NH—(CH$_2$)$_w$—, —C(=O)—NH—(CH$_2$)$_w$O—

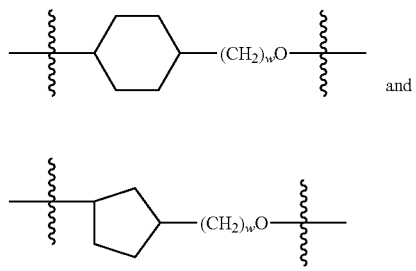

wherein v is 1, 2, 3 or 4 and w is 1, 2 or 3.

14. A method as claimed in claim 1 wherein the radical —Y-L$^1$-X$^1$-[CH$_2$]$_z$—, is —CH$_2$—, —CH$_2$O—, —C(=O)—CH$_2$—, —C(=O)—CH$_2$O—, —C(=O)—NH—CH$_2$—, or —C(=O)—NH—CH$_2$O—.

15. A method as claimed in claim 1 wherein $R_1$ is an ester group of formula —(C=O)OR$_9$ wherein R$_9$ is (i) $R_7R_8CH$— wherein $R_7$ is optionally substituted ($C_1$-$C_3$) alkyl-($Z^1$)$_a$—($C_1$-$C_3$)alkyl- or ($C_2$-$C_3$)alkenyl-($Z^1$)$_a$—($C_1$-$C_3$)alkyl- wherein a is 0 or 1 and $Z^1$ is —O—, —S—, or —NH—, and $R_8$ is hydrogen or ($C_1$-$C_3$)alkyl- or $R_7$ and $R_8$ taken together with the carbon to which they are attached form an optionally substituted $C_3$-$C_7$ cycloalkyl ring or an optionally substituted heterocyclic ring of 5- or 6-ring atoms; or (ii) optionally substituted phenyl or monocyclic heterocyclic having 5 or 6 ring atoms.

16. A method as claimed in claim 15 wherein R$_9$ is methyl, ethyl, n- or iso-propyl, n- or sec-butyl, cyclohexyl, allyl, phenyl, benzyl, 2-, 3- or 4-pyridylmethyl, N-methylpiperidin-4-yl, tetrahydrofuran-3-yl or methoxyethyl.

17. A method as claimed in claim 15 wherein R$_9$ is cyclopentyl.

18. A method as claimed in claim 1 wherein R$_2$ is cyclohexylmethyl, cyclohexyl, pyridin-3-ylmethyl, sec-butyl, tert-butyl, 1-benzylthio-1-methylethyl, 1-methylthio-1-methylethyl, or 1-mercapto-1-methylethyl.

19. A method as claimed in claim 1 wherein R$_2$ is phenyl, benzyl, phenylethyl, tert-butoxymethyl or iso-butyl.

20. A method as claimed in claim 15, wherein the compound is of formula (ID):

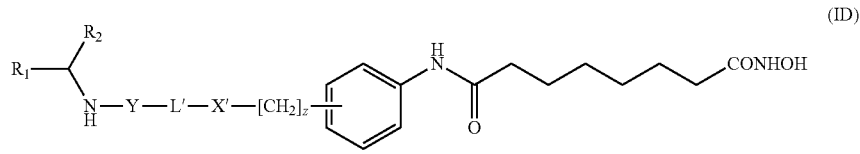

(ID)

wherein —Y-L¹-X¹-[CH₂]_z—, is —CH₂—, —CH₂O—, —C(=O)—CH₂—, —C(=O)—CH₂O—, —C(=O)—NH—CH₂—, or —C(=O)—NH—CH₂O—; and $R_2$ is phenyl, benzyl, phenylethyl, tert-butoxymethyl or iso-butyl.

21. A method as claimed in claim 20, wherein $R_1$ is an ester group of formula —(C=O)OR₉ wherein $R_9$ is cyclopentyl.

22. A method as claimed in claim 1, wherein the compound is (S)-[4-(7-hydroxy carbamoyl-heptanoylamino)-benzylamino]-phenyl-acetic acid cyclopentyl ester or a pharmaceutically acceptable salt thereof.

23. A method as claimed in claim 4, wherein x is 0.

24. A method as claimed in claim 4, wherein Z is —C(=O)—, —NHC(=O)— or —C(=O)NH—.

25. A method as claimed in claim 4, wherein $L^2$ is —(CH₂)₅—, —(CH₂)₆—, or —(CH₂)₇—.

26. A method as claimed in claim 4, wherein x is 0 and Z is —C(=O)—, —NHC(=O)— or —C(=O)NH—.

27. A method as claimed in claim 4 wherein A is one of the following, optionally substituted:

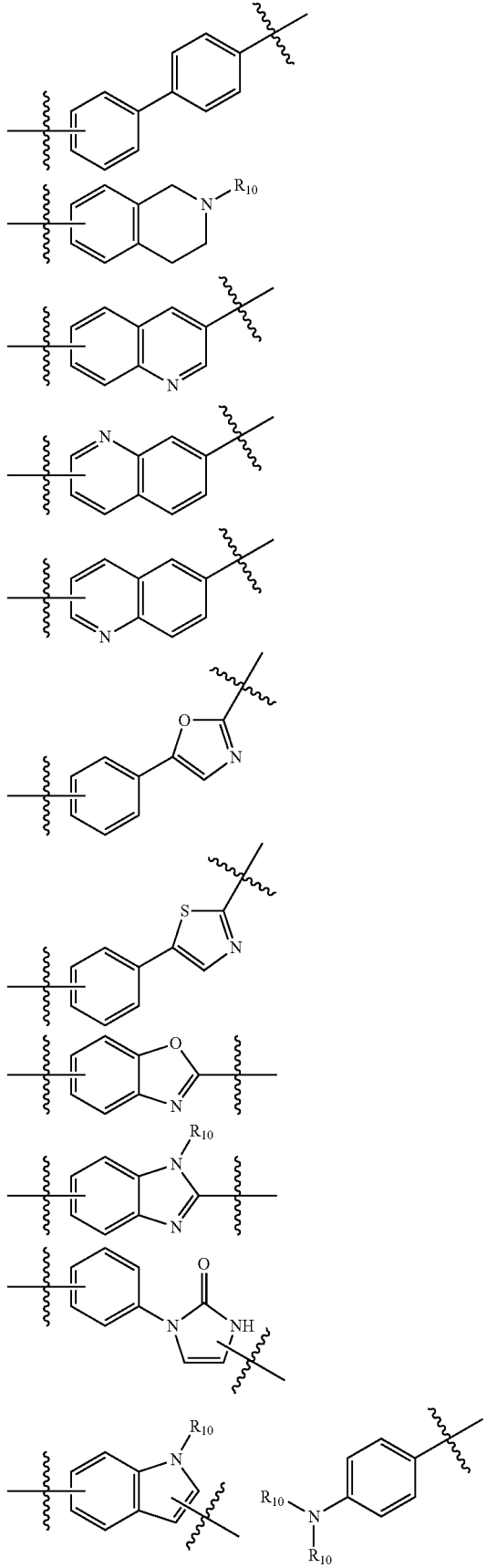

-continued

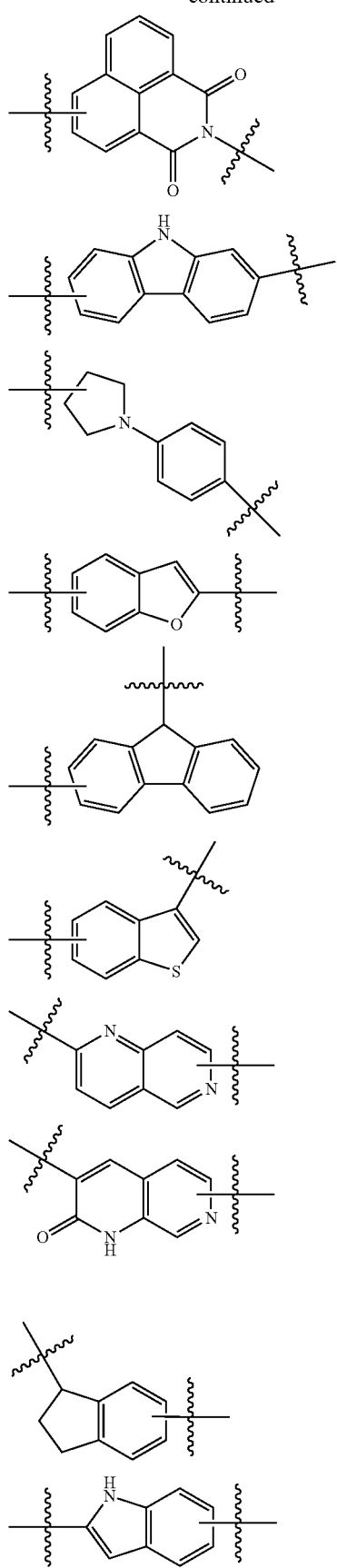
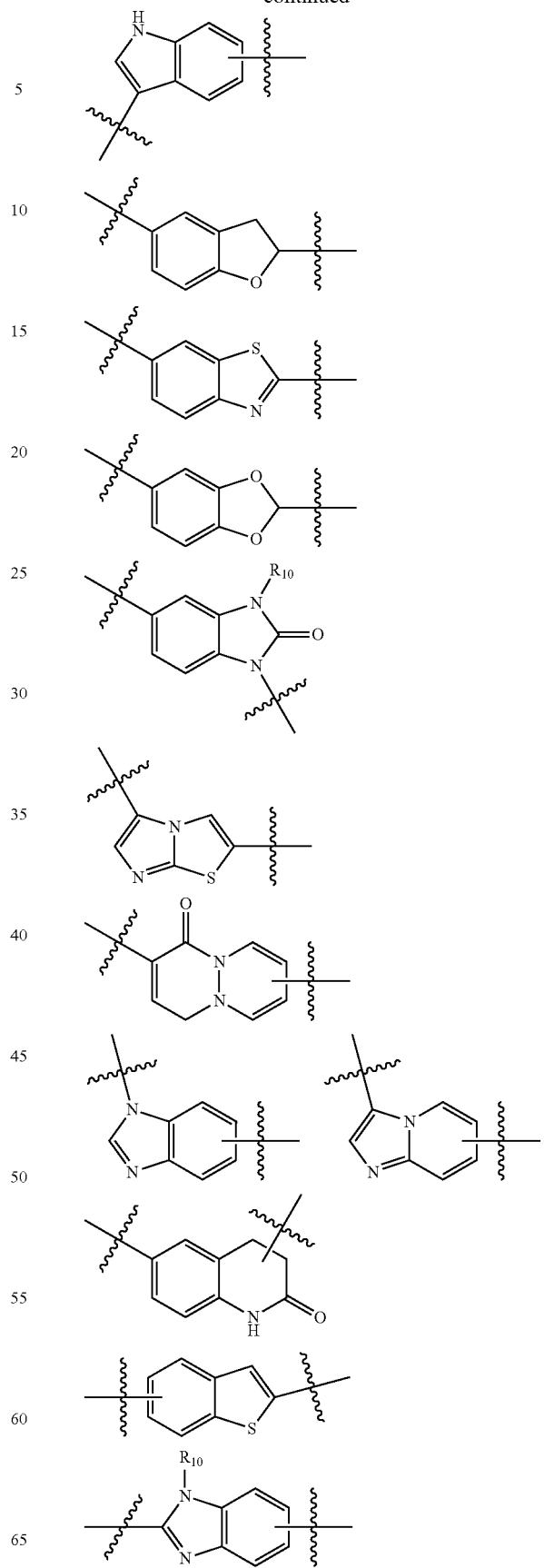

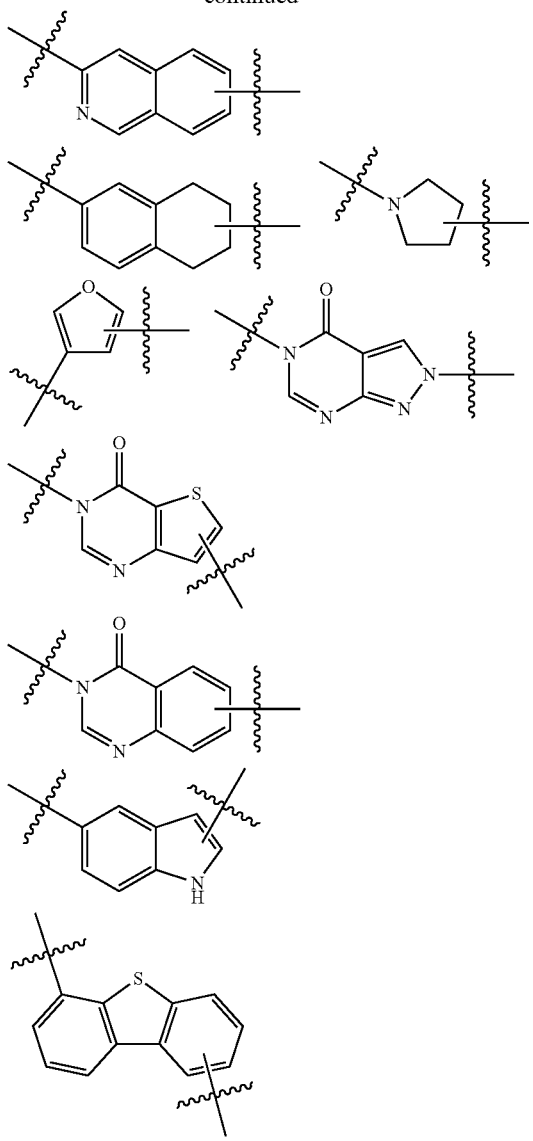

wherein R₁₀ is hydrogen or optionally substituted $C_1$-$C_6$ alkyl, the bond intersected by the wavy lines shown as connected to a fixed atom connects to the Linker radical in the compounds (I), and the other bond shown as floating links any convenient ring atom of the ring system shown to the grouping $R_1R_2CHNHYL^1X^1[CH_2]_z$.

28. A method as claimed in claim 4, wherein A is phenyl.

29. A method as claimed in claim 4 wherein the radical —Y-L¹-X¹-[CH₂]ᵤ— is selected from —C(=O)—, —C(=O)NH—, —(CH₂)ᵥ—, —(CH₂)ᵥO—, —C(=O)—

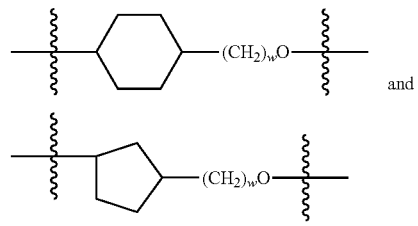

(CH₂)ᵥ—, —C(=O)—(CH₂)ᵥO—, —C(=O)—NH—(CH₂)₅—, —C(=O)—NH—(CH₂)ᵥO— wherein v is 1, 2, 3 or 4 and w is 1, 2 or 3.

30. A method as claimed in claim 4 wherein the radical —Y-L¹-X¹-[CH₂]ᵤ—, is —CH₂—, —CH₂O—, —C(=O)—CH₂—, —C(=O)—CH₂O—, —C(=O)—NH—CH₂—, or —C(=O)—NH—CH₂O—.

31. A method as claimed in claim 4 wherein R₁ is an ester group of formula —(C=O)OR₉ wherein R₉ is (i) R₇R₈CH— wherein R₇ is optionally substituted ($C_1$-$C_3$) alkyl-(Z¹)ₐ—($C_1$-$C_3$)alkyl- or ($C_2$-$C_3$)alkenyl-(Z¹)ₐ—($C_1$-$C_3$)alkyl- wherein a is 0 or 1 and Z¹ is —O—, —S—, or —NH—, and R₈ is hydrogen or ($C_1$-$C_3$)alkyl- or R₇ and R₈ taken together with the carbon to which they are attached form an optionally substituted $C_3$-$C_7$ cycloalkyl ring or an optionally substituted heterocyclic ring of 5- or 6-ring atoms; or (ii) optionally substituted phenyl or monocyclic heterocyclic having 5 or 6 ring atoms.

32. A method as claimed in claim 31 wherein R₉ is methyl, ethyl, n- or iso-propyl, n- or sec-butyl, cyclohexyl, allyl, phenyl, benzyl, 2-, 3- or 4-pyridylmethyl, N-methylpiperidin-4-yl, tetrahydrofuran-3-yl or methoxyethyl.

33. A method as claimed in claim 31 wherein R₉ is cyclopentyl.

34. A method as claimed in claim 4 wherein R₂ is cyclohexylmethyl, cyclohexyl, pyridin-3-ylmethyl, sec-butyl, tert-butyl, 1-benzylthio-1-methylethyl, 1-methylthio-1-methylethyl, or 1-mercapto-1-methylethyl.

35. A method as claimed in claim 4 wherein R₂ is phenyl, benzyl, phenylethyl, tert-butoxymethyl or iso-butyl.

36. A method as claimed in claim 31, wherein the compound is of formula (ID):

(ID)

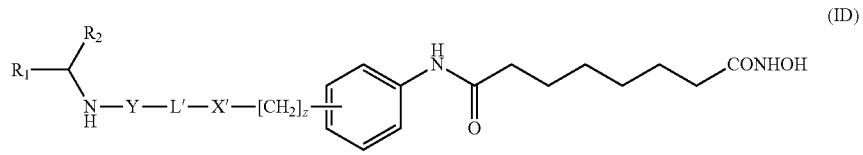

wherein the radical —Y-L¹-X¹-[CH₂]ᵤ— is —CH₂—, —CH₂O—, —C(=O)—CH₂—, —C(=O)—CH₂O—, —C(=O)—NH—CH₂—, or —C(=O)—NH—CH₂O—; and R₂ is phenyl, benzyl, phenylethyl, tert-butoxymethyl or iso-butyl.

37. A method as claimed in claim 36, wherein $R_1$ is an ester group of formula —(C=O)$OR_9$ and $R_9$ is cyclopentyl.

38. A method as claimed in claim 4, wherein the compound is (S)-[4-(7-hydroxy carbamoyl-heptanoylamino)-benzylamino]-phenyl-acetic acid cyclopentyl ester or a pharmaceutically acceptable salt thereof.

39. A method as claimed in claim 5, wherein the compound is (S)-[4-(7-hydroxy carbamoyl-heptanoylamino)-benzylamino]-phenyl-acetic acid cyclopentyl ester or a pharmaceutically acceptable salt thereof.

40. A method as claimed in claim 6, wherein the compound is (S)-[4-(7-hydroxy carbamoyl-heptanoylamino)-benzylamino]-phenyl-acetic acid cyclopentyl ester or a pharmaceutically acceptable salt thereof.

* * * * *